(12) United States Patent
Choi

(10) Patent No.: US 6,833,253 B2
(45) Date of Patent: Dec. 21, 2004

(54) STAPHYLOCOCCUS AUREUS POLYNUCLEOTIDES AND POLYPEPTIDES

(75) Inventor: Gil H. Choi, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 186 days.

(21) Appl. No.: 09/925,637

(22) Filed: Aug. 10, 2001

(65) Prior Publication Data

US 2002/0103338 A1 Aug. 1, 2002

Related U.S. Application Data

(63) Continuation-in-part of application No. PCT/US00/23773, filed on Aug. 31, 2000, and a continuation-in-part of application No. 08/956,171, filed on Oct. 20, 1997, now Pat. No. 6,593,114, and a continuation-in-part of application No. 08/781,986, filed on Jan. 3, 1997, now Pat. No. 6,737,248.

(60) Provisional application No. 60/151,933, filed on Sep. 1, 1999, and provisional application No. 60/009,861, filed on Jan. 5, 1996.

(51) Int. Cl.$^7$ ................................................. C12P 21/06
(52) U.S. Cl. ................ 435/69.1; 435/252.3; 435/320.1; 435/6; 536/23.1; 536/23.4; 536/23.7
(58) Field of Search ........................ 435/6, 69.1, 252.3, 435/320.1; 536/23.1, 23.4, 23.7

(56) References Cited

FOREIGN PATENT DOCUMENTS

EP          0 786 519 A2 *    7/1997

* cited by examiner

*Primary Examiner*—James Martinell
(74) *Attorney, Agent, or Firm*—Human Genome Sciences, Inc.

(57) ABSTRACT

The present invention relates to novel genes from *S. aureus* and the polypeptides they encode. Also provided are vectors, host cells, antibodies and recombinant methods for producing the same. The invention further relates to screening methods for identifying agonists and antagonists of *S. aureus* polypeptide activity. The invention additionally relates to diagnostic methods for detecting *Staphylococcus* nucleic acids, polypeptides and antibodies in a biological sample. The present invention further relates to novel vaccines for the prevention or attenuation of infection by *Staphylococcus*.

64 Claims, No Drawings

SEQUENCE LISTING

<160> NUMBER OF SEQ ID NOS: 74

<210> SEQ ID NO 1
<211> LENGTH: 1318
<212> TYPE: DNA
<213> ORGANISM: Homo sapiens

<400> SEQUENCE: 1

```
atgacacact atcattttgt cggaattaaa ggttctggca tgagttcatt agcacaaatc      60
atgcatgatt taggacatga agttcaagga tcggatattg agaactacgt atttacagaa     120
gttgctctta gaaataaggg gataaaaata ttaccatttg atgctaataa cataaaagaa     180
gatatggtag ttatacaagg taatgcattc gcgagtagcc atgaagaaat agtacgtgca     240
catcaattga aattagatgt tgtaagttat aatgattttt taggacagat tattgatcaa     300
tatacttcag tagctgtaac tggtgcacat ggtaaaactt ctacaacagg tttattatca     360
```

-continued

```
catgttatga atggtgataa aaagacttca ttttaattg gtgatggcac aggtatggga    420
ttgcctgaaa gtgattattt cgcttttgag gcatgtgaat atagacgtca ctttttaagt    480
tataaacctg attacgcaat tatgacaaat attgatttcg atcatcctga ttattttaaa    540
gatattaatg atgttttga tgcattccaa gaaatggcac ataatgttaa aaaggtatt    600 attgcttggg gtgatgatga acatctacgt aaaattgaag cagatgttcc aatttattat    660
tatggattta agattcgga tgacatttat gctcaaaata ttcaaattac ggataaaggt    720
actgcttttg atgtgtatgt ggatggtgag ttttatgatc acttcctgtc tccacaatat    780
ggtgaccata cagttttaaa tgcattagct gtaattgcga ttagttattt agagaagcta    840
gatgttacaa atattaaaga agcattagaa acgtttggtg gtgttaaacg tcgtttcaat    900
gaaactacaa ttgcaaatca agttattgta gatgattatg cacaccatcc aagagaaatt    960
agtgctacaa ttgaaacagc acgaaagaaa tatccacata agaagttgt tgcagtattt   1020 caaccacaca ctttctctag aacacaggca tttttaaatg aatttgcaga agtttaagt   1080 aaagcagatc gtgtattctt atgtgaaatt tttggatcaa ttagagaaaa tactggcgca   1140
ttaacgatac aagatttaat tgataaaatt gaaggtgcat cgttaattaa tgaagattct   1200
attaatgtat tagaacaatt tgataatgct gttattttat ttatgggtgc aggtgatatt   1260
caaaaattac aaaatgcata tttagataaa ttaggcatga aaaatgcgtt ttaagctt     1318
```

<210> SEQ ID NO 2
<211> LENGTH: 437
<212> TYPE: PRT
<213> ORGANISM: Homo sapiens

<400> SEQUENCE: 2

```
Met Thr His Tyr His Phe Val Gly Ile Lys Gly Ser Gly Met Ser Ser
 1               5                  10                  15

Leu Ala Gln Ile Met His Asp Leu Gly His Glu Val Gln Gly Ser Asp
             20                  25                  30

Ile Glu Asn Tyr Val Phe Thr Glu Val Ala Leu Arg Asn Lys Gly Ile
         35                  40                  45

Lys Ile Leu Pro Phe Asp Ala Asn Asn Ile Lys Glu Asp Met Val Val
     50                  55                  60

Ile Gln Gly Asn Ala Phe Ala Ser Ser His Glu Glu Ile Val Arg Ala
 65                  70                  75                  80

His Gln Leu Lys Leu Asp Val Val Ser Tyr Asn Asp Phe Leu Gly Gln
                 85                  90                  95

Ile Ile Asp Gln Tyr Thr Ser Val Ala Val Thr Gly Ala His Gly Lys
            100                 105                 110

Thr Ser Thr Thr Gly Leu Leu Ser His Val Met Asn Gly Asp Lys Lys
        115                 120                 125

Thr Ser Phe Leu Ile Gly Asp Gly Thr Gly Met Gly Leu Pro Glu Ser
    130                 135                 140

Asp Tyr Phe Ala Phe Glu Ala Cys Glu Tyr Arg Arg His Phe Leu Ser
145                 150                 155                 160

Tyr Lys Pro Asp Tyr Ala Ile Met Thr Asn Ile Asp Phe Asp His Pro
                165                 170                 175

Asp Tyr Phe Lys Asp Ile Asn Asp Val Phe Asp Ala Phe Gln Glu Met
            180                 185                 190

Ala His Asn Val Lys Lys Gly Ile Ile Ala Trp Gly Asp Asp Glu His
        195                 200                 205
```

```
Leu Arg Lys Ile Glu Ala Asp Val Pro Ile Tyr Tyr Gly Phe Lys
    210                 215                 220

Asp Ser Asp Asp Ile Tyr Ala Gln Asn Ile Gln Ile Thr Asp Lys Gly
225                 230                 235                 240

Thr Ala Phe Asp Val Tyr Val Asp Gly Glu Phe Tyr Asp His Phe Leu
                245                 250                 255

Ser Pro Gln Tyr Gly Asp His Thr Val Leu Asn Ala Leu Ala Val Ile
            260                 265                 270

Ala Ile Ser Tyr Leu Glu Lys Leu Asp Val Thr Asn Ile Lys Glu Ala
        275                 280                 285

Leu Glu Thr Phe Gly Gly Val Lys Arg Arg Phe Asn Glu Thr Thr Ile
    290                 295                 300

Ala Asn Gln Val Ile Val Asp Asp Tyr Ala His His Pro Arg Glu Ile
305                 310                 315                 320

Ser Ala Thr Ile Glu Thr Ala Arg Lys Lys Tyr Pro His Lys Glu Val
                325                 330                 335

Val Ala Val Phe Gln Pro His Thr Phe Ser Arg Thr Gln Ala Phe Leu
            340                 345                 350

Asn Glu Phe Ala Glu Ser Leu Ser Lys Ala Asp Arg Val Phe Leu Cys
        355                 360                 365

Glu Ile Phe Gly Ser Ile Arg Glu Asn Thr Gly Ala Leu Thr Ile Gln
    370                 375                 380

Asp Leu Ile Asp Lys Ile Glu Gly Ala Ser Leu Ile Asn Glu Asp Ser
385                 390                 395                 400

Ile Asn Val Leu Glu Gln Phe Asp Asn Ala Val Ile Leu Phe Met Gly
                405                 410                 415

Ala Gly Asp Ile Gln Lys Leu Gln Asn Ala Tyr Leu Asp Lys Leu Gly
            420                 425                 430

Met Lys Asn Ala Phe
        435

<210> SEQ ID NO 3
<211> LENGTH: 1074
<212> TYPE: DNA
<213> ORGANISM: Homo sapiens

<400> SEQUENCE: 3
atgcattttg atcaattaga tattgtagaa gaaagatacg aacagttaaa tgaactgtta      60
agtgacccag atgttgtaaa tgattcagat aaattacgta atattctaa agagcaagct     120 gatttacaaa aaactgtaga tgtttatcgt aactataaag ctaaaaaaga gaattagct     180 gatattgaag aaatgttaag tgagactgat gataaagaag aagtagaaat gttaaaagag     240
gagagtaatg gtattaaagc tgaacttcca atcttgaag aagagcttaa atatattattg     300 attcctaaag atcctaatga tgacaaagac gttattgtag aaataagagc agcagcaggt     360
ggtgatgagg ctgcgatttt tgctggtgat ttaatgcgta tgtattcaa gtatgctgaa     420 tcacaaggat tcaaaactga atagtagaa gcgtctgaaa gtgaccatgg tggttacaaa     480
gaaattagtt tctcagtttc tggtaatggc gcgtatagta aattgaaatt tgaaatggt     540 gcgcaccgcg ttcaacgtgt gcctgaaaca gaatcaggtg gacgtattca tacttcaaca     600
gctacagtgg cagtttttacc agaagttgaa gatgtagaaa ttgaaattag aaatgaagat     660
ttaaaaatcg acacgtatcg ttcaagtggt gcaggtggtc agcacgtaaa cacaactgac     720
tctgcagtac gtattaccca tttaccaact ggtgtcattg caacatcttc tgagaagtct     780
```

```
caaattcaaa accgtgaaaa agcaatgaaa gtgttaaaag cacgtttata cgatatgaaa    840
gttcaagaag aacaacaaaa gtatgcgtca caacgtaaat cagcagtcgg tactggtgat    900 cgttcgaac gtattcgaac ttataattat ccacaaagcc gtgtaacaga ccatcgtata    960
ggtctaacgc ttcaaaaatt agggcaaatt atggaaggcc atttagaaga aattatagat   1020
gcactgactt tatcagagca gacagataaa ttgaaagaac ttaataatgg tgaa         1074
```

<210> SEQ ID NO 4
<211> LENGTH: 358
<212> TYPE: PRT
<213> ORGANISM: Homo sapiens

<400> SEQUENCE: 4

```
Met His Phe Asp Gln Leu Asp Ile Val Glu Glu Arg Tyr Glu Gln Leu
 1               5                  10                  15

Asn Glu Leu Leu Ser Asp Pro Asp Val Val Asn Asp Ser Asp Lys Leu
            20                  25                  30

Arg Lys Tyr Ser Lys Glu Gln Ala Asp Leu Gln Lys Thr Val Asp Val
        35                  40                  45

Tyr Arg Asn Tyr Lys Ala Lys Lys Glu Glu Leu Ala Asp Ile Glu Glu
    50                  55                  60

Met Leu Ser Glu Thr Asp Asp Lys Glu Glu Val Glu Met Leu Lys Glu
65                  70                  75                  80

Glu Ser Asn Gly Ile Lys Ala Glu Leu Pro Asn Leu Glu Glu Glu Leu
                85                  90                  95

Lys Ile Leu Leu Ile Pro Lys Asp Pro Asn Asp Lys Asp Val Ile
           100                 105                 110

Val Glu Ile Arg Ala Ala Ala Gly Gly Asp Glu Ala Ala Ile Phe Ala
       115                 120                 125

Gly Asp Leu Met Arg Met Tyr Ser Lys Tyr Ala Glu Ser Gln Gly Phe
   130                 135                 140

Lys Thr Glu Ile Val Glu Ala Ser Glu Ser Asp His Gly Gly Tyr Lys
145                 150                 155                 160

Glu Ile Ser Phe Ser Val Ser Gly Asn Gly Ala Tyr Ser Lys Leu Lys
                165                 170                 175

Phe Glu Asn Gly Ala His Arg Val Gln Arg Val Pro Glu Thr Glu Ser
            180                 185                 190

Gly Gly Arg Ile His Thr Ser Thr Ala Thr Val Ala Val Leu Pro Glu
        195                 200                 205

Val Glu Asp Val Glu Ile Glu Ile Arg Asn Glu Asp Leu Lys Ile Asp
    210                 215                 220

Thr Tyr Arg Ser Ser Gly Ala Gly Gly Gln His Val Asn Thr Thr Asp
225                 230                 235                 240

Ser Ala Val Arg Ile Thr His Leu Pro Thr Gly Val Ile Ala Thr Ser
                245                 250                 255

Ser Glu Lys Ser Gln Ile Gln Asn Arg Glu Lys Ala Met Lys Val Leu
            260                 265                 270

Lys Ala Arg Leu Tyr Asp Met Lys Val Gln Glu Glu Gln Gln Lys Tyr
        275                 280                 285

Ala Ser Gln Arg Lys Ser Ala Val Gly Thr Gly Asp Arg Ser Glu Arg
    290                 295                 300

Ile Arg Thr Tyr Asn Tyr Pro Gln Ser Arg Val Thr Asp His Arg Ile
305                 310                 315                 320
```

```
Gly Leu Thr Leu Gln Lys Leu Gly Gln Ile Met Glu Gly His Leu Glu
                325                 330                 335

Glu Ile Ile Asp Ala Leu Thr Leu Ser Glu Gln Thr Asp Lys Leu Lys
            340                 345                 350

Glu Leu Asn Asn Gly Glu
        355

<210> SEQ ID NO 5
<211> LENGTH: 555
<212> TYPE: DNA
<213> ORGANISM: Homo sapiens

<400> SEQUENCE: 5
atggggagtg acattattaa tgaaactaaa tcaagaatgc aaaaatcaat cgaaagctta      60
tcacgtgaat tagctaacat cagtgcagga agagctaatt caaatttatt aaacggcgta    120
acagttgatt actatggtgc accaacacct gtacaacaat tagcaagcat caatgttcca    180
gaagcacgtt tacttgttat ttctccatac gacaaaactt ctgtagctga catcgaaaaa    240
gcgataatag cagctaactt aggtgttaac ccaacaagtg atggtgaagt gatacgtatt    300
gctgtacctg ccttaacaga agaacgtaga aaagagcgcg ttaaagatgt taagaaaatt    360
ggtgaagaag ctaaagtatc tgttcgaaat attcgtcgtg atatgaatga tcagttgaaa    420
aaagatgaaa aaaatggcga cattactgaa gatgagttga aagtggcac tgaagatgtt    480 cagaaagcaa cagacaattc aataaaagaa attgatcaaa tgattgctga taaagaaaaa    540
gatattatgt cagta                                                     555

<210> SEQ ID NO 6
<211> LENGTH: 185
<212> TYPE: PRT
<213> ORGANISM: Homo sapiens

<400> SEQUENCE: 6

Met Gly Ser Asp Ile Ile Asn Glu Thr Lys Ser Arg Met Gln Lys Ser
  1               5                  10                  15

Ile Glu Ser Leu Ser Arg Glu Leu Ala Asn Ile Ser Ala Gly Arg Ala
             20                  25                  30

Asn Ser Asn Leu Leu Asn Gly Val Thr Val Asp Tyr Tyr Gly Ala Pro
         35                  40                  45

Thr Pro Val Gln Gln Leu Ala Ser Ile Asn Val Pro Glu Ala Arg Leu
     50                  55                  60

Leu Val Ile Ser Pro Tyr Asp Lys Thr Ser Val Ala Asp Ile Glu Lys
 65                  70                  75                  80

Ala Ile Ile Ala Ala Asn Leu Gly Val Asn Pro Thr Ser Asp Gly Glu
                 85                  90                  95

Val Ile Arg Ile Ala Val Pro Ala Leu Thr Glu Glu Arg Arg Lys Glu
            100                 105                 110

Arg Val Lys Asp Val Lys Lys Ile Gly Glu Glu Ala Lys Val Ser Val
        115                 120                 125

Arg Asn Ile Arg Arg Asp Met Asn Asp Gln Leu Lys Lys Asp Glu Lys
    130                 135                 140

Asn Gly Asp Ile Thr Glu Asp Glu Leu Arg Ser Gly Thr Glu Asp Val
145                 150                 155                 160

Gln Lys Ala Thr Asp Asn Ser Ile Lys Glu Ile Asp Gln Met Ile Ala
                165                 170                 175

Asp Lys Glu Lys Asp Ile Met Ser Val
```

-continued

```
                    180                 185
```

<210> SEQ ID NO 7
<211> LENGTH: 1176
<212> TYPE: DNA
<213> ORGANISM: Homo sapiens

<400> SEQUENCE: 7

| | | | | | |
|---|---|---|---|---|---|
| atgggtcaa | gtaatgaatt | attattagct | actgagtatt | tagaaaaaga | aagaagatt | 60 |
| cctagagcag | tattaattga | tgctattgaa | gcagctttaa | ttactgcata | caaaaagaac | 120 |
| tatgatagtg | caagaaatgt | ccgtgtggaa | ttaaatatgg | atcaaggtac | tttcaaagtt | 180 |
| atcgctcgta | aagatgttgt | tgaagaagta | tttgacgaca | gagatgaagt | ggatttaagt | 240 |
| acagcgcttg | ttaaaaaccc | tgcatatgaa | attggtgata | tatacgaaga | agatgtaaca | 300 |
| cctaaagatt | ttggtcgtgt | aggtgctcaa | gcagcgaaac | aagcagtaat | gcaacgtctt | 360 |
| cgtgatgctg | aacgtgaaat | tttatttgaa | gaatttatag | acaaagaaga | agacatactt | 420 |
| actggaatta | ttgaccgtgt | tgaccatcgt | tatgtatatg | tgaatttagg | tcgtatcgaa | 480 |
| gctgttttat | ctgaagcaga | aagaagtcct | aacgaaaaat | atattcctaa | cgaacgtatc | 540 |
| aaagtatatg | ttaacaaagt | ggaacaaacg | acaaaaggtc | ctcaaatcta | tgtttctcgt | 600 |
| agccatccag | gtttattaaa | acgtttattt | gaacaagaag | ttccagaaat | ttacgatggt | 660 |
| actgtaattg | ttaaatcagt | agcacgtgaa | gctggcgatc | gctctaaaat | tagtgtcttc | 720 |
| tctgaaaaca | atgatataga | tgctgttggt | gcatgtgttg | gtgctaaagg | cgcacgtgtt | 780 |
| gaagctgttg | ttgaagagct | aggtggtgaa | aaaatcgaca | tcgttcaatg | gaatgaagat | 840 |
| ccaaaagtat | ttgtaaaaaa | tgctttaagc | ccttctcaag | ttttagaagt | tattgttgat | 900 |
| gaaacaaatc | aatctacagt | agttgttgtt | cctgattatc | aattgtcatt | agcgattggt | 960 |
| aaaagaggac | aaaacgcacg | tctagctgct | aaattaaccg | gctggaaaat | tgatattaaa | 1020 |
| tcagaaacag | atgcgcgtga | agcgggtatc | tatccagtag | ttgaagctga | aaaagtaact | 1080 |
| gaagaagatg | ttgctttaga | agatgctgac | acaacagaat | caaccgaaga | ggtaaatgat | 1140 |
| gtttcagttg | aaacaaatgt | agagaaagaa | tctgaa | | | 1176 |

<210> SEQ ID NO 8
<211> LENGTH: 392
<212> TYPE: PRT
<213> ORGANISM: Homo sapiens

<400> SEQUENCE: 8

Met Gly Ser Ser Asn Glu Leu Leu Ala Thr Glu Tyr Leu Glu Lys
  1               5                  10                  15

Glu Lys Lys Ile Pro Arg Ala Val Leu Ile Asp Ala Ile Glu Ala Ala
                 20                  25                  30

Leu Ile Thr Ala Tyr Lys Lys Asn Tyr Asp Ser Ala Arg Asn Val Arg
             35                  40                  45

Val Glu Leu Asn Met Asp Gln Gly Thr Phe Lys Val Ile Ala Arg Lys
         50                  55                  60

Asp Val Val Glu Glu Val Phe Asp Asp Arg Asp Glu Val Asp Leu Ser
 65                  70                  75                  80

Thr Ala Leu Val Lys Asn Pro Ala Tyr Glu Ile Gly Asp Ile Tyr Glu
                 85                  90                  95

Glu Asp Val Thr Pro Lys Asp Phe Gly Arg Val Gly Ala Gln Ala Ala
                100                 105                 110

```
Lys Gln Ala Val Met Gln Arg Leu Arg Asp Ala Glu Arg Glu Ile Leu
        115                 120                 125
Phe Glu Glu Phe Ile Asp Lys Glu Asp Ile Leu Thr Gly Ile Ile
        130                 135                 140
Asp Arg Val Asp His Arg Tyr Val Tyr Val Asn Leu Gly Arg Ile Glu
145                 150                 155                 160
Ala Val Leu Ser Glu Ala Glu Arg Ser Pro Asn Glu Lys Tyr Ile Pro
                165                 170                 175
Asn Glu Arg Ile Lys Val Tyr Val Asn Lys Val Glu Gln Thr Thr Lys
                180                 185                 190
Gly Pro Gln Ile Tyr Val Ser Arg Ser His Pro Gly Leu Leu Lys Arg
                195                 200                 205
Leu Phe Glu Gln Glu Val Pro Glu Ile Tyr Asp Gly Thr Val Ile Val
        210                 215                 220
Lys Ser Val Ala Arg Glu Ala Gly Asp Arg Ser Lys Ile Ser Val Phe
225                 230                 235                 240
Ser Glu Asn Asn Asp Ile Asp Ala Val Gly Ala Cys Val Gly Ala Lys
                245                 250                 255
Gly Ala Arg Val Glu Ala Val Val Glu Glu Leu Gly Gly Glu Lys Ile
                260                 265                 270
Asp Ile Val Gln Trp Asn Glu Asp Pro Lys Val Phe Val Lys Asn Ala
        275                 280                 285
Leu Ser Pro Ser Gln Val Leu Glu Val Ile Val Asp Glu Thr Asn Gln
        290                 295                 300
Ser Thr Val Val Val Pro Asp Tyr Gln Leu Ser Leu Ala Ile Gly
305                 310                 315                 320
Lys Arg Gly Gln Asn Ala Arg Leu Ala Ala Lys Leu Thr Gly Trp Lys
                325                 330                 335
Ile Asp Ile Lys Ser Glu Thr Asp Ala Arg Glu Ala Gly Ile Tyr Pro
                340                 345                 350
Val Val Glu Ala Glu Lys Val Thr Glu Glu Asp Val Ala Leu Glu Asp
        355                 360                 365
Ala Asp Thr Thr Glu Ser Thr Glu Glu Val Asn Asp Val Ser Val Glu
        370                 375                 380
Thr Asn Val Glu Lys Glu Ser Glu
385                 390

<210> SEQ ID NO 9
<211> LENGTH: 549
<212> TYPE: DNA
<213> ORGANISM: Homo sapiens

<400> SEQUENCE: 9
atgggatctg aagaagttgg cgcaaagcgt tggtatgcag tgcatacata ttctggatat     60
gaaaataaag ttaaaagaa tttagaaaaa agagtagaat ctatgaatat gactgaacaa    120
atctttagag tagtcatacc ggaagaagaa gaaactcaag taaagatgg caaagctaaa    180
acgactgtta aaaaaacatt ccctggatat gttttagtgg aattaatcat gacagatgaa    240
tcatggtatg tggtaagaaa tacaccaggc gttactggtt ttgtaggttc tgcaggtgca    300
gggtctaagc caaatccatt gttaccagaa gaagttcgct tcatcttaaa acaaatgggt    360
cttaaagaaa agactatcga tgttgaactc gaagttggcg agcaagttcg tattaaatca    420
ggtccatttg cgaatcaagt tggtgaagtt caagaaattg aaacagataa gtttaagcta    480
acagtattag tagatatgtt tggccgagaa acaccagtag aagttgaatt cgatcaaatt    540
```

```
gaaaagctg                                                                         549
```

<210> SEQ ID NO 10
<211> LENGTH: 183
<212> TYPE: PRT
<213> ORGANISM: Homo sapiens

<400> SEQUENCE: 10

```
Met Gly Ser Glu Glu Val Gly Ala Lys Arg Trp Tyr Ala Val His Thr
  1               5                  10                  15

Tyr Ser Gly Tyr Glu Asn Lys Val Lys Lys Asn Leu Glu Lys Arg Val
             20                  25                  30

Glu Ser Met Asn Met Thr Glu Gln Ile Phe Arg Val Val Ile Pro Glu
         35                  40                  45

Glu Glu Glu Thr Gln Val Lys Asp Gly Lys Ala Lys Thr Thr Val Lys
     50                  55                  60

Lys Thr Phe Pro Gly Tyr Val Leu Val Glu Leu Ile Met Thr Asp Glu
 65                  70                  75                  80

Ser Trp Tyr Val Val Arg Asn Thr Pro Gly Val Thr Gly Phe Val Gly
                 85                  90                  95

Ser Ala Gly Ala Gly Ser Lys Pro Asn Pro Leu Leu Pro Glu Glu Val
            100                 105                 110

Arg Phe Ile Leu Lys Gln Met Gly Leu Lys Glu Lys Thr Ile Asp Val
        115                 120                 125

Glu Leu Glu Val Gly Glu Gln Val Arg Ile Lys Ser Gly Pro Phe Ala
    130                 135                 140

Asn Gln Val Gly Glu Val Gln Glu Ile Glu Thr Asp Lys Phe Lys Leu
145                 150                 155                 160

Thr Val Leu Val Asp Met Phe Gly Arg Glu Thr Pro Val Glu Val Glu
                165                 170                 175

Phe Asp Gln Ile Glu Lys Leu
            180
```

<210> SEQ ID NO 11
<211> LENGTH: 822
<212> TYPE: DNA
<213> ORGANISM: Homo sapiens

<400> SEQUENCE: 11

```
atgggtagta aattacaaga cgttattgta caagaaatga agtgaaaaaa gcgtatcgat    60
agtgctgaag aaattatgga attaaagcaa tttataaaaa attatgtaca atcacattca   120
tttataaaat ctttagtgtt aggtatttca ggaggacagg attctacatt agttggaaaa   180
ctagtacaaa tgtctgttaa cgaattacgt gaagaaggca ttgattgtac gtttattgca   240
gttaaattac cttatggagt tcaaaaagat gctgatgaag ttgagcaagc tttgcgattc   300
attgaaccag atgaaatagt aacagtcaat attaagcctg cagttgatca agtgtgcaa    360 tcattaaaag aagccggtat tgttcttaca gatttccaaa aggaaatgaa aaagcgcgt    420 gaacgtatga agtacaatt tcaattgct tcaaaccgac aaggtattgt agtaggaaca    480
gatcattcag ctgaaaatat aactgggttt tatacgaagt acggtgatgg tgctgcagat   540
atcgcaccta tatttggttt gaataaaacga caaggtcgtc aattattagc gtatcttggt   600
gcgccaaagg aattatatga aaaaacgcca actgctgatt tagagatgta taaaccacag   660
cttccagatg aagatgcatt aggtgtaact tatgaggcga ttgataatta tttagaaggt   720
```

```
aagccagtta cgccagaaga acaaaaagta attgaaaatc attatatacg aaatgcacac    780
aaacgtgaac ttgcatatac aagatacacg tggccaaaat cc                      822
```

<210> SEQ ID NO 12
<211> LENGTH: 274
<212> TYPE: PRT
<213> ORGANISM: Homo sapiens

<400> SEQUENCE: 12

```
Met Gly Ser Lys Leu Gln Asp Val Ile Val Gln Glu Met Lys Val Lys
 1               5                  10                  15

Lys Arg Ile Asp Ser Ala Glu Glu Ile Met Glu Leu Lys Gln Phe Ile
            20                  25                  30

Lys Asn Tyr Val Gln Ser His Ser Phe Ile Lys Ser Leu Val Leu Gly
        35                  40                  45

Ile Ser Gly Gly Gln Asp Ser Thr Leu Val Gly Lys Leu Val Gln Met
    50                  55                  60

Ser Val Asn Glu Leu Arg Glu Glu Gly Ile Asp Cys Thr Phe Ile Ala
65                  70                  75                  80

Val Lys Leu Pro Tyr Gly Val Gln Lys Asp Ala Asp Glu Val Glu Gln
                85                  90                  95

Ala Leu Arg Phe Ile Glu Pro Asp Glu Ile Val Thr Val Asn Ile Lys
            100                 105                 110

Pro Ala Val Asp Gln Ser Val Gln Ser Leu Lys Glu Ala Gly Ile Val
        115                 120                 125

Leu Thr Asp Phe Gln Lys Gly Asn Glu Lys Ala Arg Glu Arg Met Lys
    130                 135                 140

Val Gln Phe Ser Ile Ala Ser Asn Arg Gln Gly Ile Val Val Gly Thr
145                 150                 155                 160

Asp His Ser Ala Glu Asn Ile Thr Gly Phe Tyr Thr Lys Tyr Gly Asp
                165                 170                 175

Gly Ala Ala Asp Ile Ala Pro Ile Phe Gly Leu Asn Lys Arg Gln Gly
            180                 185                 190

Arg Gln Leu Leu Ala Tyr Leu Gly Ala Pro Lys Glu Leu Tyr Glu Lys
        195                 200                 205

Thr Pro Thr Ala Asp Leu Glu Asp Lys Pro Gln Leu Pro Asp Glu
    210                 215                 220

Asp Ala Leu Gly Val Thr Tyr Glu Ala Ile Asp Asn Tyr Leu Glu Gly
225                 230                 235                 240

Lys Pro Val Thr Pro Glu Glu Gln Lys Val Ile Glu Asn His Tyr Ile
                245                 250                 255

Arg Asn Ala His Lys Arg Glu Leu Ala Tyr Thr Arg Tyr Thr Trp Pro
            260                 265                 270

Lys Ser
```

<210> SEQ ID NO 13
<211> LENGTH: 936
<212> TYPE: DNA
<213> ORGANISM: Homo sapiens

<400> SEQUENCE: 13

```
atgggtactg aaatagattt tgatatagca attatcggtg caggtccagc tggtatgact     60
gctgcagtat acgcatcacg tgctaattta aaaacagtta tgattgaaag aggtattcca    120
ggcggtcaaa tggctaatac agaagaagta gagaacttcc ctggtttcga aatgattaca    180
```

-continued

```
ggtccagatt tatctacaaa aatgtttgaa cacgctaaaa agtttggtgc agtttatcaa    240
tatggagata ttaaatctgt agaagataaa ggcgaatata aagtgattaa ctttggtaat    300
aaagaattaa cagcgaaagc ggttattatt gctacaggtg cagaatacaa gaaaattggt    360
gttccgggtg aacaagaact tggtggacgc ggtgtaagtt attgtgcagt atgtgatggt    420
gcattcttta aaaataaacg cctattcgtt atcggtggtg gtgattcagc agtagaagag    480
ggaacattct taactaaatt tgctgacaaa gtaacaatcg ttcaccgtcg tgatgagtta    540
cgtgcacagc gtattttaca agatagagca ttcaaaaatg ataaaatcga ctttatttgg    600
agtcatactt tgaaatcaat taatgaaaaa gacggcaaag tgggttctgt gacattaacg    660
tctacaaaag atggttcaga agaaacacac gaggctgatg gtgtattcat ctatattggt    720
atgaaaccat taacagcgcc atttaaagac ttaggtatta caaatgatgt tggttatatt    780
gtaacaaaag atgatatgac aacatcagta ccaggtattt ttgcagcagg agatgttcgc    840
gacaaaggtt tacgccaaat tgtcactgct actggcgatg gtagtattgc agcgcaaagt    900
gcagcggaat atattgaaca tttaaacgat caagct                              936
```

<210> SEQ ID NO 14
<211> LENGTH: 312
<212> TYPE: PRT
<213> ORGANISM: Homo sapiens

<400> SEQUENCE: 14

```
Met Gly Thr Glu Ile Asp Phe Asp Ile Ala Ile Ile Gly Ala Gly Pro
  1               5                  10                  15

Ala Gly Met Thr Ala Ala Val Tyr Ala Ser Arg Ala Asn Leu Lys Thr
                 20                  25                  30

Val Met Ile Glu Arg Gly Ile Pro Gly Gly Gln Met Ala Asn Thr Glu
             35                  40                  45

Glu Val Glu Asn Phe Pro Gly Phe Glu Met Ile Thr Gly Pro Asp Leu
         50                  55                  60

Ser Thr Lys Met Phe Glu His Ala Lys Phe Gly Ala Val Tyr Gln
 65                  70                  75                  80

Tyr Gly Asp Ile Lys Ser Val Glu Asp Lys Gly Glu Tyr Lys Val Ile
                 85                  90                  95

Asn Phe Gly Asn Lys Glu Leu Thr Ala Lys Ala Val Ile Ala Thr
                100                 105                 110

Gly Ala Glu Tyr Lys Lys Ile Gly Val Pro Gly Glu Gln Glu Leu Gly
            115                 120                 125

Gly Arg Gly Val Ser Tyr Cys Ala Val Cys Asp Gly Ala Phe Phe Lys
        130                 135                 140

Asn Lys Arg Leu Phe Val Ile Gly Gly Gly Asp Ser Ala Val Glu Glu
145                 150                 155                 160

Gly Thr Phe Leu Thr Lys Phe Ala Asp Lys Val Thr Ile Val His Arg
                165                 170                 175

Arg Asp Glu Leu Arg Ala Gln Arg Ile Leu Gln Asp Arg Ala Phe Lys
            180                 185                 190

Asn Asp Lys Ile Asp Phe Ile Trp Ser His Thr Leu Lys Ser Ile Asn
        195                 200                 205

Glu Lys Asp Gly Lys Val Gly Ser Val Thr Leu Thr Ser Thr Lys Asp
    210                 215                 220

Gly Ser Glu Glu Thr His Glu Ala Asp Gly Val Phe Ile Tyr Ile Gly
225                 230                 235                 240
```

```
Met Lys Pro Leu Thr Ala Pro Phe Lys Asp Leu Gly Ile Thr Asn Asp
                245                 250                 255

Val Gly Tyr Ile Val Thr Lys Asp Asp Met Thr Thr Ser Val Pro Gly
            260                 265                 270

Ile Phe Ala Ala Gly Asp Val Arg Asp Lys Gly Leu Arg Gln Ile Val
        275                 280                 285

Thr Ala Thr Gly Asp Gly Ser Ile Ala Ala Gln Ser Ala Ala Glu Tyr
        290                 295                 300

Ile Glu His Leu Asn Asp Gln Ala
305                 310

<210> SEQ ID NO 15
<211> LENGTH: 1356
<212> TYPE: DNA
<213> ORGANISM: Homo sapiens

<400> SEQUENCE: 15 atgggggaa  aatattttgg  tacagacgga  gtaagaggtg  tcgcaaacca  agaactaaca      60
cctgaattgg  catttaaatt  aggaagatac  ggtggctatg  ttctagcaca  taataaaggt     120
gaaaaacacc  cacgtgtact  tgtaggtcgc  gatactagag  tttcaggtga  aatgttagaa     180
tcagcattaa  tagctggttt  gatttcaatt  ggtgcagaag  tgatgcgatt  aggtattatt     240
tcaacaccag  gtgttgcata  tttaacacgc  gatatgggtg  cagagttagg  tgtaatgatt     300
tcagcctctc  ataatccagt  tgcagataat  ggtattaaat  tctttggatc  agatggtttt     360
aaactatcag  atgaacaaga  aaatgaaatt  gaagcattat  tggatcaaga  aaacccagaa     420
ttaccaagac  cagttggcaa  tgatattgta  cattattcag  attactttga  agggcacaa      480 aaatatttga  gctatttaaa  atcaacagta  gatgttaact  ttgaaggttt  gaaaattgct     540
ttagatggtg  caaatggttc  aacatcatca  ctagcgccat  tcttatttgg  tgacttagaa     600
gcagatactg  aaacaattgg  atgtagtcct  gatggatata  atatcaatga  gaatgtggc      660 tctacacatc  ctgaaaaatt  agctgaaaaa  gtagttgaaa  ctgaaagtga  ttttgggtta     720
gcatttgacg  gcgatggaga  cagaatcata  gcagtagatg  agaatggtca  aatcgttgac     780
ggtgaccaaa  ttatgtttat  tattggtcaa  gaaatgcata  aaaatcaaga  attgaataat     840
gacatgattg  tttctactgt  tatgagtaat  ttaggttttt  acaaagcgct  tgaacaagaa     900
ggaattaaat  ctaataaaac  taaagttggc  gacagatatg  tagtagaaga  aatgcgtcgc     960 gtaattata   acttaggtgg  agaacaatct  ggacatatcg  ttatgatgga  ttacaataca    1020
actggtgatg  gtttattaac  tggtattcaa  ttagcttctg  taataaaaat  gactggtaaa    1080
tcactaagtg  aattagctgg  acaaatgaaa  aaatatccac  aatcattaat  taacgtacgc    1140
gtaacagata  aatatcgtgt  tgaagaaaat  gttgacgtta  agaagttat   gactaaagta    1200 gaagtagaaa  tgaatggaga  aggtcgaatt  ttagtaagac  cttctggaac  agaaccatta    1260
gttcgtgtca  tggttgaagc  agcaactgat  gaagatgctg  aaagatttgc  acaacaaata    1320
gctgatgtgg  ttcaagataa  aatgggatta  gataaa                                1356

<210> SEQ ID NO 16
<211> LENGTH: 452
<212> TYPE: PRT
<213> ORGANISM: Homo sapiens

<400> SEQUENCE: 16

Met Gly Gly Lys Tyr Phe Gly Thr Asp Gly Val Arg Gly Val Ala Asn
  1               5                  10                  15
```

```
Gln Glu Leu Thr Pro Glu Leu Ala Phe Lys Leu Gly Arg Tyr Gly Gly
             20                  25                  30
Tyr Val Leu Ala His Asn Lys Gly Glu Lys His Pro Arg Val Leu Val
         35                  40                  45
Gly Arg Asp Thr Arg Val Ser Gly Glu Met Leu Glu Ser Ala Leu Ile
     50                  55                  60
Ala Gly Leu Ile Ser Ile Gly Ala Glu Val Met Arg Leu Gly Ile Ile
 65                  70                  75                  80
Ser Thr Pro Gly Val Ala Tyr Leu Thr Arg Asp Met Gly Ala Glu Leu
                 85                  90                  95
Gly Val Met Ile Ser Ala Ser His Asn Pro Val Ala Asp Asn Gly Ile
            100                 105                 110
Lys Phe Phe Gly Ser Asp Gly Phe Lys Leu Ser Asp Glu Gln Glu Asn
        115                 120                 125
Glu Ile Glu Ala Leu Leu Asp Gln Glu Asn Pro Glu Leu Pro Arg Pro
    130                 135                 140
Val Gly Asn Asp Ile Val His Tyr Ser Asp Tyr Phe Glu Gly Ala Gln
145                 150                 155                 160
Lys Tyr Leu Ser Tyr Leu Lys Ser Thr Val Asp Val Asn Phe Glu Gly
                165                 170                 175
Leu Lys Ile Ala Leu Asp Gly Ala Asn Gly Ser Thr Ser Ser Leu Ala
            180                 185                 190
Pro Phe Leu Phe Gly Asp Leu Glu Ala Asp Thr Glu Thr Ile Gly Cys
        195                 200                 205
Ser Pro Asp Gly Tyr Asn Ile Asn Glu Lys Cys Gly Ser Thr His Pro
    210                 215                 220
Glu Lys Leu Ala Glu Lys Val Val Glu Thr Glu Ser Asp Phe Gly Leu
225                 230                 235                 240
Ala Phe Asp Gly Asp Gly Asp Arg Ile Ile Ala Val Asp Glu Asn Gly
                245                 250                 255
Gln Ile Val Asp Gly Asp Gln Ile Met Phe Ile Ile Gly Gln Glu Met
            260                 265                 270
His Lys Asn Gln Glu Leu Asn Asn Asp Met Ile Val Ser Thr Val Met
        275                 280                 285
Ser Asn Leu Gly Phe Tyr Lys Ala Leu Glu Gln Glu Gly Ile Lys Ser
    290                 295                 300
Asn Lys Thr Lys Val Gly Asp Arg Tyr Val Val Glu Glu Met Arg Arg
305                 310                 315                 320
Gly Asn Tyr Asn Leu Gly Gly Glu Gln Ser Gly His Ile Val Met Met
                325                 330                 335
Asp Tyr Asn Thr Thr Gly Asp Gly Leu Leu Thr Gly Ile Gln Leu Ala
            340                 345                 350
Ser Val Ile Lys Met Thr Gly Lys Ser Leu Ser Glu Leu Ala Gly Gln
        355                 360                 365
Met Lys Lys Tyr Pro Gln Ser Leu Ile Asn Val Arg Val Thr Asp Lys
    370                 375                 380
Tyr Arg Val Glu Glu Asn Val Asp Val Lys Glu Val Met Thr Lys Val
385                 390                 395                 400
Glu Val Glu Met Asn Gly Glu Gly Arg Ile Leu Val Arg Pro Ser Gly
                405                 410                 415
Thr Glu Pro Leu Val Arg Val Met Val Glu Ala Ala Thr Asp Glu Asp
            420                 425                 430
```

-continued

Ala Glu Arg Phe Ala Gln Gln Ile Ala Asp Val Val Gln Asp Lys Met
        435                 440                 445

Gly Leu Asp Lys
    450

<210> SEQ ID NO 17
<211> LENGTH: 1359
<212> TYPE: DNA
<213> ORGANISM: Homo sapiens

<400> SEQUENCE: 17

| | | | | | |
|---|---|---|---|---|---|
| atgggtttca | tgcgaagaca | cgcgataatt | ttggcagcag | gtaaaggcac | aagaatgaaa |     60 |
| tctaaaaagt | ataaagtgct | acacgaggtt | gctgggaaac | ctatggtcga | acatgtattg |    120 |
| gaaagtgtga | aaggctctgg | tgtcgatcaa | gttgtaacca | tcgtaggaca | tggtgctgaa |    180 |
| agtgtaaaag | gacatttagg | cgagcgttct | ttatacagtt | ttcaagagga | acaactcggt |    240 |
| actgcgcatg | cagtgcaaat | ggcgaaatca | cacttagaag | acaaggaagg | tacgacaatc |    300 |
| gttgtatgtg | gtgacacacc | gctcatcaca | aaggaaacat | tagtaacatt | gattgcgcat |    360 |
| cacgaggatg | ctaatgctca | agcaactgta | ttatctgcat | cgattcaaca | accatatgga |    420 |
| tacggaagaa | tcgttcgaaa | tgcgtcaggt | cgtttagaac | gcatagttga | agagaaagat |    480 |
| gcaacgcaag | ctgaaaagga | tattaatgaa | attagttcag | gtattttgc  | gtttaataat |    540 |
| aaaacgttgt | ttgaaaaatt | aacacaagtg | aaaaatgata | atgcgcaagg | tgaatattac |    600 |
| ctccctgatg | tattgtcgtt | aattttaaat | gatggcggca | tcgtagaagt | ctatcgtacc |    660 |
| aatgatgttg | aagaaatcat | gggtgtaaat | gatcgtgtaa | tgcttagtca | ggctgagaag |    720 |
| gcgatgcaac | gtcgtacgaa | tcattatcac | atgctaaatg | gtgtgacaat | catcgatcct |    780 |
| gacagcactt | atattggtcc | agacgttaca | attggtagtg | atacagtcat | tgaaccaggc |    840 |
| gtacgaatta | atggtcgtac | agaaattggc | gaagatgttg | ttattggtca | gtactctgaa |    900 |
| attaacaata | gtacgattga | aaatggtgca | tgtattcaac | agtctgttgt | taatgatgct |    960 |
| agcgtaggag | cgaatactaa | ggtcggaccg | tttgcgcaat | tgagaccagg | cgcgcaatta |   1020 |
| ggtgcagatg | ttaaggttgg | aaattttgta | gaaattaaaa | aagcagatct | taaagatggt |   1080 |
| gccaaggttt | cacatttaag | ttatattggc | gatgctgtaa | ttggcgaacg | tactaatatt |   1140 |
| ggttgcggaa | cgattacagt | taactatgat | ggtgaaaata | aatttaaaac | tatcgtcggc |   1200 |
| aaagattcat | ttgtaggttg | caatgttaat | ttagtagcac | ctgtaacaat | tggtgatgat |   1260 |
| gtattggtgg | cagctggttc | cacaatcaca | gatgacgtac | aaatgacag  | tttagctgtg |   1320 |
| gcaagagcaa | gacaaacaac | aaaagaagga | tataggaaa  |            |            |   1359 |

<210> SEQ ID NO 18
<211> LENGTH: 453
<212> TYPE: PRT
<213> ORGANISM: Homo sapiens

<400> SEQUENCE: 18

Met Gly Phe Met Arg Arg His Ala Ile Ile Leu Ala Ala Gly Lys Gly
  1               5                  10                  15

Thr Arg Met Lys Ser Lys Lys Tyr Lys Val Leu His Glu Val Ala Gly
                20                  25                  30

Lys Pro Met Val Glu His Val Leu Glu Ser Val Lys Gly Ser Gly Val
            35                  40                  45

Asp Gln Val Val Thr Ile Val Gly His Gly Ala Glu Ser Val Lys Gly
        50                  55                  60

```
His Leu Gly Glu Arg Ser Leu Tyr Ser Phe Gln Glu Gln Leu Gly
 65                  70                  75                  80

Thr Ala His Ala Val Gln Met Ala Lys Ser His Leu Glu Asp Lys Glu
             85                  90                  95

Gly Thr Thr Ile Val Val Cys Gly Asp Thr Pro Leu Ile Thr Lys Glu
            100                 105                 110

Thr Leu Val Thr Leu Ile Ala His His Glu Asp Ala Asn Ala Gln Ala
            115                 120                 125

Thr Val Leu Ser Ala Ser Ile Gln Gln Pro Tyr Gly Tyr Gly Arg Ile
            130                 135                 140

Val Arg Asn Ala Ser Gly Arg Leu Glu Arg Ile Val Glu Glu Lys Asp
145                 150                 155                 160

Ala Thr Gln Ala Glu Lys Asp Ile Asn Glu Ile Ser Ser Gly Ile Phe
                165                 170                 175

Ala Phe Asn Asn Lys Thr Leu Phe Glu Lys Leu Thr Gln Val Lys Asn
            180                 185                 190

Asp Asn Ala Gln Gly Glu Tyr Tyr Leu Pro Asp Val Leu Ser Leu Ile
            195                 200                 205

Leu Asn Asp Gly Gly Ile Val Glu Val Tyr Arg Thr Asn Asp Val Glu
210                 215                 220

Glu Ile Met Gly Val Asn Asp Arg Val Met Leu Ser Gln Ala Glu Lys
225                 230                 235                 240

Ala Met Gln Arg Arg Thr Asn His Tyr His Met Leu Asn Gly Val Thr
                245                 250                 255

Ile Ile Asp Pro Asp Ser Thr Tyr Ile Gly Pro Asp Val Thr Ile Gly
            260                 265                 270

Ser Asp Thr Val Ile Glu Pro Gly Val Arg Ile Asn Gly Arg Thr Glu
            275                 280                 285

Ile Gly Glu Asp Val Val Ile Gly Gln Tyr Ser Glu Ile Asn Asn Ser
290                 295                 300

Thr Ile Glu Asn Gly Ala Cys Ile Gln Gln Ser Val Val Asn Asp Ala
305                 310                 315                 320

Ser Val Gly Ala Asn Thr Lys Val Gly Pro Phe Ala Gln Leu Arg Pro
                325                 330                 335

Gly Ala Gln Leu Gly Ala Asp Val Lys Val Gly Asn Phe Val Glu Ile
            340                 345                 350

Lys Lys Ala Asp Leu Lys Asp Gly Ala Lys Val Ser His Leu Ser Tyr
            355                 360                 365

Ile Gly Asp Ala Val Ile Gly Glu Arg Thr Asn Ile Gly Cys Gly Thr
            370                 375                 380

Ile Thr Val Asn Tyr Asp Gly Glu Asn Lys Phe Lys Thr Ile Val Gly
385                 390                 395                 400

Lys Asp Ser Phe Val Gly Cys Asn Val Asn Leu Val Ala Pro Val Thr
                405                 410                 415

Ile Gly Asp Asp Val Leu Val Ala Ala Gly Ser Thr Ile Thr Asp Asp
            420                 425                 430

Val Pro Asn Asp Ser Leu Ala Val Ala Arg Ala Arg Gln Thr Thr Lys
            435                 440                 445

Glu Gly Tyr Arg Lys
    450

<210> SEQ ID NO 19
<211> LENGTH: 1317
<212> TYPE: DNA
```

<213> ORGANISM: Homo sapiens

<400> SEQUENCE: 19

```
atgggccca aaatagtcgt agtcggagca gtcgctggcg gtgcaacatg tgccagccaa    60
attcgacgtt tagataaaga aagtgacatt attattttg aaaaagatcg tgatatgagc   120
tttgctaatt gtgcattgcc ttatgtcatt ggcgaagttg ttgaagatag aagatatgct   180
ttagcgtata cacctgaaaa attttatgat agaaagcaaa ttacagtaaa aacttatcat   240
gaagttattg caatcaatga tgaaagacaa actgtatctg tattaaatag aaagacaaac   300
gaacaatttg aagaatctta cgataaactc attttaagcc tggtgcaag tgcaaatagc    360
cttggctttg aaagtgatat tacatttaca cttagaaatt tagaagacac tgatgctatc   420
gatcaattca tcaaagcaaa tcaagttgat aaagtattgg ttgtaggtgc aggttatgtt   480
tcattagaag ttcttgaaaa tctttatgaa cgtggtttac accctacttt aattcatcga   540
tctgataaga taaataaatt aatggatgcc gacatgaatc aacctatact tgatgaatta   600
gataagcggg agattccata ccgtttaaat gaggaaatta atgctatcaa tggaaatgaa   660
attcacttta aatcaggaaa agttgaacat acgatatga ttattgaagg tgtcggtact    720
caccccaatt caaaatttat cgaaagttca aatatcaaac ttgatcgaaa aggtttcata   780
ccggtaaacg ataaatttga aacaaatgtt ccaaacattt atgcaatagg cgatattgca   840
acatcacatt atcgacatgt cgatctaccg gctagtgttc ctttagcttg ggcgctcac    900
cgtgcagcaa gtattgttgc cgaacaaatt gctggaaatg acactattga attcaaaggc   960
ttcttaggca acaatattgt gaagttcttt gattatacat ttgcgagtgt cggcgttaaa  1020
ccaaacgaac taaagcaatt tgactataaa atggtagaag tcactcaagg tgcacacgcg  1080
aattattacc aggaaattc ccctttacac ttaagagtat attatgacac ttcaaaccgt  1140
cagattttaa gagcagctgc agtaggaaaa gaaggtgcag ataaacgtat tgatgtacta  1200
tcgatggcaa tgatgaacca gctaactgta gatgagttaa ctgagtttga agtggcttat  1260
gcaccaccat atagccaccc taaagattta atcaatatga ttggttacaa agctaaa    1317
```

<210> SEQ ID NO 20
<211> LENGTH: 439
<212> TYPE: PRT
<213> ORGANISM: Homo sapiens

<400> SEQUENCE: 20

```
Met Gly Pro Lys Ile Val Val Gly Ala Val Ala Gly Gly Ala Thr
  1               5                  10                  15

Cys Ala Ser Gln Ile Arg Arg Leu Asp Lys Glu Ser Asp Ile Ile
                 20                  25                  30

Phe Glu Lys Asp Arg Asp Met Ser Phe Ala Asn Cys Ala Leu Pro Tyr
                 35                  40                  45

Val Ile Gly Glu Val Val Glu Asp Arg Arg Tyr Ala Leu Ala Tyr Thr
                 50                  55                  60

Pro Glu Lys Phe Tyr Asp Arg Lys Gln Ile Thr Val Lys Thr Tyr His
 65                  70                  75                  80

Glu Val Ile Ala Ile Asn Asp Glu Arg Gln Thr Val Ser Val Leu Asn
                 85                  90                  95

Arg Lys Thr Asn Glu Gln Phe Glu Glu Ser Tyr Asp Lys Leu Ile Leu
                100                 105                 110

Ser Pro Gly Ala Ser Ala Asn Ser Leu Gly Phe Glu Ser Asp Ile Thr
                115                 120                 125
```

```
Phe Thr Leu Arg Asn Leu Glu Asp Thr Asp Ala Ile Asp Gln Phe Ile
    130                 135                 140
Lys Ala Asn Gln Val Asp Lys Val Leu Val Val Gly Ala Gly Tyr Val
145                 150                 155                 160
Ser Leu Glu Val Leu Glu Asn Leu Tyr Glu Arg Gly Leu His Pro Thr
                165                 170                 175
Leu Ile His Arg Ser Asp Lys Ile Asn Lys Leu Met Asp Ala Asp Met
            180                 185                 190
Asn Gln Pro Ile Leu Asp Glu Leu Asp Lys Arg Glu Ile Pro Tyr Arg
        195                 200                 205
Leu Asn Glu Glu Ile Asn Ala Ile Asn Gly Asn Glu Ile Thr Phe Lys
    210                 215                 220
Ser Gly Lys Val Glu His Tyr Asp Met Ile Ile Glu Gly Val Gly Thr
225                 230                 235                 240
His Pro Asn Ser Lys Phe Ile Glu Ser Ser Asn Ile Lys Leu Asp Arg
                245                 250                 255
Lys Gly Phe Ile Pro Val Asn Asp Lys Phe Glu Thr Asn Val Pro Asn
            260                 265                 270
Ile Tyr Ala Ile Gly Asp Ile Ala Thr Ser His Tyr Arg His Val Asp
        275                 280                 285
Leu Pro Ala Ser Val Pro Leu Ala Trp Gly Ala His Arg Ala Ala Ser
    290                 295                 300
Ile Val Ala Glu Gln Ile Ala Gly Asn Asp Thr Ile Glu Phe Lys Gly
305                 310                 315                 320
Phe Leu Gly Asn Asn Ile Val Lys Phe Phe Asp Tyr Thr Phe Ala Ser
                325                 330                 335
Val Gly Val Lys Pro Asn Glu Leu Lys Gln Phe Asp Tyr Lys Met Val
            340                 345                 350
Glu Val Thr Gln Gly Ala His Ala Asn Tyr Tyr Pro Gly Asn Ser Pro
        355                 360                 365
Leu His Leu Arg Val Tyr Tyr Asp Thr Ser Asn Arg Gln Ile Leu Arg
    370                 375                 380
Ala Ala Ala Val Gly Lys Glu Gly Ala Asp Lys Arg Ile Asp Val Leu
385                 390                 395                 400
Ser Met Ala Met Met Asn Gln Leu Thr Val Asp Glu Leu Thr Glu Phe
                405                 410                 415
Glu Val Ala Tyr Ala Pro Pro Tyr Ser His Pro Lys Asp Leu Ile Asn
            420                 425                 430
Met Ile Gly Tyr Lys Ala Lys
        435

<210> SEQ ID NO 21
<211> LENGTH: 1353
<212> TYPE: DNA
<213> ORGANISM: Homo sapiens

<400> SEQUENCE: 21
atgaaagacg aacaattata ttattttgag aaatcgccag tatttaaagc gatgatgcat    60
ttctcattgc caatgatgat agggacttta ttaagcgtta tttatggcat attaaatatt    120
tactttatag gatttttaga agatagccac atgatttctg ctatctctct aacactgcca    180
gtatttgcta tcttaatggg gttaggtaat ttatttggcg ttggtgcagg aacttatatt    240
tcacgtttat taggtgcgaa agactatagt aagagtaaat tgtaagtag tttctctatt    300 tatggtggta ttgcactagg acttatcgtg atttagtta ctttaccatt cagtgatcaa    360
```

-continued

```
atcgcagcaa ttttagggc gagaggtgaa acgttagctt taacaagtaa ttatttgaaa      420
gtaatgtttt taagtgcacc ttttgtaatt ttgttcttca tattagaaca atttgcacgt      480
gcaattgggg caccaatggt ttctatgatt ggtatgttag ctagtgtagg cttaaatatt      540
attttagatc caattttaat ttttggtttt gatttaaacg ttgttggtgc agctttgggt      600
actgcaatca gtaatgttgc tgctgctctg ttctttatca tttatttat  gaaaaatagt      660 gacgttgtgt cagttaatat taaacttgcg aaacctaata agaaatgct  ttctgaaatc      720 tttaaaatcg gtattcctgc attttaatg  agtatcttaa tgggattcac aggattagtt      780
ttaaatttat ttttagcaca ttatggaaac ttcgcgattg caagttatgg tatctcattt      840
agacttgtgc aatttccaga acttattatc atgggattat gtgaaggtgt tgtaccacta      900
attgcatata actttatggc aaataaaggc cgtatgaaag acgttatcaa agcagttatc      960
atgtctatcg gcgttatctt tgttgtatgt atgagtgctg tatttacaat tggacatcat     1020
atggtcggac tatttactac tgatcaagcc attgttgaga tggcgacatt tattttgaaa     1080
gtaacaatgg catcattatt attaaatggt ataggtttct tgtttactgg tatgcttcaa     1140
gcgactgggc aaggtcgtgg tgctacaatt atggccattt tacaaggtgc aattatcatt     1200
ccagtattat ttattatgaa tgctttgttt ggactaacag gtgtcatttg gtcattatta     1260
attgctgagt cactttgtgc tttagcagca atgttaatcg tctatttatt acgtgatcgt     1320
ttgacagttg atacatctga attaatagaa ggt                                  1353
```

<210> SEQ ID NO 22
<211> LENGTH: 451
<212> TYPE: PRT
<213> ORGANISM: Homo sapiens

<400> SEQUENCE: 22

```
Met Lys Asp Glu Gln Leu Tyr Tyr Phe Glu Lys Ser Pro Val Phe Lys
  1               5                  10                  15

Ala Met Met His Phe Ser Leu Pro Met Met Ile Gly Thr Leu Leu Ser
             20                  25                  30

Val Ile Tyr Gly Ile Leu Asn Ile Tyr Phe Ile Gly Phe Leu Glu Asp
         35                  40                  45

Ser His Met Ile Ser Ala Ile Ser Leu Thr Leu Pro Val Phe Ala Ile
     50                  55                  60

Leu Met Gly Leu Gly Asn Leu Phe Gly Val Gly Ala Gly Thr Tyr Ile
 65                  70                  75                  80

Ser Arg Leu Leu Gly Ala Lys Asp Tyr Ser Lys Ser Lys Phe Val Ser
                 85                  90                  95

Ser Phe Ser Ile Tyr Gly Gly Ile Ala Leu Gly Leu Ile Val Ile Leu
            100                 105                 110

Val Thr Leu Pro Phe Ser Asp Gln Ile Ala Ala Ile Leu Gly Ala Arg
        115                 120                 125

Gly Glu Thr Leu Ala Leu Thr Ser Asn Tyr Leu Lys Val Met Phe Leu
    130                 135                 140

Ser Ala Pro Phe Val Ile Leu Phe Ile Leu Glu Gln Phe Ala Arg
145                 150                 155                 160

Ala Ile Gly Ala Pro Met Val Ser Met Ile Gly Met Leu Ala Ser Val
                165                 170                 175

Gly Leu Asn Ile Ile Leu Asp Pro Ile Leu Ile Phe Gly Phe Asp Leu
            180                 185                 190
```

```
Asn Val Val Gly Ala Ala Leu Gly Thr Ala Ile Ser Asn Val Ala Ala
        195                 200                 205
Ala Leu Phe Phe Ile Ile Tyr Phe Met Lys Asn Ser Asp Val Val Ser
    210                 215                 220
Val Asn Ile Lys Leu Ala Lys Pro Asn Lys Glu Met Leu Ser Glu Ile
225                 230                 235                 240
Phe Lys Ile Gly Ile Pro Ala Phe Leu Met Ser Ile Leu Met Gly Phe
                245                 250                 255
Thr Gly Leu Val Leu Asn Leu Phe Leu Ala His Tyr Gly Asn Phe Ala
            260                 265                 270
Ile Ala Ser Tyr Gly Ile Ser Phe Arg Leu Val Gln Phe Pro Glu Leu
        275                 280                 285
Ile Ile Met Gly Leu Cys Glu Gly Val Val Pro Leu Ile Ala Tyr Asn
    290                 295                 300
Phe Met Ala Asn Lys Gly Arg Met Lys Asp Val Ile Lys Ala Val Ile
305                 310                 315                 320
Met Ser Ile Gly Val Ile Phe Val Val Cys Met Ser Ala Val Phe Thr
                325                 330                 335
Ile Gly His His Met Val Gly Leu Phe Thr Thr Asp Gln Ala Ile Val
            340                 345                 350
Glu Met Ala Thr Phe Ile Leu Lys Val Thr Met Ala Ser Leu Leu Leu
        355                 360                 365
Asn Gly Ile Gly Phe Leu Phe Thr Gly Met Leu Gln Ala Thr Gly Gln
    370                 375                 380
Gly Arg Gly Ala Thr Ile Met Ala Ile Leu Gln Gly Ala Ile Ile Ile
385                 390                 395                 400
Pro Val Leu Phe Ile Met Asn Ala Leu Phe Gly Leu Thr Gly Val Ile
                405                 410                 415
Trp Ser Leu Leu Ile Ala Glu Ser Leu Cys Ala Leu Ala Ala Met Leu
            420                 425                 430
Ile Val Tyr Leu Leu Arg Asp Arg Leu Thr Val Asp Thr Ser Glu Leu
        435                 440                 445
Ile Glu Gly
    450

<210> SEQ ID NO 23
<211> LENGTH: 1479
<212> TYPE: DNA
<213> ORGANISM: Homo sapiens

<400> SEQUENCE: 23
ttggatgcaa gtacgttgtt taagaaagta aaagtaaagc gtgtattggg ttctttagaa      60
caacaaatag atgatatcac tactgattca cgtacagcga gagaaggtag cattttgtc     120
gcttcagttg gatatactgt agacagtcat aagttctgtc aaaatgtagc tgatcaaggg     180
tgtaagttgg tagtggtcaa taagaacaa tcattaccag ctaacgtaac acaagtggtt     240
gtgccggaca cattaagagt agctagtatt ctagcacaca cattatatga ttatccgagt     300
catcagttag tgacatttgg tgtaacgggt acaaatggta aaacttctat tgcgacgatg     360
attcatttaa ttcaaagaaa gttacaaaaa aatagtgcat atttaggaac taatggtttc     420
caaattaatg aaacaaagac aaaaggtgca aatacgacac cagaaacagt ttctttaact     480
aagaaaatta agaagcagt tgatgcaggc gctgaatcta tgacattaga agtatcaagc     540
catggcttag tattaggacg actgcgaggc gttgaatttg acgttgcaat attttcaaat     600
```

-continued

```
ttaacacaag accatttaga ttttcatggc acaatggaag catacggaca cgcgaagtct    660
ttattgttta gtcaattagg tgaagatttg tcgaaagaaa agtatgtcgt gttaaacaat    720
gacgattcat tttctgagta tttaagaaca gtgacgcctt atgaagtatt tagttatgga    780
attgatgagg aagcccaatt tatggctaaa aatattcaag aatctttaca aggtgtcagc    840
tttgattttg taacgccttt tggaacttac ccagtaaaat cgccttatgt tggtaagttt    900
aatatttcta atattatggc ggcaatgatt gcggtgtgga gtaaaggtac atctttagaa    960
acgattatta aagctgttga aaatttagaa cctgttgaag ggcgattaga agtttttagat  1020
ccttcgttac ctattgattt aattatcgat tatgcacata cagctgatgg tatgaacaaa   1080
ttaatcgatg cagtacagcc ttttgtaaag caaaagttga tatttttagt tggtatggca   1140
ggcgaacgtg atttaactaa aacgcctgaa atggggcgag ttgcctgtcg tgcagattat   1200
gtcattttca caccggataa tccggcaaat gatgacccga aaatgttaac ggcagaatta   1260
gccaaaggtg caacacatca aaactatatt gaatttgatg atcgtgcaga agggataaaa   1320
catgcaattg acatagctga gcctggggat actgtcgttt tagcatcaaa aggaagagaa   1380
ccatatcaaa tcatgccagg gcatattaag gtgccacatc gagatgattt aattggcctt   1440
gaagcagctt acaaaaagtt cggtggtggc cctgttgat                          1479
```

<210> SEQ ID NO 24
<211> LENGTH: 493
<212> TYPE: PRT
<213> ORGANISM: Homo sapiens

<400> SEQUENCE: 24

```
Leu Asp Ala Ser Thr Leu Phe Lys Lys Val Lys Val Lys Arg Val Leu
 1               5                  10                  15

Gly Ser Leu Glu Gln Gln Ile Asp Asp Ile Thr Thr Asp Ser Arg Thr
            20                  25                  30

Ala Arg Glu Gly Ser Ile Phe Val Ala Ser Val Gly Tyr Thr Val Asp
        35                  40                  45

Ser His Lys Phe Cys Gln Asn Val Ala Asp Gln Gly Cys Lys Leu Val
    50                  55                  60

Val Val Asn Lys Glu Gln Ser Leu Pro Ala Asn Val Thr Gln Val Val
65                  70                  75                  80

Val Pro Asp Thr Leu Arg Val Ala Ser Ile Leu Ala His Thr Leu Tyr
                85                  90                  95

Asp Tyr Pro Ser His Gln Leu Val Thr Phe Gly Val Thr Gly Thr Asn
            100                 105                 110

Gly Lys Thr Ser Ile Ala Thr Met Ile His Leu Ile Gln Arg Lys Leu
        115                 120                 125

Gln Lys Asn Ser Ala Tyr Leu Gly Thr Asn Gly Phe Gln Ile Asn Glu
    130                 135                 140

Thr Lys Thr Lys Gly Ala Asn Thr Thr Pro Glu Thr Val Ser Leu Thr
145                 150                 155                 160

Lys Lys Ile Lys Glu Ala Val Asp Ala Gly Ala Glu Ser Met Thr Leu
                165                 170                 175

Glu Val Ser Ser His Gly Leu Val Leu Gly Arg Leu Arg Gly Val Glu
            180                 185                 190

Phe Asp Val Ala Ile Phe Ser Asn Leu Thr Gln Asp His Leu Asp Phe
        195                 200                 205

His Gly Thr Met Glu Ala Tyr Gly His Ala Lys Ser Leu Leu Phe Ser
    210                 215                 220
```

-continued

```
Gln Leu Gly Glu Asp Leu Ser Lys Glu Lys Tyr Val Leu Asn Asn
225                 230                 235                 240

Asp Asp Ser Phe Ser Glu Tyr Leu Arg Thr Val Thr Pro Tyr Glu Val
                245                 250                 255

Phe Ser Tyr Gly Ile Asp Glu Glu Ala Gln Phe Met Ala Lys Asn Ile
                260                 265                 270

Gln Glu Ser Leu Gln Gly Val Ser Phe Asp Phe Val Thr Pro Phe Gly
            275                 280                 285

Thr Tyr Pro Val Lys Ser Pro Tyr Val Gly Lys Phe Asn Ile Ser Asn
        290                 295                 300

Ile Met Ala Ala Met Ile Ala Val Trp Ser Lys Gly Thr Ser Leu Glu
305                 310                 315                 320

Thr Ile Ile Lys Ala Val Glu Asn Leu Glu Pro Val Glu Gly Arg Leu
                325                 330                 335

Glu Val Leu Asp Pro Ser Leu Pro Ile Asp Leu Ile Ile Asp Tyr Ala
                340                 345                 350

His Thr Ala Asp Gly Met Asn Lys Leu Ile Asp Ala Val Gln Pro Phe
            355                 360                 365

Val Lys Gln Lys Leu Ile Phe Leu Val Gly Met Ala Gly Glu Arg Asp
        370                 375                 380

Leu Thr Lys Thr Pro Glu Met Gly Arg Val Ala Cys Arg Ala Asp Tyr
385                 390                 395                 400

Val Ile Phe Thr Pro Asp Asn Pro Ala Asn Asp Pro Lys Met Leu
                405                 410                 415

Thr Ala Glu Leu Ala Lys Gly Ala Thr His Gln Asn Tyr Ile Glu Phe
                420                 425                 430

Asp Asp Arg Ala Glu Gly Ile Lys His Ala Ile Asp Ile Ala Glu Pro
            435                 440                 445

Gly Asp Thr Val Val Leu Ala Ser Lys Gly Arg Glu Pro Tyr Gln Ile
        450                 455                 460

Met Pro Gly His Ile Lys Val Pro His Arg Asp Leu Ile Gly Leu
465                 470                 475                 480

Glu Ala Ala Tyr Lys Lys Phe Gly Gly Pro Val Asp
                485                 490
```

<210> SEQ ID NO 25
<211> LENGTH: 1356
<212> TYPE: DNA
<213> ORGANISM: Homo sapiens

<400> SEQUENCE: 25

```
atgattaatg ttacattaaa gcaaattcaa tcatggattc cttgtgaaat tgaagatcaa      60
tttttaaatc aagagataaa tggagtcaca attgattcac gagcaatttc taaaaatatg     120
ttatttatac catttaaagg tgaaatgtt  gacggtcatc gctttgtctc taaagcatta     180
caagatggtg ctgggctgc  ttttatcaa  agagggacac ctatagatga aatgtaagc      240
gggcctatta tatgggttga agacacatta acggcattac aacaattggc acaagcttac    300
ttgagacatg taaaccctaa agtaattgcc gtcacagggt ctaatggtaa acaacgact      360
aaagatatga ttgaaagtgt attgcatacc gaatttaaag ttagaaaaac gcaaggtaat    420
tacaataatg aaattggttt accttaact  atttggaat  tagataatga tactgaaata    480
tcaatattgg agatggggat gtcaggtttc catgaaattg aatttctgtc aaacctcgct    540
caaccagata ttgcagttat aactaatatt ggtgagtcac atatgcaaga tttaggttcg    600
```

-continued

```
cgcgagggga ttgctaaagc taaatctgaa attacaatag gtctaaaaga taatggtacg    660
tttatatatg atggcgatga accattattg aaaccacatg ttaaagaagt tgaaaatgca    720
aaatgtatta gtattggtgt tgctactgat aatgcattag tttgttctgt tgatgataga    780
gatactacag gtatttcatt tacgattaat aataaagaac attacgatct gccaatatta    840
ggaaagcata atatgaaaaa tgcgacgatt gccattgcgg ttggtcatga attaggtttg    900
acatataaca caatctatca aaatttaaaa aatgtcagct taactggtat gcgtatggaa    960
caacatacat tagaaaatga tattactgtg ataaatgatg cctataatgc aagtcctaca   1020
agtatgagag cagctattga tacactgagt actttgacag ggcgtcgcat tctaatttta   1080
ggagatgttt tagaattagg tgaaaatagc aaagaaatgc atatcggtgt aggtaattat   1140
ttagaagaaa agcatataga tgtgttgtat acgtttggta atgaagcgaa gtatatttat   1200
gattcgggcc agcaacatgt cgaaaaagca caacacttca attctaaaga cgatatgata   1260
gaagttttaa taaacgattt aaaagcgcat gaccgtgtat tagttaaagg atcacgtggt   1320
atgaaattag aagaagtggt aaatgcttta atttca                            1356
```

<210> SEQ ID NO 26
<211> LENGTH: 452
<212> TYPE: PRT
<213> ORGANISM: Homo sapiens

<400> SEQUENCE: 26

```
Met Ile Asn Val Thr Leu Lys Gln Ile Gln Ser Trp Ile Pro Cys Glu
  1               5                  10                  15

Ile Glu Asp Gln Phe Leu Asn Gln Glu Ile Asn Gly Val Thr Ile Asp
                 20                  25                  30

Ser Arg Ala Ile Ser Lys Asn Met Leu Phe Ile Pro Phe Lys Gly Glu
             35                  40                  45

Asn Val Asp Gly His Arg Phe Val Ser Lys Ala Leu Gln Asp Gly Ala
         50                  55                  60

Gly Ala Ala Phe Tyr Gln Arg Gly Thr Pro Ile Asp Glu Asn Val Ser
     65                  70                  75                  80

Gly Pro Ile Ile Trp Val Glu Asp Thr Leu Thr Ala Leu Gln Gln Leu
                 85                  90                  95

Ala Gln Ala Tyr Leu Arg His Val Asn Pro Lys Val Ile Ala Val Thr
                100                 105                 110

Gly Ser Asn Gly Lys Thr Thr Thr Lys Asp Met Ile Glu Ser Val Leu
            115                 120                 125

His Thr Glu Phe Lys Val Lys Lys Thr Gln Gly Asn Tyr Asn Asn Glu
        130                 135                 140

Ile Gly Leu Pro Leu Thr Ile Leu Glu Leu Asp Asn Asp Thr Glu Ile
145                 150                 155                 160

Ser Ile Leu Glu Met Gly Met Ser Gly Phe His Glu Ile Glu Phe Leu
                165                 170                 175

Ser Asn Leu Ala Gln Pro Asp Ile Ala Val Ile Thr Asn Ile Gly Glu
            180                 185                 190

Ser His Met Gln Asp Leu Gly Ser Arg Glu Gly Ile Ala Lys Ala Lys
        195                 200                 205

Ser Glu Ile Thr Ile Gly Leu Lys Asp Asn Gly Thr Phe Ile Tyr Asp
    210                 215                 220

Gly Asp Glu Pro Leu Leu Lys Pro His Val Lys Glu Val Glu Asn Ala
225                 230                 235                 240
```

```
Lys Cys Ile Ser Ile Gly Val Ala Thr Asp Asn Ala Leu Val Cys Ser
                245                 250                 255

Val Asp Asp Arg Asp Thr Thr Gly Ile Ser Phe Thr Ile Asn Asn Lys
            260                 265                 270

Glu His Tyr Asp Leu Pro Ile Leu Gly Lys His Asn Met Lys Asn Ala
        275                 280                 285

Thr Ile Ala Ile Ala Val Gly His Glu Leu Gly Leu Thr Tyr Asn Thr
    290                 295                 300

Ile Tyr Gln Asn Leu Lys Asn Val Ser Leu Thr Gly Met Arg Met Glu
305                 310                 315                 320

Gln His Thr Leu Glu Asn Asp Ile Thr Val Ile Asn Asp Ala Tyr Asn
                325                 330                 335

Ala Ser Pro Thr Ser Met Arg Ala Ala Ile Asp Thr Leu Ser Thr Leu
            340                 345                 350

Thr Gly Arg Arg Ile Leu Ile Leu Gly Asp Val Leu Glu Leu Gly Glu
        355                 360                 365

Asn Ser Lys Glu Met His Ile Gly Val Gly Asn Tyr Leu Glu Glu Lys
    370                 375                 380

His Ile Asp Val Leu Tyr Thr Phe Gly Asn Glu Ala Lys Tyr Ile Tyr
385                 390                 395                 400

Asp Ser Gly Gln Gln His Val Glu Lys Ala Gln His Phe Asn Ser Lys
                405                 410                 415

Asp Asp Met Ile Glu Val Leu Ile Asn Asp Leu Lys Ala His Asp Arg
            420                 425                 430

Val Leu Val Lys Gly Ser Arg Gly Met Lys Leu Glu Glu Val Val Asn
        435                 440                 445

Ala Leu Ile Ser
    450

<210> SEQ ID NO 27
<211> LENGTH: 399
<212> TYPE: DNA
<213> ORGANISM: Homo sapiens

<400> SEQUENCE: 27
atgacaatga cagatccaat cgcagatatg cttactcgtg taagaaacgc aaacatggtg      60
cgtcacgaga agttagaatt acctgcatca aatattaaaa agaaattgc tgaaatctta     120 aagagtgaag gtttcattaa aaatgttgaa tacgtagaag atgataaaca aggtgtactt     180
cgtttattct taaaatatgg tcaaaacgat gagcgtgtta tcacaggatt aaaacgtatt     240
tcaaaaccag gttacgtgt ttatgcaaaa gctagcgaaa tgcctaaagt attaaatggt     300
ttaggtattg cattagtatc aacttctgaa ggtgtaatca ctgacaaaga agcaagaaaa     360
cgtaatgttg gtggagaaat tatcgcatac gtttggtaa                          399

<210> SEQ ID NO 28
<211> LENGTH: 132
<212> TYPE: PRT
<213> ORGANISM: Homo sapiens

<400> SEQUENCE: 28

Met Thr Met Thr Asp Pro Ile Ala Asp Met Leu Thr Arg Val Arg Asn
  1               5                  10                  15

Ala Asn Met Val Arg His Glu Lys Leu Glu Leu Pro Ala Ser Asn Ile
             20                  25                  30
```

```
Lys Lys Glu Ile Ala Glu Ile Leu Lys Ser Glu Gly Phe Ile Lys Asn
    35                  40                  45

Val Glu Tyr Val Glu Asp Asp Lys Gln Gly Val Leu Arg Leu Phe Leu
    50                  55                  60

Lys Tyr Gly Gln Asn Asp Glu Arg Val Ile Thr Gly Leu Lys Arg Ile
 65                  70                  75                  80

Ser Lys Pro Gly Leu Arg Val Tyr Ala Lys Ala Ser Glu Met Pro Lys
                85                  90                  95

Val Leu Asn Gly Leu Gly Ile Ala Leu Val Ser Thr Ser Glu Gly Val
                100                 105                 110

Ile Thr Asp Lys Glu Ala Arg Lys Arg Asn Val Gly Glu Ile Ile
                115                 120                 125

Ala Tyr Val Trp
    130

<210> SEQ ID NO 29
<211> LENGTH: 267
<212> TYPE: DNA
<213> ORGANISM: Homo sapiens

<400> SEQUENCE: 29
atggcaattt cacaagaacg taaaaacgaa atcattaaag aataccgtgt acacgaaact      60
gatactggtt caccagaagt acaaatcgct gtacttactg cagaaatcaa cgcagtaaac     120
gaacacttac gtacacacaa aaaagaccac cattcacgtc gtggattatt aaaaatggta     180
ggtcgtcgta gacatttatt aaactactta cgtagtaaag atattcaacg ttaccgtgaa     240
ttaattaaat cacttggcat ccgtcgt                                          267

<210> SEQ ID NO 30
<211> LENGTH: 89
<212> TYPE: PRT
<213> ORGANISM: Homo sapiens

<400> SEQUENCE: 30

Met Ala Ile Ser Gln Glu Arg Lys Asn Glu Ile Ile Lys Glu Tyr Arg
  1               5                  10                  15

Val His Glu Thr Asp Thr Gly Ser Pro Glu Val Gln Ile Ala Val Leu
                20                  25                  30

Thr Ala Glu Ile Asn Ala Val Asn Glu His Leu Arg Thr His Lys Lys
            35                  40                  45

Asp His His Ser Arg Arg Gly Leu Leu Lys Met Val Gly Arg Arg
    50                  55                  60

His Leu Leu Asn Tyr Leu Arg Ser Lys Asp Ile Gln Arg Tyr Arg Glu
 65                  70                  75                  80

Leu Ile Lys Ser Leu Gly Ile Arg Arg
                85

<210> SEQ ID NO 31
<211> LENGTH: 666
<212> TYPE: DNA
<213> ORGANISM: Homo sapiens

<400> SEQUENCE: 31
taaggaggga atactgtggg tcaaaaaatt aatccaatcg acttcgtgt tggtattatc       60 cgtgattggg aagctaaatg gtatgctgaa aaagacttcg cttcactttt acacgaagat    120
ttaaaaatcc gtaaatttat tgataatgaa ttaaagaag catcagtttc tcacgtagag     180
```

```
attgaacgtg ctgcaaaccg tatcaacatt gcaattcata ctggtaaacc tggtatggta    240
attggtaaag gcggttcaga aatcgaaaaa ttacgcaaca aattaaatgc gttaactgat    300
aaaaaagtac acatcaacgt aattgaaatc aaaaaagttg atcttgacgc tcgtttagta    360
gctgaaaaca tcgcacgtca attagaaaac cgtgcttcat tccgtcgtgt acaaaaacaa    420
gcaatcacta gagctatgaa acttggtgct aaaggtatca aaactcaagt atctggtcgt    480
ttaggcggag ctgacatcgc tcgtgctgaa caatattcag aaggaactgt tccacttcat    540
acgttacgtg ctgacatcga ttatgcacac gctgaagctg acactactta cggtaaatta    600
ggcgttaaag tatggattta tcgtggagaa gttcttccta ctaagaacac tagtggagga    660
ggaaaa                                                               666
```

<210> SEQ ID NO 32
<211> LENGTH: 217
<212> TYPE: PRT
<213> ORGANISM: Homo sapiens
<400> SEQUENCE: 32

```
Val Gly Gln Lys Ile Asn Pro Ile Gly Leu Arg Val Gly Ile Ile Arg
 1               5                  10                  15

Asp Trp Glu Ala Lys Trp Tyr Ala Glu Lys Asp Phe Ala Ser Leu Leu
            20                  25                  30

His Glu Asp Leu Lys Ile Arg Lys Phe Ile Asp Asn Glu Leu Lys Glu
        35                  40                  45

Ala Ser Val Ser His Val Glu Ile Glu Arg Ala Ala Asn Arg Ile Asn
    50                  55                  60

Ile Ala Ile His Thr Gly Lys Pro Gly Met Val Ile Gly Lys Gly Gly
65                  70                  75                  80

Ser Glu Ile Glu Lys Leu Arg Asn Lys Leu Asn Ala Leu Thr Asp Lys
                85                  90                  95

Lys Val His Ile Asn Val Ile Glu Ile Lys Lys Val Asp Leu Asp Ala
            100                 105                 110

Arg Leu Val Ala Glu Asn Ile Ala Arg Gln Leu Glu Asn Arg Ala Ser
        115                 120                 125

Phe Arg Arg Val Gln Lys Gln Ala Ile Thr Arg Ala Met Lys Leu Gly
    130                 135                 140

Ala Lys Gly Ile Lys Thr Gln Val Ser Gly Arg Leu Gly Gly Ala Asp
145                 150                 155                 160

Ile Ala Arg Ala Glu Gln Tyr Ser Glu Gly Thr Val Pro Leu His Thr
                165                 170                 175

Leu Arg Ala Asp Ile Asp Tyr Ala His Ala Glu Ala Asp Thr Thr Tyr
            180                 185                 190

Gly Lys Leu Gly Val Lys Val Trp Ile Tyr Arg Gly Glu Val Leu Pro
        195                 200                 205

Thr Lys Asn Thr Ser Gly Gly Lys
    210                 215
```

<210> SEQ ID NO 33
<211> LENGTH: 498
<212> TYPE: DNA
<213> ORGANISM: Homo sapiens
<400> SEQUENCE: 33

```
atggctcgta gagaagaaga gacgaaagaa tttgaagaac gcgttgttac aatcaaccgt    60
gtagcaaaag ttgtaaaagg tggtcgtcgt ttccgtttca ctgcattagt tgtagttgga   120
```

```
gacaaaaatg gtcgtgtagg tttcggtact ggtaaagctc aagaggtacc agaagcaatc      180
aaaaaagctg ttgaagcagc taaaaaagat ttagtagttg ttccacgtgt tgaaggtaca      240
actccacaca caattactgg ccgttacggt tcaggaagcg tatttatgaa accggctgca      300
cctggtacag gagttatcgc tggtggtcct gttcgtgccg tacttgaatt agcaggtatc      360
actgatatct taagtaaatc attaggatca aacacaccaa tcaacatggt tcgtgctaca      420
atcgatggtt tacaaaacct taaaaatgct gaagatgttg cgaaattacg tggcaaaaca      480
gtagaagaat tatacaat                                                   498
```

<210> SEQ ID NO 34
<211> LENGTH: 166
<212> TYPE: PRT
<213> ORGANISM: Homo sapiens

<400> SEQUENCE: 34

```
Met Ala Arg Arg Glu Glu Thr Lys Glu Phe Glu Glu Arg Val Val
 1               5                  10                  15

Thr Ile Asn Arg Val Ala Lys Val Val Lys Gly Gly Arg Arg Phe Arg
             20                  25                  30

Phe Thr Ala Leu Val Val Gly Asp Lys Asn Gly Arg Val Gly Phe
         35                  40                  45

Gly Thr Gly Lys Ala Gln Glu Val Pro Glu Ala Ile Lys Lys Ala Val
     50                  55                  60

Glu Ala Ala Lys Lys Asp Leu Val Val Pro Arg Val Glu Gly Thr
 65                  70                  75                  80

Thr Pro His Thr Ile Thr Gly Arg Tyr Gly Ser Gly Ser Val Phe Met
                 85                  90                  95

Lys Pro Ala Ala Pro Gly Thr Gly Val Ile Ala Gly Gly Pro Val Arg
             100                 105                 110

Ala Val Leu Glu Leu Ala Gly Ile Thr Asp Ile Leu Ser Lys Ser Leu
         115                 120                 125

Gly Ser Asn Thr Pro Ile Asn Met Val Arg Ala Thr Ile Asp Gly Leu
     130                 135                 140

Gln Asn Leu Lys Asn Ala Glu Asp Val Ala Lys Leu Arg Gly Lys Thr
145                 150                 155                 160

Val Glu Glu Leu Tyr Asn
                165
```

<210> SEQ ID NO 35
<211> LENGTH: 390
<212> TYPE: DNA
<213> ORGANISM: Homo sapiens

<400> SEQUENCE: 35

```
atggcacaag ttgaatatag aggcacaggc cgtcgtaaaa actcagtagc acgtgtacgt       60
ttagtaccag gtgaaggtaa catcacagtt aataaccgtg acgtacgcga atacttacca      120
ttcgaatcat taattttaga cttaaaccaa ccatttgatg taactgaaac taaaggtaac      180
tatgatgttt tagttaacgt tcatggtggt ggtttcactg acaagctcag agctatccgt      240
cacggaatcg ctcgtgcatt attagaagca gatcctgaat acagaggttc tttaaaacgc      300
gctggattac ttactcgtga cccacgtatg aaagaacata aaaaaccagg tcttaaagca      360
gctcgtcgtt caccgcaatt ctcaaaacgt                                      390
```

<210> SEQ ID NO 36
<211> LENGTH: 130
<212> TYPE: PRT
<213> ORGANISM: Homo sapiens

<400> SEQUENCE: 36

Met Ala Gln Val Glu Tyr Arg Gly Thr Gly Arg Arg Lys Asn Ser Val
1               5                   10                  15

Ala Arg Val Arg Leu Val Pro Gly Glu Gly Asn Ile Thr Val Asn Asn
            20                  25                  30

Arg Asp Val Arg Glu Tyr Leu Pro Phe Glu Ser Leu Ile Leu Asp Leu
        35                  40                  45

Asn Gln Pro Phe Asp Val Thr Glu Thr Lys Gly Asn Tyr Asp Val Leu
    50                  55                  60

Val Asn Val His Gly Gly Gly Phe Thr Gly Gln Ala Gln Ala Ile Arg
65                  70                  75                  80

His Gly Ile Ala Arg Ala Leu Leu Glu Ala Asp Pro Glu Tyr Arg Gly
                85                  90                  95

Ser Leu Lys Arg Ala Gly Leu Leu Thr Arg Asp Pro Arg Met Lys Glu
            100                 105                 110

His Lys Lys Pro Gly Leu Lys Ala Ala Arg Arg Ser Pro Gln Phe Ser
        115                 120                 125

Lys Arg
    130

<210> SEQ ID NO 37
<211> LENGTH: 306
<212> TYPE: DNA
<213> ORGANISM: Homo sapiens

<400> SEQUENCE: 37
atggcaaaac aaaaaatcag aatcagatta aaggcttatg atcaccgcgt aattgatcaa      60
tcagcagaga agattgtaga aacagcgaaa cgttctggtg cagatgtttc tggaccaatt     120
ccgttaccaa ctgagaaatc agtttacaca atcatccgtg ccgtgcataa gtataaagat     180
tcacgtgaac aattcgaaca acgtacacac aaacgtttaa tcgatattgt aaacccaaca     240
ccaaaaacag ttgacgcttt aatgggctta aacttaccat ctggtgtaga catcgaaatc     300
aaatta                                                               306

<210> SEQ ID NO 38
<211> LENGTH: 102
<212> TYPE: PRT
<213> ORGANISM: Homo sapiens

<400> SEQUENCE: 38

Met Ala Lys Gln Lys Ile Arg Ile Arg Leu Lys Ala Tyr Asp His Arg
1               5                   10                  15

Val Ile Asp Gln Ser Ala Glu Lys Ile Val Glu Thr Ala Lys Arg Ser
            20                  25                  30

Gly Ala Asp Val Ser Gly Pro Ile Pro Leu Pro Thr Glu Lys Ser Val
        35                  40                  45

Tyr Thr Ile Ile Arg Ala Val His Lys Tyr Lys Asp Ser Arg Glu Gln
    50                  55                  60

Phe Glu Gln Arg Thr His Lys Arg Leu Ile Asp Ile Val Asn Pro Thr
65                  70                  75                  80

Pro Lys Thr Val Asp Ala Leu Met Gly Leu Asn Leu Pro Ser Gly Val
                85                  90                  95

Asp Ile Glu Ile Lys Leu
            100

<210> SEQ ID NO 39
<211> LENGTH: 267
<212> TYPE: DNA
<213> ORGANISM: Homo sapiens

<400> SEQUENCE: 39
atggctaaga aatctaaaat agcaaaagag agaaaaagag aagagttagt aaataaatat     60
tacgaattac gtaaagagtt aaaagcaaaa ggtgattacg aagcgttaag aaaattacca    120
agagattcat cacctacacg tttaactaga agatgtaaag taactggaag acctagaggt    180
gtattacgta aatttgaaat gtctcgtatt gcgtttagag aacatgcgca caaggacaa     240
attccaggtg ttaaaaaatc aagttgg                                        267

<210> SEQ ID NO 40
<211> LENGTH: 89
<212> TYPE: PRT
<213> ORGANISM: Homo sapiens

<400> SEQUENCE: 40

Met Ala Lys Lys Ser Lys Ile Ala Lys Glu Arg Lys Arg Glu Leu
  1               5                  10                  15

Val Asn Lys Tyr Tyr Glu Leu Arg Lys Glu Leu Lys Ala Lys Gly Asp
                 20                  25                  30

Tyr Glu Ala Leu Arg Lys Leu Pro Arg Asp Ser Ser Pro Thr Arg Leu
             35                  40                  45

Thr Arg Arg Cys Lys Val Thr Gly Arg Pro Arg Gly Val Leu Arg Lys
         50                  55                  60

Phe Glu Met Ser Arg Ile Ala Phe Arg Glu His Ala His Lys Gly Gln
 65                  70                  75                  80

Ile Pro Gly Val Lys Lys Ser Ser Trp
                 85

<210> SEQ ID NO 41
<211> LENGTH: 276
<212> TYPE: DNA
<213> ORGANISM: Homo sapiens

<400> SEQUENCE: 41
atggctcgta gtattaaaaa aggacctttc gtcgatgagc atttaatgaa aaagttgaa      60
gctcaagaag gaagcgaaaa gaaacaagta atcaaaacat ggtcacgtcg ttctacaatt    120
ttccctaatt tcatcggaca tacttttgca gtatacgacg gacgtaaaca cgtacctgta    180
tatgtaactg aagatatggt aggtcataaa ttaggtgagt ttgctcctac tcgtacattc    240
aaaggacacg ttgcagacga caagaaaaca agaaga                              276

<210> SEQ ID NO 42
<211> LENGTH: 92
<212> TYPE: PRT
<213> ORGANISM: Homo sapiens

<400> SEQUENCE: 42

Met Ala Arg Ser Ile Lys Lys Gly Pro Phe Val Asp Glu His Leu Met
  1               5                  10                  15

Lys Lys Val Glu Ala Gln Glu Gly Ser Glu Lys Lys Gln Val Ile Lys
                 20                  25                  30

```
Thr Trp Ser Arg Arg Ser Thr Ile Phe Pro Asn Phe Ile Gly His Thr
            35                  40                  45

Phe Ala Val Tyr Asp Gly Arg Lys His Val Pro Val Tyr Val Thr Glu
    50                  55                  60

Asp Met Val Gly His Lys Leu Gly Glu Phe Ala Pro Thr Arg Thr Phe
65                  70                  75                  80

Lys Gly His Val Ala Asp Asp Lys Lys Thr Arg Arg
                85                  90
```

```
<210> SEQ ID NO 43
<211> LENGTH: 183
<212> TYPE: DNA
<213> ORGANISM: Homo sapiens

<400> SEQUENCE: 43
atggctaaaa cttcaatggt tgctaagcaa caaaaaaaac aaaaatatgc agttcgtgaa      60
tacactcgtt gtgaacgttg tggccgtcca cattctgtat atcgtaaatt taaattatgc     120
cgtatttgtt tccgtgaatt agcttacaaa ggccaaatcc ctggcgttcg taaagctagc     180
tgg                                                                  183
```

```
<210> SEQ ID NO 44
<211> LENGTH: 61
<212> TYPE: PRT
<213> ORGANISM: Homo sapiens

<400> SEQUENCE: 44

Met Ala Lys Thr Ser Met Val Ala Lys Gln Gln Lys Gln Lys Tyr
1               5                   10                  15

Ala Val Arg Glu Tyr Thr Arg Cys Glu Arg Cys Gly Arg Pro His Ser
                20                  25                  30

Val Tyr Arg Lys Phe Lys Leu Cys Arg Ile Cys Phe Arg Glu Leu Ala
            35                  40                  45

Tyr Lys Gly Gln Ile Pro Gly Val Arg Lys Ala Ser Trp
        50                  55                  60
```

```
<210> SEQ ID NO 45
<211> LENGTH: 699
<212> TYPE: DNA
<213> ORGANISM: Homo sapiens

<400> SEQUENCE: 45
atggctagaa aagttgttgt agttgatgat gaaaaaccga ttgctgatat tttagaattt      60
aacttaaaaa agaaggata cgatgtgtac tgtgcatacg atggtaatga tgcagtcgac     120
ttaatttatg aagaagaacc agacatcgta ttactagata tcatgttacc tggtcgtgat     180
ggtatggaag tatgtcgtga agtgcgcaaa aaatacgaaa tgccaataat aatgcttact     240
gctaaagatt cagaaattga taagtgcttg gtttagaac taggtgcaga tgactatgta     300
acgaaaccgt ttagtacgcg tgaattaatc gcacgtgtga aagcgaactt acgtcgtcat     360
tactcacaac cagcacaaga cactggaaat gtaacgaatg aaatcacaat taaagatatt     420 gtgattatc cagacgcata ttctattaaa aacgtggcg aagatattga attaacacat     480
cgtgaatttg aattgttcca ttatttatca aaacatatgg acaagtaat gacacgtgaa     540 catttattac aaacagtatg gggctatgat tactttggcg atgtacgtac ggtcgatgta     600
acgattcgtc gtttacgtga aaagattgaa gatgatccgt cacatcctga atatattgtg     660
```

```
acgcgtagag gcgttggata tttcctccaa caacatgag                              699
```

<210> SEQ ID NO 46
<211> LENGTH: 233
<212> TYPE: PRT
<213> ORGANISM: Homo sapiens

<400> SEQUENCE: 46

```
Met Ala Arg Lys Val Val Val Asp Asp Glu Lys Pro Ile Ala Asp
  1               5                  10                  15

Ile Leu Glu Phe Asn Leu Lys Lys Gly Tyr Asp Val Tyr Cys Ala
                 20                  25                  30

Tyr Asp Gly Asn Asp Ala Val Asp Leu Ile Tyr Glu Glu Pro Asp
                 35                  40                  45

Ile Val Leu Leu Asp Ile Met Leu Pro Gly Arg Asp Gly Met Glu Val
 50                  55                  60

Cys Arg Glu Val Arg Lys Lys Tyr Glu Met Pro Ile Ile Met Leu Thr
 65                  70                  75                  80

Ala Lys Asp Ser Glu Ile Asp Lys Val Leu Gly Leu Glu Leu Gly Ala
                 85                  90                  95

Asp Asp Tyr Val Thr Lys Pro Phe Ser Thr Arg Glu Leu Ile Ala Arg
                100                 105                 110

Val Lys Ala Asn Leu Arg Arg His Tyr Ser Gln Pro Ala Gln Asp Thr
                115                 120                 125

Gly Asn Val Thr Asn Glu Ile Thr Ile Lys Asp Ile Val Ile Tyr Pro
                130                 135                 140

Asp Ala Tyr Ser Ile Lys Lys Arg Gly Glu Asp Ile Glu Leu Thr His
145                 150                 155                 160

Arg Glu Phe Glu Leu Phe His Tyr Leu Ser Lys His Met Gly Gln Val
                165                 170                 175

Met Thr Arg Glu His Leu Leu Gln Thr Val Trp Gly Tyr Asp Tyr Phe
                180                 185                 190

Gly Asp Val Arg Thr Val Asp Val Thr Ile Arg Arg Leu Arg Glu Lys
                195                 200                 205

Ile Glu Asp Asp Pro Ser His Pro Glu Tyr Ile Val Thr Arg Arg Gly
210                 215                 220

Val Gly Tyr Phe Leu Gln Gln His Glu
225                 230
```

<210> SEQ ID NO 47
<211> LENGTH: 937
<212> TYPE: DNA
<213> ORGANISM: Homo sapiens

<400> SEQUENCE: 47

```
atgccattat ttttacaacc aattttaaaa acaaaattat ggggcggtca acgtctaagt    60
gagtttggat atcaattaga caatgataca actgggggaa tgttggtgtg tgtcagcaca   120
tccaaatggt acgagcgaga ttattaatgg accatatcaa ggtcaaacat tagaccgtat   180
ttggtcagaa catcgtgaat tgtttggtga tttcccaagc aaagattttc cgcttctaac   240
taaaatagtg gatgcaagag aatcactttc tattcatgtg caccctgata attcttatgc   300
ttatgagcat gaaaacgggc aatatggcaa atctgaatgt tggtatatta tagatgcaga   360
agaagatgca gaaatagtta tagggacatt agcagagtct agagaagaag ttgcgaatca   420
tgttcaacac ggaacgatag agtcgatact tagatatatt aaagtaaaac ctggagaatt   480
```

```
ctattttatt ccagcaggaa cagtwcatac tatttcttca ggaatattag catacgaaac    540
gatgcaatcg tcagacatta catatagact ttatgatttc aatcgtcaag ataatcaata    600
taatgataga ccgttaaata ttgaaaaagc tttagacgtt attcagtaca atgcaccatt    660
acctaatatt ttgcctgaaa gcgaaattat tgaaaaccat aagtgtacac acattgtatc    720
gaatgatttc tttacattgg ttaaatggga aatttctggc acgttaaatt atatgaagcc    780
tagagagttc tgtttagtta cagtgttgga aggcgaaggg caaatgattg tctatggtga    840
aattttcaaa ctgactactg gtacaaactt tattttgact tctgaagatt tggatagtgt    900
ctttgaaggt gatttcacat tgatgattag ctatgtg                             937
```

<210> SEQ ID NO 48
<211> LENGTH: 312
<212> TYPE: PRT
<213> ORGANISM: Homo sapiens

<400> SEQUENCE: 48

```
Met Pro Leu Phe Leu Gln Pro Ile Leu Lys Thr Lys Leu Trp Gly Gly
  1               5                  10                  15

Gln Arg Leu Ser Glu Phe Gly Tyr Gln Leu Asp Asn Asp Thr Thr Gly
             20                  25                  30

Glu Cys Trp Cys Val Ser Ala His Pro Asn Gly Thr Ser Glu Ile Ile
         35                  40                  45

Asn Gly Pro Tyr Gln Gly Gln Thr Leu Asp Arg Ile Trp Ser Glu His
     50                  55                  60

Arg Glu Leu Phe Gly Asp Phe Pro Ser Lys Asp Phe Pro Leu Leu Thr
 65                  70                  75                  80

Lys Ile Val Asp Ala Arg Glu Ser Leu Ser Ile His Val His Pro Asp
                 85                  90                  95

Asn Ser Tyr Ala Tyr Glu His Glu Asn Gly Gln Tyr Gly Lys Ser Glu
            100                 105                 110

Cys Trp Tyr Ile Ile Asp Ala Glu Glu Asp Ala Glu Ile Val Ile Gly
        115                 120                 125

Thr Leu Ala Glu Ser Arg Glu Glu Val Ala Asn His Val Gln His Gly
    130                 135                 140

Thr Ile Glu Ser Ile Leu Arg Tyr Ile Lys Val Lys Pro Gly Glu Phe
145                 150                 155                 160

Tyr Phe Ile Pro Ala Gly Thr Val His Thr Ile Ser Ser Gly Ile Leu
                165                 170                 175

Ala Tyr Glu Thr Met Gln Ser Ser Asp Ile Thr Tyr Arg Leu Tyr Asp
            180                 185                 190

Phe Asn Arg Gln Asp Asn Gln Tyr Asn Asp Arg Pro Leu Asn Ile Glu
        195                 200                 205

Lys Ala Leu Asp Val Ile Gln Tyr Asn Ala Pro Leu Pro Asn Ile Leu
    210                 215                 220

Pro Glu Ser Glu Ile Ile Glu Asn His Lys Cys Thr His Ile Val Ser
225                 230                 235                 240

Asn Asp Phe Phe Thr Leu Val Lys Trp Glu Ile Ser Gly Thr Leu Asn
                245                 250                 255

Tyr Met Lys Pro Arg Glu Phe Cys Leu Val Thr Val Leu Glu Gly Glu
            260                 265                 270

Gly Gln Met Ile Val Asp Gly Glu Ile Phe Lys Leu Thr Thr Gly Thr
        275                 280                 285

Asn Phe Ile Leu Thr Ser Glu Asp Leu Asp Ser Val Phe Glu Gly Asp
```

-continued

```
         290                 295                 300
Phe Thr Leu Met Ile Ser Tyr Val
305                 310

<210> SEQ ID NO 49
<211> LENGTH: 837
<212> TYPE: DNA
<213> ORGANISM: Homo sapiens

<400> SEQUENCE: 49
atggctgtat tatatttagt gggcacacca attggtaatt tagcagatat tacttataga     60
gcagttgatg tattgaaacg tgttgatatg attgcttgtg aagacactag agtaactagt    120
aaactgtgta atcattatga tattccaact ccattaaagt catatcacga acataacaag    180
gataagcaga ctgcttttat cattgaacag ttagaattag gtcttgacgt tgcgctcgta    240
tctgatgctg gattgccctt aattagtgat cctggatacg aattagtagt ggcagccaga    300
gaagctaata ttaaagtaga gactgtgcct ggacctaatg ctgggctgac ggctttgatg    360
gctagtggat taccttcata tgtatataca ttttaggat ttttgccacg aaaagagaaa     420
gaaaaaagtg ctgtattaga gcaacgtatg catgaaaata gcacattaat tatatacgaa    480
tcaccgcatc gtgtgacaga tacattaaaa acaattgcaa agatagatgc aacacgacaa    540
gtatcactag gcgtgaatt aactaagaag ttcgaacaaa ttgtaactga tgatgtaaca     600
caattacaag cattgattca gcaaggcgat gtaccattga aaggcgaatt cgttatctta    660
attgaaggtg ctaaagcgaa caatgagata tcgtggtttg atgatttatc tatcaatgag    720
catgttgatc attatattca aacttcacag atgaaaccaa acaagctat taaaaaagtt    780 gctgaagaac gacaacttaa aacgaatgaa gtatataata tttatcatca aataagt       837

<210> SEQ ID NO 50
<211> LENGTH: 279
<212> TYPE: PRT
<213> ORGANISM: Homo sapiens

<400> SEQUENCE: 50

Met Ala Val Leu Tyr Leu Val Gly Thr Pro Ile Gly Asn Leu Ala Asp
1               5                  10                  15

Ile Thr Tyr Arg Ala Val Asp Val Leu Lys Arg Val Asp Met Ile Ala
            20                  25                  30

Cys Glu Asp Thr Arg Val Thr Ser Lys Leu Cys Asn His Tyr Asp Ile
        35                  40                  45

Pro Thr Pro Leu Lys Ser Tyr His Glu His Asn Lys Asp Lys Gln Thr
    50                  55                  60

Ala Phe Ile Ile Glu Gln Leu Glu Leu Gly Leu Asp Val Ala Leu Val
65                  70                  75                  80

Ser Asp Ala Gly Leu Pro Leu Ile Ser Asp Pro Gly Tyr Glu Leu Val
                85                  90                  95

Val Ala Ala Arg Glu Ala Asn Ile Lys Val Glu Thr Val Pro Gly Pro
            100                 105                 110

Asn Ala Gly Leu Thr Ala Leu Met Ala Ser Gly Leu Pro Ser Tyr Val
        115                 120                 125

Tyr Thr Phe Leu Gly Phe Leu Pro Arg Lys Glu Lys Glu Lys Ser Ala
    130                 135                 140

Val Leu Glu Gln Arg Met His Glu Asn Ser Thr Leu Ile Ile Tyr Glu
145                 150                 155                 160
```

```
Ser Pro His Arg Val Thr Asp Thr Leu Lys Thr Ile Ala Lys Ile Asp
                165                 170                 175

Ala Thr Arg Gln Val Ser Leu Gly Arg Glu Leu Thr Lys Lys Phe Glu
            180                 185                 190

Gln Ile Val Thr Asp Val Thr Gln Leu Gln Ala Leu Ile Gln Gln
        195                 200                 205

Gly Asp Val Pro Leu Lys Gly Glu Phe Val Ile Leu Ile Glu Gly Ala
    210                 215                 220

Lys Ala Asn Asn Glu Ile Ser Trp Phe Asp Asp Leu Ser Ile Asn Glu
225                 230                 235                 240

His Val Asp His Tyr Ile Gln Thr Ser Gln Met Lys Pro Lys Gln Ala
                245                 250                 255

Ile Lys Lys Val Ala Glu Glu Arg Gln Leu Lys Thr Asn Glu Val Tyr
            260                 265                 270

Asn Ile Tyr His Gln Ile Ser
            275
```

<210> SEQ ID NO 51
<211> LENGTH: 624
<212> TYPE: DNA
<213> ORGANISM: Homo sapiens

<400> SEQUENCE: 51

```
atgaaatttg gaaaaacaat cgcagtagta ttagcatcta gtgtcttgct tgcaggatgt      60
actacggata aaaagaaat  taaggcatat ttaaagcaag tggataaaat taaagatgat    120
gaagaaccaa ttaaaactgt tggtaagaaa attgctgaat tagatgagaa aaagaaaaaa    180
ttaactgaag atgtcaatag taaagataca gcagttcgcg gtaaagcagt aaaggattta    240
attaaaaatg ccgatgatcg tctaaaggaa tttgaaaaag aagaagacgc aattaagaag    300
tctgaacaag actttaagaa agcaaaaagt cacgttgata acattgataa tgatgttaaa    360
cgtaaagaag taaacaatt  agatgatgta ttaaaagaaa aatataagtt acacagtgat    420
tacgcgaaag catataaaaa ggctgtaaac tcagagaaaa cattatttaa atatttaaat    480
caaaatgacg cgacacaaca aggtgttaac gaaaaatcaw aagcaataga acagaactat    540
aaaaagttaa aagaagtatc agataagtat acaaaagtac taaataaggt tggtaaagaa    600
aagcaagacg ttgatcaatt taaa                                           624
```

<210> SEQ ID NO 52
<211> LENGTH: 208
<212> TYPE: PRT
<213> ORGANISM: Homo sapiens
<220> FEATURE:
<221> NAME/KEY: MISC_FEATURE
<222> LOCATION: (174)..(174)
<223> OTHER INFORMATION: Xaa equals any amino acid

<400> SEQUENCE: 52

```
Met Lys Phe Gly Lys Thr Ile Ala Val Val Leu Ala Ser Ser Val Leu
  1               5                  10                  15

Leu Ala Gly Cys Thr Thr Asp Lys Lys Glu Ile Lys Ala Tyr Leu Lys
            20                  25                  30

Gln Val Asp Lys Ile Lys Asp Asp Glu Glu Pro Ile Lys Thr Val Gly
        35                  40                  45

Lys Lys Ile Ala Glu Leu Asp Glu Lys Lys Lys Leu Thr Glu Asp
    50                  55                  60

Val Asn Ser Lys Asp Thr Ala Val Arg Gly Lys Ala Val Lys Asp Leu
```

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |

Ile Lys Asn Ala Asp Asp Arg Leu Lys Glu Phe Glu Lys Glu Asp
                 85                  90                  95

Ala Ile Lys Lys Ser Glu Gln Asp Phe Lys Ala Lys Ser His Val
            100                 105                 110

Asp Asn Ile Asp Asn Asp Val Lys Arg Lys Glu Val Lys Gln Leu Asp
        115                 120                 125

Asp Val Leu Lys Glu Lys Tyr Lys Leu His Ser Asp Tyr Ala Lys Ala
    130                 135                 140

Tyr Lys Lys Ala Val Asn Ser Glu Lys Thr Leu Phe Lys Tyr Leu Asn
145                 150                 155                 160

Gln Asn Asp Ala Thr Gln Gln Gly Val Asn Glu Lys Ser Xaa Ala Ile
                165                 170                 175

Glu Gln Asn Tyr Lys Lys Leu Lys Glu Val Ser Asp Lys Tyr Thr Lys
            180                 185                 190

Val Leu Asn Lys Val Gly Lys Glu Lys Gln Asp Val Asp Gln Phe Lys
        195                 200                 205

<210> SEQ ID NO 53
<211> LENGTH: 717
<212> TYPE: DNA
<213> ORGANISM: Homo sapiens

<400> SEQUENCE: 53
atcgaggaca gaatattgtt aaagtatgaa catattgcta agcagcttaa tgcgtttata      60
catcaatcta atttcaaacc cggtgataaa ttgccaagcg tgacgcaatt aaaagaacgt     120
tatcaagtaa gtaagagtac tatcattaaa gcattaggct tattggaaca agatggtttg     180
atctatcaag cacaaggcag tggtatttat gtgagaaata ttgctgatgc caatcgtatc     240
aacgtcttta agactaatgg tttctctaaa agtttaggtg aacaccgaat gacaagtaag     300
gtacttgttt ttaaggagat tgcaacgcca cctaaatctg tacaagatga gctccaatta     360
aatgcagatg ataccgtcta ctatttagag cgattaagat tcgtggacga tgatgtttta     420
tgtatcgaat attcttatta tcataaagaa atcgtgaaat atttaaatga tgatattgct     480
aagggctcta tcttcgacta tttagaatca aacatgaaac ttcgtattgg tttttcagat     540
attttctttta atgtagatca actcacttca agtgaagctt cattactaca attgtctaca     600
ggtgaaccat gtttacgtta ccaccagact ttttatacaa tgactggcaa acccttttgat    660
tcatctgaca tcgtatttca ttatcgtcat gcacagtttt atattcctag taaaaag        717

<210> SEQ ID NO 54
<211> LENGTH: 239
<212> TYPE: PRT
<213> ORGANISM: Homo sapiens

<400> SEQUENCE: 54

Ile Glu Asp Arg Ile Leu Leu Lys Tyr Glu His Ile Ala Lys Gln Leu
1               5                  10                  15

Asn Ala Phe Ile His Gln Ser Asn Phe Lys Pro Gly Asp Lys Leu Pro
            20                  25                  30

Ser Val Thr Gln Leu Lys Glu Arg Tyr Gln Val Ser Lys Ser Thr Ile
        35                  40                  45

Ile Lys Ala Leu Gly Leu Leu Glu Gln Asp Gly Leu Ile Tyr Gln Ala
    50                  55                  60

Gln Gly Ser Gly Ile Tyr Val Arg Asn Ile Ala Asp Ala Asn Arg Ile

-continued

```
                65                  70                  75                  80
Asn Val Phe Lys Thr Asn Gly Phe Ser Lys Ser Leu Gly Glu His Arg
                    85                  90                  95
Met Thr Ser Lys Val Leu Val Phe Lys Glu Ile Ala Thr Pro Pro Lys
                100                 105                 110
Ser Val Gln Asp Glu Leu Gln Leu Asn Ala Asp Asp Thr Val Tyr Tyr
                115                 120                 125
Leu Glu Arg Leu Arg Phe Val Asp Asp Val Leu Cys Ile Glu Tyr
            130                 135                 140
Ser Tyr Tyr His Lys Glu Ile Val Lys Tyr Leu Asn Asp Asp Ile Ala
145                 150                 155                 160
Lys Gly Ser Ile Phe Asp Tyr Leu Glu Ser Asn Met Lys Leu Arg Ile
                165                 170                 175
Gly Phe Ser Asp Ile Phe Phe Asn Val Asp Gln Leu Thr Ser Ser Glu
                180                 185                 190
Ala Ser Leu Leu Gln Leu Ser Thr Gly Glu Pro Cys Leu Arg Tyr His
                195                 200                 205
Gln Thr Phe Tyr Thr Met Thr Gly Lys Pro Phe Asp Ser Ser Asp Ile
            210                 215                 220
Val Phe His Tyr Arg His Ala Gln Phe Tyr Ile Pro Ser Lys Lys
225                 230                 235
```

<210> SEQ ID NO 55
<211> LENGTH: 716
<212> TYPE: DNA
<213> ORGANISM: Homo sapiens

<400> SEQUENCE: 55

| | | |
|---|---|---|
| atgactgtag aatggttagc agaacaatta aaagaacata atattcaatt aactgagact | 60 |
| caaaaacaac agtttcaaac atattatcgt ttacttgttg aatggaatga aaagatgaat | 120 |
| ttgacaagta ttacagatga acacgatgta tatttgaaac attttttatga ttccattgca | 180 |
| cctagttttt atttttgattt taatcagcct ataagtatat gtgatgtagg cgctggagct | 240 |
| ggttttccaa gtattccgtt aaaaataatg tttccgcagt taaaagtgac gattgttgat | 300 |
| tcattaaata agcgtattca attttttaaac catttagcgt cagaattaca attacaggat | 360 |
| gtcagctttta tacacgatag agcagaaaca tttggtaagg gtgtctacag ggagtcttat | 420 |
| gatgttgtta ctgcaagagc agtagctaga ttatccgtgt taagtgaatt gtgtttaccg | 480 |
| ctagttaaaa aaggtggaca gtttgttgca ttaaaatctt caaaaggtga agaagaatta | 540 |
| gaagaagcaa aatttgcaat tagtgtgtta ggtggtaatg ttacagaaac acataccttt | 600 |
| gaattgccag aagatgctgg agagcgccag atgttcatta ttgataaaaa aagacagacg | 660 |
| ccgaaaaagt atccaagaaa accagggacg ctaataagac tcctttactt gaaaaa | 716 |

<210> SEQ ID NO 56
<211> LENGTH: 239
<212> TYPE: PRT
<213> ORGANISM: Homo sapiens

<400> SEQUENCE: 56

```
Met Thr Val Glu Trp Leu Ala Glu Gln Leu Lys Glu His Asn Ile Gln
  1               5                  10                  15
Leu Thr Glu Thr Gln Lys Gln Gln Phe Gln Thr Tyr Tyr Arg Leu Leu
                20                  25                  30
Val Glu Trp Asn Glu Lys Met Asn Leu Thr Ser Ile Thr Asp Glu His
```

```
                 35                  40                  45
Asp Val Tyr Leu Lys His Phe Tyr Asp Ser Ile Ala Pro Ser Phe Tyr
             50                  55                  60

Phe Asp Phe Asn Gln Pro Ile Ser Ile Cys Asp Val Gly Ala Gly Ala
 65                  70                  75                  80

Gly Phe Pro Ser Ile Pro Leu Lys Ile Met Phe Pro Gln Leu Lys Val
                 85                  90                  95

Thr Ile Val Asp Ser Leu Asn Lys Arg Ile Gln Phe Leu Asn His Leu
            100                 105                 110

Ala Ser Glu Leu Gln Leu Gln Asp Val Ser Phe Ile His Asp Arg Ala
        115                 120                 125

Glu Thr Phe Gly Lys Gly Val Tyr Arg Glu Ser Tyr Asp Val Val Thr
    130                 135                 140

Ala Arg Ala Val Ala Arg Leu Ser Val Leu Ser Glu Leu Cys Leu Pro
145                 150                 155                 160

Leu Val Lys Lys Gly Gly Gln Phe Val Ala Leu Lys Ser Ser Lys Gly
                165                 170                 175

Glu Glu Glu Leu Glu Glu Ala Lys Phe Ala Ile Ser Val Leu Gly Gly
            180                 185                 190

Asn Val Thr Glu Thr His Thr Phe Glu Leu Pro Glu Asp Ala Gly Glu
        195                 200                 205

Arg Gln Met Phe Ile Ile Asp Lys Lys Arg Gln Thr Pro Lys Lys Tyr
    210                 215                 220

Pro Arg Lys Pro Gly Thr Pro Asn Lys Thr Pro Leu Leu Glu Lys
225                 230                 235

<210> SEQ ID NO 57
<211> LENGTH: 1191
<212> TYPE: DNA
<213> ORGANISM: Homo sapiens

<400> SEQUENCE: 57
atggcacata ccattacgat tgttggctta ggaaactatg gcattgatga tttgccgcta      60
gggatatata aatttttaaa gacacaagat aaagtttatg caagaacgtt agatcatcca     120
gttatagaat cattgcaaga tgaattaaca tttcagagtt ttgaccatgt ttatgaagca     180
cataaccaat ttgaagatgt ctatattgat attgtggcgc aattggttga agctgctaat     240
gaaaaagata ttgtctatgc ggttccgggt catcctagag ttgctgagac aactacagtg     300
aaattactgg ctttagcaaa ggacaatact gatatagatg tgaaagtttt aggtgggaaa     360
agctttattg atgatgtgtt tgaagcagtt aatgtagatc caaatgatgg cttcacactg     420
ttagatgcga catcattaca agaagtaaca cttaatgtta gaacgcatac attgattacg     480
caagtttata gtgcaatggt tgctgctaat ttgaaaatca ctttaatgga acgatatcct     540
gatgattacc ctgttcaaat tgtcactggt gcacgaagcg atggtgcgga taacgttgtg     600
acatgcccat tatatgaatt ggatcatgat gaaaatgcat tcaataattt gacgagtgta     660
ttcgtaccaa aaatcataac atcgacatat ttgtatcatg actttgattt tgcaacggaa     720
gtgattgata ctttagttga tgaagataaa ggttgtccat gggataaagt gcaaacgcat     780
gmaacgctaa agcgttattt acttgaagaa catttgaat tgttcgaagc tattgacaat     840
gaagatgatt ggcatatgat tgaagaacta ggagatattt tattacaagt gttattgcat     900
actagtattg gtaaaaaaga agggtatatc gacattaaag aagtgattac aagtcttaat     960
gctaaaatga ttcgtagaca cccacacata tttggtgatg ccaatgctga aactatcgat    1020
```

-continued

```
gacttaaaag aaatttggtc taaggcgaaa gatgctgaag gtaaacagcc aagagttaaa      1080
tttgaaaaag tatttgcaga gcatttttta aatttatatg agaagacgaa ggataagtca      1140
tttgatgagg ccgcgttaaa gcagtggcta gaaaaagggg agagtaatac a              1191
```

<210> SEQ ID NO 58
<211> LENGTH: 397
<212> TYPE: PRT
<213> ORGANISM: Homo sapiens
<220> FEATURE:
<221> NAME/KEY: MISC_FEATURE
<222> LOCATION: (261)..(261)
<223> OTHER INFORMATION: Xaa equals any amino acid

<400> SEQUENCE: 58

```
Met Ala His Thr Ile Thr Ile Val Gly Leu Gly Asn Tyr Gly Ile Asp
  1               5                  10                  15

Asp Leu Pro Leu Gly Ile Tyr Lys Phe Leu Lys Thr Gln Asp Lys Val
             20                  25                  30

Tyr Ala Arg Thr Leu Asp His Pro Val Ile Glu Ser Leu Gln Asp Glu
         35                  40                  45

Leu Thr Phe Gln Ser Phe Asp His Val Tyr Glu Ala His Asn Gln Phe
     50                  55                  60

Glu Asp Val Tyr Ile Asp Ile Val Ala Gln Leu Val Glu Ala Ala Asn
 65                  70                  75                  80

Glu Lys Asp Ile Val Tyr Ala Val Pro Gly His Pro Arg Val Ala Glu
                 85                  90                  95

Thr Thr Thr Val Lys Leu Leu Ala Leu Ala Lys Asp Asn Thr Asp Ile
            100                 105                 110

Asp Val Lys Val Leu Gly Gly Lys Ser Phe Ile Asp Asp Val Phe Glu
        115                 120                 125

Ala Val Asn Val Asp Pro Asn Asp Gly Phe Thr Leu Leu Asp Ala Thr
    130                 135                 140

Ser Leu Gln Glu Val Thr Leu Asn Val Arg Thr His Thr Leu Ile Thr
145                 150                 155                 160

Gln Val Tyr Ser Ala Met Val Ala Ala Asn Leu Lys Ile Thr Leu Met
                165                 170                 175

Glu Arg Tyr Pro Asp Asp Tyr Pro Val Gln Ile Val Thr Gly Ala Arg
            180                 185                 190

Ser Asp Gly Ala Asp Asn Val Val Thr Cys Pro Leu Tyr Glu Leu Asp
        195                 200                 205

His Asp Glu Asn Ala Phe Asn Asn Leu Thr Ser Val Phe Val Pro Lys
    210                 215                 220

Ile Ile Thr Ser Thr Tyr Leu Tyr His Asp Phe Asp Phe Ala Thr Glu
225                 230                 235                 240

Val Ile Asp Thr Leu Val Asp Glu Asp Lys Gly Cys Pro Trp Asp Lys
                245                 250                 255

Val Gln Thr His Xaa Thr Leu Lys Arg Tyr Leu Leu Glu Thr Phe
            260                 265                 270

Glu Leu Phe Glu Ala Ile Asp Asn Glu Asp Asp Trp His Met Ile Glu
        275                 280                 285

Glu Leu Gly Asp Ile Leu Leu Gln Val Leu Leu His Thr Ser Ile Gly
    290                 295                 300

Lys Lys Glu Gly Tyr Ile Asp Ile Lys Glu Val Ile Thr Ser Leu Asn
305                 310                 315                 320
```

| Ala | Lys | Met | Ile | Arg | Arg | His | Pro | His | Ile | Phe | Gly | Asp | Ala | Asn | Ala |
|     |     |     | 325 |     |     |     | 330 |     |     |     |     |     | 335 |     |     |

| Glu | Thr | Ile | Asp | Asp | Leu | Lys | Glu | Ile | Trp | Ser | Lys | Ala | Lys | Asp | Ala |
|     |     |     | 340 |     |     |     |     | 345 |     |     |     |     | 350 |     |     |

| Glu | Gly | Lys | Gln | Pro | Arg | Val | Lys | Phe | Glu | Lys | Val | Phe | Ala | Glu | His |
|     |     |     | 355 |     |     |     |     | 360 |     |     |     |     | 365 |     |     |

| Phe | Leu | Asn | Leu | Tyr | Glu | Lys | Thr | Lys | Asp | Lys | Ser | Phe | Asp | Glu | Ala |
|     |     | 370 |     |     |     |     | 375 |     |     |     |     | 380 |     |     |     |

| Ala | Leu | Lys | Gln | Trp | Leu | Glu | Lys | Gly | Glu | Ser | Asn | Thr |
| 385 |     |     |     |     | 390 |     |     |     |     | 395 |     |     |

<210> SEQ ID NO 59
<211> LENGTH: 804
<212> TYPE: DNA
<213> ORGANISM: Homo sapiens

<400> SEQUENCE: 59

```
aatgtaaatc attctaataa aacgacaact gtgtcttctt tacttgtata tgttacatat      60
attcacgata gagaggataa gaaaatggct caaatttcta aatataaacg tgtagttttg     120
aaactaagtg gtgaagcgtt agctggagaa aaaggatttg gcataaatcc agtaattatt     180
aaaagtgttg ctgagcaagt ggctgaagtt gctaaaatgg actgtgaaat cgcagtaatc     240
gttggtggcg gaaacatttg gagaggtaaa acaggtagtg acttaggtat ggaccgtgga     300
actgctgatt acatgggtat gcttgcaact gtaatgaatg ccttagcatt acaagatagt     360
ttagaacaat tggattgtga tacacgagta ttaacatcta ttgaaatgaa gcaagtggct     420
gaaccttata ttcgtcgtcg tgcaattaga cacttagaaa agaaacgcgt agttatttt     480
gctgcaggta ttggaaaccc atacttctct acagatacta cagcggcatt acgtgctgca     540
gaagttgaag cagatgttat tttaatgggc aaaaataatg tagatggtgt atattctgca     600
gatcctaaag taaacaaaga tgcggtaaaa tatgaacatt taacgcatat tcaaatgctt     660
caagaaggtt tacaagtaat ggattcaaca gcatcctcat tctgtatgga taataacatt     720
ccgttaactg ttttctctat tatggaagaa ggaaatatta acgtgctgt tatgggtgaa     780
aagataggta cgttaattac aaaa                                              804
```

<210> SEQ ID NO 60
<211> LENGTH: 268
<212> TYPE: PRT
<213> ORGANISM: Homo sapiens

<400> SEQUENCE: 60

| Asn | Val | Asn | His | Ser | Asn | Lys | Thr | Thr | Thr | Val | Ser | Ser | Leu | Leu | Val |
| 1   |     |     |     | 5   |     |     |     |     | 10  |     |     |     |     | 15  |     |

| Tyr | Val | Thr | Tyr | Ile | His | Asp | Arg | Glu | Asp | Lys | Lys | Met | Ala | Gln | Ile |
|     |     |     | 20  |     |     |     |     | 25  |     |     |     |     | 30  |     |     |

| Ser | Lys | Tyr | Lys | Arg | Val | Val | Leu | Lys | Leu | Ser | Gly | Glu | Ala | Leu | Ala |
|     |     | 35  |     |     |     |     | 40  |     |     |     |     | 45  |     |     |     |

| Gly | Glu | Lys | Gly | Phe | Gly | Ile | Asn | Pro | Val | Ile | Lys | Ser | Val | Ala |
|     | 50  |     |     |     |     | 55  |     |     |     |     | 60  |     |     |     |

| Glu | Gln | Val | Ala | Glu | Val | Ala | Lys | Met | Asp | Cys | Glu | Ile | Ala | Val | Ile |
| 65  |     |     |     |     | 70  |     |     |     |     | 75  |     |     |     |     | 80  |

| Val | Gly | Gly | Gly | Asn | Ile | Trp | Arg | Gly | Lys | Thr | Gly | Ser | Asp | Leu | Gly |
|     |     |     |     | 85  |     |     |     |     | 90  |     |     |     |     | 95  |     |

| Met | Asp | Arg | Gly | Thr | Ala | Asp | Tyr | Met | Gly | Met | Leu | Ala | Thr | Val | Met |
|     |     |     | 100 |     |     |     |     | 105 |     |     |     |     | 110 |     |     |

```
Asn Ala Leu Ala Leu Gln Asp Ser Leu Glu Gln Leu Asp Cys Asp Thr
        115                 120                 125
Arg Val Leu Thr Ser Ile Glu Met Lys Gln Val Ala Glu Pro Tyr Ile
    130                 135                 140
Arg Arg Arg Ala Ile Arg His Leu Glu Lys Lys Arg Val Val Ile Phe
145                 150                 155                 160
Ala Ala Gly Ile Gly Asn Pro Tyr Phe Ser Thr Asp Thr Ala Ala
                165                 170                 175
Leu Arg Ala Ala Glu Val Glu Ala Asp Val Ile Leu Met Gly Lys Asn
            180                 185                 190
Asn Val Asp Gly Val Tyr Ser Ala Asp Pro Lys Val Asn Lys Asp Ala
        195                 200                 205
Val Lys Tyr Glu His Leu Thr His Ile Gln Met Leu Gln Glu Gly Leu
    210                 215                 220
Gln Val Met Asp Ser Thr Ala Ser Ser Phe Cys Met Asp Asn Asn Ile
225                 230                 235                 240
Pro Leu Thr Val Phe Ser Ile Met Glu Glu Gly Asn Ile Lys Arg Ala
                245                 250                 255
Val Met Gly Glu Lys Ile Gly Thr Leu Ile Thr Lys
            260                 265

<210> SEQ ID NO 61
<211> LENGTH: 1068
<212> TYPE: DNA
<213> ORGANISM: Homo sapiens

<400> SEQUENCE: 61
atgacaaaag aaaatatttg tatcgttttt ggagggaaaa gtgcagaaca cgaagtatcg      60
attctgacag cacaaaatgt attaaatgca atagataaag acaaatatca tgttgatatc     120
atttatatta ccaatgatgg tgattggaga aagcaaaata atattacagc tgaaattaaa     180
tctactgatg agcttcattt agaaaatgga gaggcgcttg agatttcaca gctattgaaa     240
gaaagtagtt caggacaacc atacgatgca gtattcccat tattacatgg tcctaatggt     300
gaagatggca cgattcaagg gcttttgaa gttttggatg taccatatgt aggaaatggt     360
gtattgtcag ctgcaagttc tatggacaaa cttgtaatga acaattatt tgaacatcga     420 gggttaccac agttacctta tattagtttc ttacgttctg aatatgaaaa atatgaacat     480 aacatttaa aattagtaaa tgataaatta aattacccag tctttgttaa acctgctaac     540
ttagggtcaa gtgtaggtat cagtaaatgt aataatgaag cggaacttaa agaaggtatt     600
aaagaagcat tccaatttga ccgtaagctt gttatagaac aaggcgttaa cgcacgtgaa     660
attgaagtag cagttttagg aaatgactat cctgaagcga catggccagg tgaagtcgta     720
aaagatgtcg cgttttacga ttacaaatca aaatataaag atggtaaggt tcaattacaa     780
attccagctg acttagacga agatgttcaa ttaacgctta gaaatatggc attagaggca     840
ttcaaagcga cagattgttc tggttttagtc cgtgctgatt tctttgtaac agaagacaac     900
caaatatata ttaatgaaac aaatgcaatg cctggattta cggctttcag tatgtatcca     960
aagttatggg aaaatatggg cttatcttat ccagaattga ttacaaaact tatcgagctt    1020
gctaaagaac gtcaccagga taaacagaaa aataaataca aaattgac                1068

<210> SEQ ID NO 62
<211> LENGTH: 356
<212> TYPE: PRT
```

<213> ORGANISM: Homo sapiens

<400> SEQUENCE: 62

```
Met Thr Lys Glu Asn Ile Cys Ile Val Phe Gly Gly Lys Ser Ala Glu
  1               5                  10                  15
His Glu Val Ser Ile Leu Thr Ala Gln Asn Val Leu Asn Ala Ile Asp
             20                  25                  30
Lys Asp Lys Tyr His Val Asp Ile Ile Tyr Ile Thr Asn Asp Gly Asp
         35                  40                  45
Trp Arg Lys Gln Asn Asn Ile Thr Ala Glu Ile Lys Ser Thr Asp Glu
     50                  55                  60
Leu His Leu Glu Asn Gly Glu Ala Leu Glu Ile Ser Gln Leu Leu Lys
 65                  70                  75                  80
Glu Ser Ser Ser Gly Gln Pro Tyr Asp Ala Val Phe Pro Leu Leu His
                 85                  90                  95
Gly Pro Asn Gly Glu Asp Gly Thr Ile Gln Gly Leu Phe Glu Val Leu
            100                 105                 110
Asp Val Pro Tyr Val Gly Asn Gly Val Leu Ser Ala Ala Ser Ser Met
        115                 120                 125
Asp Lys Leu Val Met Lys Gln Leu Phe Glu His Arg Gly Leu Pro Gln
    130                 135                 140
Leu Pro Tyr Ile Ser Phe Leu Arg Ser Glu Tyr Glu Lys Tyr Glu His
145                 150                 155                 160
Asn Ile Leu Lys Leu Val Asn Asp Lys Leu Asn Tyr Pro Val Phe Val
                165                 170                 175
Lys Pro Ala Asn Leu Gly Ser Ser Val Gly Ile Ser Lys Cys Asn Asn
            180                 185                 190
Glu Ala Glu Leu Lys Glu Gly Ile Lys Glu Ala Phe Gln Phe Asp Arg
        195                 200                 205
Lys Leu Val Ile Glu Gln Gly Val Asn Ala Arg Glu Ile Glu Val Ala
    210                 215                 220
Val Leu Gly Asn Asp Tyr Pro Glu Ala Thr Trp Pro Gly Glu Val Val
225                 230                 235                 240
Lys Asp Val Ala Phe Tyr Asp Tyr Lys Ser Lys Tyr Lys Asp Gly Lys
                245                 250                 255
Val Gln Leu Gln Ile Pro Ala Asp Leu Asp Glu Asp Val Gln Leu Thr
            260                 265                 270
Leu Arg Asn Met Ala Leu Glu Ala Phe Lys Ala Thr Asp Cys Ser Gly
        275                 280                 285
Leu Val Arg Ala Asp Phe Phe Val Thr Glu Asp Asn Gln Ile Tyr Ile
    290                 295                 300
Asn Glu Thr Asn Ala Met Pro Gly Phe Thr Ala Phe Ser Met Tyr Pro
305                 310                 315                 320
Lys Leu Trp Glu Asn Met Gly Leu Ser Tyr Pro Glu Leu Ile Thr Lys
                325                 330                 335
Leu Ile Glu Leu Ala Lys Glu Arg His Gln Asp Lys Gln Lys Asn Lys
            340                 345                 350
Tyr Lys Ile Asp
        355
```

<210> SEQ ID NO 63
<211> LENGTH: 861
<212> TYPE: DNA
<213> ORGANISM: Homo sapiens

```
<400> SEQUENCE: 63
atgacgaatc taccgatgaa taaattaata gatgaagtca ataatgaatt atcggttgcg      60
ataaataaat cagtaatgga tactcagcta gaagaaagta tgttgtattc attaaatgct     120
ggaggtaaac gcatccgacc agttctgtta ttactcactt tagattcact aaataccgag     180
tatgagttag gtatgaagag cgcaattgca ctagaaatga ttcatacata ttcacttatt     240
catgatgacc taccagcgat ggataatgat gattatcgac gaggaaaatt aacaaatcat     300
aaagtatatg gtgagtggac tgcgatatta gcaggtgatg ctttattaac taaagcattt     360
gaacttattt caagtgatga tagattaact gatgaagtaa aaataaaagt tctacaacgg     420
ctgtcaatag caagtggtca tgttggaatg gtcggcggtc aaatgttaga tatgcaaagc     480
gaaggccaac caattgatct tgaaactttg gaaatgatac acaaaacaaa acaggagca      540 ttattaactt ttgcggttat gagtgcagca gatatcgcta atgtcgatga tacaactaaa     600
gaacatttag aaagttatag ttatcattta ggtatgatgt tccagattaa agatgattta     660
ttagactgct atggtgatga agcaaagtta ggtaaaaaag tgggcagcga tcttgaaaat     720
aataaaagta cgtacgtgag tttattaggg aaagatggcg cagaagataa attgacttat     780
catagagacg cagcagtgga tgaactaacg caaattgatg aacaattcaa tacaaaacac     840
ttattagaaa tcgttgattt a                                              861

<210> SEQ ID NO 64
<211> LENGTH: 287
<212> TYPE: PRT
<213> ORGANISM: Homo sapiens

<400> SEQUENCE: 64

Met Thr Asn Leu Pro Met Asn Lys Leu Ile Asp Glu Val Asn Asn Glu
  1               5                  10                  15

Leu Ser Val Ala Ile Asn Lys Ser Val Met Asp Thr Gln Leu Glu Glu
             20                  25                  30

Ser Met Leu Tyr Ser Leu Asn Ala Gly Gly Lys Arg Ile Arg Pro Val
         35                  40                  45

Leu Leu Leu Leu Thr Leu Asp Ser Leu Asn Thr Glu Tyr Glu Leu Gly
     50                  55                  60

Met Lys Ser Ala Ile Ala Leu Glu Met Ile His Thr Tyr Ser Leu Ile
 65                  70                  75                  80

His Asp Asp Leu Pro Ala Met Asp Asn Asp Asp Tyr Arg Arg Gly Lys
                 85                  90                  95

Leu Thr Asn His Lys Val Tyr Gly Glu Trp Thr Ala Ile Leu Ala Gly
            100                 105                 110

Asp Ala Leu Leu Thr Lys Ala Phe Glu Leu Ile Ser Ser Asp Asp Arg
        115                 120                 125

Leu Thr Asp Glu Val Lys Ile Lys Val Leu Gln Arg Leu Ser Ile Ala
    130                 135                 140

Ser Gly His Val Gly Met Val Gly Gly Gln Met Leu Asp Met Gln Ser
145                 150                 155                 160

Glu Gly Gln Pro Ile Asp Leu Glu Thr Leu Glu Met Ile His Lys Thr
                165                 170                 175

Lys Thr Gly Ala Leu Leu Thr Phe Ala Val Met Ser Ala Ala Asp Ile
            180                 185                 190

Ala Asn Val Asp Asp Thr Thr Lys Glu His Leu Glu Ser Tyr Ser Tyr
        195                 200                 205
```

```
His Leu Gly Met Met Phe Gln Ile Lys Asp Asp Leu Asp Cys Tyr
    210                 215                 220

Gly Asp Glu Ala Lys Leu Gly Lys Lys Val Gly Ser Asp Leu Glu Asn
225                 230                 235                 240

Asn Lys Ser Thr Tyr Val Ser Leu Leu Gly Lys Asp Gly Ala Glu Asp
                245                 250                 255

Lys Leu Thr Tyr His Arg Asp Ala Ala Val Asp Glu Leu Thr Gln Ile
                260                 265                 270

Asp Glu Gln Phe Asn Thr Lys His Leu Leu Glu Ile Val Asp Leu
            275                 280                 285
```

<210> SEQ ID NO 65
<211> LENGTH: 819
<212> TYPE: DNA
<213> ORGANISM: Homo sapiens
<220> FEATURE:
<221> NAME/KEY: misc_feature
<222> LOCATION: (811)..(811)
<223> OTHER INFORMATION: n equals a, t, g, or c

<400> SEQUENCE: 65

```
tttgttattc tgagtagcca atttggcaaa gatgaacaaa cgtctgaaca aacgtatcaa      60
gttgcagtcg cattagagtt aattcatatg gcaacacttg ttcatgatga cgttattgat     120
aaaagcgaca agcgtcgagg caagttaacc atatcaaaga aatgggatca gacaactgct     180
attttaactg ggaattttt attggcatta ggacttgaac acttaatggc cgttaaagat     240
aatcgtgtac atcaattgat atctgaatct atcgttgatg tttgtagagg ggaacttttc     300
caatttcaag accaatttaa cagtcaacag acaattatta attatttacg acgtatcaat     360
cgcaaaacag cactgttaat tcaaatatca actgaagttg gtgcaattac ttctcaatct     420
gataaagaga ctgtacgaaa attgaaaatg attggtcatt atataggtat gagcttccaa     480
atcattgatg atgtattaga cttcacaagt accgaaaaga aattaggtaa gccggtcgga     540
agtgatttgc ttaatggtca tattacgtta ccgatttat tagaaatgcg taaaaatcca     600
gacttcaaat tgaaaatcga acagttacgt cgtgatagtg aacgcaaaga atttgaagaa     660
tgtatccaaa tcattagaaa atctgacagc atcgatgagg ctaaggcagt aagttcgaag     720
tatttaagta aagcyttgaa tttgatttcy gagttaccag atggacatcc gagatcacta     780
cytttaagtt tgacgaaaaa aatgggttca anaaacacg                           819
```

<210> SEQ ID NO 66
<211> LENGTH: 273
<212> TYPE: PRT
<213> ORGANISM: Homo sapiens
<220> FEATURE:
<221> NAME/KEY: MISC_FEATURE
<222> LOCATION: (261)..(261)
<223> OTHER INFORMATION: Xaa equals any amino acid
<221> NAME/KEY: MISC_FEATURE
<222> LOCATION: (271)..(271)
<223> OTHER INFORMATION: Xaa equals any amino acid

<400> SEQUENCE: 66

```
Phe Val Ile Leu Ser Ser Gln Phe Gly Lys Asp Glu Gln Thr Ser Glu
  1               5                  10                  15

Gln Thr Tyr Gln Val Ala Val Ala Leu Glu Leu Ile His Met Ala Thr
                 20                  25                  30

Leu Val His Asp Asp Val Ile Asp Lys Ser Asp Lys Arg Arg Gly Lys
             35                  40                  45
```

-continued

```
Leu Thr Ile Ser Lys Lys Trp Asp Gln Thr Thr Ala Ile Leu Thr Gly
 50                  55                  60

Asn Phe Leu Leu Ala Leu Gly Leu Glu His Leu Met Ala Val Lys Asp
 65                  70                  75                  80

Asn Arg Val His Gln Leu Ile Ser Glu Ser Ile Val Asp Val Cys Arg
                 85                  90                  95

Gly Glu Leu Phe Gln Phe Gln Asp Gln Phe Asn Ser Gln Gln Thr Ile
            100                 105                 110

Ile Asn Tyr Leu Arg Arg Ile Asn Arg Lys Thr Ala Leu Leu Ile Gln
        115                 120                 125

Ile Ser Thr Glu Val Gly Ala Ile Thr Ser Gln Ser Asp Lys Glu Thr
130                 135                 140

Val Arg Lys Leu Lys Met Ile Gly His Tyr Ile Gly Met Ser Phe Gln
145                 150                 155                 160

Ile Ile Asp Asp Val Leu Asp Phe Thr Ser Thr Glu Lys Lys Leu Gly
                165                 170                 175

Lys Pro Val Gly Ser Asp Leu Leu Asn Gly His Ile Thr Leu Pro Ile
            180                 185                 190

Leu Leu Glu Met Arg Lys Asn Pro Asp Phe Lys Leu Lys Ile Glu Gln
        195                 200                 205

Leu Arg Arg Asp Ser Glu Arg Lys Glu Phe Glu Glu Cys Ile Gln Ile
210                 215                 220

Ile Arg Lys Ser Asp Ser Ile Asp Glu Ala Lys Ala Val Ser Ser Lys
225                 230                 235                 240

Tyr Leu Ser Lys Ala Leu Asn Leu Ile Ser Glu Leu Pro Asp Gly His
                245                 250                 255

Pro Arg Ser Leu Xaa Leu Ser Leu Thr Lys Lys Met Gly Ser Xaa Asn
            260                 265                 270

Thr
```

<210> SEQ ID NO 67
<211> LENGTH: 504
<212> TYPE: DNA
<213> ORGANISM: Homo sapiens

<400> SEQUENCE: 67

```
gtaaattata ttatgaattt gcctgtcaat tcttaaaga cattcttacc ggaactaatt      60
gaaaaaaatg tcaaagttga acaattgga tttactgata agttgccaaa atcaacgata    120
gaagcaatta ataatgcyma agaaaagaca gctaataata ccggcttaaa attaatattt    180
gcaattaatt atggtggcag agcagaactt gttcatagta ttaaaaatat gtttgacgag    240
cttcatcaac aaggtttaaa tagtgatatc atagatgaaa catatataaa caatcattta    300
atgacaaaag actatcctga tccagagttg ttaattcgta cttcaggaga acaaagaata    360
agtaatttct tgatttggca gtttcgtat agtgaattta tctttaatca aaaattatgg    420
cctgactttg acgaagatga attaattaaa tgtataaaaa tttatcagtc acgtcaaaga    480
cgctttggcg gattgagtga ggag                                          504
```

<210> SEQ ID NO 68
<211> LENGTH: 168
<212> TYPE: PRT
<213> ORGANISM: Homo sapiens
<220> FEATURE:
<221> NAME/KEY: MISC_FEATURE
<222> LOCATION: (47)..(47)
<223> OTHER INFORMATION: Xaa equals any amino acid

<400> SEQUENCE: 68

| Val | Asn | Tyr | Ile | Met | Asn | Leu | Pro | Val | Asn | Phe | Leu | Lys | Thr | Phe | Leu |
|---|---|---|---|---|---|---|---|---|---|---|---|---|---|---|---|
| 1 | | | | 5 | | | | | 10 | | | | | 15 | |

Pro Glu Leu Ile Glu Lys Asn Val Lys Val Glu Thr Ile Gly Phe Thr
            20                    25                  30

Asp Lys Leu Pro Lys Ser Thr Ile Glu Ala Ile Asn Asn Ala Xaa Glu
        35                    40                    45

Lys Thr Ala Asn Asn Thr Gly Leu Lys Leu Ile Phe Ala Ile Asn Tyr
50                  55                    60

Gly Gly Arg Ala Glu Leu Val His Ser Ile Lys Asn Met Phe Asp Glu
65                70                    75                  80

Leu His Gln Gln Gly Leu Asn Ser Asp Ile Ile Asp Glu Thr Tyr Ile
            85                    90                95

Asn Asn His Leu Met Thr Lys Asp Tyr Pro Asp Pro Glu Leu Leu Ile
            100                105            110

Arg Thr Ser Gly Glu Gln Arg Ile Ser Asn Phe Leu Ile Trp Gln Val
            115                120            125

Ser Tyr Ser Glu Phe Ile Phe Asn Gln Lys Leu Trp Pro Asp Phe Asp
      130                135                140

Glu Asp Glu Leu Ile Lys Cys Ile Lys Ile Tyr Gln Ser Arg Gln Arg
145                  150                155            160

Arg Phe Gly Gly Leu Ser Glu Glu
            165

<210> SEQ ID NO 69
<211> LENGTH: 1823
<212> TYPE: DNA
<213> ORGANISM: Homo sapiens

<400> SEQUENCE: 69

| atgaagtggc | taaacaact | acaatccctt | catactaaat | ttgtaattgt | ttatgtatta | 60 |
| ctgattatca | ttggtatgca | aattatcggg | ttatatttta | caaataacct | tgaaaaagag | 120 |
| ctgcttgata | attttaagaa | gaatattacg | cagtacgcga | acaattaga | aattagtatt | 180 |
| gaaaaagtat | atgacgaaaa | gggctccgta | aatgcacaaa | aagatattca | aaatttatta | 240 |
| agtgagtatg | ccaaccgtca | agaaattgga | gaaattcgtt | ttatagataa | agaccaaatt | 300 |
| attattgcga | cgacgaagca | gtctaaccgt | agtctaatca | atcaaaaagc | gaatgatagt | 360 |
| tctgtccaaa | aagcactatc | actaggacaa | tcaaacgatc | atttaatttt | aaaagattat | 420 |
| ggcggtggta | aggaccgtgt | ctgggtatat | aatatcccag | ttaaagtcga | taaaaggta | 480 |
| attggtaata | tttatatcga | atcaaaaatt | aatgacgttt | ataaccaatt | aaataatata | 540 |
| aatcaaatat | tcattgttgg | tacagctatt | tcattattaa | tcacagtcat | cctaggattc | 600 |
| tttatagcgc | gaacgattac | caaaccaatc | accgatatgc | gtaaccagac | ggtcgaaatg | 660 |
| tccagaggta | actatacgca | acgtgtgaag | atttatggta | atgatgaaat | tggcgaatta | 720 |
| gctttagcat | ttaataactt | gtctaaacgt | gtacaagaag | cgcaggctaa | tactgaaagt | 780 |
| gagaaacgta | gactggactc | agttatcacc | catatgagtg | atggtattat | tgcaacagac | 840 |
| cgccgtggac | gtattcgtat | cgtcaatgat | atggcactca | agatgcttgg | tatggcgaaa | 900 |
| gaagacatca | tcggatatta | catgttaagt | gtattaagtc | ttgaagatga | atttaaactg | 960 |
| gaagaaattc | aagagaataa | tgatagtttc | ttattagatt | taaatgaaga | agaaggtcta | 1020 |
| atcgcacgtg | ttaactttag | tacgattgtg | caggaaacag | gatttgtaac | tggttatatc | 1080 |

-continued

```
gctgtgttac atgacgtaac tgaacaacaa caagttgaac gtgagcgtcg tgaatttgtt   1140
gccaatgtat cacatgagtt acgtacacct ttaacttcta tgaatagtta cattgaagca   1200
cttgaagaag gtgcatggaa agatgaggaa cttgcgccac aattttatc tgttacccgt    1260 gaagaaacag aacgaatgat tcgactggtc aatgacttgc tacagttatc taaaatggat   1320
aatgagtctg atcaaatcaa caagaaaatt acgactttaa catgttcatt aataaaatta   1380
ttaatcgaca tgaaatgtct gcgaaagata caacatttat tcgagatatt ccgaaaaaga   1440
cgattttcac agaatttgat cctgataaaa tgacgcaagt atttgataat gtcattacaa   1500
atgcgatgaa atattctaga ggcgataaac gtgtcgagtt ccacgtgaaa caaaatccac   1560
tttataatcg aatgacgatt cgtattaaag ataatggcat tggtattcct atcaataaag   1620
tcgataagat attcgaccga ttctatcgtg tagataaggc acgtacgcgt aaaatgggtg   1680
gtactggatt aggactagcc atttcgaaag agattgtgga agcgcacaat ggtcgtattt   1740
gggcaaacag tgtagaaggt caaggtacat ctatctttat cacacttcca tgtgaagtca   1800
ttgaagacgg tgattgggat gaa                                           1823
```

<210> SEQ ID NO 70
<211> LENGTH: 608
<212> TYPE: PRT
<213> ORGANISM: Homo sapiens

<400> SEQUENCE: 70

```
Met Lys Trp Leu Lys Gln Leu Gln Ser Leu His Thr Lys Phe Val Ile
  1               5                  10                  15

Val Tyr Val Leu Leu Ile Ile Ile Gly Met Gln Ile Ile Gly Leu Tyr
                 20                  25                  30

Phe Thr Asn Asn Leu Glu Lys Glu Leu Leu Asp Asn Phe Lys Lys Asn
             35                  40                  45

Ile Thr Gln Tyr Ala Lys Gln Leu Glu Ile Ser Ile Glu Lys Val Tyr
         50                  55                  60

Asp Glu Lys Gly Ser Val Asn Ala Gln Lys Asp Ile Gln Asn Leu Leu
 65                  70                  75                  80

Ser Glu Tyr Ala Asn Arg Gln Glu Ile Gly Glu Ile Arg Phe Ile Asp
                 85                  90                  95

Lys Asp Gln Ile Ile Ile Ala Thr Thr Lys Gln Ser Asn Arg Ser Leu
            100                 105                 110

Ile Asn Gln Lys Ala Asn Asp Ser Ser Val Gln Lys Ala Leu Ser Leu
        115                 120                 125

Gly Gln Ser Asn Asp His Leu Ile Leu Lys Asp Tyr Gly Gly Gly Lys
    130                 135                 140

Asp Arg Val Trp Val Tyr Asn Ile Pro Val Lys Val Asp Lys Lys Val
145                 150                 155                 160

Ile Gly Asn Ile Tyr Ile Glu Ser Lys Ile Asn Asp Val Tyr Asn Gln
                165                 170                 175

Leu Asn Asn Ile Asn Gln Ile Phe Ile Val Gly Thr Ala Ile Ser Leu
            180                 185                 190

Leu Ile Thr Val Ile Leu Gly Phe Phe Ile Ala Arg Thr Ile Thr Lys
        195                 200                 205

Pro Ile Thr Asp Met Arg Asn Gln Thr Val Glu Met Ser Arg Gly Asn
    210                 215                 220

Tyr Thr Gln Arg Val Lys Ile Tyr Gly Asn Asp Glu Ile Gly Glu Leu
225                 230                 235                 240
```

-continued

```
Ala Leu Ala Phe Asn Asn Leu Ser Lys Arg Val Gln Glu Ala Gln Ala
                245                 250                 255

Asn Thr Glu Ser Glu Lys Arg Arg Leu Asp Ser Val Ile Thr His Met
            260                 265                 270

Ser Asp Gly Ile Ile Ala Thr Asp Arg Gly Arg Ile Arg Ile Val
        275                 280                 285

Asn Asp Met Ala Leu Lys Met Leu Gly Met Ala Lys Glu Asp Ile Ile
    290                 295                 300

Gly Tyr Tyr Met Leu Ser Val Leu Ser Leu Glu Asp Glu Phe Lys Leu
305                 310                 315                 320

Glu Glu Ile Gln Glu Asn Asn Asp Ser Phe Leu Leu Asp Leu Asn Glu
                325                 330                 335

Glu Glu Gly Leu Ile Ala Arg Val Asn Phe Ser Thr Ile Val Gln Glu
            340                 345                 350

Thr Gly Phe Val Thr Gly Tyr Ile Ala Val Leu His Asp Val Thr Glu
        355                 360                 365

Gln Gln Gln Val Glu Arg Glu Arg Glu Phe Val Ala Asn Val Ser
    370                 375                 380

His Glu Leu Arg Thr Pro Leu Thr Ser Met Asn Ser Tyr Ile Glu Ala
385                 390                 395                 400

Leu Glu Glu Gly Ala Trp Lys Asp Glu Glu Leu Ala Pro Gln Phe Leu
                405                 410                 415

Ser Val Thr Arg Glu Glu Thr Glu Arg Met Ile Arg Leu Val Asn Asp
            420                 425                 430

Leu Leu Gln Leu Ser Lys Met Asp Asn Glu Ser Asp Gln Ile Asn Lys
        435                 440                 445

Glu Ile Ile Asp Phe Asn Met Phe Ile Asn Lys Ile Ile Asn Arg His
    450                 455                 460

Glu Met Ser Ala Lys Asp Thr Thr Phe Ile Arg Asp Ile Pro Lys Lys
465                 470                 475                 480

Thr Ile Phe Thr Glu Phe Asp Pro Asp Lys Met Thr Gln Val Phe Asp
                485                 490                 495

Asn Val Ile Thr Asn Ala Met Lys Tyr Ser Arg Gly Asp Lys Arg Val
            500                 505                 510

Glu Phe His Val Lys Gln Asn Pro Leu Tyr Asn Arg Met Thr Ile Arg
        515                 520                 525

Ile Lys Asp Asn Gly Ile Gly Ile Pro Ile Asn Lys Val Asp Lys Ile
    530                 535                 540

Phe Asp Arg Phe Tyr Arg Val Asp Lys Ala Arg Thr Arg Lys Met Gly
545                 550                 555                 560

Gly Thr Gly Leu Gly Leu Ala Ile Ser Lys Glu Ile Val Glu Ala His
                565                 570                 575

Asn Gly Arg Ile Trp Ala Asn Ser Val Glu Gly Gln Gly Thr Ser Ile
            580                 585                 590

Phe Ile Thr Leu Pro Cys Glu Val Ile Glu Asp Gly Asp Trp Asp Glu
        595                 600                 605
```

<210> SEQ ID NO 71
<211> LENGTH: 2232
<212> TYPE: DNA
<213> ORGANISM: Homo sapiens

<400> SEQUENCE: 71
atggcgaagc aaaaaattaa aattaaaaaa aataaaatag gggcagtcct acttgttggt    60

-continued

```
ttattcggac tgctcttttt tatattggtt ttaagaattt catatatcat gattactgga      120
cattctaatg gtcaagattt agtcatgaag gcaaatgaaa agtatttagt taagaatgca      180
caacaaccag aacgaggaaa gatatatgat cgtaatggta aagtgctagc agaagatgta      240
gaaagatata aacttgttgc agtaatagat aaaaaggcga gtgccaattc taaaaaacct      300
aggcatgtag ttgataaaaa agagactgca agaaaattat ctacagtcat taatatgaag      360
ccagaggaaa ttgaaaagag acttagtcaa agaaagcttt tccaaattga atttggacgc      420
aaaggaacaa atttaacgta tcaggacaaa ttgaaaatag agaaaatgaa tttgcctggt      480
atttctttat tgcctgaaac agaacgcttt tatccaaatg gcaattttgc atcacactta      540
attggtagag ctcagaaaaa tccggatact ggtgaactta aggtgcact tggagttgaa       600 aagattttg atagttattt aagtggatct aaaggatcat tgagatatat tcatgatatt      660
tggggatata tcgcaccaaa tactaaaaaa gagaagcagc ctaaacgtgg tgatgatgtc      720
catttaacaa tcgattcaaa tattcaagta tttgttgaag aagctttaga tggcatggtt      780
gaaagatacc agccgaaaga tttatttgcg gttgtcatgg atgccaaaac tggagaaatt      840
ttagcataca gtcagcgacc aacatttaat cctgaaactg gtaaagactt tggtaaaaag      900
tgggcaaatg acctttatca aaacacatac gagcctggat caacatttaa atcatatggg      960
ttagcagctg ctattcaaga aggtgctttt gatcctgata gaaatataa atctggacat     1020 agagatatta tgggttcacg tatttcagac tggaatagag tcggttgggg tgaaatccca     1080
atgtcactcg gatttactta ttcatctaat acattgatga tgcatttaca agatttagtt     1140
ggtgcagaca aaatgaaatc ttggtatgaa cgatttggat ttggaaaatc aactaaaggt     1200
atgtttgatg gagaagcacc tggtcaaatt ggatggagta atgagttgca acaaaaaacg     1260
tcatcatttg gtcaatcgac aacagtaaca cctgttcaaa tgttacaagc gcaatcagcg     1320
ttctttaatg atggtaatat gttaaaacca tggtttgtga atagcgttga aaatcctgtt     1380
agtaaaagac aattttataa agggcaaaaa caaatcgcag gcaaaccaat aacaaaagat     1440
actgctgaaa aagttgaaaa gcaattggat ttagttgtga atagtaagaa gagtcacgct     1500
gcaaactatc gtattgatgg ttatgaggtc gaaggtaaga ctggtacagc acaagtcgct     1560
gcacctaatg gtggtggata cgttaaaggt ccaaacccat attttgtaag ttttatgggt     1620
gacgcgccga agaaaaatcc taaagttatt gtatacgctg gtatgagctt ggcacaaaaa     1680
aatgaccaag aagcttatga attaggtgtt agtaaagcgt ttaaaccaat aatggaaaat     1740
actttgaaat atttaaatgt aggtaaatca aaagatgaca catctaatgc agagtatagt     1800
aaagtgccag atgttgaagg tcaagacaaa caaaaagcta ttgataatgt gagtgcaaaa     1860
tcattagaac cagttactat tggttctggc acacaaataa aagcacaatc tataaaagca     1920
gggaataaag tcttacctca tagtaaagta ctgttattaa cagatggaga cttaactatg     1980
cctgacatgt caggatggac gaaagaagat gtcattgctt tgaaaacct aacaaatatt      2040 aaagtaaatt taaaggtag cggttttgtg tcccaccaat caattagtaa gggacaaaaa     2100
cttactgaaa aagataaaat agacgtagaa ttttcatcag agaatgtaga cagcaattcg     2160
acgaataatt ctgattcaaa ttcagatgat aagaagaaat ctgacagtaa aactgacaag     2220
gataagtcgg ac                                                         2232
```

<210> SEQ ID NO 72
<211> LENGTH: 744
<212> TYPE: PRT
<213> ORGANISM: Homo sapiens

<400> SEQUENCE: 72

| | | | | | | | | | | | | | | |
|---|---|---|---|---|---|---|---|---|---|---|---|---|---|---|
| Met | Ala | Lys | Gln | Lys | Ile | Lys | Ile | Lys | Lys | Asn | Lys | Ile | Gly | Ala | Val |
| 1 | | | | 5 | | | | | 10 | | | | | 15 | |
| Leu | Leu | Val | Gly | Leu | Phe | Gly | Leu | Leu | Phe | Ile | Leu | Val | Leu | Arg |
| | | | 20 | | | | | 25 | | | | | 30 | |
| Ile | Ser | Tyr | Ile | Met | Ile | Thr | Gly | His | Ser | Asn | Gly | Gln | Asp | Leu | Val |
| | | 35 | | | | | 40 | | | | | 45 | | | |
| Met | Lys | Ala | Asn | Glu | Lys | Tyr | Leu | Val | Lys | Asn | Ala | Gln | Gln | Pro | Glu |
| 50 | | | | | 55 | | | | | 60 | | | | | |
| Arg | Gly | Lys | Ile | Tyr | Asp | Arg | Asn | Gly | Lys | Val | Leu | Ala | Glu | Asp | Val |
| 65 | | | | | 70 | | | | | 75 | | | | | 80 |
| Glu | Arg | Tyr | Lys | Leu | Val | Ala | Val | Ile | Asp | Lys | Lys | Ala | Ser | Ala | Asn |
| | | | | 85 | | | | | 90 | | | | | 95 | |
| Ser | Lys | Lys | Pro | Arg | His | Val | Val | Asp | Lys | Lys | Glu | Thr | Ala | Lys | Lys |
| | | | 100 | | | | | 105 | | | | | 110 | | |
| Leu | Ser | Thr | Val | Ile | Asn | Met | Lys | Pro | Glu | Glu | Ile | Glu | Lys | Arg | Leu |
| | | 115 | | | | | 120 | | | | | 125 | | | |
| Ser | Gln | Lys | Lys | Ala | Phe | Gln | Ile | Glu | Phe | Gly | Arg | Lys | Gly | Thr | Asn |
| | 130 | | | | | 135 | | | | | 140 | | | | |
| Leu | Thr | Tyr | Gln | Asp | Lys | Leu | Lys | Ile | Glu | Lys | Met | Asn | Leu | Pro | Gly |
| 145 | | | | | 150 | | | | | 155 | | | | | 160 |
| Ile | Ser | Leu | Leu | Pro | Glu | Thr | Glu | Arg | Phe | Tyr | Pro | Asn | Gly | Asn | Phe |
| | | | | 165 | | | | | 170 | | | | | 175 | |
| Ala | Ser | His | Leu | Ile | Gly | Arg | Ala | Gln | Lys | Asn | Pro | Asp | Thr | Gly | Glu |
| | | | 180 | | | | | 185 | | | | | 190 | | |
| Leu | Lys | Gly | Ala | Leu | Gly | Val | Glu | Lys | Ile | Phe | Asp | Ser | Tyr | Leu | Ser |
| | | 195 | | | | | 200 | | | | | 205 | | | |
| Gly | Ser | Lys | Gly | Ser | Leu | Arg | Tyr | Ile | His | Asp | Ile | Trp | Gly | Tyr | Ile |
| | 210 | | | | | 215 | | | | | 220 | | | | |
| Ala | Pro | Asn | Thr | Lys | Lys | Glu | Lys | Gln | Pro | Lys | Arg | Gly | Asp | Asp | Val |
| 225 | | | | | 230 | | | | | 235 | | | | | 240 |
| His | Leu | Thr | Ile | Asp | Ser | Asn | Ile | Gln | Val | Phe | Val | Glu | Glu | Ala | Leu |
| | | | | 245 | | | | | 250 | | | | | 255 | |
| Asp | Gly | Met | Val | Glu | Arg | Tyr | Gln | Pro | Lys | Asp | Leu | Phe | Ala | Val | Val |
| | | | 260 | | | | | 265 | | | | | 270 | | |
| Met | Asp | Ala | Lys | Thr | Gly | Glu | Ile | Leu | Ala | Tyr | Ser | Gln | Arg | Pro | Thr |
| | | 275 | | | | | 280 | | | | | 285 | | | |
| Phe | Asn | Pro | Glu | Thr | Gly | Lys | Asp | Phe | Gly | Lys | Lys | Trp | Ala | Asn | Asp |
| | 290 | | | | | 295 | | | | | 300 | | | | |
| Leu | Tyr | Gln | Asn | Thr | Tyr | Glu | Pro | Gly | Ser | Thr | Phe | Lys | Ser | Tyr | Gly |
| 305 | | | | | 310 | | | | | 315 | | | | | 320 |
| Leu | Ala | Ala | Ala | Ile | Gln | Glu | Gly | Ala | Phe | Asp | Pro | Asp | Lys | Lys | Tyr |
| | | | | 325 | | | | | 330 | | | | | 335 | |
| Lys | Ser | Gly | His | Arg | Asp | Ile | Met | Gly | Ser | Arg | Ile | Ser | Asp | Trp | Asn |
| | | | 340 | | | | | 345 | | | | | 350 | | |
| Arg | Val | Gly | Trp | Gly | Glu | Ile | Pro | Met | Ser | Leu | Gly | Phe | Thr | Tyr | Ser |
| | | 355 | | | | | 360 | | | | | 365 | | | |
| Ser | Asn | Thr | Leu | Met | Met | His | Leu | Gln | Asp | Leu | Val | Gly | Ala | Asp | Lys |
| | 370 | | | | | 375 | | | | | 380 | | | | |
| Met | Lys | Ser | Trp | Tyr | Glu | Arg | Phe | Gly | Phe | Gly | Lys | Ser | Thr | Lys | Gly |
| 385 | | | | | 390 | | | | | 395 | | | | | 400 |
| Met | Phe | Asp | Gly | Glu | Ala | Pro | Gly | Gln | Ile | Gly | Trp | Ser | Asn | Glu | Leu |

-continued

```
            405                 410                 415
Gln Gln Lys Thr Ser Ser Phe Gly Gln Ser Thr Thr Val Thr Pro Val
            420                 425                 430
Gln Met Leu Gln Ala Gln Ser Ala Phe Phe Asn Asp Gly Asn Met Leu
            435                 440                 445
Lys Pro Trp Phe Val Asn Ser Val Glu Asn Pro Val Ser Lys Arg Gln
            450                 455                 460
Phe Tyr Lys Gly Gln Lys Gln Ile Ala Gly Lys Pro Ile Thr Lys Asp
465                 470                 475                 480
Thr Ala Glu Lys Val Glu Lys Gln Leu Asp Leu Val Val Asn Ser Lys
                    485                 490                 495
Lys Ser His Ala Ala Asn Tyr Arg Ile Asp Gly Tyr Glu Val Glu Gly
                500                 505                 510
Lys Thr Gly Thr Ala Gln Val Ala Ala Pro Asn Gly Gly Gly Tyr Val
                515                 520                 525
Lys Gly Pro Asn Pro Tyr Phe Val Ser Phe Met Gly Asp Ala Pro Lys
            530                 535                 540
Lys Asn Pro Lys Val Ile Val Tyr Ala Gly Met Ser Leu Ala Gln Lys
545                 550                 555                 560
Asn Asp Gln Glu Ala Tyr Glu Leu Gly Val Ser Lys Ala Phe Lys Pro
                    565                 570                 575
Ile Met Glu Asn Thr Leu Lys Tyr Leu Asn Val Gly Lys Ser Lys Asp
                580                 585                 590
Asp Thr Ser Asn Ala Glu Tyr Ser Lys Val Pro Asp Val Glu Gly Gln
            595                 600                 605
Asp Lys Gln Lys Ala Ile Asp Asn Val Ser Ala Lys Ser Leu Glu Pro
            610                 615                 620
Val Thr Ile Gly Ser Gly Thr Gln Ile Lys Ala Gln Ser Ile Lys Ala
625                 630                 635                 640
Gly Asn Lys Val Leu Pro His Ser Lys Val Leu Leu Leu Thr Asp Gly
                    645                 650                 655
Asp Leu Thr Met Pro Asp Met Ser Gly Trp Thr Lys Glu Asp Val Ile
                660                 665                 670
Ala Phe Glu Asn Leu Thr Asn Ile Lys Val Asn Leu Lys Gly Ser Gly
            675                 680                 685
Phe Val Ser His Gln Ser Ile Ser Lys Gly Gln Lys Leu Thr Glu Lys
            690                 695                 700
Asp Lys Ile Asp Val Glu Phe Ser Ser Glu Asn Val Asp Ser Asn Ser
705                 710                 715                 720
Thr Asn Asn Ser Asp Ser Asn Ser Asp Asp Lys Lys Ser Asp Ser
                    725                 730                 735
Lys Thr Asp Lys Asp Lys Ser Asp
            740
```

<210> SEQ ID NO 73
<211> LENGTH: 1677
<212> TYPE: DNA
<213> ORGANISM: Homo sapiens

<400> SEQUENCE: 73

```
attcgcaaat tgctttattg cgattaaatt ttttggtgg tactatatag aagttgatga      60
aatattaatg aacttatatg caaaagtata ttgagaaata aacaggtaaa aaggagaatt    120
attttgcaaa atttaaaga actagggatt tcggataata cggttcagtc acttgaatca    180
```

-continued

```
atgggatttta aagagccgac acctatccaa aaagacagta tcccttatgc gttacaagga      240
attgatatcc ttgggcaagc tcaaaccggt acaggtaaaa caggagcatt cggtattcct      300
ttaattgaga agtagtaggg aaacaaggg gttcaatcgt tgattttagc acctacaaga       360
gaattggcaa tgcaggtagc tgaacaatta agagaattta gccgtggaca aggtgtccaa      420
gttgttactg tattcggtgg tatgcctatc gaacgccaaa ttaaagcctt gaaaaaggc       480
ccacaaatcg tagtcggaac acctgggcgt gttatcgacc atttaaatcg tcgcacatta      540
aaaacggacg gaattcatac tttgatttta gatgaagctg atgaaatgat gaatatggga      600
ttcatcgatg atatgagatt tattatggat aaaattccag cagtcaacg tcaaacaatg       660
ttgttctcag ctacaatgcc taaagcaatc caagctttag tacaacaatt tatgaaatca      720
ccaaaaatca ttaagacaat gaataatgaa atgtctgatc cacaaatcga agaattctat     780
acaattgtta agaattaga gaaatttgat acatttacaa atttcctaga tgttcatcaa       840
cctgaattag caatcgtatt cggacgtaca aaacgtcgtg ttgatgaatt aacaagtgct      900
ttgatttcta aaggatataa agctgaaggt ttacatggtg atattacaca agcgaaacgt     960
ttagaagtat taaagaaatt taaaaatgac caaattaata ttttagtcgc tactgatgta    1020
gcagcaagag gactagatat ttctggtgtg agtcatgttt ataactttga tatacctcaa    1080
gatactgaaa gctatacaca ccgtattggt cgtacgggtc gtgctggtaa agaaggtatc    1140
gctgtaacgt ttgttaatcc aatcgaaatg gattatatca gacaaattga agatgcaaac    1200
ggtagaaaaa tgagtgcact tcgtccacca catcgtaaag aagtacttca agcacgtgaa    1260
gatgacatca agaaaaagt tgaaaactgg atgtctaaag agtcagaatc acgcttgaaa    1320
cgcatttcta cagagttgtt aaatgaatat aacgatgttg attagttgc tgcactttta    1380
caagagttag tagaagcaaa cgatgaagtt gaagttcaat taacttttga aaaaccatta    1440
tctcgcaaag gccgtaacgg taaccaagt ggttctcgta acagaaatag taagcgtggt     1500
aatcctaaat ttgacagtaa gagtaaacgt tcaaaggat actcaagtaa aagaaaagt      1560
acaaaaaaat tcgaccgtaa agagaagagc agcggtggaa gcagaccat gaaaggtcgc    1620
acatttgctg accatcaaaa ataatttata gattaagagc ttaaagatgt aatgtct       1677
```

<210> SEQ ID NO 74
<211> LENGTH: 526
<212> TYPE: PRT
<213> ORGANISM: Homo sapiens

<400> SEQUENCE: 74

```
Asn Ile Asn Glu Leu Ile Cys Lys Ser Ile Leu Arg Asn Lys Gln Val
 1               5                  10                  15

Lys Arg Arg Ile Ile Leu Gln Asn Phe Lys Glu Leu Gly Ile Ser Asp
            20                  25                  30

Asn Thr Val Gln Ser Leu Glu Ser Met Gly Phe Lys Glu Pro Thr Pro
        35                  40                  45

Ile Gln Lys Asp Ser Ile Pro Tyr Ala Leu Gln Gly Ile Asp Ile Leu
    50                  55                  60

Gly Gln Ala Gln Thr Gly Thr Gly Lys Thr Gly Ala Phe Gly Ile Pro
65                  70                  75                  80

Leu Ile Glu Lys Val Val Gly Lys Gln Gly Val Gln Ser Leu Ile Leu
                85                  90                  95

Ala Pro Thr Arg Glu Leu Ala Met Gln Val Ala Glu Gln Leu Arg Glu
            100                 105                 110
```

-continued

```
Phe Ser Arg Gly Gln Gly Val Gln Val Val Thr Val Phe Gly Gly Met
            115                 120                 125

Pro Ile Glu Arg Gln Ile Lys Ala Leu Lys Lys Gly Pro Gln Ile Val
130                 135                 140

Val Gly Thr Pro Gly Arg Val Ile Asp His Leu Asn Arg Arg Thr Leu
145                 150                 155                 160

Lys Thr Asp Gly Ile His Thr Leu Ile Leu Asp Glu Ala Asp Glu Met
                165                 170                 175

Met Asn Met Gly Phe Ile Asp Asp Met Arg Phe Ile Met Asp Lys Ile
                180                 185                 190

Pro Ala Val Gln Arg Gln Thr Met Leu Phe Ser Ala Thr Met Pro Lys
            195                 200                 205

Ala Ile Gln Ala Leu Val Gln Gln Phe Met Lys Ser Pro Lys Ile Ile
210                 215                 220

Lys Thr Met Asn Asn Glu Met Ser Asp Pro Gln Ile Glu Glu Phe Tyr
225                 230                 235                 240

Thr Ile Val Lys Glu Leu Glu Lys Phe Asp Thr Phe Thr Asn Phe Leu
                245                 250                 255

Asp Val His Gln Pro Glu Leu Ala Ile Val Phe Gly Arg Thr Lys Arg
            260                 265                 270

Arg Val Asp Glu Leu Thr Ser Ala Leu Ile Ser Lys Gly Tyr Lys Ala
            275                 280                 285

Glu Gly Leu His Gly Asp Ile Thr Gln Ala Lys Arg Leu Glu Val Leu
290                 295                 300

Lys Lys Phe Lys Asn Asp Gln Ile Asn Ile Leu Val Ala Thr Asp Val
305                 310                 315                 320

Ala Ala Arg Gly Leu Asp Ile Ser Gly Val Ser His Val Tyr Asn Phe
                325                 330                 335

Asp Ile Pro Gln Asp Thr Glu Ser Tyr Thr His Arg Ile Gly Arg Thr
            340                 345                 350

Gly Arg Ala Gly Lys Glu Gly Ile Ala Val Thr Phe Val Asn Pro Ile
            355                 360                 365

Glu Met Asp Tyr Ile Arg Gln Ile Glu Asp Ala Asn Gly Arg Lys Met
370                 375                 380

Ser Ala Leu Arg Pro Pro His Arg Lys Glu Val Leu Gln Ala Arg Glu
385                 390                 395                 400

Asp Asp Ile Lys Glu Lys Val Glu Asn Trp Met Ser Lys Glu Ser Glu
                405                 410                 415

Ser Arg Leu Lys Arg Ile Ser Thr Glu Leu Leu Asn Glu Tyr Asn Asp
            420                 425                 430

Val Asp Leu Val Ala Ala Leu Leu Gln Glu Leu Val Glu Ala Asn Asp
            435                 440                 445

Glu Val Glu Val Gln Leu Thr Phe Glu Lys Pro Leu Ser Arg Lys Gly
            450                 455                 460

Arg Asn Gly Lys Pro Gly Ser Arg Asn Arg Asn Ser Lys Arg Gly
465                 470                 475                 480

Asn Pro Lys Phe Asp Ser Lys Ser Lys Arg Ser Lys Gly Tyr Ser Ser
                485                 490                 495

Lys Lys Lys Ser Thr Lys Lys Phe Asp Arg Lys Glu Lys Ser Ser Gly
            500                 505                 510

Gly Ser Arg Pro Met Lys Gly Arg Thr Phe Ala Asp His Gln
            515                 520                 525
```

STAPHYLOCOCCUS AUREUS POLYNUCLEOTIDES AND POLYPEPTIDES

CROSS-REFERENCE TO RELATED APPLICATIONS

The present application is a continuation-in-part of and claims priority under 35 U.S.C. § 120 to U.S. application Ser. No. 08/956,171, filed Oct. 20, 1997, now U.S. Pat. No. 6,593,114, and U.S. application Ser. No. 08/781,986, filed Jan. 3, 1997, now U.S. Pat. No. 6,737,248, each of which claims benefit under 35 U.S.C. § 119(e) to U.S. Provisional Application No. 60/009,861, filed Jan. 5, 1996; the present application is also a continuation-in-part of and claims priority under 35 U.S.C. § 120 to International Application No. PCT/US00/23773, filed Aug. 31, 2000 (published by the International Bureau in the English language on Mar. 8, 2001 as International Publication No. WO 01/16292), which claims benefit under 35 U.S.C. § 119(e) of U.S. Provisional Application No. 60/151,933, filed Sep. 1, 1999, each of which is hereby incorporated by reference in its entirety.

FIELD OF THE INVENTION

The present invention relates to novel *Staphylococcus aureus* genes (*S. aureus*) nucleic acids and polypeptides. Also provided are vectors, host cells and recombinant or synthetic methods for producing the same. Further provided are diagnostic methods for detecting *S. aureus* using probes, primers, and antibodies to the *S. aureus* nucleic acids and polypeptides of the present invention. The invention further relates to screening methods for identifying agonists and antagonists of *S. aureus* polypeptide activity and to vaccines using *S. aureus* nucleic acids and polypeptides and to therapeutics using agonists and/or antagonists of the invention.

BACKGROUND OF THE INVENTION

The genus *Staphylococcus* includes at least 20 distinct species. (For a review see Novick, R. P., The *Staphylococcus* as a Molecular Genetic System in MOLECULAR BIOLOGY OF THE STAPHYLOCOCCI, 1–37 (R. Novick, Ed., VCH Publishers, New York (1990)). Species differ from one another by 80% or more, by hybridization kinetics, whereas strains within a species are at least 90% identical by the same measure.

The species *S. aureus*, a gram-positive, facultatively aerobic, clump-forming cocci, is among the most important etiological agents of bacterial infection in humans, as discussed briefly below.

Human Health and *S. aureus*

*Staphylococcus aureus* is a ubiquitous pathogen. See, e.g., Mims et al., MEDICAL MICROBIOLOGY (Mosby-Year Book Europe Limited, London, UK 1993). It is an etiological agent of a variety of conditions, ranging in severity from mild to fatal. A few of the more common conditions caused by *S. aureus* infection are burns, cellulitis, eyelid infections, food poisoning, joint infections, neonatal conjunctivitis, osteomyelitis, skin infections, surgical wound infection, scalded skin syndrome and toxic shock syndrome, some of which are described further below.

Burns: Burn wounds generally are sterile initially. However, they generally compromise physical and immune barriers to infection, cause loss of fluid and electrolytes and result in local or general physiological dysfunction. After cooling, contact with viable bacteria results in mixed colonization at the injury site. Infection may be restricted to the non-viable debris on the burn surface ("eschar"), it may progress into full skin infection and invade viable tissue below the eschar and it may reach below the skin, enter the lymphatic and blood circulation and develop into septicemia. *S. aureus* is among the most important pathogens typically found in burn wound infections. It can destroy granulation tissue and produce severe septicemia.

Cellulitis: Cellulitis, an acute infection of the skin that expands from a typically superficial origin to spread below the cutaneous layer, most commonly is caused by *S. aureus* in conjunction with *S. pyrogenes*. Cellulitis can lead to systemic infection. In fact, cellulitis can be one aspect of synergistic bacterial gangrene. This condition typically is caused by a mixture of *S. aureus* and microaerophilic *Streptococci*. It causes necrosis and treatment is limited to excision of the necrotic tissue. The condition often is fatal.

Eyelid infections: *S. aureus* is the cause of styes and of "sticky eye" in neonates, among other eye infections. Typically such infections are limited to the surface of the eye, and may occasionally penetrate the surface with more severe consequences.

Food poisoning: Some strains of *S. aureus* produce one or more of five serologically distinct, heat and acid stable enterotoxins that are not destroyed by digestive process of the stomach and small intestine (enterotoxins A–E). Ingestion of the toxin, in sufficient quantities, typically results in severe vomiting, but not diarrhea. The effect does not require viable bacteria. Although the toxins are known, their mechanism of action is not understood.

Joint infections: *S. aureus* infects bone joints causing diseases such osteomyelitis. See, e.g., R. Cunningham et al., (1996) J. Med. Microbiol. 44:157–164.

Osteomyelitis: *S. aureus* is the most common causative agent of haematogenous osteomyelitis. The disease tends to occur in children and adolescents more than adults and it is associated with non-penetrating injuries to bones. Infection typically occurs in the long end of growing bone, hence its occurrence in physically immature populations. Most often, infection is localized in the vicinity of sprouting capillary loops adjacent to epiphysis growth plates in the end of long, growing bones.

Skin infections: *S. aureus* is the most common pathogen of such minor skin infections as abscesses and boils. Such infections often are resolved by normal host response mechanisms, but they also can develop into severe internal infections. Recurrent infections of the nasal passages plague nasal carriers of *S. aureus*.

Surgical Wound Infections: Surgical wounds often penetrate far into the body. Infection of such wound thus poses a grave risk to the patient. *S. aureus* is the most important causative agent of infections in surgical wounds. *S. aureus* is unusually adept at invading surgical wounds; sutured wounds can be infected by far fewer *S. aureus* cells then are necessary to cause infection in normal skin. Invasion of surgical wound can lead to severe *S. aureus* septicemia. Invasion of the blood stream by *S. aureus* can lead to seeding and infection of internal organs, particularly heart valves and bone, causing systemic diseases, such as endocarditis and osteomyelitis.

Scalded Skin Syndrome: *S. aureus* is responsible for "scalded skin syndrome" (also called toxic epidermal necrosis, Ritter's disease and Lyell's disease). This diseases occurs in older children, typically in outbreaks caused by flowering of *S. aureus* strains produce exfoliation(also called scalded skin syndrome toxin). Although the bacteria initially may infect only a minor lesion, the toxin destroys intercellular connections, spreads epidermal layers and allows the infection to penetrate the outer layer of the skin, producing the desquamation that typifies the diseases. Shedding of the outer layer of skin generally reveals normal skin below, but fluid lost in the process can produce severe injury in young children if it is not treated properly.

Toxic Shock Syndrome: Toxic shock syndrome is caused by strains of S. aureus that produce the so-called toxic shock syndrome toxin. The disease can be caused by S. aureus infection at any site, but it is too often erroneously viewed exclusively as a disease solely of women who use tampons. The disease involves toxemia and septicemia, and can be fatal.

Nosocomial Infections: In the 1984 National Nosocomial Infection Surveillance Study ("NNIS") S. aureus was the most prevalent agent of surgical wound infections in many hospital services, including medicine, surgery, obstetrics, pediatrics and newborns.

Other Infections: Other types of infections, risk factors, etc. involving S. aureus are discussed in: A. Trilla (1995) J. Chemotherapy 3:37–43; F. Espersen (1995) J. Chemotherapy 3:11–17; D. E. Craven (1995) J. Chemotherapy 3:19–28; J. D. Breen et al. (1995) Infect. Dis. Clin. North Am. 9(1):11–24 (each incorporated herein in their entireties).

Resistance to Drugs of S. aureus Strains

Prior to the introduction of penicillin the prognosis for patients seriously infected with S. aureus was unfavorable. Following the introduction of penicillin in the early 1940s even the worst S. aureus infections generally could be treated successfully. The emergence of penicillin-resistant strains of S. aureus did not take long, however. Most strains of S. aureus encountered in hospital infections today do not respond to penicillin; although, fortunately, this is not the case for S. aureus encountered in community infections. It is well-known now that penicillin-resistant strains of S. aureus produce a lactamase which converts penicillin to pencillinoic acid, and thereby destroys antibiotic activity. Furthermore, the lactamase gene often is propagated episomally, typically on a plasmid, and often is only one of several genes on an episomal element that, together, confer multidrug resistance.

Methicillins, introduced in the 1960s, largely overcame the problem of penicillin resistance in S. aureus. These compounds conserve the portions of penicillin responsible for antibiotic activity and modify or alter other portions that make penicillin a good substrate for inactivating lactamases. However, methicillin resistance has emerged in S. aureus, along with resistance to many other antibiotics effective against this organism, including aminoglycosides, tetracycline, chloramphenicol, macrolides and lincosamides. In fact, methicillin-resistant strains of S. aureus generally are multiply drug resistant.

Methicillian-resistant S. aureus (MRSA) has become one of the most important nosocomial pathogens worldwide and poses serious infection control problems. Today, many strains are multiresistant against virtually all antibiotics with the exception of vancomycin-type glycopeptide antibiotics.

Recent reports that transfer of vancomycin resistance genes from enterococci to S. aureus has been observed in the laboratory sustain the fear that MRSA might become resistant against vancomycin, too, a situation generally considered to result in a public health disaster. MRSA owe their resistance against virtually all β-lactam antibiotics to the expression of an extra penicillin binding protein (PBP) 2a, encoded by the mecA gene. This additional very low affinity PBP, which is found exclusively in resistant strains, appears to be the only pbp still functioning in cell wall peptidoglycan synthesis at β-lactam concentrations high enough to saturate the normal set of S. aureus PBP 1–4. In 1983 it was shown by insertion mutagenesis using transposon Tn551 that several additional genes independent of mecA are needed to sustain the high level of methicillin resistance of MRSA. Interruption of these genes did not influence the resistance level by interfering with PBP2a expression, and were therefore called fem (factor essential for expression of methicillin resistance) or aux (auxiliary genes).

In the meantime six fem genes (femA-through F) have been described and the minimal number of additional aux genes has been estimated to be more than 10. Interference with femA and femB results in a strong reduction of methicillin resistance, back to sensitivity of strains without PBP2a. The fem genes are involved in specific steps of cell wall synthesis. Consequently, inactivation of fem encoded factors induce β-lactam hypersensitivity in already sensitive strains. Both femA and femB have been shown to be involved in peptidoglycan pentaglycine interpeptide bridge formation. FemA is responsible for the formation of glycines 2 and 3, and FemB is responsible for formation of glycines 4 and 5. S. aureus may be involved in the formation of a monoglycine muropeptide precursors. FemC–F influence amidation of the iso-D-glutamic acid residue of the peptidoglycan stem peptide, formation of a minor muropeptide with L-alanine instead of glycine at position 1 of the interpeptide bridge, perform a yet unknown function, or are involved in an early step of peptidoglycan precursors biosynthesis (addition of L-lysine), respectively.

SUMMARY OF THE INVENTION

The present invention provides isolated S. aureus polynucleotides and polypeptides shown in Table 1 and SEQ ID NO:1 through SEQ ID NO:74. Polynucleotide sequences are shown as the odd numbered SEQ ID NOs (e.g., SEQ ID NO:1, SEQ ID NO:3, SEQ ID NO:5, and so on up to SEQ ID NO:73). The polypeptide sequences are shown as the even numbered SEQ ID NOs (e.g., SEQ ID NO:2, SEQ ID NO:4, SEQ ID NO:6, and so on up to SEQ ID NO:74). One aspect of the invention provides isolated nucleic acid molecules comprising or alternatively, consisting of, polynucleotides having a nucleotide sequence selected from the group consisting of: (a) a nucleotide sequence shown in Table 1; (b) a nucleotide sequence encoding any of the amino acid sequences of the polypeptides shown in Table 1; (c) a nucleotide sequence encoding an antigenic fragment of any of the polypeptides shown in Table 1; (d) a nucleotide sequence encoding a biologically active fragment of any of the polypeptides shown in Table 1; and (e) a nucleotide sequence complementary to any of the nucleotide sequences in (a), (b), (c) and/or (d). The invention further provides for fragments of the nucleic acid molecules of (a), (b), (c), (d) and/or (e) above.

Further embodiments of the invention include isolated nucleic acid molecules that comprise or alternatively, consist of, a polynucleotide having a nucleotide sequence at least 90% identical, and more preferably at least 95%, 96%, 97%, 98%, 99% or 100% identical, to any of the nucleotide sequences in (a), (b), (c), (d), or (e) above, or a polynucleotide which hybridizes under stringent hybridization conditions to a polynucleotide in (a), (b), (c), (d) or (e) above. Additional nucleic acid embodiments of the invention relate to isolated nucleic acid molecules comprising polynucleotides which encode the amino acid sequences of epitope-bearing portions of a S. aureus polypeptide having an amino acid sequence in Table 1, and including but not limited to those epitope-bearing portions shown in Table 4.

The present invention also relates to recombinant vectors, which include the isolated nucleic acid molecules of the present invention, and to host cells containing the recombinant vectors, as well as to methods of making such vectors and host cells. The present invention further relates to the use of these vectors in the production of *S. aureus* polypeptides or peptides by recombinant techniques.

The invention further provides isolated *S. aureus* polypeptides having an amino acid sequence selected from the group consisting of an amino acid sequence described in (a), (b), (c), (d), or (e) above, any of the polypeptides described in Table 1 or the complement thereof, and/or fragments thereof.

The polypeptides of the present invention also include polypeptides having an amino acid sequence with at least 70% similarity, and more preferably at least 75%, 80%, 85%, 90%, 95%, 96%, 97%, 98%, 99%, or 100% similarity to those described in Table 1, as well as polypeptides having an amino acid sequence at least 70% identical, more preferably at least 75% identical, and still more preferably 80%, 85%, 90%, 95%, 96%, 97%, 98%, or 99% identical to those above; as well as isolated nucleic acid molecules encoding such polypeptides.

The present invention provides antagonists of the polypeptides of the invention (e.g., including but not limited to antibodies to the polypeptides of the invention, small molecule inhibitors of the polypeptides of the invention) as therapeutic treatment in a *S. aureus* mediated disease.

The present invention further provides methods for the identification of antagonists of the polypeptides of the invention (e.g., including but not limited to, for example, small molecule inhibitors of the polypeptides of the invention) using polypeptides of the invention in screening assays.

The present invention further provides a vaccine, preferably a multi-component vaccine comprising one or more of the *S. aureus* polynucleotides or polypeptides described in Table 1, or fragments thereof, together with a pharmaceutically acceptable diluent, carrier, or excipient, wherein the *S. aureus* polypeptide(s) are present in an amount effective to elicit an immune response to members of the *Staphylococcus* genus, or at least *S. aureus*, in an animal. The *S. aureus* polypeptides of the present invention may further be combined with one or more immunogens of one or more other staphylococcal or non-staphylococcal organisms to produce a multi-component vaccine intended to elicit an immunological response against members of the *Staphylococcus* genus and, optionally, one or more non-staphylococcal organisms.

The vaccines of the present invention can be administered in a DNA form, e.g., "naked" DNA, wherein the DNA encodes one or more staphylococcal polypeptides and, optionally, one or more polypeptides of a non-staphylococcal organism. The DNA encoding one or more polypeptides may be constructed such that these polypeptides are expressed as fusion proteins.

The vaccines of the present invention may also be administered as a component of a genetically engineered organism or host cell. Thus, a genetically engineered organism or host cell which expresses one or more *S. aureus* polypeptides may be administered to an animal. For example, such a genetically engineered organism or host cell may contain one or more *S. aureus* polypeptides of the present invention intracellularly, on its cell surface, or in its periplasmic space. Further, such a genetically engineered organism or host cell may secrete one or more *S. aureus* polypeptides. The vaccines of the present invention may also be co-administered to an animal with an immune system modulator (e.g., CD86 and GM-CSF).

The invention also provides a method of inducing an immunological response in an animal to one or more members of the *Staphylococcus* genus, preferably one or more isolates of the *S. aureus* species, comprising administering to the animal a vaccine as described above.

The invention further provides a method of inducing a protective immune response in an animal, sufficient to prevent, attenuate, or control an infection by members of the *Staphylococcus* genus, preferably at least *S. aureus* species, comprising administering to the animal a composition comprising one or more of the polynucleotides or polypeptides described in Table 1, or fragments thereof (e.g., including, but not limited to, fragments which comprise the epitopes shown in Table 4). Further, these polypeptides, or fragments thereof, may be conjugated to another immunogen and/or administered in admixture with an adjuvant.

The invention further relates to antibodies elicited in an animal by the administration of one or more *S. aureus* polypeptides of the present invention and to methods for producing such antibodies and fragments thereof. The invention further relates to recombinant antibodies and fragments thereof and to methods for producing such antibodies and fragments thereof.

The invention also provides diagnostic methods for detecting the expression of the polynucleotides and polypeptides of Table 1 by members of the *Staphylococcus* genus in a biological or environmental sample. One such method involves assaying for the expression of a polynucleotide encoding *S. aureus* polypeptides in a sample from an animal. This expression may be assayed either directly (e.g., by assaying polypeptide levels using antibodies elicited in response to amino acid sequences described in Table 1) or indirectly (e.g., by assaying for antibodies having specificity for amino acid sequences described in Table 1). The expression of polynucleotides can also be assayed by detecting the nucleic acids of Table 1. An example of such a method involves the use of the polymerase chain reaction (PCR) to amplify and detect *Staphylococcus* nucleic acid sequences in a biological or environmental sample.

The invention also includes a kit for analyzing samples for the presence of members of the *Staphylococcus* genus in a biological or environmental sample. In a general embodiment, the kit includes at least one polynucleotide probe containing a nucleotide sequence that will specifically hybridize with a *S. aureus* nucleic acid molecule of Table 1 and a suitable container. In a specific embodiment, the kit includes two polynucleotide probes defining an internal region of the *S. aureus* nucleic acid molecule of Table 1, where each probe has one strand containing a 31' mer-end internal to the region. In a further embodiment, the probes may be useful as primers for polymerase chain reaction amplification.

The present invention also relates to nucleic acid probes having all or part of a nucleotide sequence described in Table 1 which are capable of hybridizing under stringent conditions to *Staphylococcus* nucleic acids. The invention further relates to a method of detecting one or more *Staphylococcus* nucleic acids in a biological sample obtained from an animal, said one or more nucleic acids encoding *Staphylococcus* polypeptides, comprising: (a) contacting the sample with one or more of the above-described nucleic acid probes, under conditions such that hybridization occurs, and (b) detecting hybridization of said one or more probes to the *Staphylococcus* nucleic acid present in the biological sample.

By "biological sample" is intended any biological sample obtained from an individual, body fluid, cell line, tissue culture, or other source which contains *S. aureus* polypeptides or polynucleotides of the invention. As indicated, biological samples include body fluids (such as semen, lymph, sera, plasma, urine, synovial fluid and spinal fluid) which contain the *S. aureus* polypeptides or polynucleotides of the invention, and tissue sources found to contain the expressed *S. aureus* polypeptides shown in Table 1. Methods for obtaining tissue biopsies and body fluids from mammals are well-known in the art. Where the biological sample is to include mRNA, a tissue biopsy is the preferred source.

The method(s) provided above may preferably be applied in a diagnostic method and/or kits in which *S. aureus* polynucleotides and/or polypeptides of the invention are attached to a solid support. In one exemplary method, the support may be a "gene chip" or a "biological chip" as described in U.S. Pat. Nos. 5,837,832, 5,874,219, and 5,856,174. Further, such a gene chip with *S. aureus* polynucleotides of Table 1 attached may be used to diagnose *S. aureus* infection in a mammal, preferably a human. The U.S. Patents referenced above are incorporated herein by reference in their entirety.

DETAILED DESCRIPTION

The present invention relates to recombinant *S. aureus* polypeptides and fragments thereof. The invention also relates to methods for using these polypeptides to produce immunological responses and to confer immunological protection to disease caused by members of the genus *Staphylococcus*. The invention further relates to nucleic acid sequences which encode antigenic *S. aureus* polypeptides and to methods for detecting *Staphylococcus* nucleic acids and polypeptides in biological samples. The invention also relates to *Staphylococcus* specific antibodies and methods for detecting such antibodies produced in a host animal. The invention relates to antagonists of polypeptides of the invention, including but not limited to antibodies and small molecule inhibitors. The invention further relates to methods of identifying and isolating antagonists of polypeptides of the invention.

Definitions

The following definitions are provided to clarify the subject matter which the inventors consider to be the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection). Further included are species and strains of the genus *Staphylococcus* which produce disease states in animals.

As used herein, the term "organism" means any living biological system, including viruses, regardless of whether it is a pathogenic agent.

As used herein, the term "*Staphylococcus*" means any species or strain of bacteria which is a member of the genus *Staphylococcus* regardless of whether it is a known pathogenic agent.

As used herein, the phrase "one or more *S. aureus* polypeptides of the present invention" means the amino acid sequence of one or more of the *S. aureus* polypeptides disclosed in Table 1. These polypeptides may be expressed as fusion proteins wherein the *S. aureus* polypeptides of the present invention are linked to additional amino acid sequences which may be of Staphylococcal or non-Staphylococcal origin (e.g. His tagged fusion proteins). This phrase further includes fragments of the *S. aureus* polypeptides of the present invention.

As used herein, the phrase "full-length amino acid sequence" and "full-length polypeptide" refer to an amino acid sequence or polypeptide encoded by a full-length open reading frame (ORF). For purposes of the present invention, polynucleotide ORFs in Table 1 are defined by the corresponding polypeptide sequences of Table 1 encoded by said polynucleotide. Therefore, a polynucleotide ORF is defined at the 5' end by the first base coding for the initiation codon of the corresponding polypeptide sequence of Table 1 and is defined at the 3' end by the last base of the last codon of said polypeptide sequence. As is well-known in the art, initiation codons for bacterial species may include, but are not limited to, those encoding Methionine, Valine, or Leucine. As discussed below for polynucleotide fragments, the ORFs of the present invention may be claimed by a 5' and 3' position of a polynucleotide sequence of the present invention wherein the first base of said sequence is position 1.

As used herein, the phrase "truncated amino acid sequence" and "truncated polypeptide" refer to a subsequence of a full-length amino acid sequence or polypeptide. Several criteria may also be used to define the truncated amino acid sequence or polypeptide. For example, a truncated polypeptide may be defined as a mature polypeptide (e.g., a polypeptide which lacks a leader sequence). A truncated polypeptide may also be defined as an amino acid sequence which is a portion of a longer sequence that has been selected for ease of expression in a heterologous system but retains regions which render the polypeptide useful for use in vaccines (e.g., antigenic regions which are expected to elicit a protective immune response).

Additional definitions are provided throughout the specification.

Explanation of Table 1

Table 1 lists the full-length *S. aureus* polynucleotide and polypeptide sequences of the present invention and their associated SEQ ID NOs. Each polynucleotide and polypeptide sequence is preceeded by a gene identifier. Each polynucleotide sequence is followed by at least one polypeptide sequence encoded by said polynucleotide. For some of the sequences of Table 1, a known biological activity and the name of the homolog with similar activity is listed after the gene sequence identifier.

Explanation of Table 2

Table 2 lists accession numbers for the closest matching sequences between the polypeptides of the present invention and those available through GenBank and GeneSeq databases. These reference numbers are the database entry numbers commonly used by those of skill in the art, who will be familar with their denominations. The descriptions of the nomenclature for GenBank are available from the National Center for Biotechnology Information. Column 1 lists the polynucleotide sequence of the present invention. Column 2 lists the accession number of a "match" gene sequence in GenBank or GeneSeq databases. Column 3 lists the description of the "match" gene sequence. Columns 4 and 5 are the high score and smallest sum probability, respectively, calculated by BLAST. Polypeptides of the present invention that do not share significant identity/similarity with any polypeptide sequences of GenBank and GeneSeq are not represented in Table 2. Polypeptides of the present invention that share significant identity/similarity with more than one of the polypeptides of GenBank and GeneSeq may be represented more than once.

Explanation of Table 3.

The *S. aureus* polypeptides of the present invention may include one or more conservative amino acid substitutions from natural mutations or human manipulation as indicated in Table 3. Changes are preferably of a minor nature, such as conservative amino acid substitutions that do not significantly affect the folding or activity of the protein. Residues from the following groups, as indicated in Table 3, may be substituted for one another: Aromatic, Hydrophobic, Polar, Basic, Acidic, and Small, Explanation of Table 4

Table 4 lists residues comprising antigenic epitopes of antigenic epitope-bearing fragments present in each of the full-length *S. aureus* polypeptides described in Table 1 as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power MacIntosh, DNASTAR, Inc., 1228 South Park Street Madison, Wis.). *S. aureus* polypeptides shown in Table 1 may possess one or more antigenic epitopes comprising residues described in Table 4. It will be appreciated that depending on the analytical criteria used to predict antigenic determinants, the exact address of the determinant may vary slightly. The residues and locations shown described in Table 4 correspond to the amino acid sequences for each full-length polypeptide sequence shown in Table 1 and in the Sequence Listing. Polypeptides of the present invention that do not have antigenic epitopes recognized by the Jameson-Wolf algorithm are not represented in Table 2.

Nucleic Acid Molecules

Sequenced *S. aureus* genomic DNA was obtained from the *S. aureus* strain ISP3. *S. aureus* strain ISP3, has been deposited at the American Type Culture Collection, as a convenience to those of skill in the art. The *S. aureus* strain ISP3 was deposited on Apr. 7, 1998 at the ATCC, 10801 University Blvd. Manassas, Va. 20110–2209, and given accession number 202108. As discussed elsewhere herein, polynucleotides of the present invention readily may be obtained by routine application of well-known and standard procedures for cloning and sequencing DNA. A wide variety of *S. aureus* strains can be used to prepare *S. aureus* genomic DNA for cloning and for obtaining polynucleotides and polypeptides of the present invention. A wide variety of *S. aureus* strains are available to the public from recognized depository institutions, such as the American Type Culture Collection (ATCC). It is recognized that minor variations is the nucleic acid and amino acid sequence may be expected from *S. aureus* strain to strain. The present invention provides for genes, including both polynucleotides and polypeptides, of the present invention from all the *S. aureus* strains.

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. By "nucleotide sequence" of a nucleic acid molecule or polynucleotide is intended to mean either a DNA or RNA sequence. Using the information provided herein, such as the nucleotide sequence in Table 1, a nucleic acid molecule of the present invention encoding a *S. aureus* polypeptide may be obtained using standard cloning and screening procedures, such as those for cloning DNAs using genomic DNA as starting material. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, New York 1989). Illustrative of the invention, the nucleic acid molecule described in Table 1 was discovered in a DNA library derived from a *S. aureus* ISP3 genomic DNA.

Nucleic acid molecules of the present invention may be in the form of RNA, such as mRNA, or in the form of DNA, including, for instance, DNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

TABLE 1

| Nucleotide and Amino Acid Sequences of *S. aureus* Genes. |
|---|
| >22HGS010 murC (SEQ ID NO:1) |
| ATGACACACTATCATTTTGTCGGAATTAAAGGTTCTGGCATGAGTTCATTAGCACAAATCATGCATGATTTAGGACATGA |
| AGTTCAAGGATCGGATATTGAGAACTACGTATTTACAGAAGTTGCTCTTAGAAATAAGGGGATAAAAATATTACCATTTG |
| ATGCTAATAACATAAAAGAAGATATGGTAGTTATACAAGGTAATGCATTCGCGAGTAGCCATGAAGAAATAGTACGTGCA |
| CATCAATTGAAATTAGATGTTGTAAGTTATAATGATTTTTTAGGACAGATTATTGATCAATATACTTCAGTAGCTGTAAC |
| TGGTGCACATGGTAAAACTTCTACAACAGGTTTATTATCACATGTTATGAATGGTGATAAAAAGACTTCATTTTTAATTG |
| GTGATGGCACAGGTATGGGATTGCCTGAAAGTGATTATTTCGCTTTTGAGGCATGTGAATATAGACGTCACTTTTTAAGT |
| TATAAACCTGATTACGCAATTATGACAAATATTGATTTCGATCATCCTGATTATTTTAAAGATATTAATGATGTTTTTGA |
| TGCATTCCAAGAAATGGCACATAATGTTAAAAAAGGTATTATTGCTTGGGGTGATGATGAACATCTACGTAAAATTGAAG |

TABLE 1-continued

Nucleotide and Amino Acid Sequences of S. aureus Genes.

CAGATGTTCCAATTTATTATTATGGATTTAAAGATTCGGATGACATTTATGCTCAAAATATTCAAATTACGGATAAAGGT

ACTGCTTTTGATGTGTATGTGGATGGTGAGTTTTATGATCACTTCCTGTCTCCACAATATGGTGACCATACAGTTTTAAA

TGCATTAGCTGTAATTGCGATTAGTTATTTAGAGAAGCTAGATGTTACAAATATTAAAGAAGCATTAGAAACGTTTGGTG

GTGTTAAACGTCGTTTCAATGAAACTACAATTGCAAATCAAGTTATTGTAGATGATTATGCACACCATCCAAGAGAAATT

AGTGCTACAATTGAAACAGCACGAAAGAAATATCCACATAAAGAAGTTGTTGCAGTATTTCAACCACACACTTTCTCTAG

AACACAGGCATTTTTAAATGAATTTGCAGAAAGTTTAAGTAAAGCAGATCGTGTATTCTTATGTGAAATTTTTGGATCAA

TTAGAGAAAATACTGGCGCATTAACGATACAAGATTTAATTGATAAAATTGAAGGTGCATCGTTAATTAATGAAGATTCT

ATTAATGTATTAGAACAATTTGATAATGCTGTTATTTTATTTATGGGTGCAGGTGATATTCAAAAATTACAAAATGCATA

TTTAGATAAATTAGGCATGAAAAATGCGTTTTAAGCTT

>HGS010 MurC (SEQ ID NO:2)

MTHYHFVGIKGSGMSSLAQIMHDLGHEVQGSDIENYVFTEVALRNKGIKILPFDANNIKEDMV

VIQGNAFASSHEEIVRAHQLKLDVVSYNDFLGQIIDQYTSVAVTGAHGKTSTTGLLSHVMNGDKKTSFLIGDTG

MGLPESDYFAFEACEYRRHFLSYKPDYAIMTNIDFDHPDYFKDINDVFDAFQEMAHNVKKGIIAWGDDEHLRKIE

ADVPIYYYGFKDSDDIYAQNIQITDKGTAFDVYVDGEFYDHFLSPQYGDHTVLNALAVIAISYLEKLDVTNIKEA

LETFGGVKRRFNETTIANQVIVDDYAHHPREISATIETARKKYPHKEVVAVFQPHTFSRTQAFLNEFAESLSKAD

RVFLCEIFGSIRENTGALTIQDLIDKIEGASLINEDSINVLEQFDNAVILFMGAGDIQKLQNAYLDKLGMKNAF

>HGS027 RF1 (peptide chain release factor1) (SEQ ID NO:3)

ATGCATTTTGATCAATTAGATATTGTAGAAGAAAGATACGAACAGTTAAATGAACTGTTAAGTGACCCAGATGTTGTAAA

TGATTCAGATAAAATTACGTAAATATTCTAAAGAGCAAGCTGATTTACAAAAAACTGTAGATGTTTATCGTAACTATAAAG

CTAAAAAAGAAGAATTAGCTGATATTGAAGAAATGTTAAGTGAGACTGATGATAAAGAAGAAGTAGAAATGTTAAAAGAG

GAGAGTAATGGTATTAAAGCTGAACTTCCAAATCTTGAAGAAGAGCTTAAAATATTATTGATTCCTAAAGATCCTAATGA

TGACAAAGACGTTATTGTAGAAATAAGAGCAGCAGCAGGTGGTGATGAGGCTGCGATTTTTGCTGGTGATTTAATGCGTA

TGTATTCAAAGTATGCTGAATCACAAGGATTCAAAACTGAAATAGTAGAAGCGTCTGAAAGTGACCATGGTGGTTACAAA

GAAATTAGTTTCTCAGTTTCTGGTAATGGCGCGTATAGTAAATTGAAATTTGAAAATGGTGCGCACCGCGTTCAACGTGT

GCCTGAAACAGAATCAGGTGGACGTATTCATACTTCAACAGCTACAGTGGCAGTTTTACCAGAAGTTGAAGATGTAGAAA

TTGAAATTAGAAATGAAGATTTAAAAATCGACACGTATCGTTCAAGTGGTGCAGGTGGTCAGCACGTAAACACAACTGAC

TCTGCAGTACGTATTACCCATTTACCAACTGGTGTCATTGCAACATCTTCTGAGAAGTCTCAAATTCAAAACCGTGAAAA

AGCAATGAAAGTGTTAAAAGCACGTTTATACGATATGAAAGTTCAAGAAGAACAACAAAAGTATGCGTCACAACGTAAAT

CAGCAGTCGGTACTGGTGATCGTTCAGAACGTATTCGAACTTATAATTATCCACAAAGCCGTGTAACAGACCATCGTATA

GGTCTAACGCTTCAAAAATTAGGGCAAATTATGGAAGGCCATTTAGAAGAAATTATAGATGCACTGACTTTATCAGAGCA

GACAGATAAATTGAAAGAACTTAATAATGGTGAA

>HGS027 Rfi (peptide chain release factor1) (SEQ ID NO:4)

MHFDQLDIVEERYEQLNELLSDPDVVNDSDKLRKYSKEQADLQKTVDVYRNYKAKKEELADIEEMLSETDDKEEV

EMLKEESNGIKAELPNLEEELKILLIPKDPNDDKDVIVEIRAAAGGDEAAIFAGDLMRMYSKYAESQGFKTEIVE

ASESDHGGYKEISFSVSGNGAYSKLKFENGAHRVQRVPETESGGRIHTSTATVAVLPEVEDVEIEIRNEDLKIDT

YRSSAGGQHVNTTDSAVRITHLPTGVIATSSEKSQIQNREKAMKVLKARLYDMKVQEEQQKYASQRKSAVGTGD

RSERIRTYNYPQSRVTDHRIGLTLQKLGQIMEGHLEEIIDALTLSEQTDKLKELNNGE

>HGS029 Rrf (ribosome recycling factor) (SEQ ID NO:5)

ATGGGGAGTGACATTATTAATGAAACTAAATCAAGAATGCAAAAATCAATCGAAAGCTTATCACGTGAATTAGCTAACAT

TABLE 1-continued

Nucleotide and Amino Acid Sequences of *S. aureus* Genes.

CAGTGCAGGAAGAGCTAATTCAAATTTATTAAACGGCGTAACAGTTGATTACTATGGTGCACCAACACCTGTACAACAAT

TAGCAAGCATCAATGTTCCAGAAGCACGTTTACTTGTTATTTCTCCATACGACAAAACTTCTGTAGCTGACATCGAAAAA

GCGATAATAGCAGCTAACTTAGGTGTTAACCCAACAAGTGATGGTGAAGTGATACGTATTGCTGTACCTGCCTTAACAGA

AGAACGTAGAAAAGAGCGCGTTAAAGATGTTAAGAAAATTGGTGAAGAAGCTAAAGTATCTGTTCGAAATATTCGTCGTG

ATATGAATGATCAGTTGAAAAAAGATGAAAAAAATGGCGACATTACTGAAGATGAGTTGAGAAGTGGCACTGAAGATGTT

CAGAAAGCAACAGACAATTCAATAAAAGAAATTGATCAAATGATTGCTGATAAAGAAAAAGATATTATGTCAGTA

>HGS029 Rrf (ribosome recycling factor) (SEQ ID NO:6)

MGSDIINETKSRMQKSIESLSRELANISAGRANSNLLNGVTVDYYGAPTPVQQLASINVPEARLLVISPYDKTSV

ADIEKAIIAANLGVNPTSDGEVIRIAVPALTEERRKERVKDVKKIGEEAKVSVRNIRRDMNDQLKKDEKNGDITE

DELRSGTEDVQKATDNSIKEIDQMIADKEKDIMSV

>HGS038 nusA (SEQ ID NO:7)

ATGGGGTCAAGTAATGAATTATTATTAGCTACTGAGTATTTAGAAAAAGAAAAGAAGATTCCTAGAGCAGTATTAATTGA

TGCTATTGAAGCAGCTTTAATTACTGCATACAAAAAGAACTATGATAGTGCAAGAAATGTCCGTGTGGAATTAAATATGG

ATCAAGGTACTTTCAAAGTTATCGCTCGTAAAGATGTTGTTGAAGAAGTATTTGACGACAGAGATGAAGTGGATTTAAGT

ACAGCGCTTGTTAAAAACCCTGCATATGAAATTGGTGATATATACGAAGAAGATGTAACACCTAAAGATTTTGGTCGTGT

AGGTGCTCAAGCAGCGAAACAAGCAGTAATGCAACGTCTTCGTGATGCTGAACGTGAAATTTTATTTGAAGAATTTATAG

ACAAAGAAGAAGACATACTTACTGGAATTATTGACCGTGTTGACCATCGTTATGTATATGTGAATTTAGGTCGTATCGAA

GCTGTTTTATCTGAAGCAGAAAGAAGTCCTAACGAAAAATATATTCCTAACGAACGTATCAAAGTATATGTTAACAAAGT

GGAACAAACGACAAAAGGTCCTCAAATCTATGTTTCTCGTAGCCATCCAGGTTTATTAAAACGTTTATTTGAACAAGAAG

TTCCAGAAATTTACGATGGTACTGTAATTGTTAAATCAGTAGCACGTGAAGCTGGCGATCGCTCTAAAATTAGTGTCTTC

TCTGAAAACAATGATATAGATGCTGTTGGTGCATGTGTTGGTGCTAAAGGCGCACGTGTTGAAGCTGTTGTTGAAGAGCT

AGGTGGTGAAAAAATCGACATCGTTCAATGGAATGAAGATCCAAAAGTATTTGTAAAAAATGCTTTAAGCCCTTCTCAAG

TTTTAGAAGTTATTGTTGATGAAACAAATCAATCTACAGTAGTTGTTGTTCCTGATTATCAATTGTCATTAGCGATTGGT

AAAAGAGGACAAAACGCACGTCTAGCTGCTAAATTAACCGGCTGGAAAATTGATATTAAATCAGAAACAGATGCGCGTGA

AGCGGGTATCTATCCAGTAGTTGAAGCTGAAAAAGTAACTGAAGAAGATGTTGCTTTAGAAGATGCTGACACAACAGAAT

CAACCGAAGAGGTAAATGATGTTTCAGTTGAAACAAATGTAGAGAAAGAATCTGAA

>HGS038 NusA (SEQ ID NO:8)

MGSSNELLLATEYLEKEKKIPRAVLIDAIEAALITAYKKNYDSARNVRVELNMDQGTFKVIARKDVVEEVFDDRD

EVDLSTALVKNPAYEIGDIYEEDVTPKDFGRVGAQAAKQAVMQRLRDAEREILFEEFIDKEEDILTGIIDRVDHR

YVYVNLGRIEAVLSEAERSPNEKYIPNERIKVYVNKVEQTTKGPQIYVSRSHPGLLKRLFEQEVPEIYDGTVIVK

SVAREAGDRSKISVFSENNDIDAVGACVGAKGARVEAVVEELGGEKIDIVQWNEDPKVFVKNALSPSQVLEVIVD

ETNQSTVVVVPDYQLSLAIGKRGQNARLAAKLTGWKIDIKSETDAREAGIYPVVEAEKVTEEDVALEDADTTEST

EEVNDVSVETNVEKESE

>HGS039 nusG (SEQ ID NO:9)

ATGGGATCTGAAGAAGTTGGCGCAAAGCGTTGGTATGCAGTGCATACATATTCTGGATATGAAAATAAAGTTAAAAAGAA

TTTAGAAAAAAGAGTAGAATCTATGAATATGACTGAACAAATCTTTAGAGTAGTCATACCGGAAGAAGAAGAAACTCAAG

TAAAAGATGGCAAAGCTAAAACGACTGTTAAAAAAACATTCCCTGGATATGTTTTAGTGGAATTAATCATGACAGATGAA

TCATGGTATGTGGTAAGAAATACACCAGGCGTTACTGGTTTTGTAGGTTCTGCAGGTGCAGGGTCTAAGCCAAATCCATT

TABLE 1-continued

Nucleotide and Amino Acid Sequences of S. aureus Genes.

GTTACCAGAAGAAGTTCGCTTCATCTTAAAACAAATGGGTCTTAAAGAAAAGACTATCGATGTTGAACTCGAAGTTGGCG

AGCAAGTTCGTATTAAATCAGGTCCATTTGCGAATCAAGTTGGTGAAGTTCAAGAAATTGAAACAGATAAGTTTAAGCTA

ACAGTATTAGTAGATATGTTTGGCCGAGAAACACCAGTAGAAGTTGAATTCGATCAAATTGAAAAGCTG

>HGS039 NusG (SEQ ID NO:10)

MGSEEVGAKRWYAVHTYSGYENKVKKNLEKRVESMNMTEQIFRVVIPEEEETQVKDGKAKTTVKKTFPGYVLVEL

IMTDESWYVVRNTPGVTGFVGSAGAGSKPNPLLPEEVRFILKQMGLKEKTIDVELEVGEQVRIKSGPFANQVGEV

QEIETDKFKLTVDMFGRETPVEVEFDQIEKL

>HGS041 nadE (NH3-Dependent NAD Synthetase) (SEQ ID NO:11)

ATGGGTAGTAAATTACAAGACGTTATTGTACAAGAAATGAAAGTGAAAAAGCGTATCGATAGTGCTGAAGAAATTATGGA

ATTAAAGCAATTTATAAAAAATTATGTACAATCACATTCATTTATAAAATCTTTAGTGTTAGGTATTTCAGGAGGACAGG

ATTCTACATTAGTTGGAAAACTAGTACAAATGTCTGTTAACGAATTACGTGAAGAAGGCATTGATTGTACGTTTATTGCA

GTTAAATTACCTTATGGAGTTCAAAAAGATGCTGATGAAGTTGAGCAAGCTTTGCGATTCATTGAACCAGATGAAATAGT

AACAGTCAATATTAAGCCTGCAGTTGATCAAAGTGTGCAATCATTAAAAGAAGCCGGTATTGTTCTTACAGATTTCCAAA

AAGGAAATGAAAAAGCGCGTGAACGTATGAAAGTACAATTTTCAATTGCTTCAAACCGACAAGGTATTGTAGTAGGAACA

GATCATTCAGCTGAAAATATAACTGGGTTTTATACGAAGTACGGTGATGGTGCTGCAGATATCGCACCTATATTTGGTTT

GAATAAACGACAAGGTCGTCAATTATTAGCGTATCTTGGTGCGCCAAAGGAATTATATGAAAAAACGCCAACTGCTGATT

TAGAAGATGATAAACCACAGCTTCCAGATGAAGATGCATTAGGTGTAACTTATGAGGCGATTGATAATTATTTAGAAGGT

AAGCCAGTTACGCCAGAAGAACAAAAAGTAATTGAAAATCATTATATACGAAATGCACACAAACGTGAACTTGCATATAC

AAGATACACGTGGCCAAAATCC

>HGS041 NadE (NH3-Dependent NAD Synthetase) (SEQ ID NO:12)

MGSKLQDVIVQEMKVKKRIDSAEEIMELKQFIKNYVQSHSFIKSLVLGISGGQDSTLVGKLVQMSVNELREEGID

CTFIAVKLPYGVQKDADEVEQALRFIEPDEIVTVNIKPAVDQSVQSLKEAGIVLTDFQKGNEKARERMKVQFSIA

SNRQGIVVGTDHSAENITGFYTKYGDGAADIAPIFGLNKRQGRQLLAYLGAPKELYEKTPTADLEDDKPQLPDED

ALGVTYEAIDNYLEGKPVTPEEQKVIENHYIRNAHKRELAYTRYTWPKS

>HGS042 trxB (Thioredoxin Reductase) (SEQ ID NO:13)
ATGGGTACTGAAATAGATTTTGATATAGCAATTATCGGTGCAGGTCCAGCTGGTATGACTGCTGCAGTATACGCATCACG

TGCTAATTTAAAAACAGTTATGATTGAAAGAGGTATTCCAGGCGGTCAAATGGCTAATACAGAAGAAGTAGAGAACTTCC

CTGGTTTCGAAATGATTACAGGTCCAGATTTATCTACAAAAATGTTTGAACACGCTAAAAAGTTTGGTGCAGTTTATCAA

TATGGAGATATTAAATCTGTAGAAGATAAAGGCGAATATAAAGTGATTAACTTTGGTAATAAAGAATTAACAGCGAAAGC

GGTTATTATTGCTACAGGTGCAGAATACAAGAAAATTGGTGTTCCGGGTGAACAAGAACTTGGTGGACGCGGTGTAAGTT

ATTGTGCAGTATGTGATGGTGCATTCTTTAAAAATAAACGCCTATTCGTTATCGGTGGTGGTGATTCAGCAGTAGAAGAG

GGAACATTCTTAACTAAATTTGCTGACAAAGTAACAATCGTTCACCGTCGTGATGAGTTACGTGCACAGCGTATTTTACA

AGATAGAGCATTCAAAAATGATAAAATCGACTTTATTTGGAGTCATACTTTGAAATCAATTAATGAAAAAGACGGCAAAG

TGGGTTCTGTGACATTAACGTCTACAAAAGATGGTTCAGAAGAAACACACGAGGCTGATGGTGTATTCATCTATATTGGT

ATGAAACCATTAACAGCGCCATTTAAAGACTTAGGTATTACAAATGATGTTGGTTATATTGTAACAAAAGATGATATGAC

AACATCAGTACCAGGTATTTTTGCAGCAGGAGATGTTCGCGACAAAGGTTTACGCCAAATTGTCACTGCTACTGGCGATG

GTAGTATTGCAGCGCAAAGTGCAGCGGAATATATTGAACATTTAAACGATCAAGCT

>HGS042 TrxB (Thioredoxin Reductase) (SEQ ID NO:14)

MGTEIDFDIAIIGAGPAGMTAAVYASRANLKTVMIERGIPGGQMANTEEVENFPGFEMITGPDLSTKMFEHAKKF

TABLE 1-continued

Nucleotide and Amino Acid Sequences of S. aureus Genes.

GAVYQYGDIKSVEDKGEYKVINFGNKELTAKAVIIATGAEYKKIGVPGEQELGGRGVSYCAVCDGAFFKNKRLFV

IGGGDSAVEEGTFLTKFADKVTIVHRRDELRAQRILQDRAFKNDKIDFIWSHTLKSINEKDGKVGSVTLTSTKDG

SEETHEADGVFIYIGMKPLTAPFKDLGITNDVGYIVTKDDMTTSVPGIFAAGDVRDKGLRQIVTATGDGSIAAQS

AAEYIEHLNDQA

>HGS043 femD/glmM (Phosphoglucosamine Mutase) (SEQ ID NO:15)

ATGGGGGGAAAATATTTTGGTACAGACGGAGTAAGAGGTGTCGCAAACCAAGAACTAACACCTGAATTGGCATTTAAATT

AGGAAGATACGGTGGCTATGTTCTAGCACATAATAAAGGTGAAAAACACCCACGTGTACTTGTAGGTCGCGATACTAGAG

TTTCAGGTGAAATGTTAGAATCAGCATTAATAGCTGGTTTGATTTCAATTGGTGCAGAAGTGATGCGATTAGGTATTATT

TCAACACCAGGTGTTGCATATTTAACACGCGATATGGGTGCAGAGTTAGGTGTAATGATTTCAGCCTCTCATAATCCAGT

TGCAGATAATGGTATTAAATTCTTTGGATCAGATGGTTTTAAACTATCAGATGAACAAGAAAATGAAATTGAAGCATTAT

TGGATCAAGAAAACCCAGAATTACCAAGACCAGTTGGCAATGATATTGTACATTATTCAGATTACTTTGAAGGGCACAA

AAATATTTGAGCTATTTAAAATCAACAGTAGATGTTAACTTTGAAGGTTTGAAAATTGCTTTAGATGGTGCAAATGGTTC

AACATCATCACTAGCGCCATTCTTATTTGGTGACTTAGAAGCAGATACTGAAACAATTGGATGTAGTCCTGATGGATATA

ATATCAATGAGAAATGTGGCTCTACACATCCTGAAAAATTAGCTGAAAAAGTAGTTGAAACTGAAAGTGATTTTGGGTTA

GCATTTGACGGCGATGGAGACAGAATCATAGCAGTAGATGAGAATGGTCAAATCGTTGACGGTGACCAAATTATGTTTAT

TATTGGTCAAGAAATGCATAAAAATCAAGAATTGAATAATGACATGATTGTTTCTACTGTTATGAGTAATTTAGGTTTTT

ACAAAGCGCTTGAACAAGAAGGAATTAAATCTAATAAAACTAAAGTTGGCGACAGATATGTAGTAGAAGAAATGCGTCGC

GGTAATTATAACTTAGGTGGAGAACAATCTGGACATATCGTTATGATGGATTACAATACAACTGGTGATGGTTTATTAAC

TGGTATTCAATTAGCTTCTGTAATAAAAATGACTGGTAAATCACTAAGTGAATTAGCTGGACAAATGAAAAAATATCCAC

AATCATTAATTAACGTACGCGTAACAGATAAATATCGTGTTGAAGAAAATGTTGACGTTAAAGAAGTTATGACTAAAGTA

GAAGTAGAAATGAATGGAGAAGGTCGAATTTTAGTAAGACCTTCTGGAACAGAACCATTAGTTCGTGTCATGGTTGAAGC

AGCAACTGATGAAGATGCTGAAAGATTTGCACAACAAATAGCTGATGTGGTTCAAGATAAAATGGGATTAGATAAA

>HGS043 FemD/GlmM (Phosphoglucosamine Mutase) (SEQ ID NO:16)

MGGKYFGTDGVRGVANQELTPELAFKLGRYGGYVLAHNKGEKHPRVLVGRDTRVSGEMLESALIAGLISIGAEVM

RLGIISTPGVAYLTRDMGAELGVMISASHNPVADNGIKFFGSDGFKLSDEQENEIEALLDQENPELPRPVGNDIV

HYSDYFEGAQKYLSYLKSTVDVNFEGLKIALDGANGSTSSLAPFLFGDLEADTETIGCSPDGYNINEKCGSTHPE

KLAEKVVETESDFGLAFDGDGDRIIAVDENGQIVDGDQIMFIIGQEMHKNQELNNDMIVSTVMSNLGFYKALEQE

GIKSNKTKVGDRYVVEEMRRGNYNLGGEQSGHIVMMDYNTTGDGLLTGIQLASVIKMTGKSLSELAGQMKKYPQS

LINVRVTDKYRVEENVDVKEVMTKVEVEMNGEGRILVRPSGTEPLVRVMVEAATDEDAERFAQQIADVVQDKMGL

DK

>HGS044 glmU (Glucosamine N-acetyly/uridylate transferase) (SEQ ID NO:17)

ATGGGTTTCATGCGAAGACACGCGATAATTTTGGCAGCAGGTAAAGGCACAAGAATGAAATCTAAAAAGTATAAAGTGCT

ACACGAGGTTGCTGGGAAACCTATGGTCGAACATGTATTGGAAAGTGTGAAAGGCTCTGGTGTCGATCAAGTTGTAACCA

TCGTAGGACATGGTGCTGAAAGTGTAAAAGGACATTTAGGCAGCGTTCTTTATACAGTTTTCAAGAGGAACAACTCGGT

ACTGCGCATGCAGTGCAAATGGCGAAATCACACTTAGAAGACAAGGAAGGTACGACAATCGTTGTATGTGGTGACACACC

GCTCATCACAAAGGAAACATTAGTAACATTGATTGCGCATCACGAGGATGCTAATGCTCAAGCAACTGTATTATCTGCAT

CGATTCAACAACCATATGGATACGGAAGAATCGTTCGAAATGCGTCAGGTCGTTTAGAACGCATAGTTGAAGAGAAAGAT

GCAACGCAAGCTGAAAGGATATTAATGAAATTAGTTCAGGTATTTTGCGTTTAATAATAAAACGTTGTTTGAAAAATT

AACACAAGTGAAAAATGATAATGCGCAAGGTGAATATTACCTCCCTGATGTATTGTCGTTAATTTTAAATGATGGCGGCA

TABLE 1-continued

Nucleotide and Amino Acid Sequences of *S. aureus* Genes.

```
TCGTAGAAGTCTATCGTACCAATGATGTTGAAGAAATCATGGGTGTAAATGATCGTGTAATGCTTAGTCAGGCTGAGAAG
GCGATGCAACGTCGTACGAATCATTATCACATGCTAAATGGTGTGACAATCATCGATCCTGACAGCACTTATATTGGTCC
AGACGTTACAATTGGTAGTGATACAGTCATTGAACCAGGCGTACGAATTAATGGTCGTACAGAAATTGGCGAAGATGTTG
TTATTGGTCAGTACTCTGAAATTAACAATAGTACGATTGAAAATGGTGCATGTATTCAACAGTCTGTTGTTAATGATGCT
AGCGTAGGAGCGAATACTAAGGTCGGACCGTTTGCGCAATTGAGACCAGGCGCGCAATTAGGTGCAGATGTTAAGGTTGG
AAATTTTGTAGAAATTAAAAAAGCAGATCTTAAAGATGGTGCCAAGGTTTCACATTTAAGTTATATTGGCGATGCTGTAA
TTGGCGAACGTACTAATATTGGTTGCGGAACGATTACAGTTAACTATGATGGTGAAAATAAATTTAAAACTATCGTCGGC
AAAGATTCATTTGTAGGTTGCAATGTTAATTTAGTAGCACCTGTAACAATTGGTGATGATGTATTGGTGGCAGCTGGTTC
CACAATCACAGATGACGTACCAAATGACAGTTTAGCTGTGGCAAGAGCAAGACAAACAACAAAAGAAGGATTATAGGAAA
```

>HGS044 GlmU (Glucosamine N-acetyly/uridylate transterase) (SEQ ID NO:18)

```
MGFMRRHAIILAAGKGTRMKSKKYKVLHEVAGKPMVEHVLESVKGSGVDQVVTIVGHGAESVKGHLGERSLYSFQ
EEQLGTAHAVQMAKSHLEDKEGTTIVVCGDTPLITKETLVTLIAHHEDANAQATVLSASIQQPYGYGRIVRNASG
RLERIVEEKDATQAEKDINEISSGIFAFNNKTLFEKLTQVKNDNAQGEYYLPDVLSLILNDGGIVEVYRTNDVEE
IMGVNDRVMLSQAEKAMQRRTNHYHMLNGVTIIDPDSTYIGPDVTIGSDTVIEPGVRINGRTEIGEDVVIGQYSE
INNSTIENGACIQQSVVNDASVGANTKVGPFAQLRPGAQLGADVKVGNFVEIKKADLKDGAKVSHLSYIGDAVIG
ERTNIGCGTITVNYDGENKFKTIVGKDSFVGCNVNLVAPVTIGDDVLVAAGSTITDDVPNDSLAVARARQTTKEG
YRK
```

>HGS045 CoADR (CoenzyrneA Disulfide Reductase) (SEQ ID NO:19)

```
ATGGGGCCCAAAATAGTCGTAGTCGGAGCAGTCGCTGGCGGTGCAACATGTGCCAGCCAAATTCGACGTTTAGATAAAGA
AAGTGACATTATTATTTTTGAAAAAGATCGTGATATGAGCTTTGCTAATTGTGCATTGCCTTATGTCATTGGCGAAGTTG
TTGAAGATAGAAGATATGCTTTAGCGTATACACCTGAAAAATTTTATGATAGAAAGCAAATTACAGTAAAAACTTATCAT
GAAGTTATTGCAATCAATGATGAAAGACAAACTGTATCTGTATTAAATAGAAAGACAAACGAACAATTTGAAGAATCTTA
CGATAAACTCATTTTAAGCCCTGGTGCAAGTGCAAATAGCCTTGGCTTTGAGTGATATTACATTTAACTTAGAAATT
CGATAAACTCATTTTAAGCCCTGGTGCAAGTGCAAATAGCCTTGGCTTTGAAAGTGATATTACATTTACACTTAGAAATT
TAGAAGACACTGATGCTATCGATCAATTCATCAAAGCAAATCAAGTTGATAAAGTATTGGTTGTAGGTGCAGGTTATGTT
TCATTAGAAGTTCTTGAAAATCTTTATGAACGTGGTTTACACCCTACTTTAATTCATCGATCTGATAAGATAAATAAATT
AATGGATGCCGACATGAATCAACCTATACTTGATGAATTAGATAAGCGGGAGATTCCATACCGTTTAAATGAGGAAATTA
ATGCTATCAATGGAAATGAAATTACATTTAAATCAGGAAAAGTTGAACATTACGATATGATTATTGAAGGTGTCGGTACT
CACCCCAATTCAAAATTTATCGAAAGTTCAAATATCAAACTTGATCGAAAAGGTTTCATACCGGTAAACGATAAATTTGA
AACAAATGTTCCAAACATTTATGCAATAGGCGATATTGCAACATCACATTATCGACATGTCGATCTACCGGCTAGTGTTC
CTTTAGCTTGGGCGCTCACCGTGCAGCAAGTATTGTTGCCGAACAAATTGCTGGAAATGACACTATTGAATTCAAAGGC
TTCTTAGGCAACAATATTGRGAAGTTCTTTGATTATACATTTGCGAGTGTCGGCGTTAAACCAAACGAACTAAAGCAATT
TGACTATAAAATGGTAGAAGTCACTCAAGGTGCACACGCGAATTATTACCCAGGAAATTCCCCTTTACACTTAAGAGTAT
ATTATGACACTTCAAACCGTCAGATTTTAAGAGCAGCTGCAGTAGGAAAAGAAGGTGCAGATAAACGTATTGATGTACTA
TCGATGGCAATGATGAACCAGCTAACTGTAGATGAGTTAACTGAGTTTGAAGTGGCTTATGCACCACCATATAGCCACCC
TAAAGATTTAATCAATATGATTGGTTACAAAGCTAAA
```

>HGS045 CoADR (CoenzyrneA Disulfide Reductase) (SEQ ID NO:20)

MGPKIVVVGAVAGGATCASQIRRLDKESDIIIFEKDRDMSFANCALPYVIGEVVEDRRYALAYTPEKFYDRKQIT

TABLE 1-continued

Nucleotide and Amino Acid Sequences of *S. aureus* Genes.

VKTYHEVIAINDERQTVSVLNRKTNEQFEESYDKLILSPGASANSLGFESDITFTLRNLEDTDAIDQFIKANQVD

KVLVVGAGYVSLEVLENLYERGLHPTLIHRSDKINKLMDADMNQPILDELDKREIPYRLNEEINAINGNEITFKS

GKVEHYDMIIEGVGTHPNSKFIESSNIKLDRKGFIPVNDKFETNVPNIYAIGDIATSHYRHVDLPASVPLAWGAH

RAASIVAEQIAGNDTIEFKGFLGNNIVKFFDYTFASVGVKPNELKQFDYKMVEVTQGAHANYYPGNSPLHLRVYY

DTSNRQILRAAAVGKEGADKRIDVLSMAMMNQLTVDELTEFEVAYAPPYSHPKDLINMIGYKAK

>HGS046 SVR (SEQ ID NO:21)

ATGAAAGACGAACAATTATATTATTTTGAGAAATCGCCAGTATTTAAAGCGATGATGCATTTCTCATTGCCAATGATGAT

AGGGACTTTATTAAGCGTTATTTATGGCATATTAAATATTTACTTTATAGGATTTTTAGAAGATAGCCACATGATTTCTG

CTATCTCTCTAACACTGCCAGTATTTGCTATCTTAATGGGGTTAGGTAATTTATTTGGCGTTGGTGCAGGAACTTATATT

TCACGTTTATTAGGTGCGAAAGACTATAGTAAGAGTAAATTTGTAAGTAGTTTCTCTATTTATGGTGGTATTGCACTAGG

ACTTATCGTGATTTTAGTTACTTTACCATTCAGTGATCAAATCGCAGCAATTTTAGGGGCGAGAGGTGAAACGTTAGCTT

TAACAAGTAATTATTTGAAAGTAATGTTTTTAAGTGCACCTTTTGTAATTTTGTTCTTCATATTAGAACAATTTGCACGT

GCAATTGGGGCACCAATGGTTTCTATGATTGGTATGTTAGCTAGTGTAGGCTTAAATATTATTTTAGATCCAATTTTAAT

TTTTGGTTTTGATTTAAACGTTGTTGGTGCAGCTTTGGGTACTGCAATCAGTAATGTTGCTGCTGCTCTGTTCTTTATCA

TTTATTTTATGAAAAATAGTGACGTTGTGTCAGTTAATATTAAACTTGCGAAACCTAATAAAGAAATGCTTTCTGAAATC

TTTAAAATCGGTATTCCTGCATTTTTAATGAGTATCTTAATGGGATTCACAGGATTAGTTTTAAATTTATTTTAGCACA

TTATGGAAACTTCGCGATTGCAAGTTATGGTATCTCATTTAGACTTGTGCAATTTCCAGAACTTATTATCATGGGATTAT

GTGAAGGTGTTGTACCACTAATTGCATATAACTTTATCGCAAATAAAGGCCGTATGAAAGACGTTATCAAAGCAGTTATC

ATGTCTATCGGCGTTATCTTTGTTGTATGTATGAGTGCTGTATTTACAATTGGACATCATATGGTCGGACTATTTACTAC

TGATCAAGCCATTGTTGAGATGGCGACATTTATTTTGAAAGTAACAATGGCATCATTATTATTAAATGGTATAGGTTTCT

TGTTTACTGGTATGCTTCAAGCGACTGGGCAAGGTCGTGGTGCTACAATTATGGCCATTTTACAAGGTGCAATTATCATT

CCAGTATTTATTTATTATGAATGCTTTGTTTGGACTAACAGGTGTCATTTGGTCATTATTAATTGCTGAGTCACTTTGTGC

TTTAGCAGCAATGTTAATCGTCTATTTATTACGTGATCGTTTGACAGTTGATACATCTGAATTATAAGGGT

>HGS046 SVR (SEQ ID NO:22)

MKDEQLYYFEKSPVFKAMMHFSLPMMIGTLLSVIYGILNIYFIGFLEDSHMISAISLTLPVFAILMGLGNLFGVG

AGTYISRLLGAKDYSKSKFVSSFSIYGGIALGLIVILVTLPFSDQIAAILGARGETLALTSNYLKFMFLSAPFVI

LFFILEQFARIAGAPMVSMIGMLASVGLNIILDPILIFGFDLNVVGAALGTAISNVAAALFFIIYFMKNSDVVSV

NIKLAKPNKEMLSEIFKIGIPAFLMSILMGFTGLVLNLFLAHYGNFAIASYGISFRLVQFPELIIMGLCEGVVPL

IAYNFMANKGRMKDVIKAVIMSIGVIFVVCMSAVFTIGHHMVGLFTTDQAIVEMATFILKVTMASLLLNGIGFLF

TGMLQATGQGRGATIMAILQGAIIPVLFIMNALFGLTGVIWSLLIAESLCALAAMLIVYLLRDRLTVDTSELIE

G

HGS049 murE (SEQ ID NO:23)

TTGGATGCAAGTACGTTGTTTAAGAAAGTAAAAGTAAAGCGTGTATTGGGTTCTTTAGAACAACAAATAGATGATATCAC

TACTGATTCACGTACAGCGAGAGAAGGTAGCATTTTTGTCGCTTCAGTTGGATATACTGTAGACAGTCATAAGTTCTGTC

AAAATGTAGCTGATCAAGGGTGTAAGTTGGTAGTGGTCAATAAAGAACAATCATTACCAGCTAACGTAACACAAGTGGTT

GTGCCGGACACATTAAGAGTAGCTAGTATTCTAGCACACACATTATATGATTATCCGAGTCATCAGTTAGTGACATTTGG

TGTAACGGGTACAAATGGTAAAACTTCTATTGCGACGATGATTCATTTAATTCAAAGAAAGTTACAAAAAAATAGTGCAT

ATTTAGGAACTAATGGTTTCCAAATTAATGAAACAAAGACAAAAGGTGCAAATACGACACCAGAAACAGTTTCTTTAACT

AAGAAAATTAAAGAAGCAGTTGATGCAGGCGCTGAATCTATGACATTAGAAGTATCAAGCCATGGCTTAGTATTAGGACG

TABLE 1-continued

Nucleotide and Amino Acid Sequences of *S. aureus* Genes.

ACTGCGAGGCGTTGAATTTGACGTTGCAATATTTTCAAATTTAACACAAGACCATTTAGATTTTCATGGCACAATGGAAG

CATACGGACACGCGAAGTCTTTATTGTTTAGTCAATTAGGTGAAGATTTGTCGAAAGAAAAGTATGTCGTGTTAAACAAT

GACGATTCATTTTCTGAGTATTTAAGAACAGTGACGCCTTATGAAGTATTTAGTTATGGAATTGATGAGGAAGCCCAATT

TATGGCTAAAAATATTCAAGAATCTTTACAAGGTGTCAGCTTTGATTTTGTAACGCCTTTTGGAACTTACCCAGTAAAAT

CGCCTTATGTTGGTAAGTTTAATATTTCTAATATTATGGCGGCAATGATTGCGGTGTGGAGTAAAGGTACATCTTTAGAA

ACGATTATTAAAGCTGTTGAAAATTTAGAACCTGTTGAAGGGCGATTAGAAGTTTTAGATCCTTCGTTACCTATTGATTT

AATTATCGATTATGCACATACAGCTGATGGTATGAACAAATTAATCGATGCAGTACAGCCTTTTGTAAAGCAAAAGTTGA

TATTTTTAGTTGGTATGGCAGGCGAACGTGATTTAACTAAAACGCCTGAAATGGGGCGAGTTGCCTGTCGTGCAGATTAT

GTCATTTTCACACCGGATAATCCGGCAAATGATGACCCGAAAATGTTAACGGCAGAATTAGCCAAAGGTGCAACACATCA

AAACTATATTGAATTTGATGATCGTGCAGAAGGGATAAAACATGCAATTGACATAGCTGAGCCTGGGGATACTGTCGTTT

TAGCATCAAAAGGAAGAGAACCATATCAAATCATGCCAGGGCATATTAAGGTGCCACATCGAGATGATTTAATTGGCCTT

GAAGCAGCTTACAAAAAGTTCGGTGGTGGCCCTGTTGAT

>HGS049 MurE (SEQ ID NO:24)

LDASTLFKKVKVKRVLGSLEQQIDDITTDSRTAREGSIFVASVGYTVDSHKFCQNVADQGCKLVVVNKEQSLPANVTQVV

VPDTLRVASILAHTLYDYPSHQLVTFGVTGTNGKTSIATMIHLIQRKLQKNSAYLGTNGFQINETKTKGANTTPETVSLT

KKIKEAVDAGAESMTLEVSSHGLVLGRLRGVEFDVAIFSNLTQDHLDFHGTMEAYGHAKSLLFSQLGEDLSKEKYVVLNN

DDSFSEYLRTVTPYEVFSYGIDEEAQFMAKNIQESLQGVSFDFVTPFGTYPVKSPYVGKFNISNIMAAMIAVWSKGTSLE

TIIKAVENLEPVEGRLEVLDPSLPIDLIIDYAHTADGMNKLIDAVQPFVKQKLIFLVGMAGERDLTKTPEMGRVACRADY

VIFTPDNPANDDPKMLTAELAKGATHQNYIEFDDRAEGIKHAIDIAEPGDTVVLASKGREPYQIMPGHIKVPHRDDLIGL

EAAYKKFGGGPVD

>HGS050 MurF (SEQ ID NO:25)

ATGATTAATGTTACATTAAAGCAAATTCAATCATGGATTCCTTGTGAAATTGAAGATCAATTTTTAAATCAAGAGATAAA

TGGAGTCACAATTGATTCACGAGCAATTTCTAAAAATATGTTATTTATACCATTTAAAGGTGAAAATGTTGACGGTCATC

GCTTTGTCTCTAAAGCATTACAAGATGGTGCTGGGGCTGCTTTTTATCAAAGAGGGACACCTATAGATGAAAATGTAAGC

GGGCCTATTATATGGGTTGAAGACACATTAACGGCATTACAACAATTGGCACAAGCTTACTTGAGACATGTAAACCCTAA

AGTAATTGCCGTCACAGGGTCTAATGGTAAAACAACGACTAAAGATATGATTGAAAGTGTATTGCATACCGAATTTAAAG

TTAAGAAAACGCAAGGTAATTACAATAATGAAATTGGTTTACCTTTAACTATTTTGGAATTAGATAATGATACTGAAATA

TCAATATTGGAGATGGGGATGTCAGGTTTCCATGAAATTGAATTTCTGTCAAACCTCGCTCAACCAGATATTGCAGTTAT

AACTAATATTGGTGAGTCACATATGCAAGATTTAGGTTCGCGCGAGGGGATTGCTAAAGCTAAATCTGAAATTACAATAG

GTCTAAAAGATAATGGTACGTTTATATATGATGGCGATGAACCATTATTGAAACCACATGTTAAAGAAGTTGAAAATGCA

AAATGTATTAGTATTGGTGTTGCTACTGATAATGCATTAGTTTGTTCTGTTGATGATAGAGATACTACAGGTATTTCATT

TACGATTAATAATAAAGAACATTACGATCTGCCAATATTAGGAAAGCATAATATGAAAAATGCGACGATTGCCATTGCGG

TTGGTCATGAATTAGGTTTGACATATAACACAATCTATCAAAATTTAAAAAATGTCAGCTTAACTGGTATGCGTATGGAA

CAACATACATTAGAAAATGATATTACTGTGATAAATGATGCCTATAATGCAAGTCCTACAAGTATGAGAGCAGCTATTGA

TACACTGAGTACTTTGACAGGGCGTCGCATTCTAATTTTAGGAGATGTTTTAGAATTAGGTGAAAATAGCAAAGAAATGC

ATATCGGTGTAGGTAATTATTTAGAAGAAAAGCATATAGATGTGTTGTATACGTTTGGTAATGAAGCGAAGTATATTTAT

GATTCGGGCCAGCAACATGTCGAAAAAGCACAACACTTCAATTCTAAAGACGATATGATAGAAGTTTTAATAAACGATTT

AAAAGCGCATGACCGTGTATTAGTTAAAGGATCACGTGGTATGAAATTAGAAGAAGTGGTAAATGCTTTAATTTCA

TABLE 1-continued

Nucleotide and Amino Acid Sequences of *S. aureus* Genes.

>HGS050 MurF (SEQ ID NO:26)

MINVTLKQIQSWIPCEIEDQFLNQEINGVTIDSRAISKNMLFIPFKGENVDGHRFVSKALQDGAGAAFYQRGTPIDENVS

GPIIWVEDTLTALQQLAQAYLRHVNPKVIAVTGSNGKTTTKDMIESVLHTEFKVKKTQGNYNNEIGLPLTILELDNDTEI

SILEMGMSGFHEIEFLSNLAQPDIAVITNIGESHMQDLGSREGIAKAKSEITIGLKDNGTFIYDGDEPLLKPHVKEVENA

KCISIGVATDNALVCSVDDRDTTGISFTINNKEHYDLPILGKHNMKNATIAIAVGHELGLTYNTIYQNLKNVSLTGMRME

QHTLENDITVINDAYNASPTSMRAAIDTLSTLTGRRILILGDVLELGENSKEMHIGVGNYLEEKHIDVLYTFGNEAKYIY

DSGQQHVEKAQHFNSKDDMIEVLINDLKAHDRVLVKGSRGMKLEEVVNALIS

>HGS052 Ribosomal Protein S8 (SEQ ID NO:27)

ATGACAATGACAGATCCAATCGCAGATATGCTTACTCGTGTAAGAAACGCAAACATGGTGCGTCACGAGAAGTTAGAATT

ACCTGCATCAAATATTAAAAAGAAATTGCTGAAATCTTAAAGAGTGAAGGTTTCATTAAAAATGTTGAATACGTAGAAG

ATGATAAACAAGGTGTACTTCGTTTATTCTTAAAAATATGGTCAAAACGATGAGCGTGTTATCACAGGATTAAAACGTATT

TCAAAACCAGGTTTACGTGTTTATGCAAAAGCTAGCGAAATGCCTAAAGTATTAAATGGTTTAGGTATTGCATTAGTATC

AACTTCTGAAGGTGTAATCACTGACAAAGAAGCAAGAAAACGTAATGTTGGTGGAGAAATTATCGCATACGTTTG

>HGS052 Ribosomal Protein S8 (SEQ ID NO:28)

MTMTDPIADMLTRVRNANMVRHEKLELPASNIKKEIAEILKSEGFIKNVEYVEDDKQGVLRLFLKYGQNDERVIT

GLKRISKPGLRVYAKASEMPKVLNGLGIALVSTSEGVITDKEARKRNVGGEIIAYVW

>HGS053 Ribosomal Protein S15 (SEQ ID NO:29)

ATGGCAATTTCACAAGAACGTAAAAACGAAATCATTAAAGAATACCGTGTACACGAAACTGATACTGGTTCACCAGAAGT

ACAAATCGCTGTACTTACTGCAGAAATCAACGCAGTAAACGAACACTTACGTACACACAAAAAAGACCACCATTCACGTC

GTGGATTATTAAAAATGGTAGGTCGTCGTAGACATTTATTAAACTACTTACGTAGTAAAGATATTCAACGTTACCGTGAA

TTAATTAAATCACTTGGCATCCGTCGT

>HGS053 Ribosomal Protein S15 (SEQ ID NO:30)

MAISQERKNEIIKEYRVHETDTGSPEVQIAVLTAEINAVNEHLRTHKKDHHSRRGLLKMVGRRRHLLNYLRSKDI

QRYRELIKSLGIRR

>HGS055 Ribosomal Protein S3 (SEQ ID NO:31)

TAAGGAGGGAATACTGTGGGTCAAAAAATTAATCCAATCGGACTTCGTGTTGGTATTATCCGTGATTGGGAAGCTAAATG

GTATGCTGAAAAAGACTTCGCTTCACTTTTACACGAAGATTTAAAAATCCGTAAATTTATTGATAATGAATTAAAAGAAG

CATCAGTTTCTCACGTAGAGATTGAACGTGCTGCAAACCGTATCAACATTGCAATTCATACTGGTAAACCTGGTATGGTA

ATTGGTAAAGGCGGTTCAGAAATCGAAAAATTACGCAACAAATTAAATGCGTTAACTGATAAAAAAGTACACATCAACGT

AATTGAAATCAAAAAAGTTGATCTTGACGCTCGTTTAGTAGCTGAAAACATCGCACGTCAATTAGAAAACCGTGCTTCAT

TCCGTCGTGTACAAAAACAAGCAATCACTAGAGCTATGAAACTTGGTGCTAAAGGTATCAAAACTCAAGTATCTGGTCGT

TTAGGCGGAGCTGACATCGCTCGTGCTGAACAATATTCAGAAGGAACTGTTCCACTTCATACGTTACGTGCTGACATCGA

TTATGCACACGCTGAAGCTGACACTACTTACGGTAAATTAGGCGTTAAAGTATGGATTTATCGTGGAGAAGTTCTTCCTA

CTAAGAACACTAGTGGAGGAGGAAAA

>HGS055 Ribosomal Protein S3 (SEQ ID NO:32)

VGQKINPIGLRVGIIRDWEAKWYAEKDFASLLHEDLKIRKFIDNELKEASVSHVEIERAANRINIAIHTGKPGMVIGKGG

SEIEKLRNKLNALTDKKVHINVIEIKKVDLDARLVAENIARQLENRASFRRVQKQAITRAMKLGAKGIKTQVSGRLGGAD

IARAEQYSEGTVPLHTLRADIDYAHAEADTTYGKLGVKVWIYRGEVLPTKNTSGGGK

TABLE 1-continued

Nucleotide and Amino Acid Sequences of S. aureus Genes.

>HGS056 Ribosomal Protein S5 (SEQ ID NO:33)

ATGGCTCGTAGAGAAGAAGAGACGAAAGAATTTGAAGAACGCGTTGTTACAATCAACCGTGTAGCAAAAGTTGTAAAAGG

TGGTCGTCGTTTCCGTTTCACTGCATTAGTTGTAGTTGGAGACAAAAATGGTCGTGTAGGTTTCGGTACTGGTAAAGCTC

AAGAGGTACCAGAAGCAATCAAAAAAGCTGTTGAAGCAGCTAAAAAAGATTTAGTAGTTGTTCCACGTGTTGAAGGTACA

ACTCCACACACAATTACTGGCCGTTACGGTTCAGGAAGCGTATTTATGAAACCGGCTGCACCTGGTACAGGAGTTATCGC

TGGTGGTCCTGTTCGTGCCGTACTTGAATTAGCAGGTATCACTGATATCTTAAGTAAATCATTAGGATCAAACACACCAA

TCAACATGGTTCGTGCTACAATCGATGGTTTACAAAACCTTAAAAATGCTGAAGATGTTGCGAAATTACGTGGCAAAACA

GTAGAAGAATTATACAAT

>HGS056 Ribosomal Protein S5 (SEQ ID NO:34)

MARREEETKEFEERVVTINRVAKVVKGGRRFRFTALVVVGDKNGRVGFGTGKAQEVPEAIKKAVEAAKKDLVVVP

RVEGTTPHTITGRYGSGSVFMKPAAPGTGVIAGGPVRAVLELAGITDILSKSLGSNTPINMVRATIDGLQNLKNA

EDVAKLRGKTVEELYN

>HGS057 Ribosomal Protein S9 (SEQ ID NO:35)

ATGGCACAAGTTGAATATAGAGGCACAGGCCGTCGTAAAAACTCAGTAGCACGTGTACGTTTAGTACCAGGTGAAGGTAA

CATCACAGTTAATAACCGTGACGTACGCGAATACTTACCATTCGAATCATTAATTTTAGACTTAAACCAACCATTTGATG

TAACTGAAACTAAAGGTAACTATGATGTTTTAGTTAACGTTCATGGTGGTGGTTTCACTGGACAAGCTCAAGCTATCCGT

CACGGAATCGCTCGTGCATTATTAGAAGCAGATCCTGAATACAGAGGTTCTTTAAAACGCGCTGGATTACTTACTCGTGA

CCCACGTATGAAAGAACATAAAAAACCAGGTCTTAAAGCAGCTCGTCGTTCACCTCAATTCTCAAAACGT

HGS057 Ribosomal Protein S9 (SEQ ID NO:36)

MAQVEYRGTGRRKNSVARVRLVPGEGNITVNNRDVREYLPFESLILDLNQPFDVTETKGNYDVLVNVHGGGFTGQ

AQAIRHGIARALLEADPEYRGSLKRAGLLTRDPRMKEHKKPGLKAARRSPQFSKR

>HGS058 Ribosomal Protein S10 (SEQ ID NO:37)

ATGGCAAAACAAAAAATCAGAATCAGATTAAAGGCTTATGATCACCGCGTAATTGATCAATCAGCAGAGAAGATTGTAGA

AACAGCGAAACGTTCTGGTGCAGATGTTTCTGGACCAATTCCGTTACCAACTGAGAAATCAGTTTACACAATCATCCGTG

CCGTGCATAAGTATAAAGATTCACGTGAACAATTCGAACAACGTACACACAAACGTTTAATCGATATTGTAAACCCAACA

CCAAAAACAGTTGACGCTTTAATGGGCTTAAACTTACCATCTGGTGTAGACATCGAAATCAAATTA

>HGS058 Ribosomal Protein S10 (SEQ ID NO:38)

MAKQKIRIRLKAYDHRVIDQSAEKIVETAKRSGADVSGPIPLPTEKSVYTIIRAVHKYKDSREOFEORTHKRLID

IVNPTPKTVDALMGLNLPSGVDIEIKL

>HGS059 Ribosomal Protein S14 (SEQ ID NO:39)

ATGGCTAAGAAATCTAAAATAGCAAAAGAGAGAAAAAGAGAAGAGTTAGTAAATAAATATTACGAATTACGTAAAGAGTT

AAAAGCAAAAGGTGATTACGAAGCGTTAAGAAAATTACCAAGAGATTCATCACCTACACGTTTAACTAGAAGATGTAAAG

TAACTGGAAGACCTAGAGGTGTATTACGTAAATTTGAAATGTCTCGTATTGCGTTTAGAGAACATGCGCACAAAGGACAA

ATTCCAGGTGTTAAAAAATCAAGTTGG

>HGS059 Ribosomal Protein S14 (SEQ ID NO:40)

MAKKSKIAKERKREELVNKYYELRKELKAKGDYEALRKLPRDSSPTRLTRRCKVTGRPRGVLRKFEMSRIAFREH

AHKGQIPGVKKSSW

>HGS060 Ribosomal Protein S19 (SEQ ID NO:41)

ATGGCTCGTAGTATTAAAAAAGGACCTTTCGTCGATGAGCATTTAATGAAAAAAGTTGAAGCTCAAGAAGGAAGCGAAAA

TABLE 1-continued

Nucleotide and Amino Acid Sequences of *S. aureus* Genes.

GAAACAAGTAATCAAAACATGGTCACGTCGTTCTACAATTTTCCCTAATTTCATCGGACATACTTTTGCAGTATACGACG

GACGTAAACACGTACCTGTATATGTAACTGAAGATATGGTAGGTCATAAATTAGGTGAGTTTGCTCCTACTCGTACATTC

AAAGGACACGTTGCAGACGACAAGAAAACAAGAAGA

>HGS060 Ribosomal Protein S19 (SEQ ID NO:42)

MARSIKKGPFVDEHLMKKVEAQEGSEKKQVIKTWSRRSTIFPNFIGHTFAVYDGRKHVPVYVTEDMVGHKLGEFA

PTRTFKGHVADDKKTRR

>HGS062 Ribosomal Protein S14 Homolog (SEQ ID NO:43)

ATGGCTAAAACTTCAATGGTTGCTAAGCAACAAAAAAAACAAAAATATGCAGTTCGTGAATACACTCGTTGTGAACGTTG

TGGCCGTCCACATTCTGTATATCGTAAATTTAAATTATGCCGTATTTGTTTCCGTGAATTAGCTTACAAAGGCCAAATCC

CTGGCGTTCGTAAAGCTAGCTGG

>HGS062 Ribosomal Protein S14 Homolog (SEQ ID NO:44)

MAKTSMVAKQQKKQKYAVREYTRCERCGRPHSVYRKFKLCRICFRELAYKGQIPGVRKASW

>HGS064 YycF (SEQ ID NO:45)

ATGGCTAGAAAAGTTGTTGTAGTTGATGATGAAAAACCGATTGCTGATATTTTAGAATTTAACTTAAAAAAAGAAGGATA

CGATGTGTACTGTGCATACGATGGTAATGATGCAGTCGACTTAATTTATGAAGAAGAACCAGACATCGTATTACTAGATA

TCATGTTACCTGGTCGTGATGGTATGGAAGTATGTCGTGAAGTGCGCAAAAAATACGAAATGCCAATAATAATGCTTACT

GCTAAAGATTCAGAAATTGATAAAGTGCTTGGTTTAGAACTAGGTGCAGATGACTATGTAACGAAACCGTTTAGTACGCG

TGAATTAATCGCACGTGTGAAAGCGAACTTACGTCGTCATTACTCACAACCAGCACAAGACACTGGAAATGTAACGAATG

AAATCACAATTAAAGATATTGTGATTTATCCAGACGCATATTCTATTAAAAAACGTGGCGAAGATATTGAATTAACACAT

CGTGAATTTGAATTGTTCCATTATTTATCAAAACATATGGGACAAGTAATGACACGTGAACATTTATTACAAACAGTATG

GGGCTATGATTACTTTGGCGATGTACGTACGGTCGATGTAACGATTCGTCGTTTACGTGAAAAGATTGAAGATGATCCGT

CACATCCTGAATATATTGTGACGCGTAGAGGCGTTGGATATTTCCTCCAACAACATGAG

>HGS064 YycF (SEQ ID NO:46)

MARKVVVVDDEKPIADILEFNLKKEGYDVYCAYDGNDAVDLIYEEEPDIVLLDIMLPGRDGMEVCREVRKKYEMP

IIMLTAKDSEIDKVLGLELGADDYVTKPFSTRELIARVKANLRRHYSQPAQDTGNVTNEITIKDIVIYPDAYSIK

KRGEDIELTHREFELFHYLSKHMGQVMTREHLLQTVWGYDYFGDVRTVDVTIRRLREKIEDDPSHPEYIVTRRGV

GYFLQQHE

>HGS063 (SEQ ID NO:47)

ATGCCATTATTTTTACAACCAATTTTAAAAACAAAATTATGGGGCGGTCAACGTCTAAGTGAGTTTGGATATCAATTAGA

CAATGATACAACTGGGGGAATGTTGGTGTGTGTCAGCACATCCAAATGGTACGAGCGAGATTATTAATGGACCATATCAA

GGTCAAACATTAGACCGTATTTGGTCAGAACATCGTGAATTGTTTGGTGATTTCCCAAGCAAAGATTTTCCGCTTCTAAC

TAAAATAGTGGATGCAAGAGAATCACTTTCTATTCATGTGCACCCTGATAATTCTTATGCTTATGAGCATGAAAACGGGC

AATATGGCAAATCTGAATGTTGGTATATTATAGATGCAGAAGAAGATGCAGAAATAGTTATAGGGACATTAGCAGAGTCT

AGAGAAGAAGTTGCGAATCATGTTCAACACGGAACGATAGAGTCGATACTTAGATATATTAAAGTAAAACCTGGAGAATT

CTATTTTATTCCAGCAGGAACAGTWCATACTATTTCTTCAGGAATATTAGCATACGAAACGATGCAATCGTCAGACATTA

CATATAGACTTTATGATTTCAATCGTCAAGATAATCAATATAATGATAGACCGTTAAATATTGAAAAAGCTTTAGACGTT

ATTCAGTACAATGCACCATTACCTAATATTTTGCCTGAAAGCGAAATTATTGAAAACCATAAGTGTACACACATTGTATC

GAATGATTTCTTTACATTGGTTAAATGGGAAATTTCTGGCACGTTAAATTATATGAAGCCTAGAGAGTTCTGTTTAGTTA

CAGTGTTGGAAGGCGAAGGGCAAATGATTGTCTATGGTGAAATTTTCAAACTGACTACTGGTACAAACTTTATTTTGACT

TCTGAAGATTTGGATAGTGTCTTTGAAGGTGATTTCACATTGATGATTAGCTATGTG

>HGS063 (SEQ ID NO:48)

MPLFLQPILKTKLWGGQRLSEFGYQLDNDTTGECWCVSAHPNGTSEIINGPYQGQTLDRIWSEHRELFGDFPSKD

FPLLTKIVDARESLSIHVHPDNSYAYEHENGQYGKSECWYIIDAEEDAEIVIGTLAESREEVANHVOHGTIESIL

RYIKVKPGEFYFIPAGTVHTISSGILAYETMQSSDITYRLYDFNRQDNQYNDRPLNIEKALDVIQYNAPLPNILP

ESEIIENHKCTHIVSNDFFTLVKWEISGTLNYMKPREFCLVTVLEGEGQMIVDGEIFKLTTGTNFILTSEDLDSV

FEGDFTLMISYV

>HGS065 (SEQ ID NO:49)

ATGGCTGTATTATATTTAGTGGGCACACCAATTGGTAATTTAGCAGATATTACTTATAGAGCAGTTGATGTATTGAAACG

TGTTGATATGATTGCTTGTGAAGACACTAGAGTAACTAGTAAACTGTGTAATCATTATGATATTCCAACTCCATTAAAGT

CATATCACGAACATAACAAGGATAAGCAGACTGCTTTTATCATTGAACAGTTAGAATTAGGTCTTGACGTTGCGCTCGTA

TCTGATGCTGGATTGCCCTTAATTAGTGATCCTGGATACGAATTAGTAGTGGCAGCCAGAGAAGCTAATATTAAAGTAGA

GACTGTGCCTGGACCTAATGCTGGGCTGACGGCTTTGATGGCTAGTGGATTACCTTCATATGTATATACATTTTTAGGAT

TTTTGCCACGAAAAGAGAAAGAAAAAAGTGCTGTATTAGAGCAACGTATGCATGAAAATAGCACATTAATTATATACGAA

TCACCGCATCGTGTGACAGATACATTAAAAACAATTGCAAAGATAGATGCAACACGACAAGTATCACTAGGGCGTGAATT

AACTAAGAAGTTCGAACAAATTGTAACTGATGATGTAACACAATTACAAGCATTGATTCAGCAAGGCGATGTACCATTGA

AAGGCGAATTCGTTATCTTAATTGAAGGTGCTAAAGCGAACAATGAGATATCGTGGTTTGATGATTTATCTATCAATGAG

CATGTTGATCATTATATTCAAACTTCACAGATGAAACCAAAACAAGCTATTAAAAAAGTTGCTGAAGAACGACAACTTAA

AACGAATGAAGTATATAATATTTATCATCAAATAAGT

>HGS065 (SEQ ID NO:50)

MAVLYLVGTPIGNLADITYRAVDVLKRVDMIACEDTRVTSKLCNHYDIPTPLKSYHEHNKDKQTAFIIEQLELGL

DVALVSDAGLPLISDPGYELVVAAREANIKVETVPGPNAGLTALMASGLPSYVYTFLGFLPRKEKEKSAVLEQRM

HENSTLIIYESPHRVTDTLKTIAKIDATRQVSLGRELTKKFEQIVTDDVTQLQALIQQGDVPLKGEFVILIEGAK

ANNEISWFDDLSINEHVDHYIQTSQMKPKQAIKKVAEERQLKTNEVYNIYHQIS

>HGS066 (SEQ ID NO:51)

ATGAAATTTGGAAAAACAATCGCAGTAGTATTAGCATCAGTGTCTTGCTTGCAGGATGTACTACGGATAAAAAAGAAAT

TAAGGCATATTTAAAGCAAGTGGATAAAATTAAAGATGATGAAGAACCAATTAAAACTGTTGGTAAGAAAATTGCTGAAT

TAGATGAGAAAAAGAAAAAATTAACTGAAGATGTCAATAGTAAAGATACAGCAGTTCGCGGTAAAGCAGTAAAGGATTTA

ATTAAAAATGCCGATGATCGTCTAAAGGAATTTGAAAAAGAAGAAGACGCAATTAAGAAGTCTGAACAAGACTTTAAGAA

AGCAAAAAGTCACGTTGATAACATTGATAATGATGTTAAACGTAAAGAAGTAAAACAATTAGATGATGTATTAAAAGAAA

AATATAAGTTACACAGTGATTACGCGAAAGCATATAAAAAGGCTGTAAACTCAGAGAAAACATTATTTAAATATTTAAAT

CAAAATGACGCGACACAACAAGGTGTTAACGAAAAATCAWAAGCAATAGAACAGAACTATAAAAAGTTAAAAGAAGTATC

AGATAAGTATACAAAAGTACTAAATAAGGTTGGTAAAGAAAAGCAAGACGTTGATCAATTTAAA

>HGS066 (SEQ ID NO:52)

MKFGKTIAVVLASSVLLAGCTTDKKEIKAYLKQVDKIKDDEEPIKTVGKKIAELDEKKKKLTEDVNSKDTAVRGK

AVKDLIKNADDRLKEFEKEEDAIKKSEQDFKKAKSHVDNIDNDVKRKEVKQLDDVLKEKYKLHSDYAKAYKKAVN

SEKTLFKYLNQNDATQQGVNEKSXAIEQNYKKLKEVSDKYTKVLNKVGKEKQDVDQFK

TABLE 1-continued

Nucleotide and Amino Acid Sequences of *S. aureus* Genes.

>HGS067 (SEQ ID NO:53)

ATCGAGGACAGAATATTGTTAAAGTATGAACATATTGCTAAGCAGCTTAATGCGTTTATACATCAATCTAATTTCAAACC

CGGTGATAAATTGCCAAGCGTGACGCAATTAAAAGAACGTTATCAAGTAAGTAAGAGTACTATCATTAAAGCATTAGGCT

TATTGGAACAAGATGGTTTGATCTATCAAGCACAAGGCAGTGGTATTTATGTGAGAAATATTGCTGATGCCAATCGTATC

AACGTCTTTAAGACTAATGGTTTCTCTAAAAGTTTAGGTGAACACCGAATGACAAGTAAGGTACTTGTTTTTAAGGAGAT

TGCAACGCCACCTAAATCTGTACAAGATGAGCTCCAATTAAATGCAGATGATACCGTCTACTATTTAGAGCGATTAAGAT

TCGTGGACGATGATGTTTTATGTATCGAATATTCTTATTATCATAAAGAAATCGTGAAATATTTAAATGATGATATTGCT

AAGGGCTCTATCTTCGACTATTTAGAATCAAACATGAAACTTCGTATTGGTTTTTCAGATATTTTCTTTAATGTAGATCA

ACTCACTTCAAGTGAAGCTTCATTACTACAATTGTCTACAGGTGAACCATGTTTACGTTACCACCAGACTTTTTATACAA

TGACTGGCAAACCCTTTGATTCATCTGACATCGTATTTCATTATCGTCATGCACAGTTTTATATTCCTAGTAAAAAG

>HGS067 (SEQ ID NO:54)

IEDRILLKYEHIAKQLNAFIHQSNFKPGDKLPSVTQLKERYQVSKSTIIKALGLLEQDGLIYQAQGSGIYVRNIA

DANRINVFKTNGFSKSLGEHRMTSKVLVFKEIATPPKSVQDELQLNADDTVYYLERLRFVDDDVLCIEYSYYHKE

IVKYLNDDIAKGSIFDYLESNMKLRIGFSDIFFNVDQLTSSEASLLQLSTGEPCLRYHQTFYTMTGKPFDSSDIV

FHYRHAQFYIPSKK

>HGS068 (SEQ ID NO:55)

ATGACTGTAGAATGGTTAGCAGAACAATTAAAAGAACATAATATTCAATTAACTGAGACTCAAAAACAACAGTTTCAAAC

ATATTATCGTTTACTTGTTGAATGGAATGAAAAGATGAATTTGACAAGTATTACAGATGAACACGATGTATATTTGAAAC

ATTTTTATGATTCCATTGCACCTAGTTTTTATTTTGATTTTAATCAGCCTATAAGTATATGTGATGTAGGCGCTGGAGCT

GGTTTTCCAAGTATTCCGTTAAAAATAATGTTTCCGCAGTTAAAAGTGACGATTGTTGATTCATTAAATAAGCGTATTCA

ATTTTTAAACCATTTAGCGTCAGAATTACAATTACAGGATGTCAGCTTTATACACGATAGAGCAGAAACATTTGGTAAGG

GTGTCTACAGGGAGTCTTATGATGTTGTTACTGCAAGAGCAGTAGCTAGATTATCCGTGTTAAGTGAATTGTGTTTACCG

CTAGTTAAAAAAGGTGGACAGTTTGTTGCATTAAAAATCTTCAAAAGGTGAAGAAGAATTAGAAGAAGCAAAATTTGCAAT

TAGTGTGTTAGGTGGTAATGTTACAGAAACACATACCTTTGAATTGCCAGAAGATGCTGGAGAGCGCCAGATGTTCATTA

TTGATAAAAAAAGACGACGCCGAAAAAGTATCCAAGAAAACCAGGGACGCTAATAAGACTCCTTTACTTGAAAAA

>HGS068 (SEQ ID NO:56)

MTVEWLAEQLKEHNIQLTETQKQQFQTYYRLLVEWNEKMNLTSITDEHDVYLKHFYDSIAPSFYFDFNQPISICD

VGAGAGFPSIPLKIMFPQLKVTIVDSLNKRIQFLNHLASELQLQDVSFIHDRAETFGKGVYRESYDVVTARAVAR

LSVLSELCLPLVKKGGQFVALKSSKGEEELEEAKFAISVLGGNVTETHTFELPEDAGERQMFIIDKKRQTPKKYP

RKPGTPNKTPLLEK

>HGS069 (SEQ ID NO:57)

ATGGCACATACCATTACGATTGTTGGCTTAGGAAACTATGGCATTGATGATTTGCCGCTAGGGATATATAAATTTTTAAA

GACACAAGATAAAGTTTATGCAAGAACGTTAGATCATCCAGTTATAGAATCATTGCAAGATGAATTAACATTTCAGAGTT

TTGACCATGTTTATGAAGCACATAACCAATTTGAAGATGTCTATATTGATATTGTGGCGCAATTGGTTGAAGCTGCTAAT

GAAAAAGATATTGTCTATGCGGTTCCGGGTCATCCTAGAGTTGCTGAGACAACTACAGTGAAATTACTGGCTTTAGCAAA

GGACAATACTGATATAGATGTGAAAGTTTTAGGTGGGAAAAGCTTTATTGATGATGTGTTTGAAGCAGTTAATGTAGATC

CAAATGATGGCTTCACACTGTTAGATGCGACATCATTACAAGAAGTAACACTTAATGTTAGAACGCATACATTGATTACG

CAAGTTTATAGTGCAATGGTTGCTGCTAATTTGAAAATCACTTTAATGGAACGATATCCTGATGATTACCCTGTTCAAAT

TGTCACTGGTGCACGAAGCGATGGTGCGGATAACGTTGTGACATGCCCATTATATGAATTGGATCATGATGAAAATGCAT

TABLE 1-continued

Nucleotide and Amino Acid Sequences of S. aureus Genes.

TCAATAATTTGACGAGTGTATTCGTACCAAAAATCATAACATCGACATATTTGTATCATGACTTTGATTTTGCAACGGAA

GTGATTGATACTTTAGTTGATGAAGATAAAGGTTGTCCATGGGATAAAGTGCAAACGCATGAAACGCTAAAGCGTTATTT

ACTTGAAGAAACATTTGAATTGTTCGAAGCTATTGACAATGAAGATGATTGGCATATGATTGAAGAACTAGGAGATATTT

TATTACAAGTGTTATTGCATACTAGTATTGGTAAAAAAGAAGGGTATATCGACATTAAAGAAGTGATTACAAGTCTTAAT

GCTAAAATGATTCGTAGACACCCACACATATTTGGTGATGCCAATGCTGAAACTATCGATGACTTAAAAGAAATTTGGTC

TAAGGCGAAAGATGCTGAAGGTAAACAGCCAAGAGTTAAATTTGAAAAAGTATTTGCAGAGCATTTTTTAAATTTATATG

AGAAGACGAAGGATAAGTCATTTGATGAGGCCGCGTTAAAGCAGTGGCTAGAAAAAGGGGAGAGTAATACA

>HGS069 (SEQ ID NO:58)

MAHTITIVGLGNYGIDDLPLGIYKFLKTQDKVYARTLDHPVIESLQDELTFQSFDHVYEAHNQFEDVYIDIVAQL

VEAANEKDIVYAVPGHPRVAETTTVKLLALAKDNTDIDVKVLGGKSFIDDVFEAVNVDPNDGFTLLDATSLQEVT

LNVRTHTLITQVYSAMVAANLKITLMERYPDDYPVQIVTGARSDGADNVVTCPLYELDHDENAFNNLTSVFVPKI

ITSTYLYHDFDFATEVIDTLVDEDKGCPWDKVQTHXTLKRYLLEETFELFEAIDNEDDWHMIEELGDILLQVLLH

TSIGKKEGYIDIKEVITSLNAKMIRRHPHIFGDANAETIDDLKEIWSKAKDAEGKQPRVKFEKVFAEHFLNLYEK

TKDKSFDEAALKQWLEKGESNT

>HGS070 (SEQ ID NO:59)

AATGTAAATCATTCTAATAAAACGACAACTGTGTCTTCTTTACTTGTATATGTTACATATATTCACGATAGAGAGGATAA

GAAAATGGCTCAAATTTCTAATATAAACGTGTAGTTTTGAAACTAAGTGGTGAAGCGTTAGCTGGAAAAAAGGAGATTTG

GCATAAATCCAGTAATTATTAAAAGTGTTGCTGAGCAAGTGGCTGAAGTTGCTAAAATGGACTGTGAAATCGCAGTAATC

GTTGGTGGCGGAAACATTTGGAGAGGTAAAACAGGTAGTGACTTAGGTATGGACCGTGGAACTGCTGATTACATGGGTAT

GCTTGCAACTGTAATGAATGCCTTAGCATTACAAGATAGTTTAGAACAATTGGATTGTGATACACGAGTATTAACATCTA

TTGAAATGAAGCAAGTGGCTGAACCTTATATTCGTCGTCGTGCAATTAGACACTTAGAAAAGAAACGCGTAGTTATTTTT

GCTGCAGGTATTGGAAACCCATACTTCTCTACAGATACTACAGCGGCATTACGTGCTGCAGAAGTTGAAGCAGATGTTAT

TTTAATGGGCAAAAATAATGTAGATGGTGTATATTCTGCAGATCCTAAAGTAAACAAAGATGCGGTAAAATATGAATATT

TAACGCATATTCAAATGCTTCAAGAAGGTTTACAAGTAATGGATTCAACAGCATCCTCATTCTGTATGGATAATAACATT

CCGTTAACTGTTTTCTCTATTATGGAAGAAGGAAATATTAAACGTGCTGTTATGGGTGAAAAGATAGGTACGTTAATTAC

AAAA

>HGS070 (SEQ ID NO:60)

NVNHSNKTTTVSSLLVYVTYIHDREDKKMAQISKYKRVVLKLSGEALAGEKGFGINPVIIKSVAEQVAEVAKMDC

EIAVIVGGGNIWRGKTGSDLGMDRGTADYMGMLATVMNALALQDSLEQLDCDTRVLTSIEMKQVAEPYIRRRAIR

HLEKKRVVIFAAGIGNPYFSTDTTAALRAAEVEADVILMGKNNVDGVYSADPKVNKDAVKYEHLTHIQMLQEGLQ

VMDSTASSFCMDNNIPLTVFSIMEEGNIKRAVMGEKIGTLITK

HGS071 D-alanyl-alanine ligase( Dd1A) (SEQ ID NO:61)

ATGACAAAAGAAAATATTTGTATCGTTTTTGGAGGGAAAAGTGCAGAACACGAAGTATCGATTCTGACAGCACAAAATGT

ATTAAATGCAATAGATAAAGACAAATATCATGTTGATATCATTTATATTACCAATGATGGTGATTGGAGAAAGCAAAATA

ATATTACAGCTGAAATTAAATCTACTGATGAGCTTCATTTAGAAAATGGAGAGGCGCTTGAGATTTCACAGCTATTGAAA

GAAAGTAGTTCAGGACAACCATACGATGCAGTATTCCCATTATTACATGGTCCTAATGGTGAAGATGGCAGCATTCAAGG

GCTTTTTTGAAGTTTTGGATGTACCATATGTAGGAAATGGTGTATTGTCAGCTGCAAGTTCTATGGACAAACTTGTAATGA

AACAATTATTTGAACATCGAGGGTTACCACAGTTACCTTATATTAGTTTCTTACGTTCTGAATATGAAAAATATGAACAT

TABLE 1-continued

Nucleotide and Amino Acid Sequences of S. aureus Genes.

AACATTTTAAAATTAGTAAATGATAAATTAAATTACCCAGTCTTTGTTAAACCTGCTAACTTAGGGTCAAGTGTAGGTAT

CAGTAAATGTAATAATGAAGCGGAACTTAAAGAAGGTATTAAAGAAGCATTCCAATTTGACCGTAAGCTTGTTATAGAAC

AAGGCGTTAACGCACGTGAAATTGAAGTAGCAGTTTTAGGAAATGACTATCCTGAAGCGACATGGCCAGGTGAAGTCGTA

AAAGATGTCGCGTTTTACGATTACAAATCAAAATATAAAGATGGTAAGGTTCAATTACAAATTCCAGCTGACTTAGACGA

AGATGTTCAATTAACGCTTAGAAATATGGCATTAGAGGCATTCAAAGCGACAGATTGTTCTGGTTTAGTCCGTGCTGATT

TCTTTGTAACAGAAGCAACCAAATATATATTAATGAAACAAATGCAATGCCTGGATTTACGGCTTTCAGTATGTATCCA

AAGTTATGGGAAAATATGGGCTTATCTTATCCAGAATTGATTACAAAACTTATCGAGCTTGCTAAAGAACGTCACCAGGA

TAAACAGAAAAATAAATACAAAATTGAC

>HGS071 D-alanyl-alanine ligase (DdlA) (SEQ ID NO:62)

MTKENICIVFGGKSAEHEVSILTAQNVLNAIDKDKYHVDIIYITNDGDWRKQNNITAEIKSTDELHLENGEALEI

SQLLKESSSGQPYDAVFPLLHGPNGEDGTIQGLFEVLDVPYVGNGVLSAASSMDKLVMKQLFEHRGLPQLPYISF

LRSEYEKYEHNILKLVNDKLNYPVFVKPANLGSSVGISKCNNEAELKEGIKEAFQFDRKLVIEQGVNAREIEVAV

LGNDYPEATWPGEVVKDVAFYDYKSKYKDGKVQLQIPADLDEDVQLTLRNMALEAFKATDCSGLVRADFFVTEDN

QIYINETNAMPGFTAFSMYPKLWENMGLSYPELITKLIELAKERHQDKQKNKYKID

>HGS072 Farnesyl diphosphatesynthase (IspA) (SEQ ID NO:63)

ATGACGAATCTACCGATGAATAAATTAATAGATGAAGTCAATAATGAATTATCGGTTGCGATAAATAAATCAGTAATGGA

TACTCAGCTAGAAGAAAGTATGTTGTATTCATTAAATGCTGGAGGTAAACGCATCCGACCAGTTCTGTTATTACTCACTT

TAGATTCACTAAATACCGAGTATGAGTTAGGTATGAAGAGCGCAATTGCACTAGAAATGATTCATACATATTCACTTATT

CATGATGACCTACCAGCGATGGATAATGATGATTATCGACGAGGAAAATTAACAAATCATAAAGTATATGGTGAGTGGAC

TGCGATATTAGCAGGTGATGCTTTATTAACTAAAGCATTTGAACTTATTTCAAGTGATGATAGATTAACTGATGAAGTAA

AAATAAAAGTTCTACAACGGCTGTCAATAGCAAGTGGTCATGTTGGAATGGTCGGCGGTCAAATGTTAGATATGCAAAGC

GAAGGCCAACCAATTGATCTTGAAACTTTGGAAATGATACACAAAACAAAAACAGGAGCATTATTAACTTTTGCGGTTAT

GAGTGCAGCAGATATCGCTAATGTCGATGATACAACTAAAGAACATTTAGAAAGTTATAGTTATCATTTAGGTATGATGT

TCCAGATTAAAGATGATTTATTAGACTGCTATGGTGATGAAGCAAACTTAGGTAAAAAAGTGGGCAGCGATCTTGAAAAT

AATAAAAGTACGTACGTGAGTTTATTAGGGAAAGATGGCGCAGAAGATAAATTGACTTATCATAGAGACGCAGCAGTGGA

TGAACTAACGCAAATTGATGAACAATTCAATACAAAACACTTATTAGAAATCGTTGATTTA

>HGS072 Farnesyl diphosphate synthase (IspA) (SEQ ID NO:64)

MTNLPMNKLIDEVNNELSVAINKSVMDTQLEESMLYSLNAGGKRIRPVLLLLTLDSLNTEYELGMKSAIALEMIH

TYSLIHDDLPAMDNDDYRRGKLTNHKVYGEWTAILAGDALLTKAFELISSDDRLTDEVKIKVLQRLSIASGHVGM

VGGQMLDMQSEGQPIDLETLEMIHKTKTGALLTFAVMSAADIANVDDTTKEHLESYSYHLGMMFQIKDDLLDCYG

DEAKLGKKVGSDLENNKSTYVSLLGKDGAEDKLTYHRDAAVDELTQIDEQFNTKHLLEIVDL

>HGS073 Diphosphate Synthase (IspB) (SEQ ID NO:65)

TTTGTTATTCTGAGTAGCCAATTTGGCAAAGATGAACAAACGTCTGAACAAACGTATCAAGTTGCAGTCGCATTAGAGTT

AATTCATATGGCAACACTTGTTCATGATGACGTTATTGATAAAGCGACAAGCGTCGAGGCAAGTTAACCATATCAAAGA

AATGGGATCAGACAACTGCTATTTTAACTGGGAATTTTTTATTGGCATTAGGACTTGAACACTTAATGGCCGTTAAAGAT

AATCGTGTACATCAATTGATATCTGAATCTATCGTTGATGTTTGTAGAGGGGAACTTTTCCAATTTCAAGACCAATTTAA

CAGTCAACAGACAATTATTAATTATTTACGACGTATCAATCGCAAAACAGCACTGTTAATTCAAATATCAACTGAAGTTG

GTGCAATTACTTCTCAATCTGATAAAGAGACTGTACGAAAATTGAAAATGATTGGTCATTATATAGGTATGAGCTTCCAA

ATCATTGATGATGTATTAGACTTCACAAGTACCGAAAAGAAATTAGGTAAGCCGGTCGGAAGTGATTTGCTTAATGGTCA

TABLE 1-continued

Nucleotide and Amino Acid Sequences of *S. aureus* Genes.

TATTACGTTACCGATtTTATTAGAAATGCGTAAAAATCCAGACTTCAAATTGAAAATCGAACAGTTACGTCGTGATAGTG

AACGCAAAGAATTTGAAGAATGTATCCAAATCATTAGAAAATCTGACAGCATCGATGAGGCTAAGGCAGTAAGTTCGAAG

TATTTAAGTAAAGCyTTGAATTTGATTTCyGAGTTACCAGATGGACATCCGAGATCACTACyTTTAAGTTTGACGAAAAA

AATGGGTTCAAnAAACACG

>HGS073 Diphosphate Synthase (IspB) (SEQ ID NO:66)

FVILSSQFGKDEQTSEQTYQVAVALELIHMATLVHDDVIDKSDKRRGKLTISKKWDQTTAILTGNFLLALGLEHL

MAVKDNRVHQLISESIVDVCRGELFQFQDQFNSQQTIINYLRRINRKTALLIQISTEVGAITSQSDKETVRKLKM

IGHYIGMSFQIIDDVLDFTSTEKKLGKPVGSDLLNGHITLPILLEMRKNPDFKLKIEQLRRDSERKEFEECIQII

RKSDSIDEAKAVSSKYLSKALNLISELPDGHPRSLXLSLTKKMGSXNT

>HGS074 Undecaprenyl Pyrophosphate Synthetase (UppS) (SEQ ID NO:67)

GTAAATTATATTATGAATTTGCCTGTCAATTTCTTAAAGACATTCTTACCGGAACTAATTGAAAAAAATGTCAAAGTTGA

AACAATTGGATTTACTGATAAGTTGCCAAAATCAACGATAGAAGCAATTAATAATGCYmAAGAAAAGACAGCTAATAATA

CCGGCTTAAAATTAATATTTGCAATTAATTATGGTGGCAGAGCAGAACTTGTTCATAGTATTAAAAATATGTTTGACGAG

CTTCATCAACAAGGTTTAAATAGTGATATCATAGATGAAACATATATAAACAATCATTTAATGACAAAAGACTATCCTGA

TCCAGAGTTGTTAATTCGTACTTCAGGAGAACAAAGAATAAGTAATTTCTTGATTTGGCAAGTTTCGTATAGTGAATTTA

TCTTTAATCAAAAATTATGGCCTGACTTTGACGAAGATGAATTAATTAAATGTATAAAAATTTATCAGTCACGTCAAAGA

CGCTTTGGCGGATTGAGTGAGGAG

>HGS074 Undecaprenyl Pyrophosphate Synthetase (UppS) (SEQ ID NO:68)

VNYIMNLPVNFLKTFLPELIEKNVKVETIGFTDKLPKSTIEAINNAXEKTANNTGLKLIFAINYGGRAELVHSIK

NMFDELHQQGLNSDIIDETYINNHLMTKDYPDPELLIRTSGEQRISNFLIWQVSYSEFIFNQKLWPDFDEDELIK

CIKIYQSRQRRFGGLSEE

>HGS075 YycG (SEQ ID NO:69)

ATGAAGTGGCTAAAACAACTACAATCCCTTCATACTAAATTTGTAATTGTTTATGTATTACTGATTATCATTGGTATGCA

AATTATCGGGTTATATTTTACAAATAACCTTGAAAAAGAGCTGCTTGATAATTTTAAGAAGAATATTACGCAGTACGCGA

AACAATTAGAAATTAGTATTGAAAAAGTATATGACGAAAAGGGCTCCGTAAATGCACAAAAAGATATTCAAAATTTATTA

AGTGAGTATGCCAACCGTCAAGAAATTGGAGAAATTCGTTTTATAGATAAAGACCAAATTATTATTGCGACGACGAAGCA

GTCTAACCGTAGTCTAATCAATCAAAAAGCGAATGATAGTTCTGTCCAAAAAGCACTATCACTAGGACAATCAAACGATC

ATTTAATTTTAAAAGATTATGGCGGTGGTAAGGACCGTGTCTGGGTATATAATATCCCAGTTAAAGTCGATAAAAAGGTA

ATTGGTAATATTTATATCGAATCAAAAATTAATGACGTTTATAACCAATTAAATAATATAAATCAAATATTCATTGTTGG

TACAGCTATTTCATTATTAATCACAGTCATCCTAGGATTCTTTATAGCGCGAACGATTACCAAACCAATCACCGATATGC

GTAACCAGACGGTCGAAATGTCCaGAGGTAACTATACGCAACGTGTGAAGATTTATGGTAATGATGAAATTGCGAATTA

GCTTTAGCATTTAATAACTTGTCTAAACGTGTACAAGAAGCGCAGGCTAATACTGAAAGTGAGAAACGTAGACTGGACTC

AGTTATCACCCATATGAGTGATGGTATTATTGCAACAGACCGCCGTGGACGTATTCGTATCGTCAATGATATGGCACTCA

AGATGCTTGGTATGGCGAAAGAAGACATCATCGGATATTACATGTTAAGTGTATTAAGTCTTGAAGATGAATTTAAACTG

GAAGAAATTCAAGAGAATAATGATAGTTTCTTATTAGATTTAAATGAAGAAGAAGGTCTAATCGCACGTGTTAACTTTAG

TACGATTGTGCAGGAAACAGGATTTGTAACTGGTTATATCGCTGTGTTACATGACGTAACTGAACAACAAGTTGAAC

GTGAGCGTCGTGAATTTGTTGCCAATGTATCACATGAGTTACGTACACCCTTTAACTTCTATGAATAGTTACATTGAAGCA

CTTGAAGAAGGTGCATGGAAAGATGAGGAACTTGCGCCACAATTTTTATCTGTTACCCGTGAAGAAACAGAACGAATGAT

TABLE 1-continued

Nucleotide and Amino Acid Sequences of S. aureus Genes.

TCGACTGGTCAATGACTTGCTACAGTTATCTAAAATGGATAATGAGTCTGATCAAATCAACAAAGAAATTACGACTTTAA

CATGTTCATTAATAAAATTATTAATCGACATGAAATGTCTGCGAAAGATACAACATTTATTCGAGATATTCCGAAAAAGA

CGATTTTCACAGAATTTGATCCTGATAAAATGACGCAAGTATTTGATAATGTCATTACAAATGCGATGAAATATTCTAGA

GGCGATAAACGTGTCGAGTTCCACGTGAAACAAAATCCACTTTATAATCGAATGACGATTCGTATTAAAGATAATGGCAT

TGGTATTCCTATCAATAAAGTCGATAAGATATTCGACCGATTCTATCGTGTAGATAAGGCACGTACGCGTAAAATGGGTG

GTACTGGATTAGGACTAGCCATTTCGAAAGAGATTGTGGAAGCGCACAATGGTCGTATTTGGGCAAACAGTGTAGAAGGT

CAAGGTACATCTATCTTTATCACACTTCCATGTGAAGTCATTGAAGACGGTGATTGGGATGAA

>HGS075 YycG (SEQ ID NO:70)

MKWLKQLQSLHTKFVIVYVLLIIIGMQIIGLYFTNNLEKELLDNFKKNITQYAKQLEISIEKVYDEKGSVNAQKD

IQNLLSEYANRQEIGEIRFIDKDQIIIATTKQSNRSLINQKANDSSVQKALSLGQSNDHLILKDYGGGKDRVWVY

NIPVKVDKKVIGNIYIESKINDVYNQLNNINQIFIVGTAISLLITVILGFFIARTITKPITDMRNQTVEMSRGNY

TQRVKIYGNDEIGELALAFNNLSKRVQEAQANTESEKRRLDSVITHMSDGIIATDRRGRIRIVNDMALKMLGMAK

EDIIGYYMLSVLSLEDEFKLEEIQENNDSFLLDLNEEEGLIARVNFSTIVQETGFVTGYIAVLHDVTEQQQVERE

RREFVANVSHELRTPLTSMNSYIEALEEGAWKDEELAPQFLSVTREETERMIRLVNDLLQLSKMDNESDQINKEI

IDFNMFINKIINRHEMSAKDTTFIRDIPKKTIFTEFDPDKMTQVFDNVITNAMKYSRGDKRVEFHVKQNPLYNRM

TIRIKDNGIGIPINKVDKIFDRFYRVDKARTRKMGGTGLGLAISKEIVEAHNGRIWANSVEGQGTSIFITLPCEV

IEDGDWDE

>pbp1 (SEQ ID NO:71)

ATGGCGAAGCAAAAAATTAAAATTAAAAAAAAATAAAATAGGGGCAGTCCTACTTGTTGGTTTATTCGGACTGCTCTTTTT

TATATTGGTTTTAAGAATTTCATATATCATGATTACTGGACATTCTAATGGTCAAGATTTAGTCATGAAGGCAAATGAAA

AGTATTTAGTTAAGAATGCACAACAACCAGAACGAGGAAAGATATATGATCGTAATGGTAAAGTGCTAGCAGAAGATGTA

GAAAGATATAAACTTGTTGCAGTAATAGATAAAAAGGCGAGTGCCAATTCTAAAAAACCTAGGCATGTAGTTGATAAAAA

AGAGACTGCAAAGAAATTATCTACAGTCATTAATATGAAGCCAGAGGAAATTGAAAAGAGACTTAGTCAAAAGAAAGCTT

TCCAAATTGAATTTGGACGCAAAGGAACAAATTTAACGTATCAGGACAAATTGAAAATAGAGAAATGAATTTGCCTGGT

ATTTCTTTATTGCCTGAAACAGAACGCTTTTATCCAAATGGCAATTTTGCATCACACTTAATTGGTAGAGCTCAGAAAAA

TCCGGATACTGGTGAACTTAAAGGTGCACTTGGAGTTGAAAAGATTTTTGATAGTTATTTAAGTGGATCTAAAGGATCAT

TGAGATATATTCATGATATTTGGGGATATATCGCACCAAATACTAAAAAAGAGAAGCAGCCTAAACGTGGTGATGATGTC

CATTTAACAATCGATTCAAATATTCAAGTATTTGTTGAAGAAGCTTTAGATGGCATGGTTGAAAGATACCAGCCGAAAGA

TTTATTTGCGGTTGTCATGGATGCCAAAACTGGAGAAATTTTAGCATACAGTCAGCGACCAACATTTAATCCTGAAACTG

GTAAAGACTTTGGTAAAAAGTGGGCAAATGACCTTTATCAAAACACATACGAGCCTGGATCAACATTTAAATCATATGGG

TTAGCAGCTGCTATTCAAGAAGGTGCTTTTGATCCTGATAAGAAATATAAATCTGGACATAGAGATATTATGGGTTCACG

TATTTCAGACTGGAATAGAGTCGGTTGGGGTGAAATCCCAATGTCACTCGGATTTACTTATTCATCTAATACATTGATGA

TGCATTTACAAGATTTAGTTGGTGCAGACAAAATGAAATCTTGGTATGAACGATTTGGATTTGGAAAATCAACTAAAGGT

ATGTTTGATGGAGAAGCACCTGGTCAAATTGGATGGAGTAATGAGTTGCAACAAAAAACGTCATCATTTGGTCAATCGAC

AACAGTAACACCTGTTCAAATGTTACAAGCGCAATCAGCGTTCTTTAATGATGGTAATATGTTAAAACCATGGTTTGTGA

ATAGCGTTGAAAATCCTGTTAGTAAAAGACAATTTTATAAAGGGCAAAAACAAATCGCAGGCAAACCAATAACAAAAGAT

ACTGCTGAAAAAGTTGAAAAGCAATTGGATTTAGTTGTGAATAGTAAGAAGAGTCACGCTGCAAACTATCGTATTGATGG

TTATGAGGTCGAAGGTAAGACTGGTACAGCACAAGTCGCTGCACCTAATGGTGGTGGATACGTTAAAGGTCCAAACCCAT

ATTTTGTAAGTTTTATGGGTGACGCGCCGAAGAAAAATCCTAAAGTTATTGTATACGCTGGTATGAGCTTGGCACAAAAA

TABLE 1-continued

Nucleotide and Amino Acid Sequences of *S. aureus* Genes.

AATGACCAAGAAGCTTATGAATTAGGTGTTAGTAAAGCGTTTAAACCAATAATGGAAAATACTTTGAAATATTTAAATGT

AGGTAAATCAAAAGATGACACATCTAATGCAGAGTATAGTAAAGTGCCAGATGTTGAAGGTCAAGACAAACAAAAAGCTA

TTGATAATGTGAGTGCAAAATCATTAGAACCAGTTACTATTGGTTCTGGCACACAAATAAAAGCACAATCTATAAAAGCA

GGGAATAAAGTCTTACCTCATAGTAAAGTACTGTTATTAACAGATGGAGACTTAACTATGCCTGACATGTCAGGATGGAC

GAAAGAAGATGTCATTGCTTTTGAAAACCTAACAAATATTAAAGTAAATTTAAAAGGTAGCGGTTTTGTGTCCCACCAAT

CAATTAGTAAGGGACAAAAACTTACTGAAAAAGATAAAATAGACGTAGAATTTTCATCAGAGAATGTAGACAGCAATTCG

ACGAATAATTCTGATTCAAATTCAGATGATAAGAAGAAATCTGACAGTAAAACTGACAAGGATAAGTCGGAC

>Pbp1 (SEQ ID NO:72)

MAKQKIKIKKNKIGAVLLVGLFGLLFFILVLRISYIMITGHSNGQDLVMKANEKYLVKNAQQPERGKIYDRNGKV

LAEDVERYKLVAVIDKKASANSKKPRHVVDKKETAKKLSTVINMKPEEIEKRLSQKKAFQIEFGRKGTNLTYQDK

LKIEKMNLPGISLLPETERFYPNGNFASHLIGRAQKNPDTGELKGALGVEKIFDSYLSGSKGSLRYIHDIWGYIA

PNTKKEKQPKRGDDVHLTIDSNIQVFVEEALDGMVERYQPKDLFAVVMDAKTGEILAYSQRPTFNPETGKDFGKK

WANDLYQNTYEPGSTFKSYGLAAAIQEGAFDPDKKYKSGHRDIMGSRISDWNRVGWGEIPMSLGFTYSSNTLMMH

LQDLVGADKMKSWYERFGFGKSTKGMFDGEAPGQIGWSNELQQKTSSFGQSTTVTPVQMLQAQSAFFNDGNMLKP

WFVNSVENPVSKRQFYKGQKQIAGKPITKDTAEKVEKQLDLVVNSKKSHAANYRIDGYEVEGKTGTAQVAAPNGG

GYVKGPNPYFVSFMGDAPKKNPKVIVYAGMSLAQKNDQEAYELGVSKAFKPIMENTLKYLNVGKSKDDTSNAEYS

KVPDVEGQDKQKAIDNVSAKSLEPVTIGSGTQIKAQSIKAGNKVLPHSKVLLLTDGDLTMPDMSGWTKEDVIAFE

NLTNIKVNLKGSGFVSHQSISKGQKLTEKDKIDVEFSSENVDSNSTNNSDSNSDDKKKSDSRTDKDKSD

>deaD (SEQ ID NO:73)

ATTCGCAAATTGCTTTATTGCGATTAAATTTTTTTGGTGGTACTATATAGAAGTTGATGAAATATTAATGAACTTATATG

CAAAAGTATATTGAGAAATAAACAGGTAAAAAGGAGAATTATTTTGCAAAATTTTAAAGAACTAGGGATTTCGGATAATA

CGGTTCAGTCACTTGAATCAATGGGATTTAAAGAGCCGACACCTATCCAAAAAGACAGTATCCCTTATGCGTTACAAGGA

ATTGATATCCTTGGGCAAGCTCAAACCGGTACAGGTAAAACAGGAGCATTCGGTATTCCTTTAATTGAGAAAGTAGTAGG

GAAACAAGGGGTTCAATCGTTGATTTTAGCACCTACAAGAGAATTGGCAATGCAGGTAGCTGAACAATTAAGAGAATTTA

GCCGTGGACAAGGTGTCCAAGTTGTTACTGTATTCGGTGGTATGCCTATCGAACGCAAATTAAAGCCTTGAAAAAGGC

CCACAAATCGTAGTCGGAACACCTGGGCGTGTTATCGACCATTTAAATCGTCGCACATTAAAAACGGACGGAATTCATAC

TTTGATTTTAGATGAAGCTGATGAAATGATGAATATGGGATTCATCGATGATATGAGATTTATTATGGATAAAATTCCAG

CAGTACAACGTCAAACAATGTTGTTCTCAGCTACAATGCCTAAAGCAATCCAAGCTTTAGTACAACAATTTATGAAATCA

CCAAAAATCATTAAGACAATGAATAATGAAATGTCTGATCCACAAATCGAAGAATTCTATACAATTGTTAAAGAATTAGA

GAAATTTGATACATTTACAAATTTCCTAGATGTTCATCAACCTGAATTAGCAATCGTATTCGGACGTACAAAACGTCGTG

TTGATGAATTAACAAGTGCTTTGATTTCTAAAGGATATAAAGCTGAAGGTTTACATGGTGATATTACACAAGCGAAACGT

TTAGAAGTATTAAAGAAATTTAAAAATGACCAAATTAATATTTTAGTCGCTACTGATGTAGCAGCAAGAGGACTAGATAT

TTCTGGTGTGAGTCATGTTTATAACTTTGATATACCTCAAGATACTGAAAGCTATACACACCGTATTGGTCGTACGGGTC

GTGCTGGTAAAGAAGGTATCGCTGTAACGTTTGTTAATCCAATCGAAATGGATTATATCAGACAAATTGAAGATGCAAAC

GGTAGAAAAATGAGTGCACTTCGTCCACCACATCGTAAAGAAGTACTTCAAGCACGTGAAGATGACATCAAAGAAAAGT

TGAAAACTGGATGTCTAAAGAGTCAGAATCACGCTTGAAACGCATTTCTACAGAGTTGTTAAATGAATATAACGATGTTG

ATTTAGTTGCTGCACTTTTACAAGAGTTAGTAGAAGCAAACGATGAAGTTGAAGTTCAATTAACTTTTGAAAAACCATTA

TCTCGCAAAGGCCGTAACGGTAAACCAAGTGGTTCTCGTAACAGAAATAGTAAGCGTGGTAATCCTAAATTTGACAGTAA

TABLE 1-continued

Nucleotide and Amino Acid Sequences of S. aureus Genes.

GAGTAAACGTTCAAAAGGATACTCAAGTAAGAAGAAAAGTACAAAAAAATTCGACCGTAAAGAGAAGAGCAGCGGTGGAA

GCAGACCTATGAAAGGTCGCACATTTGCTGACCATCAAAAATAATTTATAGATTAAGAGCTTAAAGATGTAATGTCT

>DeaD (SEQ ID NO:74)

NINELICKSILRNKQVKRRIILQNFKELGISDNTVQSLESMGFKEPTPIQKDSIPYALQCIDILGQAQTGTGKTG

AFGIPLIEKVVGKQGVQSLILAPTRELAMQVAEQLREFSRGQGVQVVTVFGGMPIERQIKALKKGPQIVVGTPGR

VIDHLNRRTLKTDGIHTLILDEADEMMNMGFIDDMRFIMDKIPAVQRQTMLFSATMPKAIQALVQQFMKSPKIIK

TMNNEMSDPQIEEFYTIVKELEKFDTFTNFLDVHQPELAIVFGRTKRRVDELTSALISKGYKAEGLHGDITQAKR

LEVLKKFKNDQINILVATDVAARGLDISGVSHVYNFDIPQDTESYTHRIGRTGRAGKEGIAVTFVNPIEMDYIRQ

IEDANGRKMSALRPPHRKEVLQAREDDIKEKVENWMSKESESRLKRISTELLNEYNDVDLVAALLQELVEANDEV

EVQLTFEKPLSRKGRNGKPSGSRNRNSKRGNPKFDSKSKRSKGYSSKKKSTKKFDRKEKSSGGSRPMKGRTFADH

Q

The present invention further encompasses nucleic acid molecules of the present invention that are chemically synthesized, or reproduced as peptide nucleic acids (PNA), or according to other methods known in the art. The use of PNAs would serve as the preferred form if the nucleic acid molecules of the invention are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. For general review, see, e.g., P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), hereby incorporated by reference herein.

PNAs bind specifically and tightly to complementary DNA strands and are not degraded by nucleases. In fact, a PNA binds more strongly to DNA than does DNA itself. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T^m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

By "isolated" polynucleotide sequence is intended a nucleic acid molecule, DNA or RNA, which has been removed from its native environment. This includes segments of DNA comprising the S. aureus polynucleotides of the present invention isolated from the native chromosome. These fragments include both isolated fragments consisting only of S. aureus DNA and fragments comprising heterologous sequences such as vector sequences or other foreign DNA. For example, recombinant DNA molecules contained in a vector are considered isolated for the purposes of the present invention which may be partially or substantially purified to exclude RNA or heterologous DNA. Isolated polynucleotides may be at least 10%, 20%, 30%, 40%, 50%, 60%, 70%, 75%, 80%, 85%, 90%, 95%, 96%, 97%, 98%, 99%, or 100% pure relative to heterologous polynucleotides (e.g., DNA or RNA) or relative to all materials and compounds other than the carrier solution. Further examples of isolated DNA molecules include recombinant DNA molecules introduced and maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically which may be partially or substantially purified. The term "isolated" does not refer to genomic or cDNA libraries, whole cell mRNA preparations, genomic DNA digests (including those gel separated by electrophoresis), whole chromosomes, or sheared whole cell genomic DNA preparations or other compositions where the art demonstrates no distinguishing features of the polynucleotides sequences of the present invention.

In addition, isolated nucleic acid molecules of the invention include DNA molecules which comprise a sequence substantially different from those described above but which, due to the degeneracy of the genetic code, still encode a S. aureus polypeptides and peptides of the present invention (e.g., polypeptides of Table 1). That is, all possible DNA sequences that encode the S. aureus polypeptides of the present invention. This includes the genetic code and species-specific codon preferences known in the art. Thus, it would be routine for one skilled in the art to generate the degenerate variants described above, for instance, to optimize codon expression for a particular host (e.g., change codons in the bacterial mRNA to those preferred by a mammalian or other bacterial host such as E. coli).

The invention further provides isolated nucleic acid molecules having the nucleotide sequence shown in Table 1 or a nucleic acid molecule having a sequence complementary to one of the above sequences. Such isolated molecules, particularly DNA molecules, are useful as probes for gene mapping and for identifying S. aureus in a biological sample, for instance, by PCR or hybridization analysis (e.g., including, but not limited to, Northern blot analysis). In specific embodiments, the polynucleotides of the present invention are less than 300 kb, 200 kb, 100 kb, 50 kb, 10, kb, 7.5 kb, 5 kb, 2.5 kb, and 1 kb. In another embodiment, the polynucleotides comprising the coding sequence for polypeptides of the present invention do not contain genomic flanking gene sequences or contain only genomic flanking gene sequences having regulatory control sequences for the said polynucleotides.

In further embodiments, polynucleotides of the invention comprise at least 15, at least 30, at least 50, at least 100, or at least 250, at least 500, or at least 1000 contiguous nucleotides comprising the coding sequence for polypeptides of the present invention, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in Table 1. In further embodiments, polynucleotides of the invention comprise at least 15, at least 30, at least 50, at least 100, or at least 250, at least 500, or at least 1000 contiguous nucleotides comprising the coding sequence for polypeptides of the present invention. In another embodiment, the nucleic acid comprising coding sequence for polypeptides of the present invention does not contain coding sequences of a genomic flanking gene (i.e., 5' or 3' to the Table 1 sequences in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

The present invention is further directed to nucleic acid molecules encoding portions or fragments of the nucleotide sequences described herein. Uses for the polynucleotide fragments of the present invention include, but are not limited to, probes, primers, molecular weight markers and expressing the polypeptide fragments of the present invention. Fragments include portions of the nucleotide sequences of Table 1, at least 10 contiguous nucleotides in length selected from any two integers, one of which representing a 5' nucleotide position and a second of which representing a 3' nucleotide position, where the first nucleotide for each nucleotide sequence in Table 1 is position 1. That is, every combination of a 5' and 3' nucleotide position that a fragment at least 10 contiguous nucleotides in length could occupy is included in the invention as an individual species. "At least" means a fragment may be 10 contiguous nucleotide bases in length or any integer between 10 and the length of an entire nucleotide sequence minus 1. Therefore, included in the invention are contiguous fragments specified by any 5' and 3' nucleotide base positions of a nucleotide sequences of Table 1 wherein the contiguous fragment is any integer between 10 and the length of an entire nucleotide sequence minus 1.

The polynucleotide fragments specified by 5' and 3' positions can be immediately envisaged using the clone description and are therefore not individually listed solely for the purpose of not unnecessarily lengthening the specifications.

Although it is particularly pointed out that each of the above-described species may be included in or excluded from the present invention. The above species of polynucleotides fragments of the present invention may alternatively be described by the formula "a to b"; where "a" equals the 5' nucleotide position and "b" equals the 3' nucleotide position of the polynucleotide fragment, where "a" equals as integer between 1 and the number of nucleotides of the polynucleotide sequence of the present invention minus 10, where "b" equals an integer between 10 and the number of nucleotides of the polynucleotide sequence of the present invention; and where "a" is an integer smaller than "b" by at least 10.

Again, it is particularly pointed out that each species of the above formula may be specifically included in, or excluded from, the present invention.

Further, the invention includes polynucleotides comprising sub-genuses of fragments specified by size, in nucleotides, rather than by nucleotide positions. The invention includes any fragment size, in contiguous nucleotides, selected from integers between 10 and the length of an entire nucleotide sequence minus 1. Preferred sizes of contiguous nucleotide fragments include at least 20 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, at least 500 nucleotides, at least 550 nucleotides, at least 600 nucleotides, at least 650 nucleotides, at least 700 nucleotides, at least 750 nucleotides, at least 800 nucleotides, at least 850 nucleotides, at least 900 nucleotides, at least 950 nucleotides, at least 1000 nucleotides, at least 1050 nucleotides, at least 1100 nucleotides, and at least 1150 nucleotides. Other preferred sizes of contiguous polynucleotide fragments, which may be useful as diagnostic probes and primers, include fragments 50–300 nucleotides in length which include, as discussed above, fragment sizes representing each integer between 50–300. Larger fragments are also useful according to the present invention corresponding to most, if not all, of the polynucleotide sequences of the sequence listing, shown in Table 1, or deposited clones. The preferred sizes are, of course, meant to exemplify not limit the present invention as all size fragments, representing any integer between 10 and the length of an entire nucleotide sequence minus 1 of the sequence listing or deposited clones, may be specifically included in or excluded from the invention. Additional preferred nucleic acid fragments of the present invention include nucleic acid molecules encoding epitope-bearing portions of the polypeptides (e.g., including but not limited to, nucleic acid molecules encoding epitope-bearing portions of the polypeptides which are shown in Table 4).

In another aspect, the invention provides an isolated nucleic acid molecule comprising a polynucleotide which hybridizes under stringent hybridization conditions to a portion of a polynucleotide in a nucleic acid molecules of the invention described above, for instance, nucleotide sequences of Table 1. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. Hybridizing polynucleotides are useful as diagnostic probes and primers as discussed above. Portions of a polynucleotide which hybridize to a nucleotide sequence in Table 1, which can be used as probes and primers, may be precisely specified by 5' and 3' base positions or by size in nucleotide bases as described above or precisely excluded in the same manner. Preferred hybridizing polynucleotides of the present invention are those that, when labeled and used in a hybridization assay known in the art (e.g., Southern and Northern blot analysis), display the greatest signal strength with the polynucleotides of Table 1 regardless of other heterologous sequences present in equamolar amounts.

The nucleic acid molecules of the present invention, which encode a S. aureus polypeptide, may include, but are not limited to, nucleic acid molecules encoding the full-length S. aureus polypeptides of Table 1. Also included in the present invention are nucleic acids encoding the above full-length sequences and further comprise additional sequences, such as those encoding an added secretory leader sequence, such as a pre-, or pro- or prepro-protein sequence. Further included in the present invention are nucleic acids encoding the above full-length sequences and portions thereof and further comprise additional heterologous amino acid sequences encoded by nucleic acid sequences from a different source.

Also included in the present invention are nucleic acids encoding the above protein sequences together with additional, non-coding sequences, including for example, but not limited to non-coding 5' and 3' sequences. These sequences include transcribed, non-translated sequences that may play a role in transcription, and mRNA processing, for example, ribosome binding and stability of mRNA. Also included in the present invention are additional coding sequences which provide additional functionalities.

Thus, a nucleotide sequence encoding a polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al. (1984) Cell 37:767. As discussed below, other such fusion proteins include the S. aureus fused to Fc at the N- or C-terminus.

Variant and Mutant Polynucleotides

The present invention further relates to variants of the nucleic acid molecules which encode portions, analogs or derivatives of a S. aureus polypeptides of Table 1, and variant polypeptides thereof including portions, analogs, and derivatives of the S. aureus polypeptides. Variants may occur naturally, such as a natural allelic variant. By an "allelic variant" is intended one of several alternate forms of a gene occupying a given locus on a chromosome of an organism. See, e.g., B. Lewin, Genes IV (1990). Non-naturally occurring variants may be produced using art-known mutagenesis techniques.

Such nucleic acid variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a S. aureus protein of the present invention or portions thereof. Also preferred in this regard are conservative substitutions.

Such polypeptide variants include those produced by amino acid substitutions, deletions or additions. The substitutions, deletions, or additions may involve one or more residues. Alterations may produce conservative or non-conservative amino acid substitutions, deletions, or additions. Especially preferred among these are silent substitutions, additions and deletions, which do not alter the properties and activities of a S. aureus protein of the present invention or portions thereof. Also especially preferred in this regard are conservative substitutions.

The present invention also relates to recombinant vectors, which include the isolated nucleic acid molecules of the present invention, and to host cells containing the recombinant vectors, as well as to methods of making such vectors and host cells and for using them for production of S. aureus polypeptides or peptides by recombinant techniques.

The present application is directed to nucleic acid molecules at least 90%, 95%, 96%, 97%, 98%, 99% or 100% identical to a nucleic acid sequence shown in Table 1. The above nucleic acid sequences are included irrespective of whether they encode a polypeptide having S. aureus activity. This is because even where a particular nucleic acid molecule does not encode a polypeptide having S. aureus activity, one of skill in the art would still know how to use the nucleic acid molecule, for instance, as a hybridization probe or primer. Uses of the nucleic acid molecules of the present invention that do not encode a polypeptide having S. aureus activity include, inter alia, isolating an S. aureus gene or allelic variants thereof from a DNA library, and detecting S. aureus mRNA expression in biological or environmental samples, suspected of containing S. aureus by hybridization analysis (e.g., including, but not limited to, Northern Blot analysis) or PCR.

For example, one such method involves assaying for the expression of a polynucleotide encoding S. aureus polypeptides in a sample from an animal host (e.g, including, but not limited to, human, bovine, rabbit, porcine, murine, chicken, and/or avian species). The expression of polynucleotides can be assayed by detecting the nucleic acids of Table 1. An example of such a method involves the use of the polymerase chain reaction (PCR) to amplify and detect Staphylococcus nucleic acid sequences in a biological or environmental sample.

The present invention also relates to nucleic acid probes having all or part of a nucleotide sequence described in Table 1 which are capable of hybridizing under stringent conditions to Staphylococcus nucleic acids. The invention further relates to a method of detecting one or more Staphylococcus nucleic acids in a biological sample obtained from an animal, said one or more nucleic acids encoding Staphylococcus polypeptides, comprising: (a) contacting the sample with one or more of the above-described nucleic acid probes, under conditions such that hybridization occurs, and (b) detecting hybridization of said one or more probes to the Staphylococcus nucleic acid present in the biological sample.

The invention also includes a kit for analyzing samples for the presence of members of the Staphylococcus genus in a biological or environmental sample. In a general embodiment, the kit includes at least one polynucleotide probe containing a nucleotide sequence that will specifically hybridize with a S. aureus nucleic acid molecule of Table 1 and a suitable container. In a specific embodiment, the kit includes two polynucleotide probes defining an internal region of the S. aureus nucleic acid molecule of Table 1, where each probe has one strand containing a 31'mer-end internal to the region. In a further embodiment, the probes may be useful as primers for polymerase chain reaction amplification.

The method(s) provided above may preferably be applied in a diagnostic method and/or kits in which S. aureus polynucleotides of Table 1 are attached to a solid support. In one exemplary method, the support may be a "gene chip" or a "biological chip" as described in U.S. Pat. Nos. 5,837,832, 5,874,219, and 5,856,174. Further, such a gene chip with S. aureus polynucleotides of Table 1 attached may be used to diagnose S. aureus infection in an animal host, preferably a human. The U.S. Patents referenced above are incorporated herein by reference in their entirety.

The present invention is further directed to nucleic acid molecules having sequences at least 80%, 85%, 90%, 95%, 96%, 97%, 98%, 99% or 100% identical to the nucleic acid sequence shown in Table 1, which do, in fact, encode a polypeptide having S. aureus protein activity. By "a polypeptide having S. aureus activity" is intended polypeptides exhibiting activity similar, but not necessarily identical, to an activity of the S. aureus protein of the invention, as measured in a particular biological assay suitable for measuring activity of the specified protein. The biological activities of some of the polypeptides of the present invention are listed in Table 1, after the name of the closest homolog with similar activity. The biological activities were determined using methods known in the art for the particular biological activity listed. For the remaining polypeptides of Table 1, the assays known in the art to measure the activity of the polypeptides of Table 2, sharing a high degree of identity, may be used to measure the activity of the corresponding polypeptides of Table 1.

Of course, due to the degeneracy of the genetic code, one of ordinary skill in the art will immediately recognize that a large number of the nucleic acid molecules having a sequence at least 80%, 85%, 90%, 95%, 96%, 97%, 98%, 99%, or 100% identical to the nucleic acid sequences shown in Table 1 will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly effect protein function (e.g., replacing one aliphatic amino acid with a second aliphatic amino acid), as further described below.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the S. aureus polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence shown in Table 1, the ORF (open reading frame), or any fragment specified as described herein.

Other methods of determining and defining whether any particular nucleic acid molecule or polypeptide is at least 90%, 95%, 96%, 97%, 98%, 99%, or 100% identical to a nucleotide sequence of the presence invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. A RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

TABLE 2

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| | | GenSeq | | |
| HGS010 | W87771 | UDP-N-acetylmuramate:L-alanine ligase (MurC polype... | 2238 | 9.10E − 308 |
| HGS010 | W89199 | Partial sequence of the MurC polypeptide. New isol... | 1067 | 1.20E − 144 |
| HGS010 | W55120 | *Streptococcus pneumoniae* SP0070 protein. Nucleic a... | 451 | 2.30E − 142 |
| HGS010 | W20606 | *H. pylori* cytoplasmic protein, 01ep30520orf27. *Hel.*... | 147 | 1.10E − 29 |
| HGS010 | W77686 | *Staphylococcus aureus* protein of unknown function... | 185 | 7.30E − 19 |
| HGS010 | W20102 | *H. pylori* cytoplasmic protein, 11253.aa. *Helicobac.*... | 122 | 1.10E − 12 |
| HGS010 | W24585 | *H. pylori* cytoplasmic protein, 11253.aa. *Helicobac.*... | 122 | 1.10E − 12 |
| HGS010 | W29454 | *Streptococcus pneumoniae* MurD protein. *Streptococc.*... | 99 | 7.50E − 10 |
| HGS010 | W68551 | *S. pneumoniae* MurD protein. *Streptococcus pneumoni.*... | 99 | 7.50E − 10 |
| HGS010 | W55117 | *Streptococcus pneumoniae* SP0067 protein. Nucleic a... | 99 | 4.80E − 09 |
| HGS027 | W29380 | *S. pneumoniae* peptide releasing factor RF-1. DNA e... | 593 | 1.00E − 141 |
| HGS027 | W38592 | *S. pneumoniae* peptide chain release factor 1. Nove... | 593 | 1.00E − 141 |
| HGS029 | W71494 | Helicobacter polypeptide GHPO 805. Helicobacter po... | 440 | 4.20E − 55 |
| HGS029 | R14036 | Ribosome releasing factor. Novel peptide promoting... | 437 | 1.10E − 54 |
| HGS029 | W69755 | Ribosome recycling factor protein. Expression and... | 411 | 3.20E − 51 |
| HGS029 | W69754 | Ribosome recycling factor protein. Expression and... | 410 | 4.40E − 51 |
| HGS029 | W78188 | Human secreted protein encoded by gene 63 clone HP... | 109 | 2.10E − 14 |
| HGS038 | W79340 | *Staphylococcus aureus* nusA protein homologue. New... | 667 | 1.00E − 89 |
| HGS038 | W98760 | *H. pylori* GHPO 1087 protein. New isolated *Helicoba.*... | 260 | 1.70E − 36 |
| HGS039 | W80656 | *S. pneumoniae* transcription elongation factor. *Str.*... | 246 | 2.80E − 33 |
| HGS039 | W27997 | Amino acid sequence of transcription antiterminati... | 272 | 1.00E − 32 |
| HGS041 | R58587 | Nicotinamide adenine dinucleotide synthetase N-te... | 181 | 8.10E − 38 |
| HGS042 | W21022 | *H. pylori* cytoplasmic protein, hp5e15440orf21. *Hel.*... | 295 | 1.90E − 80 |
| HGS042 | R47583 | NADH oxidase. DNA encoding NADH oxidase - used in... | 229 | 1.90E − 39 |
| HGS042 | R60863 | Hydrogen peroxide-generating NADH oxidase. A DNA f... | 309 | 6.30E − 35 |
| HGS042 | W28236 | Amino acid sequence of a mercuric reductase. Novel... | 91 | 1.60E − 15 |
| HGS042 | W29772 | *Malassezia fungus* MF-5 antigenic protein. Antigeni... | 80 | 5.60E − 14 |
| HGS042 | R43074 | *Aspergillus niger* Sulphydryl oxidase (SOX). DNA en... | 92 | 2.10E − 12 |
| HGS042 | W53251 | *Candida albicans* fungal antigen - allergen SEQ ID... | 76 | 9.80E − 11 |
| HGS042 | W98700 | *H. pylori* GHPO 698 protein. New isolated *Helicobac.*... | 65 | 3.60E − 09 |
| HGS043 | W71558 | Helicobacter polypeptide GHPO 1252. Helicobacter p... | 437 | 1.60E − 108 |
| HGS043 | W98793 | *H. pylori* GHPO 1252 protein. New isolated Helicoba... | 437 | 1.60E − 108 |
| HGS043 | W20598 | *H. pylori* protein. *Helicobacter pylori* nucleic aci... | 434 | 2.20E − 108 |
| HGS043 | W28298 | *Staphylococcus aureus* protein of unknown function... | 584 | 1.20E − 75 |
| HGS043 | W20206 | *H. pylori* derived protein. *Helicobacter pylori* nuc... | 268 | 1.20E − 37 |
| HGS043 | W88304 | *E. coli* O111 antigen gene cluster ORF5 (manB) prot... | 130 | 9.00E − 32 |
| HGS043 | W88322 | *E. coli* O157 antigen pathway ORF11 (manD) protein... | 128 | 7.60E − 29 |
| HGS043 | R04578 | Part of protein with urease activity. New nucleoti... | 175 | 2.60E − 17 |
| HGS043 | W88333 | *Salmonella enterica* O antigen gene cluster manB pr... | 69 | 2.90E − 11 |
| HGS043 | W20803 | *H. pylori* cytoplasmic protein, 09ap11406orf8. *Heli.*... | 84 | 5.60E − 09 |
| HGS044 | W19930 | N-acetylglucosamine 1-phosphate uridyltransferase... | 2281 | 8.60E − 308 |
| HGS044 | W19929 | N-acetylglucosamine 1-phosphate uridyltransferase... | 2275 | 5.70E − 307 |
| HGS044 | W89182 | *S. pneumoniae* GlmU polypeptide. New *Streptococcus.*... | 1111 | 3.50E − 148 |
| HGS044 | W89183 | *S. pneumoniae* GlmU ORF polypeptide sequence. New S... | 926 | 7.30E − 123 |
| HGS044 | W98337 | *H. pylori* GHPO 142 protein. New isolated *Helicobac.*... | 264 | 1.70E − 101 |
| HGS045 | W18209 | *Staphylococcus aureus* Coenzyme A disulphide reduct... | 2236 | 7.40E − 305 |
| HGS045 | W77578 | *Staphylococcus aureus* protein of unknown function... | 548 | 1.50E − 71 |
| HGS045 | W06425 | Water-forming NADH oxidase. DNA encoding water-for... | 101 | 4.10E − 34 |
| HGS045 | W94460 | NADH:H2O oxidase activity protein. Increasing the... | 75 | 5.00E − 22 |
| HGS045 | W02649 | Ascorbate-free-radical-reductase. New isolated tom... | 86 | 4.40E − 11 |
| HGS045 | W83401 | Human thioredoxin reductase mature protein. Prepar... | 82 | 2.10E − 08 |
| HGS045 | R92050 | KM31-7 precursor. Clover yellow vein virus nuclear... | 82 | 3.50E − 08 |
| HGS045 | W83404 | Human KM-102-derived reductase like factor. Prepar... | 82 | 3.50E − 08 |
| HGS046 | W98618 | *H. pylori* GHPO 231 protein. New isolated *Helicobac.*... | 108 | 3.20E − 14 |
| HGS046 | W20305 | *H. pylori* surface membrane protein 24409577.aa. *He.*... | 136 | 1.40E − 11 |
| HGS046 | W20809 | *H. pylori* surface or membrane protein, 09cp10502or... | 134 | 2.10E − 11 |
| HGS049 | W20733 | *H. pylori* cell envelope protein, 06cp11722orf15. *H.*... | 156 | 2.70E − 51 |
| HGS049 | W26775 | Peptidoglycan biosynthetic enzyme MurE. *Streptococ.*... | 173 | 1.10E − 31 |
| HGS049 | W20436 | *H. pylori* protein. *Helicobacter pylori* nucleic aci... | 98 | 6.00E − 17 |
| HGS049 | W29454 | *Streptococcus pneumoniae* MurD protein. *Streptococc.*... | 64 | 4.90E − 08 |
| HGS049 | W68551 | *S. pneumoniae* MurD protein. *Streptococcus pneumoni.*... | 64 | 4.90E − 08 |
| HGS050 | W34453 | MurF protein. *Brevibacterium flavum* murF gene - us... | 513 | 4.10E − 133 |
| HGS050 | W20826 | *H. pylori* cytoplasmic protein 11ep12011orf9. *Helic.*... | 99 | 3.00E − 18 |
| HGS050 | W71543 | Helicobacter polypeptide GHPO 208. Helicobacter po... | 92 | 2.30E − 16 |
| HGS050 | W98302 | *H. pylori* GHPO 208 protein. New isolated *Helicobac.*... | 92 | 2.30E − 16 |
| HGS053 | W88645 | Secreted protein encoded by gene 112 clone HUKFC71... | 114 | 4.60E − 10 |
| HGS055 | W62677 | *Streptococcus pneumoniae* polypeptide. *Streptococcu.*... | 853 | 2.10E − 113 |
| HGS057 | W38664 | *S. pneumoniae* 30S ribosomal protein S9. Novel *Stre.*... | 387 | 2.10E − 49 |
| HGS059 | W38499 | *S. pneumoniae* ribosomal protein S14 (rpS14). Novel... | 292 | 4.30E − 36 |
| HGS060 | P81003 | Sequence encoding protein uniquely expressed by hu... | 106 | 3.90E − 08 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| HGS062 | W38499 | *S. pneumoniae* ribosomal protein S14 (rpS14). Novel... | 167 | 9.90E − 24 |
| HGS064 | W89791 | *Staphylococcus aureus* protein SEQ ID #5239. Polynu... | 1219 | 7.10E − 166 |
| HGS064 | W38174 | Response regulator amino acid sequence from S. pne... | 399 | 3.30E − 105 |
| HGS064 | W57633 | *S. pneumoniae* response regulator protein. New isol... | 399 | 3.30E − 105 |
| HGS064 | W18219 | *Staphylococcus aureus* response regulator protein... | 266 | 5.30E − 85 |
| HGS064 | W68415 | *Mycobacterium bovis* regX3 protein. Mycobacterial n... | 333 | 1.10E − 71 |
| HGS064 | W38175 | Response regulator amino acid sequence. DNA encodi... | 353 | 5.70E − 64 |
| HGS064 | W57634 | *S. pneumoniae* response regulator protein. New isol... | 353 | 5.70E − 64 |
| HGS064 | W19274 | *Staphylococcus aureus* novel response regulator pro... | 303 | 1.90E − 61 |
| HGS064 | W13272 | *Rhodococcus erythropolis* SK92-B1 regulatory factor... | 298 | 6.40E − 58 |
| HGS064 | W80799 | *Rhodococcus nitrile* hydratase gene fragment produc... | 298 | 6.40E − 58 |
| HGS065 | W80663 | *S. pneumoniae* protein of unknown function. Strepto... | 368 | 1.00E − 46 |
| HGS065 | W38482 | *Streptococcus pneumoniae* protein of unknown functi... | 256 | 1.60E − 29 |
| HGS066 | W77583 | *Staphylococcus aureus* protein of unknown function... | 332 | 4.80E − 40 |
| HGS067 | W77630 | *Staphylococcus aureus* protein of unknown function... | 453 | 6.60E − 59 |
| HGS067 | R34719 | *Bacillus subtilis* srfA operon ORF8 prod. Multi-enz... | 144 | 5.00E − 12 |
| HGS068 | W74405 | *S. aureus* gidB protein sequence. New *Staphylococcu*... | 1229 | 4.70E − 166 |
| HGS068 | W74406 | *S. aureus* gidB protein sequence. New *Staphylococcu*... | 1174 | 1.90E − 158 |
| HGS068 | W89447 | A gidB polypeptide sequence. New nucleic acid enco... | 244 | 1.70E − 56 |
| HGS068 | W77522 | Glucose inhibited division protein B. New nucleic... | 269 | 1.60E − 31 |
| HGS070 | W98338 | *H. pylori* GHPO 250 protein. New isolated *Helicobac*... | 274 | 1.10E − 51 |
| HGS070 | W20646 | *H. pylori* cytoplasmic protein, 02cp11822orf26. *Hel*... | 291 | 1.60E − 46 |
| HGS070 | W38565 | *S. pneumoniae* uridylate kinase. Novel *Streptococcu*... | 246 | 5.00E − 28 |
| HGS070 | W20147 | *H. pylori* cytoplasmic protein, 14574201.aa. *Helico*... | 75 | 3.00E − 08 |
| HGS071 | W37743 | *S. pneumoniae* DDL protein. *Streptococcus pneumonia*... | 558 | 1.20E − 113 |
| HGS071 | W46752 | D-alanine-D-alanine ligase sequence of *Mycobacteri*... | 182 | 1.00E − 87 |
| HGS071 | R57151 | *Enterococcus faecalis* vanB protein. New protein Va... | 176 | 4.50E − 72 |
| HGS071 | R24298 | D-alanine-D-alanine ligase VanA from *E.faecium*. PO... | 184 | 6.40E − 70 |
| HGS071 | R24303 | D-Ala-D-Ala ligase VanC involved in antibiotic res... | 281 | 2.70E − 66 |
| HGS071 | R24305 | Translation of ORF 1 contg. *E.faecium* proteins Van... | 184 | 1.00E − 58 |
| HGS071 | R57150 | *Enterococcus faecalis* vanB protein internal fragme... | 155 | 2.00E − 30 |
| HGS071 | W98614 | *H. pylori* GHPO 205 protein. New isolated *Helicobac*... | 92 | 7.00E − 17 |
| HGS072 | W00285 | Mutant farnesyldiphosphate synthase (4). Productio... | 339 | 1.70E − 86 |
| HGS072 | W00286 | Native farnesyldiphosphate synthase. Production of... | 335 | 2.30E − 86 |
| HGS072 | W47444 | *Bacillus stearothermophilus* farnesyl diphosphate s... | 333 | 4.30E − 86 |
| HGS072 | W62532 | Farnesyl diphospate synthase of *B. stearothermophi*... | 333 | 4.30E − 86 |
| HGS072 | W00283 | Mutant farnesyldiphosphate synthase (2). Productio... | 332 | 5.90E − 86 |
| HGS072 | R35047 | FPS. New thermally stable farnesyl pyrophosphate s... | 333 | 1.10E − 85 |
| HGS072 | W00284 | Mutant farnesyldiphosphate synthase (3). Productio... | 333 | 1.50E − 85 |
| HGS072 | W00282 | Mutant farnesyldiphosphate synthase (1). Productio... | 328 | 7.30E − 85 |
| HGS072 | W62535 | Mutant farnesyl diphospate synthase of *B. stearoth*... | 331 | 8.90E − 84 |
| HGS072 | W62537 | Mutant farnesyl diphospate synthase of *B. stearoth*... | 331 | 8.90E − 84 |
| HGS073 | R92060 | Heptaprenyl diphosphate synthetase ORFIII product... | 506 | 1.10E − 81 |
| HGS073 | W47422 | *Bacillus stearothermophilus* prenyl diphosphate syn... | 506 | 1.10E − 81 |
| HGS073 | W47420 | *Micrococcus luteus* prenyl diphosphate synthetase s... | 493 | 4.30E − 70 |
| HGS073 | W53922 | Decaprenyl diphosphate synthase #3. Production of... | 292 | 1.20E − 36 |
| HGS073 | W53920 | Decaprenyl diphosphate synthase #1. Production of... | 292 | 2.80E − 36 |
| HGS073 | W53921 | Decaprenyl diphosphate synthase #2. Production of... | 292 | 6.80E − 36 |
| HGS073 | W12389 | Geranylgeranyl diphosphate synthase F77S mutant. N... | 172 | 4.30E − 34 |
| HGS073 | W12386 | Geranylgeranyl diphosphate synthase. New mutant ge... | 177 | 6.90E − 34 |
| HGS073 | W12388 | Geranylgeranyl diphosphate synthase F118L mutant... | 173 | 6.90E − 34 |
| HGS073 | R79969 | Geranylgeranyl diphosphate synthase. DNA encoding... | 174 | 2.70E − 33 |
| HGS074 | W60977 | *Streptococcus pneumoniae* encoded polypeptide. New... | 253 | 2.10E − 58 |
| HGS074 | W80710 | *S. pneumoniae* protein of unknown function. Strepto... | 248 | 9.80E − 58 |
| HGS075 | W83372 | *Streptococcus pneumoniae* histidine kinase. New *Str*... | 175 | 1.10E − 33 |
| HGS075 | W68414 | *Mycobacterium bovis* senX3 protein. *Mycobacterial n*... | 159 | 3.50E − 27 |
| HGS075 | R24296 | Regulatory protein VanS involved in glycopeptide r... | 143 | 2.60E − 25 |
| HGS075 | W68522 | *N. crassa* os1p protein. New assay for histidine ki... | 185 | 4.30E − 24 |
| HGS075 | W83377 | *Streptococcus pneumoniae* histidine kinase. New *Str*... | 135 | 8.40E − 23 |
| HGS075 | W89427 | *S. pneumoniae* histidine kinase polypeptide. New hi... | 135 | 8.40E − 23 |
| HGS075 | W89432 | *Streptococcus pneumoniae* histidine kinase. New *Str*... | 135 | 8.40E − 23 |
| HGS075 | W81600 | *Candida albicans* CaNIK1 protein involved in phenot... | 168 | 5.30E − 22 |
| HGS075 | R24306 | Translation of ORF 2 contg. *E.faecium* protein VanS... | 142 | 8.90E − 22 |
| HGS075 | W68523 | Partial *C. albicans* cos1p protein. New assay for h... | 151 | 5.90E − 21 |
| Pbp1 | W98771 | *H. pylori* GHPO 1134 protein. New isolated *Helicoba*... | 87 | 3.80E − 12 |
| Pbp1 | R27253 | Penicillin binding protein PBP2A-epi. Polynucleoti... | 78 | 1.90E − 08 |
| deaD | W60667 | *E.coli* cold shock protein CsdA. Modulating protein... | 395 | 2.40E − 119 |
| deaD | W24291 | LmelF4A. Compositions comprising LbelF4A and LmelF... | 321 | 9.80E − 81 |
| deaD | R77503 | *Leishmania sp.* antigen LbelF4A. DNA encoding prote... | 317 | 2.90E − 80 |
| deaD | W24290 | LbelF4A. Compositions comprising LbelF4A and LmelF... | 317 | 2.90E − 80 |
| deaD | W70213 | *Leishmania* antigen LbelF4A protein. New immunogeni... | 317 | 2.90E − 80 |
| deaD | W92743 | *L. braziliensis* EIF4A protein. New *Leishmania braz*... | 317 | 2.90E − 80 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| deaD | W81502 | Dead Box X (DBX) gene short transcript amino acid... | 276 | 7.40E − 80 |
| deaD | W81501 | Dead Box X (DBX) gene long transcript amino acid s... | 276 | 7.40E − 80 |
| deaD | W11218 | *Leishmania braziliensis* LbeIF4A antigen. Polypepti... | 313 | 1.20E − 79 |
| deaD | W81503 | Dead Box Y (DBY) gene product. Novel genes in the... | 279 | 5.20E − 74 |
| | | Genbank | | |
| HGS010 | gi|2642659 | (AF034076) UDP-N-acetylmuramoyl-L-alanin... | 2255 | 0.00E + 00 |
| HGS010 | gnl|PID|e1185852 | UDP-N-acetyl muramate-alanine ligase [*Ba*... | 1438 | 7.30E − 196 |
| HGS010 | gi|2688761 | (AE001180) UDP-N-acetylmuramate-alanine... | 169 | 2.30E − 56 |
| HGS010 | gi|2983764 | (AE000736) UDP-N-acetylmuramate-alanine... | 183 | 8.80E − 54 |
| HGS010 | gnl|PID|d1035273 | (AB015023) MurC [*Corynebacterium glutami*... | 108 | 1.30E − 52 |
| HGS010 | gi|42056 | (UDP-N-acetylmuramate: L-alanine ligase)... | 191 | 2.70E − 51 |
| HGS010 | gi|2177094 | UDP-MurNAc:L-alanine ligase [*Escherichia*... | 191 | 2.70E − 51 |
| HGS010 | gi|3322616 | (AE001213) UDP-N-acetylmuramate--alanine... | 165 | 1.10E − 45 |
| HGS010 | gi|1574695 | UDP-N-acetylmuramate--alanine ligase (mu... | 175 | 4.80E − 44 |
| HGS010 | gnl|PID|d1025270 | MurC [*Porphyromonas gingivalis*] > sp|Q518... | 182 | 6.40E − 44 |
| HGS027 | gnl|PID|e1184607 | peptide chain release factor 1 [*Bacillus*... | 888 | 8.80E − 160 |
| HGS027 | gnl|PID|d1009421 | Peptide Termination Factor [*Mycoplasma c*... | 715 | 1.10E − 126 |
| HGS027 | gnl|PID|d1019559 | peptide chain release factor [*Synechocys*... | 539 | 4.00E − 121 |
| HGS027 | gi|2688096 | (AE001130) peptide chain release factor... | 628 | 1.40E − 115 |
| HGS027 | gnl|PID|e1342822 | (AJ235272) PEPTIDE CHAIN RELEASE FACTOR... | 569 | 1.50E − 115 |
| HGS027 | gnl|PID|d1015453 | Peptide chain release factor 1 (RF-I) [E... | 467 | 4.30E − 113 |
| HGS027 | gi|968930 | peptide chain release factor 1 [*Escheric*... | 463 | 1.50E − 112 |
| HGS027 | gi|3328413 | (AE001277) Peptide Chain Releasing Facto... | 430 | 1.50E − 112 |
| HGS027 | gi|3322309 | (AE001190) peptide chain release factor... | 604 | 1.70E − 112 |
| HGS027 | gi|147567 | peptide chain release factor 1 [*Escheric*... | 467 | 3.60E − 112 |
| HGS029 | gi|2645713 | (AF033018) ribosome recycling factor [*St*... | 895 | 2.60E − 115 |
| HGS029 | gnl|PID|e1185243 | ribosome recycling factor [*Bacillus subt*... | 633 | 2.90E − 80 |
| HGS029 | gnl|PID|d1019290 | ribosome releasing factor [*Synechocystis*... | 486 | 1.40E − 60 |
| HGS029 | gnl|PID|e248763 | frr [*Mycobacterium tuberculosis*] | 445 | 4.10E − 55 |
| HGS029 | gi|2314423 | (AE000631) ribosome releasing factor (fr... | 440 | 1.90E − 54 |
| HGS029 | gi|1573820 | ribosome releasing factor (rrf) [*Haemoph*... | 438 | 3.60E − 54 |
| HGS029 | gi|147771 | ribosome releasing factor (gtg start cod... | 437 | 4.90E − 54 |
| HGS029 | gi|3322898 | (AE001235) ribosome recycling factor [*Tr*... | 433 | 1.70E − 53 |
| HGS029 | gnl|PID|e327819 | ribosome recycling factor [*Mycobacterium*... | 431 | 3.10E − 53 |
| HGS029 | gi|4155787 | (AE001545) RIBOSOME RECYCLING FACTOR (RI... | 430 | 4.20E − 53 |
| HGS038 | gnl|PID|e1185251 | nusA [*Bacillus subtilis*] > pir|B69668|B6... | 1218 | 1.50E − 160 |
| HGS038 | gi|49316 | ORF2 gene product [*Bacillus subtilis*] >... | 1210 | 1.80E − 159 |
| HGS038 | gnl|PID|e1342846 | (AJ235272) N UTILIZATION SUBSTANCE PROT... | 602 | 6.90E − 97 |
| HGS038 | gi|642364 | NusA protein [*Thermus aquaticus* thermop... | 502 | 6.30E − 92 |
| HGS038 | gnl|PID|e1299837 | nusA [*Mycobacterium tuberculosis*] > sp|O... | 333 | 2.40E − 89 |
| HGS038 | gi|3323210 | (AE001259) N utilization substance prot... | 288 | 3.20E − 87 |
| HGS038 | gi|606109 | L factor [*Escherichia coli*] > gi|1789560... | 412 | 5.60E − 86 |
| HGS038 | gi|515637 | transcription factor [*Salmonella typhim*... | 409 | 1.90E − 85 |
| HGS038 | pir|D64114|D64114 | transcription termination-antiterminati... | 418 | 2.00E − 83 |
| HGS038 | gnl|PID|e1172585 | NusA protein (nusA) [*Escherichia coli*] | 608 | 3.40E − 78 |
| HGS039 | gi|2078377 | NusG [*Staphylococcus aureus*] > sp|O08386|... | 924 | 4.00E − 121 |
| HGS039 | gi|426473 | nusG gene product [*Staphylococcus carnos*... | 894 | 4.80E − 117 |
| HGS039 | gnl|PID|d1003063 | transcription antitermination factor *Nus*... | 648 | 1.30E − 83 |
| HGS039 | gnl|PID|e306572 | nusG [*Mycobacterium tuberculosis*] | 289 | 1.90E − 60 |
| HGS039 | sp|P96930|P96930 | TRANSCRIPTION ANTITERMINATION PROTEIN NUSG. | 289 | 1.90E − 60 |
| HGS039 | gnl|PID|d1007561 | nusG [*Streptomyces coelicolor*] > pir|S547... | 290 | 1.20E − 53 |
| HGS039 | gi|457386 | transcription factor [*Thermus aquaticus*... | 148 | 1.50E − 53 |
| HGS039 | gnl|PID|d1004802 | NusG [*Streptomyces coelicolor*] > pir|S410... | 283 | 1.10E − 52 |
| HGS039 | gnl|PID|d1004801 | NusG [*Streptomyces griseus*] > pir|S41061|... | 282 | 1.50E − 52 |
| HGS039 | gnl|PID|e349728 | NusG [*Streptomyces griseus*]> pir|S32234|... | 282 | 1.50E − 52 |
| HGS041 | gnl|PID|d1016252 | NH(3)-dependent NAD(+) synthetase (EC 6... | 620 | 2.60E − 105 |
| HGS041 | gi|146974 | NH3-dependent NAD synthetase [*Escherich*... | 620 | 3.30E − 99 |
| HGS041 | gi|143519 | outB [*Bacillus subtilis*] > gnl|PID|d1009... | 410 | 1.50E − 87 |
| HGS041 | gnl|PID|d1030194 | (AP000001) 257aa long hypothetical NH(3... | 156 | 1.20E − 21 |
| HGS041 | pir|S77778|S77778 | probable NH(3)-dependent NAD(+) synthet... | 153 | 1.80E − 20 |
| HGS041 | gi|2649596 | (AE001035) NH(3)-dependent NAD + synthet... | 167 | 3.60E − 19 |
| HGS041 | gi|2622628 | (AE000911) NH(3)-dependent NAD + synthet... | 167 | 1.90E − 18 |
| HGS041 | gi|3844972 | NH(3)-dependent NAD + synthetase, putati... | 142 | 3.20E − 18 |
| HGS041 | gi|1673951 | (AE000027) *Mycoplasma pneumoniae*, proba... | 140 | 6.30E − 16 |
| HGS041 | gi|1591995 | NH(3)-dependent NAD + synthetase (nadE)... | 162 | 1.30E − 14 |
| HGS042 | gnl|PID|e1320012 | (AJ223781) thioredoxin reductase [*Staph*... | 1592 | 1.50E − 214 |
| HGS042 | gnl|PID|e313024 | hypothetical protein [*Bacillus subtilis*... | 1162 | 1.80E − 155 |
| HGS042 | gi|2246749 | (AF009622) thioredoxin reductase [*Liste*... | 1060 | 1.80E − 141 |
| HGS042 | gi|1353197 | thioredoxin reductase [*Eubacterium acid*... | 404 | 3.80E − 98 |
| HGS042 | pir|S38988|D35156 | thioredoxin reductase (NADPH) (EC 1.6.4... | 404 | 3.80E − 98 |
| HGS042 | gi|3323124 | (AE001252) thioredoxin reductase (trxB)... | 353 | 1.80E − 96 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| HGS042 | gi\|1171125 | thioredoxin reductase [*Clostridium lito*. . . | 397 | 3.80E − 95 |
| HGS042 | gi\|2262173 | (AC002329) NADPH thioredoxin reductase. . . | 193 | 1.80E − 84 |
| HGS042 | pir\|S44027\|S44027 | thioredoxin reductase (NADPH) (EC 1.6.4. . . | 188 | 7.10E − 84 |
| HGS042 | gnl\|PID\|d1008681 | Thioredoxin Reductase (NADPH) [*Neurospo*. . . | 145 | 5.20E − 82 |
| HGS043 | gnl\|PID\|e283110 | femD [*Staphylococcus aureus*] > gnl\|PID\|e1. . . | 2299 | 0.00E + 00 |
| HGS043 | gnl\|PID\|e284993 | phosphoglucosamine mutase [*Staphylococcu*. . . | 2295 | 0.00E + 00 |
| HGS043 | gnl\|PID\|e1182110 | similar to phosphoglucomutase [*glycolysi*. . . | 1419 | 8.30E − 211 |
| HGS043 | gnl\|PID\|d1034036 | (AB006424) ybbT [*Bacillus subtilis*] > spj. . . | 1419 | 5.50E − 210 |
| HGS043 | gnl\|PID\|e1316460 | (AL031317) putative phospho-sugar mutase. . . | 744 | 1.90E − 145 |
| HGS043 | gi\|467124 | ureD;B229_C3_234 [*Mycobacterium leprae*]. . . | 643 | 9.70E − 133 |
| HGS043 | gnl\|PID\|e316048 | mrsA [*Mycobacterium tuberculosis*] > sp\|O0. . . | 655 | 1.40E − 132 |
| HGS043 | gi\|1574798 | mrsA protein (mrsA) [*Haemophilus influen*. . . | 349 | 4.50E − 129 |
| HGS043 | gnl\|PID\|d1018426 | hypothetical protein [*Synechocystis sp.*]. . . | 422 | 7.00E − 119 |
| HGS043 | gi\|3329284 | (AE001354) Phosphoglucomutase [*Chlamydia*. . . | 598 | 5.70E − 117 |
| HGS044 | gnl\|PID\|d1005827 | temperature sensitive cell division [*Bac*. . . | 1338 | 1.70E − 178 |
| HGS044 | gi\|40217 | tms gene product (AA 1-456) [*Bacillus su*. . . | 1330 | 2.10E − 177 |
| HGS044 | gnl\|PID\|e304562 | glmU [*Mycobacterium tuberculosis*] > sp\|P9. . . | 765 | 1.50E − 122 |
| HGS044 | gi\|2983227 | (AE000698) UDP-N-acetylglucosamine pyrop. . . | 349 | 5.10E − 118 |
| HGS044 | gi\|975206 | uridyltransferase [*Neisseria gonorrhoeae*. .. | 373 | 2.90E − 117 |
| HGS044 | gnl\|PID\|d1011507 | UDP-N-acetylglucosamine pyrophosphorylas. . . | 486 | 2.30E − 114 |
| HGS044 | gi\|43267 | Eco urf 1 protein [*Escherichia coli*] | 413 | 3.50E − 111 |
| HGS044 | gi\|1790168 | (AE000450) N-acetyl glucosamine-1-phosph. . . | 413 | 6.40E − 111 |
| HGS044 | gi\|1573640 | UDP-N-acetylglucosamine pyrophosphorylas. . . | 381 | 1.60E − 110 |
| HGS044 | gi\|2313807 | (AE000581) UDP-N-acetylglucosamine pyrop. . . | 264 | 8.00E − 101 |
| HGS045 | gi\|2792490 | (AF041467) coenzyme A disulfide reductas. . . | 2243 | 3.70E − 305 |
| HGS045 | gi\|2688656 | (AE001172) NADH oxidase, water-forming (. . . | 194 | 7.30E − 91 |
| HGS045 | gi\|1591361 | NADH oxidase (nox) [*Methanococcus jannas*. . . | 153 | 1.60E − 51 |
| HGS045 | gnl\|PID\|d1031560 | (AP000006) 440aa long hypothetical NADH. . . | 113 | 8.10E − 44 |
| HGS045 | gi\|2650233 | (AE001077) NADH oxidase (noxA-3) [*Archae*. . . | 139 | 3.20E − 40 |
| HGS045 | 9i\|2650234 | (AE001077) NADH oxidase (noxA-2) [*Archae*. . . | 100 | 3.20E − 37 |
| HGS045 | gi\|642030 | NADH oxidase [*Serpulina hyodysenteriae*]. . . | 109 | 4.10E − 36 |
| HGS045 | gnl\|PID\|d1030604 | (AP000002) 445aa long hypothetical NADH. . . | 115 | 1.90E − 35 |
| HGS045 | gi\|2622461 | (AE000898) NADH oxidase [*Methanobacteriu*. . . | 130 | 4.70E − 35 |
| HGS045 | gi\|49023 | NADH peroxidase [*Enterococcus faecalis*]. . . | 96 | 1.60E − 33 |
| HGS046 | gnl\|PID\|e1183495 | similar to hypothetical proteins from B. . . | 192 | 8.00E − 39 |
| HGS046 | gi\|2688416 | (AE001152) conserved hypothetical integr. . . | 263 | 8.30E − 35 |
| HGS046 | gi\|2649097 | (AE001001) conserved hypothetical protei. . . | 132 | 3.00E − 30 |
| HGS046 | gnl\|PID\|d1030609 | (AP000002) 449aa long hypothetical damag. . . | 253 | 3.50E − 29 |
| HGS046 | gnl\|PID\|d1030607 | (AP000002) 472aa long hypothetical prote. . . | 226 | 1.40E − 26 |
| HGS046 | gi\|1591425 | conserved hypothetical protein [*Methanoc*. . . | 159 | 4.60E − 26 |
| HGS046 | gi\|2314344 | (AE000624) conserved hypothetical integr. . . | 230 | 1.90E − 25 |
| HGS046 | gi\|4155699 | (AE001538) putative [*Helicobacter pylori*. . . | 224 | 6.80E − 25 |
| HGS046 | gi\|2621368 | (AE000816) conserved protein [*Methanobac*. . . | 122 | 1.80E − 22 |
| HGS046 | gnl\|PID\|e340160 | DinF protein [*Streptococcus pneumoniae*]. . . | 219 | 2.70E − 22 |
| HGS050 | dbj\|AB001488_41 | (AB001488) PROBABLE UDP-N-ACETYLMURAMOYL. . . | 513 | 5.60E − 133 |
| HGS050 | gi\|4009466 | (AF068901) D-Ala-D-Ala adding enzyme [*St*. . . | 341 | 1.30E − 90 |
| HGS050 | gi\|1574689 | UDP-MurNAc-pentapeptide synthetase (murF. . . | 386 | 5.80E − 87 |
| HGS050 | gi\|2177096 | UDP-MurNAc-Tripeptide:D-Ala-D-Ala-Adding. . . | 265 | 1.40E − 65 |
| HGS050 | gi\|1743865 | UDP-MurNAc-Tripeptide:D-Ala-D-Ala-Adding. . . | 265 | 1.40E − 65 |
| HGS050 | gi\|42048 | UDP-MurNAC-pentapeptide presynthetase (A. . . | 263 | 5.20E − 64 |
| HGS050 | gi\|2983375 | (AE000709) UDP-MURNAC-pentapeptide sythe. . . | 244 | 3.50E − 63 |
| HGS050 | gi\|3322664 | (AE001217) UDP-N-acetylmuramoylalanyl-D-. . . | 212 | 8.30E − 55 |
| HGS050 | gi\|575416 | UDP-N-acetylmuramoylalanyl-D-glutamyl-2,. . . | 309 | 1.70E − 54 |
| HGS050 | gnl\|PID\|d1018904 | UDP-N-acetylmuramoylalanyl-D-glutamyl-2,. . . | 309 | 1.70E − 54 |
| HGS052 | gi\|1044978 | ribosomal protein S8 [*Bacillus subtilis*]. . . | 564 | 8.20E − 73 |
| HGS052 | gnl\|PID\|d1011637 | ribosomal protein S8 [*Bacillus subtilis*]. . . | 551 | 5.00E − 71 |
| HGS052 | gi\|44429 | S8 protein [*Micrococcus luteus*] > pir\|S29. . . | 339 | 9.10E − 50 |
| HGS052 | gnl\|PID\|e1358535 | ribosomal protein S8 [*Thermotoga maritim*. . . | 205 | 9.60E − 50 |
| HGS052 | gnl\|PID\|d293129 | rpsH [*Mycobacterium tuberculosis*] > sp\|P9. . . | 386 | 2.20E − 48 |
| HGS052 | gnl\|PID\|e337975 | ribosomal protein S8 [*Mycobacterium leprae*] | 385 | 3.00E − 48 |
| HGS052 | gi\|1276767 | 30S ribosomal protein S8 [*Porphyra purpu*. . . | 231 | 1.00E − 47 |
| HGS052 | dbj\|AB000111_15 | (AB000111) 30S ribosomal protein S8 [*Syn*. . . | 225 | 3.50E − 47 |
| HGS052 | gi\|498771 | ribosomal S8 protein [*Thermus aquaticus*. . . | 197 | 2.20E − 46 |
| HGS052 | gi\|48108 | ribosomal protein S8 [*Thermus aquaticus*]. . . | 190 | 5.70E − 46 |
| HGS053 | gnl\|PID\|e269878 | ribosomal protein S15 [*Bacillus subtilis*. . . | 365 | 5.10E − 46 |
| HGS053 | gnl\|PID\|e1173915 | (AL008967) rpsO [*Mycobacterium tuberculo*. . . | 290 | 1.40E − 35 |
| HGS053 | gnl\|PID\|d335030 | 30s ribosomal protein s15 [*Mycobacterium*. . . | 286 | 5.00E − 35 |
| HGS053 | gnl\|PID\|e1315092 | (AL031231) 30S ribosomal protein S15 [*St*. . . | 270 | 7.90E − 33 |
| HGS053 | gnl\|PID\|d118966 | ribosomal protein S15 [*Thermus thermophi*. . . | 266 | 3.00E − 32 |
| HGS053 | gnl\|PID\|d1017615 | 30S ribosomal protein S15 [*Synechocystis*. . . | 259 | 2.80E − 31 |
| HGS053 | gi\|147748 | ribosomal protein S15 [*Escherichia coli*] . . . | 257 | 5.40E − 31 |
| HGS053 | gnl\|PID\|e1342799 | (AJ235272) 30S RIBOSOMAL PROTEIN S15 (rp. . . | 256 | 7.30E − 31 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| HGS053 | gnl|PID|e321499 | rpsO [*Yersinia enterocolitica*] | 246 | 1.60E – 29 |
| HGS053 | gi|2982947 | (AE000679) ribosomal protein S15 [*Aquife*. . . | 245 | 2.50E – 29 |
| HGS055 | gi|1165309 | S3 [*Bacillus subtilis*] | 872 | 2.30E – 115 |
| HGS055 | gnl|PID|d1009470 | Ribosomal Protein S3 [*Bacillus subtilis*]. . . | 870 | 4.30E – 115 |
| HGS055 | gi|580921 | ribosomal protein S3 [*Bacillus stearothe*. . . | 860 | 1.00E – 113 |
| HGS055 | gi|456688 | ribosomal protein S3 [*Acholeplasma palma*. . . | 486 | 1.70E – 87 |
| HGS055 | gi|3047158 | ribosomal protein S3 [*Phytoplasma sp. ST*. . . | 492 | 1.90E – 85 |
| HGS055 | gi|149869 | rps3 [Mycoplasma-like organism] > pir|B41. . . | 494 | 8.90E – 85 |
| HGS055 | gi|456692 | ribosomal protein S3 [*Anaeroplasma abact*. . . | 468 | 8.00E – 84 |
| HGS055 | gi|1573793 | ribosomal protein S3 (rpS3) [*Haemophilus*. . . | 568 | 9.20E – 84 |
| HGS055 | gnl|PID|d1011609 | ribosomal protein S3 [*Actinobacillus act*. . . | 562 | 6.10E – 83 |
| HGS055 | gi|141818 | 5' end of coding region undetermined [*Ac*. . . | 465 | 1.60E – 81 |
| HGS056 | gi|1044981 | ribosomal protein S5 [*Bacillus subtilis*]. . . | 626 | 5.10E – 81 |
| HGS056 | gi|143575 | spc ORF1; S5 [*Bacillus subtilis*] > pir|S1. . . | 565 | 6.90E – 80 |
| HGS056 | gi|143417 | ribosomal protein S5 [*Bacillus stearothe*. . . | 613 | 3.00E – 79 |
| HGS056 | gnl|PID|1254448 | S5 ribosomal protein [*Streptomyces coeli*. . . | 487 | 4.10E – 62 |
| HGS056 | gi|44432 | S5 protein [*Micrococcus luteus*] > pir|S29. . . | 422 | 4.20E – 60 |
| HGS056 | gi|606237 | 30S ribosomal subunit protein S5 [*Escher*. . . | 470 | 1.00E – 59 |
| HGS056 | gi|1573805 | ribosomal protein S5 (rpS5) [*Haemophilus*. . . | 467 | 2.70E – 59 |
| HGS056 | gnl|PID|e1234851 | (AJ223237) ribosomal protein S5 [*Salmone*. . . | 460 | 2.40E – 58 |
| HGS056 | gi|44226 | ribosomal protein S5 (AA 1-250) [*Mycopla*. . . | 455 | 7.70E – 58 |
| HGS056 | gi|3322469 | (AE001202) ribosomal protein S5 (rpsE) [. .. | 451 | 3.90E – 57 |
| HGS057 | gnl|PID|d1011647 | ribosomal protein S9 [*Bacillus subtilis*]. . . | 505 | 4.20E – 65 |
| HGS057 | pir|S08564|R3BS9 | ribosomal protein S9 - *Bacillus stearoth*. . . | 482 | 6.30E – 62 |
| HGS057 | gi|1673892 | (AE000022) *Mycoplasma pneumoniae*, riboso. . . | 293 | 1.10E – 42 |
| HGS057 | gi|1276757 | 30S ribosomal protein S9 [*Porphyra purpu*. . . | 234 | 5.20E – 42 |
| HGS057 | gnl|PID|d1018054 | 30S ribosomal protein S9 [*Synechocystis*. . . | 241 | 7.10E – 42 |
| HGS057 | gnl|PID|e1316459 | (AL031317) 30S ribosomal protein S9 [*Str*. . . | 220 | 5.20E – 41 |
| HGS057 | gi|606169 | 30S ribosomal subunit protein S9 [*Escher*. . . | 325 | 2.90E – 40 |
| HGS057 | gi|3323359 | (AE001270) ribosomal protein S9 (rpsl) [. . . | 318 | 2.70E – 39 |
| HGS057 | gi|3845009 | ribosomal protein S9 (rpS9) [*Mycoplasma*. . . | 273 | 1.40E – 38 |
| HGS057 | gi|2688239 | (AE001140) ribosomal protein S9 (rpsl) [. . . | 308 | 6.20E – 38 |
| HGS058 | gnl|PID|d1011664 | ribosomal protein S10 [*Bacillus subtilis*. . . | 479 | 3.40E – 61 |
| HGS058 | gi|1165302 | S10 [*Bacillus subtilis*] | 472 | 3.10E – 60 |
| HGS058 | gi|467321 | S10 ribosomal protein [*Streptococcus mut*. . . | 422 | 2.40E – 53 |
| HGS058 | gnl|PID|e260119 | ribosomal protein S10 [*Planobispora rose*. . . | 393 | 2.30E – 49 |
| HGS058 | gnl|PID|e1192296 | rpsX [*Mycobacterium bovis* BCG] > gnl|PID|. . . | 385 | 3.00E – 48 |
| HGS058 | gi|581340 | ribosomal protein S10 [*Mycobacterium lep*. . . | 384 | 4.10E – 48 |
| HGS058 | gi|437922 | ribosomal protein S10 [*Thermotoga mariti*. . . | 369 | 4.60E – 46 |
| HGS058 | gi|44208 | ribosomal protein S10 (AA 1-102) [*Mycopl*. . . | 367 | 8.80E – 46 |
| HGS058 | gi|3328867 | (AE001317) S10 Ribosomal Protein [*Chlamy*. . . | 333 | 2.40E – 44 |
| HGS058 | gi|1573786 | ribosomal protein S10 (rpS10) [*Haemophil*. . . | 343 | 1.50E – 42 |
| HGS059 | gnl|PID|e1182877 | similar to ribosomal protein S14 [*Bacill*. . . | 344 | 1.30E – 42 |
| HGS059 | gi|3329252 | (AE001351) S14 Ribosomal Protein [*Chlamy*. . . | 187 | 1.60E – 29 |
| HGS059 | gi|606241 | 30S ribosomal subunit protein S14 [*Esche*. . . | 181 | 5.50E – 29 |
| HGS059 | gi|1016092 | ribosomal protein S14 [*Cyanophora paradoxa*] | 167 | 5.60E – 29 |
| HGS059 | gi|1573801 | ribosomal protein S14 (rpS14) [*Haemophil*. . . | 186 | 1.00E – 28 |
| HGS059 | gi|414859 | 30s ribosomal protein S14 [*Astasia longa*. . . | 174 | 2.70E – 28 |
| HGS059 | gi|42982 | S14 (rpSN) (aa 1-99) [*Escherichia coli*] | 165 | 8.40E – 27 |
| HGS059 | gnl|PID|d1007159 | ribosomal protein S14 [*Acyrthosiphon kon*. . . | 164 | 2.10E – 26 |
| HGS059 | gi|11670 | rps14 [*Marchantia polymorpha*] > pir|A0273. . . | 155 | 2.10E – 26 |
| HGS059 | gnl|PID|e1299756 | (AL021899) rpsN2 [*Mycobacterium tubercul*. . . | 167 | 5.40E – 26 |
| HGS060 | gnl|PID|d1009468 | Ribosomal Protein S19 [*Bacillus subtilis*. . . | 409 | 4.90E – 52 |
| HGS060 | gnl|PID|e316791 | rpsS [*Mycobacterium bovis* BCG] > gnl|PID|. . . | 401 | 6.20E – 51 |
| HGS060 | gi|40106 | ribosomal protein S19 [*Bacillus stearoth*. . . | 400 | 8.60E – 51 |
| HGS060 | bbs|137759 | S19 = 30S ribosomal protein [*Mycobacterium*. . . | 395 | 4.20E – 50 |
| HGS060 | gnl|PID|e337967 | ribosomal protein S19 [*Mycobacterium lep*. . . | 395 | 4.20E – 50 |
| HGS060 | gi|1016142 | ribosomal protein S19 [*Cyanophora parado*. . . | 344 | 5.20E – 43 |
| HGS060 | dbj||AB000111_6 | (AB000111) 30S ribosomal protein S19 [*Sy*. . . | 342 | 9.90E – 43 |
| HGS060 | gi|606250 | 30S ribosomal subunit protein S19 [*Esche*. . . | 332 | 2.40E – 41 |
| HGS060 | gi|11715 | rps19 [*Marchantia polymorpha*] > pir|A0274. . . | 330 | 4.50E – 41 |
| HGS060 | gnl|PID|d1021585 | (AB001684) 30S ribosomal protein S19 [*Ch*. . . | 329 | 6.20E – 41 |
| HGS062 | gi|580930 | S14 protein (AA 1-61) [*Bacillus subtili*. . . | 285 | 1.60E – 35 |
| HGS062 | pir|S48688|S48688 | ribosomal protein S14 - *Bacillus stearo*. . . | 279 | 1.10E – 34 |
| HGS062 | gi|2766516 | (AF036708) ribosomal protein S14 [*Mycop*. . . | 240 | 3.80E – 29 |
| HGS062 | gi|4155818 | (AE001547) 30S RIBOSOMAL PROTEIN S14 [*H*. . . | 232 | 5.20E – 28 |
| HGS062 | gnl|PID|e1358534 | ribosomal protein S14 [*Thermotoga marit*. . . | 230 | 1.00E – 27 |
| HGS062 | gi|44221 | ribosomal protein S14 (AA 1-61) [*Mycopl*. . . | 228 | 1.90E – 27 |
| HGS062 | gi|2314484 | (AE000633) ribosomal protein S14 (rpS14. . . | 228 | 1.90E – 27 |
| HGS062 | bbs|168339 | ribosomal protein S14 [*Thermus thermoph*. . . | 219 | 3.60E – 26 |
| HGS062 | gnl|PID|e293291 | rpsN [*Mycobacterium tuberculosis*] >sp|P. . . | 218 | 5.00E – 26 |
| HGS062 | gi|48107 | ribosomal protein S14 [*Thermus aquaticus*] | 217 | 7.00E – 26 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| HGS064 | gnl\|PID\|d1005715 | unknown [Bacillus subtilis] > gnl\|PID\|d10... | 950 | 8.60E − 128 |
| HGS064 | gi\|4104602 | (AF036966) putative response regulator [... | 469 | 4.80E − 121 |
| HGS064 | gnl\|PID\|e1299427 | (AJ001103) arcA [Lactococcus lactis] >sp... | 794 | 4.40E − 106 |
| HGS064 | gi\|1575577 | DNA-binding response regulator [Thermoto... | 278 | 1.50E − 82 |
| HGS064 | gnl\|PID\|d1011205 | regulatory components of sensory transdu... | 239 | 1.30E − 72 |
| HGS064 | gnl\|PID\|e321544 | RegX3 [Mycobacterium bovis BCG] > sp\|O071... | 333 | 5.00E − 71 |
| HGS064 | gnl\|PID\|e321547 | RegX3 [Mycobacterium tuberculosis] >gnl\|... | 333 | 5.00E − 71 |
| HGS064 | gnl\|PID\|d1002953 | SphR [Synechococcus sp.] > pir\|S32931\|S32... | 198 | 1.10E − 70 |
| HGS064 | gnl\|PID\|d314479 | mtrA [Mycobacterium tuberculosis] > sp\|Q5... | 329 | 8.10E − 69 |
| HGS064 | gnl\|PID\|e1181525 | (AJ002571) YkoG [Bacillus subtilis] > gnl... | 193 | 4.80E − 68 |
| HGS063 | gnl\|PID\|d1037676 | (AB016431) Hypothetical protein [Staphyl... | 870 | 9.00E − 116 |
| HGS063 | gnl\|PID\|d1004537 | Mannosephosphate Isomerase [Streptococcu... | 302 | 2.80E − 102 |
| HGS063 | gnl\|PID\|d1020490 | B. subtilis mannose-6-phosphate isomeras... | 662 | 4.80E − 96 |
| HGS063 | gnl\|PID\|e1183222 | similar to mannose-6-phosphate isomerase... | 724 | 7.00E − 96 |
| HGS063 | gi\|476092 | unknown [Bacillus subtilis] > gnl\|PID\|d10... | 659 | 1.10E − 94 |
| HGS063 | gi\|3043889 | (AF015751) Cyp4 [Lactococcus lactis] > sp... | 168 | 5.60E − 16 |
| HGS065 | gnl\|PID\|d1005813 | unknown [Bacillus subtilis] > gnl\|PID\|e11... | 545 | 1.10E − 70 |
| HGS065 | gnl\|PID\|d1018846 | hypothetical protein [Synechocystis sp.]... | 430 | 1.60E − 69 |
| HGS065 | gi\|606086 | ORF_f286 [Escherichia coli] > gi\|1789535... | 422 | 3.60E − 66 |
| HGS065 | gi\|1574503 | conserved hypothetical protein [Haemophi... | 426 | 2.00E − 63 |
| HGS065 | gnl\|PID\|d1002952 | ORF3 [Micromonospora olivasterospora] >p... | 455 | 2.50E − 58 |
| HGS065 | gi\|1045730 | conserved hypothetical protein [Mycoplas... | 163 | 1.00E − 56 |
| HGS065 | gnl\|PID\|e1343020 | (AJ235273) unknown [Rickettsia prowazeki... | 409 | 1.80E − 56 |
| HGS065 | gi\|1673738 | (AE000010) Mycoplasma pneumoniae, hypoth... | 152 | 3.50E − 54 |
| HGS065 | gi\|2983597 | (AE000724) hypothetical protein [Aquifex... | 313 | 2.60E − 51 |
| HGS065 | gi\|2688342 | (AE001148) conserved hypothetical protei... | 377 | 1.60E − 47 |
| HGS066 | gnl\|PID\|e1185047 | alternate gene name: ykrC; similar to h... | 152 | 1.70E − 14 |
| HGS066 | gi\|143376 | ORF5 [Bacillus subtilis] | 147 | 7.60E − 14 |
| HGS066 | pir\|A42771\|A42771 | reticulocyte-binding protein 1 - Plasmo... | 55 | 5.30E − 09 |
| HGS066 | gi\|160626 | reticulocyte binding protein 1 [Plasmod... | 55 | 5.70E − 09 |
| HGS067 | gnl\|PID\|d1011933 | yydK [Bacillus subtilis] > sp\|Q45591\|Q455... | 278 | 1.20E − 62 |
| HGS067 | gi\|2668604 | (AF015453) GNTR transcriptional regulato... | 143 | 6.10E − 21 |
| HGS067 | gnl\|PID\|e1186191 | similar to transcriptional regulator (Gn... | 108 | 3.30E − 16 |
| HGS067 | gi\|290533 | similar to E. coli ORF adjacent to suc o... | 104 | 4.30E − 16 |
| HGS067 | gi\|1000453 | TreR [Bacillus subtilis] > gi\|2626829 Tre... | 167 | 7.10E − 15 |
| HGS067 | gnl\|PID\|d1020488 | K. aerogenes, histidine utilization repr... | 118 | 9.40E − 15 |
| HGS067 | gi\|41519 | P30 protein (AA 1-240) [Escherichia coli... | 108 | 9.90E − 15 |
| HGS067 | gi\|1763080 | PhnR [Salmonella typhimurium] > sp\|P96061... | 99 | 1.90E − 14 |
| HGS067 | gnl\|PID\|e1184335 | similar to transcriptional regulator (Gn... | 87 | 5.00E − 12 |
| HGS067 | gi\|396486 | ORF8 [Bacillus subtilis] > gnl\|PID\|d10096... | 144 | 2.30E − 11 |
| HGS068 | gi\|40027 | homologous to E.coli gidB [Bacillus subt... | 444 | 1.50E − 102 |
| HGS068 | gi\|950065 | methyltransferases [Mycoplasma capricolu... | 164 | 2.60E − 47 |
| HGS068 | gnl\|PID\|d1011190 | glucose inhibited division protein B [Sy... | 157 | 3.20E − 38 |
| HGS068 | gi\|290589 | glucose inhibited division protein [Esch... | 136 | 1.60E − 33 |
| HGS068 | gi\|1573466 | glucose-inhibited division protein (gidB... | 117 | 1.10E − 31 |
| HGS068 | gnl\|PID\|e290777 | orf256; translated orf similarity to SWI... | 136 | 1.80E − 26 |
| HGS068 | gi\|581464 | homologous to E.coli gidB [Pseudomonas p... | 139 | 6.40E − 23 |
| HGS068 | gi\|2983927 | (AE000746) glucose inhibited division pr... | 117 | 3.70E − 21 |
| HGS068 | gi\|2898105 | (AF031590) GidB-like [Streptomyces coeli... | 130 | 2.90E − 20 |
| HGS068 | gi\|2314206 | (AE000613) glucose-inhibited division pr... | 121 | 2.40E − 17 |
| HGS069 | gnl\|PID\|d1005835 | unknown [Bacillus subtilis] > gnl\|PID\|e11... | 328 | 6.00E − 100 |
| HGS069 | gi\|2983025 | (AE000684) hypothetical protein [Aquifex... | 281 | 9.30E − 31 |
| HGS069 | gi\|2708269 | unknown [Brucella abortus] > sp\|O54384\|O5... | 259 | 1.80E − 27 |
| HGS069 | gnl\|PID\|e242767 | product is homologous to Streptococcus c... | 253 | 6.60E − 27 |
| HGS069 | gi\|416539 | homologous to a Streptomyces cacaoi beta... | 251 | 2.80E − 26 |
| HGS069 | gi\|882675 | CG Site No. 33299 [Escherichia coli] > gi... | 251 | 2.90E − 26 |
| HGS069 | gnl\|PID\|d1017776 | regulatory protein for beta-lactamase [S... | 232 | 1.70E − 23 |
| HGS069 | gi\|1573434 | mazG protein (mazG) [Haemophilus influen... | 223 | 3.20E − 22 |
| HGS069 | gnl\|PID\|d1001238 | regulatory protein for beta-lactamase [S... | 133 | 5.50E − 18 |
| HGS069 | gi\|3323087 | (AE001249) mazG protein (mazG) [Treponem... | 124 | 2.40E − 13 |
| HGS070 | gnl\|PID\|e1185242 | uridylate kinase [Bacillus subtilis] > pi... | 920 | 2.20E − 122 |
| HGS070 | gnl\|PID\|d1019291 | uridine monophosphate kinase [Synechocys... | 530 | 3.80E − 96 |
| HGS070 | gnl\|PID\|e1296663 | (AL023797) uridylate kinase [Streptomyce... | 678 | 4.50E − 89 |
| HGS070 | gnl\|PID\|e248883 | pyrH [Mycobacterium tuberculosis] | 416 | 1.30E − 88 |
| HGS070 | gnl\|PID\|e327783 | uridylate kinase [Mycobacterium leprae]... | 403 | 1.60E − 85 |
| HGS070 | gi\|473234 | uridine 5'-monophosphate (UMP) kinase [E... | 384 | 4.00E − 72 |
| HGS070 | gi\|1552748 | uridine 5'-monophosphate (UMP) kinase [E... | 375 | 6.80E − 71 |
| HGS070 | gi\|1574616 | uridylate kinase (pyrH) [Haemophilus inf... | 409 | 6.90E − 71 |
| HGS070 | gnl\|PID\|d1033306 | (AB010087) UMP kinase [Pseudomonas aerug... | 355 | 7.70E − 66 |
| HGS070 | gnl\|PID\|e1342466 | (AJ235270) URIDYLATE KINASE (pyrH) [Rick... | 461 | 3.60E − 59 |
| HGS071 | dbj\|\|AB001488_40 | (AB001488) PROBABLE D-ALANINE--D-ALANINE... | 812 | 2.70E − 123 |
| HGS071 | gi\|1244574 | D-alanine:D-alanine ligase [Enterococcus... | 732 | 2.60E − 114 |

TABLE 2-continued

Closest matching sequence between the polypeptides of the present invention an sequences in GenSeq and GenBank databases

| Sequence ID. | Antigen Accession No. | Match Gene Name | High Score | Smallest Sum Probability P (N) |
|---|---|---|---|---|
| HGS071 | gi\|460080 | D-alanine:D-alanine ligase-related prote... | 742 | 2.70E – 114 |
| HGS071 | gnl\|PID\|e304921 | unnamed protein product [unidentified]>... | 742 | 2.70E – 114 |
| HGS071 | gi\|4009465 | (AF068901) D-Ala-D-Ala ligase [Streptoco... | 554 | 9.40E – 112 |
| HGS071 | gnl\|PID\|d1018410 | D-alanine:D-alanine ligase-related prote... | 219 | 2.00E – 107 |
| HGS071 | gi\|153943 | D-alanine:D-alanine ligase (EC 6.3.2.4)... | 256 | 1.90E – 103 |
| HGS071 | gi\|145722 | D-alanine:D-alanine ligase A [Escherichi... | 240 | 4.60E – 100 |
| HGS071 | gi\|1244572 | D-alanine:D-alanine ligase [Enterococcus... | 625 | 2.00E – 98 |
| HGS071 | gnl\|PID\|e1359179 | (AL034447) D-alanine-D-alanine ligase [S... | 239 | 2.70E – 92 |
| HGS072 | gnl\|PID\|d1003054 | farnesyl diphosphate synthase [Bacillus... | 333 | 2.00E – 85 |
| HGS072 | gnl\|PID\|e1185696 | similar to geranyltranstransferase [Baci... | 335 | 2.10E – 82 |
| HGS072 | gnl\|PID\|d1026193 | (AB003187) farnesyl diphosphate synthase... | 340 | 3.70E – 82 |
| HGS072 | gi\|1016225 | CrtE [Cyanophora paradoxa] >sp\|P48368\|CR... | 302 | 2.40E – 69 |
| HGS072 | gnl\|PID\|d1017423 | geranylgeranyl pyrophosphate synthase [S... | 293 | 8.20E – 69 |
| HGS072 | gi\|3885426 | (AF020041) geranylgeranyl pyrophosphate... | 302 | 1.70E – 65 |
| HGS072 | sp\|O81099\|O81099 | GERANYLGERANYL PYROPHOSPHATE SYNTHASE... | 302 | 3.10E – 65 |
| HGS072 | gi\|1574277 | geranyltranstransferase (ispA) [Haemophi... | 344 | 5.10E – 65 |
| HGS072 | gi\|1773105 | geranyltransperase [Escherichia coli] > g... | 228 | 1.80E – 64 |
| HGS072 | gi\|1063276 | geranylgeranyl pyrophosphate synthase [C... | 288 | 1.30E – 63 |
| HGS073 | gi\|143803 | GerC3 [Bacillus subtilis] >gnl\|PID\|e118... | 517 | 1.20E – 82 |
| HGS073 | gnl\|PID\|d1009341 | component II of heptaprenyl diphosphate... | 506 | 5.20E – 81 |
| HGS073 | gnl\|PID\|d1026196 | (AB003188) component B of hexaprenyl di... | 493 | 2.00E – 69 |
| HGS073 | gi\|1813470 | spore germination protein C3 [Bacillus... | 467 | 3.10E – 60 |
| HGS073 | gi\|336639 | prephytoene pyrophosphate dehydrogenase... | 338 | 9.30E – 50 |
| HGS073 | pir\|S76966\|S76966 | geranylgeranyl pyrophosphate synthase c... | 352 | 1.20E – 47 |
| HGS073 | dbj\|\|AB001997_1 | (AB001997) solanesyl diphosphate syntha... | 211 | 7.40E – 44 |
| HGS073 | gi\|1276734 | prenyl transferase [Porphyra purpurea]... | 306 | 3.40E – 42 |
| HGS073 | gnl\|PID\|d1031114 | (AP000004) 342aa long hypothetical gera... | 202 | 4.80E – 42 |
| HGS073 | gi\|1573899 | octaprenyl-diphosphate synthase (ispB)... | 296 | 1.40E – 40 |
| HGS074 | gnl\|PID\|d1032955 | (AB004319) undecaprenyl diphosphate synt... | 533 | 2.00E – 69 |
| HGS074 | gnl\|PID\|e1185244 | similar to hypothetical proteins [Bacill... | 450 | 5.80E – 58 |
| HGS074 | gnl\|PID\|d1011480 | hypothetical protein [Synechocystis sp.]... | 340 | 1.00E – 42 |
| HGS074 | gi\|3328883 | (AE001319) YaeS family [Chlamydia tracho... | 324 | 1.60E – 40 |
| HGS074 | gi\|1786371 | (AE000127) orf, hypothetical protein [Es... | 323 | 2.20E – 40 |
| HGS074 | gnl\|PID\|d1012616 | unknown [Escherichia coli] | 315 | 4.40E – 39 |
| HGS074 | gi\|1573941 | conserved hypothetical protein [Haemophi... | 307 | 3.90E – 38 |
| HGS074 | gi\|3242704 | (AC003040) hypothetical protein [Arabido... | 220 | 3.70E – 37 |
| HGS074 | gnl\|PID\|e1342726 | (AJ235271) unknown [Rickettsia prowazeki... | 188 | 1.20E – 36 |
| HGS074 | gnl\|PID\|e315162 | hypothetical protein Rv2361c [Mycobacter... | 301 | 1.20E – 35 |
| HGS075 | gi\|4104603 | (AF036966) putative histidine kinase [La... | 426 | 1.60E – 185 |
| HGS075 | gnl\|PID\|d1011961 | homologous to sp:PHOR_BACSU [Bacillus su... | 517 | 8.60E – 180 |
| HGS075 | gi\|2182992 | histidine kinase [Lactococcus lactis cre... | 300 | 1.30E – 90 |
| HGS075 | gi\|410142 | ORFX18 [Bacillus subtilis] > gnl\|PID\|e118... | 373 | 1.20E – 63 |
| HGS075 | gi\|1575578 | histidine protein kinase [Thermotoga mar... | 248 | 6.50E – 51 |
| HGS075 | gi\|143331 | alkaline phosphatase regulatory protein... | 360 | 5.30E – 49 |
| HGS075 | gi\|3687664 | (AF049873) sensor protein [Lactococcus l... | 202 | 5.40E – 49 |
| HGS075 | gi\|288420 | drug sensory protein A [Synechocystis PC... | 114 | 5.90E – 44 |
| HGS075 | gi\|2352098 | histidine protein kinase; KinB [Pseudomo... | 118 | 3.10E – 38 |
| HGS075 | gi\|1276858 | hypothetical chloroplast ORF 26. [Porphy... | 102 | 3.20E – 38 |
| deaD | gi\|1573195 | ATP-dependent RNA helicase (deaD) [H... | 419 | 2.10E – 121 |
| deaD | gi\|145727 | deaD [Escherichia coli] | 405 | 2.00E – 120 |
| deaD | gi\|149184 | RNA helicase [Klebsiella pneumoniae]... | 403 | 2.10E – 120 |
| deaD | gnl\|PID\|d1011207 | ATP-dependent RNA helicase DeaD [Syn... | 810 | 7.20E – 117 |
| deaD | gi\|606102 | two frameshifts relative to ECODEAD... | 405 | 3.30E – 116 |
| deaD | s\|P23304\|DEAD_EC | OLI ATP-DEPENDENT RNA HELICASE DEAD.>gi... | 405 | 6.70E – 116 |
| deaD | gnl\|PID\|e254889 | deaD [Mycobacterium tuberculosis] > s... | 356 | 1.60E – 112 |
| deaD | gi\|2313340 | (AE000544) ATP-dependent RNA helicas... | 421 | 4.20E – 112 |
| deaD | gi\|2621248 | (AE000807) ATP-dependent RNA helicas... | 437 | 1.70E – 111 |
| deaD | gi\|4154758 | (AE001461) ATP-DEPENDENT RNA HELICAS... | 420 | 8.40E – 108 |

Vectors and Host Cell

The present invention also relates to vectors which include the isolated DNA molecules of the present invention, host cells comprising the recombinant vectors, and the production of S. aureus polypeptides and peptides of the present invention expressed by the host cells.

Recombinant constructs may be introduced into host cells using well-known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The S. aureus polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10 available from Qiagen; pBS vectors, Phagescript vectors, Bluescript vectors, pNH8A, pNH16a, pNH18A, pNH46A available from Stratagene Cloning Systems, Inc.; pET series of vectors available from Novagen; and ptrc99a, pKK223–3, pKK233–3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Among known bacterial promoters suitable for use in the present invention include the *E. coli* lacI and lacZ promoters, the T3, T5 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by competent cell transformation, calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)). ). It is specifically contemplated that the polypeptides of the present invention may in fact be expressed by a host cell lacking a recombinant vector.

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. A preferred fusion protein comprises a Hexa-Histidine peptide fused inframe to the polypeptide of the invention. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al. (1995) J. Molec. Recogn. 8:52–58 and Johanson, K. et al. (1995) J. Biol. Chem. 270 (16): 9459–9471.

The S. aureus polypeptides can be recovered and purified from recombinant cell cultures by well-known methods including ammonium sulfate or ethanol precipitation, acid extraction, anion or cation exchange chromatography (e.g. a Nickel anion exchange column can be used to bind the Hexa-His tagged fusion protein), phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well-known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express any plasma membrane associated protein of the invention in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a plasma membrane associated polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a plasma membrane associated polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a plasma membrane associated protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a plasma membrane associated polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses host cells that have been engineered to delete or replace endogenous genetic material (e.g. coding sequences for the polypeptides of the present invention), and/or to include genetic material (e.g. heterologous polynucleotide sequences) that is operably associated with polynucleotides of the present invention, and which activates, alters, and/or amplifies endogenous polynucleotides of the present invention. For example, techniques known in the art may be used to operably associate heterologous control regions (e.g. promoter and/or enhancer) and endogenous polynucleotide sequences via homologous recombination (see, e.g. U.S. Pat. No. 5,641,670, issued Jun. 24, 1997; Internation Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra, et al., Nature 342:435–438 (1989), the disclosures of each of which are hereby incorporated by reference in their entireties).

In addition, polypeptides of the invention can be chemically synthesized using techniques known in the art (e.g., see Creighton, 1983, Proteins: Structures and Molecular Principles, W. H. Freeman & Co., New York, and Hunkapiller et al., Nature, 310:105–111 (1984)). For example, a polypeptide corresponding to a fragment of a S. aureus polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses polypeptides of the present invention which are differentially modified during or after translation, such as for example, by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of alternative host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile, which can include, for example, the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference in their entireties.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing polypeptides corresponding to only one of the amino acid sequences of Table 1 (including fragments, variants, splice variants, and fusion proteins, corresponding to these as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., the polypeptide sequences shown in Table 1). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein. In one example, covalent associations are between the heterologous sequence contained in a fusion protein of the invention (see, e.g., U.S. Pat. No. 5,478,925). In a specific example, the covalent associations are between the heterologous sequence contained in a Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, International Publication NO: WO 98/49305, the contents of which is incorporated herein incorporated by reference in its entirety). In another embodiment, two or more polypeptides of the invention are joined through peptide linkers. Examples include those peptide linkers described in U.S. Pat. No. 5,073,627 (incorporated herein by reference in its entirety). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is incorporated herein by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is incorporated herein by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is incorporated herein by reference in its entirety). Additionally, techniques known in the art may be applied to generate liposomes containing the polypeptide components desired to be contained in the multimer of the invention (see, e.g., U.S. Pat. No. 5,478,925, which is incorporated herein by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is incorporated herein by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is incorporated herein by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is incorporated herein by reference in its entirety).

Polypeptides and Fragments

The invention further provides an isolated *S. aureus* polypeptide having an amino acid sequence in Table 1, or a peptide or polypeptide comprising a portion, fragment, variant or analog of the above polypeptides.

In the present invention, a "polypeptide fragment" refers to a short amino acid sequence contained in any one of the polypeptide sequences shown in Table 1 or encoded by the DNA contained in the deposit. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the mature form. Further preferred polypeptide fragments include the mature form having a continuous series of deleted residues from the amino or the carboxy terminus, or both. For example, any number of amino acids, ranging from 1–60, can be deleted from the amino terminus the mature form. Similarly, any number of amino acids, ranging from 1–30, can be deleted from the carboxy terminus of the mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, betasheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of the sequences shown in Table 1 falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Variant and Mutant Polypeptides

To improve or alter the characteristics of *S. aureus* polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions. Further, the polypeptides of the present invention may be produced as multimers including dimers, trimers and tetramers. Multimerization may be facilitated by linkers or recombinantly though fused heterologous polypeptides such as Fc regions.

N-Terminal and C-Terminal Deletion Mutants

It is known in the art that one or more amino acids may be deleted from the N-terminus or C-terminus without substantial loss of biological function. For instance, Ron et al. J. Biol. Chem., 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the polypeptides shown in Table 1.

Similarly, many examples of biologically functional C-terminal deletion mutants are known. For instance, Interferon gamma shows up to ten times higher activities by deleting 8–10 amino acid residues from the carboxy terminus of the protein See, e.g., Dobeli, et al. (1988) J. Biotechnology 7:199–216. Accordingly, the present invention provides polypeptides having one or more residues from the carboxy terminus of the polypeptides shown in Table 1. The invention also provides polypeptides having one or more amino acids deleted from both the amino and the carboxyl termini as described below.

The polypeptide fragments of the present invention can be immediately envisaged using the above description and are therefore not individually listed solely for the purpose of not unnecessarily lengthening the specification.

The present invention is further directed to polynucleotide encoding portions or fragments of the amino acid sequences described herein as well as to portions or fragments of the isolated amino acid sequences described herein. Fragments include portions of the amino acid sequences of Table 1, at least 7 contiguous amino acid in length, selected from any two integers, one of which representing a N-terminal position. The first codon of the polypeptides of Table 1 is position 1. Every combination of a N-terminal and C-terminal position that a fragment at least 7 contiguous amino acid residues in length could occupy, on any given amino acid sequence of Table 1 is included in the invention. At least means a fragment may be 7 contiguous amino acid residues in length or any integer between 7 and the number of residues in a full-length amino acid sequence minus 1. Therefore, included in the invention are contiguous fragments specified by any N-terminal and C-terminal positions of amino acid sequence set forth in Table 1 wherein the contiguous fragment is any integer between 7 and the number of residues in a full-length sequence minus 1.

Further, the invention includes polypeptides comprising fragments specified by size, in amino acid residues, rather than by N-terminal and C-terminal positions. The invention includes any fragment size, in contiguous amino acid residues, selected from integers between 7 and the number of residues in a full-length sequence minus 1. Preferred sizes of contiguous polypeptide fragments include about 7 amino acid residues, about 10 amino acid residues, about 20 amino acid residues, about 30 amino acid residues, about 40 amino acid residues, about 50 amino acid residues, about 100 amino acid residues, about 200 amino acid residues, about 300 amino acid residues, and about 400 amino acid residues. The preferred sizes are, of course, meant to exemplify, not limit, the present invention as all size fragments representing any integer between 7 and the number of residues in a full-length sequence minus 1 are included in the invention. The present invention also provides for the exclusion of any fragments specified by N-terminal and C-terminal positions or by size in amino acid residues as described above. Any number of fragments specified by N-terminal and C-terminal positions or by size in amino acid residues as described above may be excluded.

Moreover, polypeptide fragments can be at least 10, 20, 30, 40, 50, 60, 70, 80, 90, 100, 110, 120, 130, 140, 150, 175 or 200 amino acids in length. Polynucleotides encoding these polypeptides are also encompassed by the invention. In this context "about" includes the particularly recited ranges, larger or smaller by several (5, 4, 3, 2, or 1) amino acids, at either extreme or at both extremes.

The present invention further provides polypeptides having one or more residues deleted from the amino terminus of the amino acid sequence of a polypeptide disclosed herein (e.g., any polypeptide of Table 1). In particular, N-terminal deletions may be described by the general formula m–q, where q is a whole integer representing the total number of amino acid residues in a polypeptide of the invention (e.g., a polypeptide disclosed in Table 1), and m is defined as any integer ranging from 2 to q–6. Polynucleotides encoding these polypeptides are also encompassed by the invention.

The present invention further provides polypeptides having one or more residues from the carboxy-terminus of the amino acid sequence of a polypeptide disclosed herein (e.g., a polypeptide disclosed in Table 1). In particular, C-terminal deletions may be described by the general formula 1–n, where n is any whole integer ranging from 6 to q–1, and where n corresponds to the position of amino acid residue in a polypeptide of the invention. Polynucleotides encoding these polypeptides are also encompassed by the invention.

In addition, any of the above-described N- or C-terminal deletions can be combined to produce a N- and C-terminal deleted polypeptide. The invention also provides polypeptides having one or more amino acids deleted from both the amino and the carboxyl termini, which may be described generally as having residues m–n of a polypeptide encoded by a nucleotide sequence (e.g., including, but not limited to the preferred polypeptide disclosed in Table 1), or the cDNA contained in a deposited clone, and/or the complement thereof, where n and m are integers as described above. Polynucleotides encoding these polypeptides are also encompassed by the invention.

The polypeptide fragments of the present invention can be immediately envisaged using the above description and are therefore not individually listed solely for the purpose of not unnecessarily lengthening the specification.

The above fragments need not be active since they would be useful, for example, in immunoassays, in epitope mapping, epitope tagging, to generate antibodies to a particular portion of the polypeptide, as vaccines, and as molecular weight markers.

Other Mutants

In addition to N- and C-terminal deletion forms of the protein discussed above, it also will be recognized by one of ordinary skill in the art that some amino acid sequences of the S. aureus polypeptides of the present invention can be varied without significant effect of the structure or function of the protein. If such differences in sequence are contemplated, it should be remembered that there will be critical areas on the protein which determine activity.

Thus, the invention further includes variations of the S. aureus polypeptides which show substantial S. aureus polypeptide activity or which include regions of S. aureus protein such as the protein portions discussed below. Such mutants include deletions, insertions, inversions, repeats, and substitutions selected according to general rules known in the art so as to have little effect on activity. For example, guidance concerning how to make phenotypically silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative, analog, or homolog of the polypeptide of Table 1 may be, for example: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the S. aureus polypeptide is fused with another compound, such as a compound to increase the half-life of the polypeptide (for example, polyethylene glycol): or (iv) one in which the additional amino acids are fused to the above form of the polypeptide, such as an Hexa-Histidine tag peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the S. aureus polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the S. aureus proteins of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and may partially or substantially purified. A recombinantly produced version of the S. aureus polypeptide can be substantially purified by the one-step method described by Smith et al. (1988) Gene 67:31–40. Polypeptides of the invention also can be purified from natural or recombinant sources using antibodies directed against the polypeptides of the invention in methods which are well-known in the art of protein purification. The purity of the polypeptide of the present invention may also specified in percent purity as relative to heterologous containing polypeptides. Preferred purities include at least 25%, 50%, 75%, 80%, 85%, 90%, 91%, 92%, 93%, 94%, 95%, 96%, 97%, 98%, 99.75%, and 100% pure, as relative to heretologous containing polypeptides.

The invention provides for isolated S. aureus proteins comprising, or alternatively consisting of, polypeptides having an amino acid sequence selected from the group consisting of: (a) a full-length S. aureus polypeptide having the complete amino acid sequence shown in Table 1, (b) a full-length S. aureus polypeptide having the complete amino acid sequence shown in Table 1 excepting the N-terminal codon (e.g., including but not limited to, methionine, leucine, and/or valine), (c) an antigenic fragment of any of the polypeptides shown in Table 1, (d) a biologically active fragment of any of the polypeptides shown in Table 1, (e) a polypeptide encoded by any of the polynucleotide sequences shown in Table 1, and (f) a polypeptide shown in Table 1. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f) above. Further polypeptides of the present invention include polypeptides which have at least 90% similarity, more preferably at least 95% similarity, and still more preferably at least 96%, 97%, 98% or 99% similarity to those described above. Polynucleotides encoding these polypeptides are also encompassed by the invention.

A further embodiment of the invention relates to a polypeptide which comprises the amino acid sequence of a S. aureus polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a S. aureus polypeptide, having at least one, but not more than 10, 9, 8, 7, 6, 5, 4, 3, 2 or 1 conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequences shown in Table 1, or a fragment thereof, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to be made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have S. aureus activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting S. aureus protein expression or as agonists and antagonists capable of enhancing or inhibiting S. aureus protein function. Further, such polypeptides can be used in the yeast two-hybrid system to "capture" S. aureus protein binding proteins which are also candidate agonists and antagonists according to the present invention. See, e.g., Fields et al. (1989) Nature 340:245–246.

The present invention encompasses polypeptides comprising, or alternatively consisting of, an epitope of the polypeptide having an amino acid sequence in Table 1, or encoded by a polynucleotide that hybridizes to the complement of a nucleotide sequence shown in Table 1 under stringent hybridization conditions or alternatively, lower stringency hybridization conditions as defined supra. The present invention further encompasses polynucleotide sequences encoding an epitope of a polypeptide sequence of the invention (such as, for example, a nucleotide sequence disclosed in Table 1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications are incorporated herein by reference in its entirety). In one embodiment, alteration of polynucleotides corresponding to those shown in Table 1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Predicted antigenic epitopes are shown in Table 4, below. It is pointed out that Table 4 only lists amino acid residues comprising epitopes predicted to have the highest degree of antigenicity by a particular algorithm. The polypeptides not listed in Table 4 and portions of polypeptides not listed in Table 4 are not considered non-antigenic. This is because they may still be antigenic in vivo but merely not recognized as such by the particular algorithm used. Thus, Table 4 lists the amino acids residues comprising only preferred antigenic epitopes, not a complete list. In fact, all fragments of the polypeptide sequence of Table 1, at least 7 amino acid residues in length, are included in the present invention as being useful in epitope mapping and in making antibodies to particular portions of the polypeptides. Moreover, Table 4 lists only the critical residues of the epitopes determined by the Jameson-Wolf analysis. Thus, additional flanking residues on either the N-terminal, C-terminal, or both N- and C-terminal ends may be added to the sequences of Table 4 to generate an epitope-bearing protion a least 7 residues in length. Amino acid residues comprising other antigenic epitopes may be determined by algorithms similar to the Jameson-Wolf analysis or by in vivo testing for an antigenic response using the methods described herein or those known in the art.

Non-limiting examples of antigenic polypeptides or peptides that can be used to generate an Staphylococcal-specific immune response or antibodies include fragments of the amino acid sequences of Table 1 as discussed above. Table 4 discloses a list of non-limiting residues that are involved in the antigenicity of the epitope-bearing fragments of the present invention. Therefore, also included in the present inventions are isolated and purified antigenic epitope-bearing fragments of the polypeptides of the present invention comprising a peptide sequences of Table 4. The antigenic epitope-bearing fragments comprising a peptide sequence of Table 4 preferably contain between 7 to 50 amino acids (i.e. any integer between 7 and 50) of a polypeptide of the present invention. Also, included in the present invention are antigenic polypeptides between the integers of 7 and the full length sequence of a polypeptide of Table 1 comprising 1 or more amino acid sequences of Table 4. Therefore, in most cases, the polypeptides of Table 4 make up only a portion of the antigenic polypeptide. All combinations of sequences between the integers of 7 and the full sequence of a polypeptide sequence of Table 1 are included. The antigenic epitope-bearing fragments may be specified by either the number of contiguous amino acid residues or by specific N-terminal and C-terminal positions as described above for the polypeptide fragments of the present invention, wherein the first codon of each polypeptide sequence of Table 1 is position 1. Any number of the described antigenic epitope-bearing fragments of the present invention may also be excluded from the present invention in the same manner.

Antibodies

Further polypeptides of the invention relate to antibodies and T-cell antigen receptors (TCR) which immunospecifically bind a polypeptide, polypeptide fragment, or variant of any one of the polypeptide sequences in Table 1, and/or an epitope, of the present invention (as determined by immunoassays well-known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, the immunoglobulin molecules of the invention are IgG1. In another specific embodiment, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Table 4 below. Preferred epitopes of the invention include the predicted antigenic epitopes shown in Table 4, below. It is pointed out that Table 4 only lists amino acid residues comprising epitopes predicted to have the highest degree of antigenicity by particular algorithm.

bearing portion at least 7 residues in length. Amino acid residues comprising other antigenic epitopes may be determined by algorithms similar to the Jameson-Wolf analysis or by in vivo testing for an antigenic response using the methods described herein or those known in the art.

TABLE 4

| | Residues Comprising Antigenic Epitoes |
|---|---|
| HGS010 MurC | from about Gly-137 to about Lys-139, from about Lys-236 to about Asp-239. |
| HGS027 Rfl | from about Asn-106 to about Lys-109, from about Glu-191 to about Gly-194, from about Arg-227 to about Ala-231. |
| HGS038 NusA | from about Lys-39 to about Asp-42, from about Pro-170 to about Lys-173, from about Thr-302 to about Gln-304. |
| HGS041 NadE | from about Lys-173 to about Asp-176, from about Lys-189 to about Gly-192, from about Lys-273 to about Arg-275. |
| HGS042 TrxB | from about Lys-192 to about Asp-194, from about Lys-210 to about Gly-212. |
| HGS043 FemD/GlmM | from about Arg-29 to about Gly-31, from about Pro-210 to about Gly-212, from about Asn-305 to about Thr-307. |
| HGS044 GlmU | from about Asp-261 to about Thr-263, from about Asp-390 to about Asn-393, from about Arg-452 to about Gly-454. |
| HGS045 CoADR | from about Thr-377 to about Asn-379. |
| HGS046 SVR | from about Tyr-89 to about Ser-92. |
| HGS050 MurF | from about Asp-258 to about Thr-262. |
| HGS053 Ribosomal Protein S15 | from about Arg-53 to about Gly-55. |
| HGS057 Ribosomal Protein S9 | from about Arg-7 to about Thr-9, from about Arg-11 to about Lys-13, from about Lys-58 to about Asn-60. |
| HGS059 Ribosomal Protein S14 | from about Pro-40 to about Asp-42. |
| HGS060 Ribosomal Protein S19 | from about Asp-53 to about Arg-55. |
| HGS064 YycF | from about Asp-34 to about Asn-36, from about Gly-58 to about Asp-60. |
| HGS063 | from about Asp-27 to about Thr-31, from about Tyr-52 to about Gly-54, from about Glu-104 to about Gly-109, from about Gln-196 to about Asp-202. |
| HGS067 | from about Pro-27 to about Asp-29, from about Pro-236 to about Lys-238. |
| HGS068 | from about Pro-221 to about Lys-223. |
| HGS069 | from about Pro-180 to about Asp-182. |
| HGS071 DdlA | from about Asn-45 to about Asp-48, from about Ser-82 to about Ser-84, from about Lys-249 to about Gly-255, from about Lys-350 to about Tyr-353. |
| HGS072 IspA | from about Asp-88 to about Asp-91, from about Arg-93 to about Gly-95, from about Asn-240 to about Ser-243. |
| HGS073 IspB | from about Lys-44 to about Gly-47. |
| HGS075 YycG | from about Tyr-140 to about Gly-143, from about Ser-221 to about Asn-224, from about Ser-506 to about Asp-509. |
| Pbp1 | from about Glu-64 to about Gly-66, from about Asp-70 to about Asn-72, from about Arg-140 to about Gly-142, from about Pro-172 to about Gly-174, from about Pro-234 to about Asp-238, from about Glu-292 to about Gly-294, from about Pro-312 to about Ser-314, from about Lys-337 to about Gly-339. |
| DeaD | from about Asn-380 to about Arg-382, from about Arg-462 to about Asn-466, from about Asn-474 to about Gly-480, from about Asp-485 to about Tyr-494, from about Lys-509 to about Gly-513. |

The polypeptides not listed in Table 4 and portions of polypeptides not listed in Table 4 are not considered non-antigenic. This is because they may still be antigenic in vivo but merely not recognized as such by the particular algorithm used. Thus, Table 4 lists the amino acid residues comprising only preferred antigenic epitopes, not a complete list. In fact, all fragments of the polypeptide sequence of Table 1, at least 7 amino acids residues in length, are included in the present invention as being useful in epitope mapping and in making antibodies to particular portions of the polypeptides. Moreover, Table 4 lists only the critical residues of the epitopes determined by the Jameson-Wolf analysis. Thus, additional flanking residues on either the N-terminal, C-terminal, or both N- and C-terminal ends may be added to the sequences of Table 4 to generate a epitope- These polypeptide fragments have been determined to bear antigenic epitopes of the S. aureus proteins shown in Table 1 by the analysis of the Jameson-Wolf antigenic index. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6) :805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having any of the amino acid sequences shown in Table 1.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, New York, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthinegruanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, New York (1993); Kriegler, Gene Transfer and Expression, A Laboratory Manual, Stockton Press, New York (1990); and in Chapters 12 and 13, Dracopoli et al. (eds), Current Protocols in Human Genetics, John Wiley & Sons, New York (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of any one of the amino acid sequences shown in Table 1 may be fused or conjugated to the above antibody portions to increase the in vivo half life of the polypeptides or for use in inununoassays using methods known in the art. Further, the polypeptides corresponding to S. aureus proteins shown in Table 1 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexahistidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X- 100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, New York (1993); and Kriegler, Gene Transfer and Expression, A Laboratory Manual, Stockton Press, New York (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitate delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Diagnostic Assays

The present invention further relates to methods for assaying staphylococcal infection in an animal by detecting the expression of genes encoding staphylococcal polypeptides of the present invention. The methods comprise analyzing tissue or body fluid from the animal for *Staphylococcus*-specific antibodies, nucleic acids, or proteins. Analysis of nucleic acid specific to *Staphylococcus* is assayed by PCR or hybridization techniques using nucleic acid sequences of the present invention as either hybridization probes or primers. See, e.g., Sambrook et al. Molecular cloning: A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group *Rickettsiae* species by analysis of restriction fragment length polymorphism of PCR-amplified DNA) and Chen et al. 1994 J. Clin. Microbiol. 32:589–595 (detecting bacterial nucleic acids via PCR).

Where diagnosis of a disease state related to infection with *Staphylococcus* has already been made, the present invention is useful for monitoring progression or regression of the disease state by measuring the amount of *Staphylococcus* cells present in a patient or whereby patients exhibiting enhanced *Staphylococcus* gene expression will experience a worse clinical outcome relative to patients expressing these gene(s) at a lower level.

By "biological sample" is intended any biological sample obtained from an animal, cell line, tissue culture, or other source which contains *Staphylococcus* polypeptide, mRNA, or DNA. Biological samples include body fluids (such as saliva, blood, plasma, urine, mucus, synovial fluid, etc.) tissues (such as muscle, skin, and cartilage) and any other biological source suspected of containing *Staphylococcus* polypeptides or nucleic acids. Methods for obtaining biological samples such as tissue are well known in the art.

The present invention is useful for detecting diseases related to *Staphylococcus* infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidinium-thiocyanate-phenol-chloroform method described in Chomczynski et al. (1987) Anal. Biochem. 162:156–159. mRNA encoding *Staphylococcus* polypeptides having sufficient homology to the nucleic acid sequences identified in Table 1 to allow for hybridization between complementary sequences are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A *S. aureus* polynucleotide sequence shown in Table 1 labeled according to any appropriate method (such as the $^{32}$P-multiprimed DNA labeling system (Amersham)) is used as probe. After hybridization overnight, the filter is washed and exposed to x-ray film. DNA for use as probe according to the present invention is described in the sections above and will preferably at least 15 nucleotides in length.

S1 mapping can be performed as described in Fujita et al. (1987) Cell 49:357–367. To prepare probe DNA for use in S1 mapping, the sense strand of an above-described *S. aureus* DNA sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding polypeptides of the present invention).

Levels of mRNA encoding *Staphylococcus* polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the *Staphylococcus* polypeptides of the present invention) are quantified using an imaging analyzer. RT and PCR reaction ingredients and conditions, reagent and gel concentrations, and labeling methods are well-known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995).

The polynucleotides of the present invention, including both DNA and RNA, may be used to detect polynucleotides of the present invention or *Staphylococcus* species including *S. aureus* using bio chip technology. The present invention includes both high density chip arrays (>1000 oligonucleotides per $cm^2$) and low density chip arrays (<1000 oligonucleotides per $cm^2$). Bio chips comprising arrays of polynucleotides of the present invention may be used to detect *Staphylococcus* species, including *S. aureus*, in biological and environmental samples and to diagnose an animal, including humans, with an *S. aureus* or other *Staphylococcus* infection. The bio chips of the present invention may comprise polynucleotide sequences of other pathogens including bacteria, viral, parasitic, and fungal polynucleotide sequences, in addition to the polynucleotide sequences of the present invention, for use in rapid differential pathogenic detection and diagnosis. The bio chips can also be used to monitor an *S. aureus* or other *Staphylococcus* infections and to monitor the genetic changes (deletions, insertions, mismatches, etc.) in response to drug therapy in the clinic and drug development in the laboratory. The bio chip technology comprising arrays of polynucleotides of the present invention may also be used to simultaneously monitor the expression of a multiplicity of genes, including those of the present invention. The polynucleotides used to comprise a selected array may be specified in the same manner as for the fragments, i.e, by their 5' and 3' positions or length in contigious base pairs and include from. Methods and particular uses of the polynucleotides of the present invention to detect *Staphylococcus* species, including *S. aureus*, using bio chip technology include those known in the art and those of: U.S. Pat. Nos. 5,510,270, 5,545,531, 5,445,934, 5,677,195, 5,532,128, 5,556,752, 5,527,681, 5,451,683, 5,424,186, 5,607,646, 5,658,732 and World Patent Nos. WO/9710365, WO/9511995, WO/9743447, WO/9535505, each incorporated herein in their entireties.

Biosensors using the polynucleotides of the present invention may also be used to detect, diagnose, and monitor *S. aureus* or other *Staphylococcus* species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. Methods and particular uses of the polynucleotides of the present invention to detect *Staphylococcus* species, including *S. aureus*, using biosenors include those known in the art and those of: U.S. Pat. Nos 5,721,102, 5,658,732, 5,631,170, and World Patent Nos. WO97/35011, WO/9720203, each incorporated herein in their entireties.

Thus, the present invention includes both bio chips and biosensors comprising polynucleotides of the present invention and methods of their use.

A preferred composition of matter comprises isolated nucleic acid molecules wherein the nucleotide sequences of said nucleic acid molecules comprise a bio chip or biosensor of at least 1, 2, 3, 4, 5, 6, 7, 8, 9, 10, 15, 20, 25, 30, 40, 50, 100, 150, 200, 250, 300, 500, 1000, 2000, 3000 or 4000 nucleotide sequences, wherein at least one sequence in said DNA bio chip or biosensor is at least 95% identical to a sequence of at least 50 contiguous nucleotides in a *S. aureus* polynucleotide shown in Table 1. The nucleic acid molecules can comprise DNA molecules or RNA molecules.

Assaying *Staphylococcus* polypeptide levels in a biological sample can occur using any art-known method, such as antibody-based techniques. For example, *Staphylococcus* polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of *Staphylococcus* polypeptides for Western-blot or dot/slot assay. See, e.g., Jalkanen, M. et al. (1985) J. Cell. Biol. 101:976–985; Jalkanen, M. et al. (1987) J. Cell. Biol. 105:3087–3096. In this technique, which is based on the use of cationic solid phases, quantitation of a *Staphylococcus* polypeptide can be accomplished using an isolated *Staphylococcus* polypeptide as a standard. This technique can also be applied to body fluids.

Other antibody-based methods useful for detecting *Staphylococcus* polypeptide gene expression include immunoassays, such as the ELISA and the radioimmunoassay (RIA). For example, a *Staphylococcus* polypeptide-specific monoclonal antibodies can be used both as an immunoabsorbent and as an enzyme-labeled probe to detect and quantify a *Staphylococcus* polypeptide. The amount of a *Staphylococcus* polypeptide present in the sample can be calculated by reference to the amount present in a standard preparation using a linear regression computer algorithm. Such an ELISA is described in Iacobelli et al. (1988) Breast Cancer Research and Treatment 11:19–30. In another ELISA assay, two distinct specific monoclonal antibodies can be used to detect *Staphylococcus* polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the *Staphylococcus* polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the *Staphylococcus* polypeptide-specific antibodies of the present invention are provided below. Examples of suitable enzyme labels include malate dehydrogenase, *Staphylococcus* nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb $^{47}$Sc, $^{109}$Pd, ect. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxysuccinimide ester method, all of which methods are incorporated by reference herein.

In a related aspect, the invention includes a diagnostic kit for use in screening serum containing antibodies specific against *S. aureus* infection. Such a kit may include an isolated *S. aureus* antigen comprising an epitope which is specifically immunoreactive with at least one anti-*S. aureus* antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the *S. aureus* antigen can be detected by binding of the reporter labeled antibody to the anti-*S. aureus* polypeptide antibody.

In a related aspect, the invention includes a method of detecting *S. aureus* infection in a subject. This detection method includes reacting a body fluid, preferably serum, from the subject with an isolated *S. aureus* antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

The polypeptides and antibodies of the present invention, including fragments thereof, may be used to detect *Staphylococcus* species including *S. aureus* using bio chip and biosensor technology. Bio chip and biosensors of the present invention may comprise the polypeptides of the present invention to detect antibodies, which specifically recognize *Staphylococcus* species, including *S. aureus*. Bio chip and biosensors of the present invention may also comprise antibodies which specifically recognize the polypeptides of the present invention to detect *Staphylococcus* species, including *S. aureus* or specific polypeptides of the present invention. Bio chips or biosensors comprising polypeptides or antibodies of the present invention may be used to detect *Staphylococcus* species, including *S. aureus*, in biological and environmental samples and to diagnose an animal, including humans, with an *S. aureus* or other *Staphylococcus* infection. Thus, the present invention includes both bio chips and biosensors comprising polypeptides or antibodies of the present invention and methods of their use.

The bio chips of the present invention may further comprise polypeptide sequences of other pathogens including bacteria, viral, parasitic, and fungal polypeptide sequences, in addition to the polypeptide sequences of the present invention, for use in rapid diffenertial pathogenic detection and diagnosis. The bio chips of the present invention may further comprise antibodies or fragements thereof specific for other pathogens including bacteria, viral, parasitic, and fungal polypeptide sequences, in addition to the antibodies or fragements thereof of the present invention, for use in rapid diffenertial pathogenic detection and diagnosis. The bio chips and biosensors of the present invention may also be used to monitor an *S. aureus* or other *Staphylococcus* infection and to monitor the genetic changes (amio acid deletions, insertions, substitutions, etc.) in response to drug therapy in the clinic and drug development in the laboratory. The bio chip and biosensors comprising polypeptides or antibodies of the present invention may also be used to simultaneously monitor the expression of a multiplicity of polypeptides, including those of the present invention. The polypeptides used to comprise a bio chip or biosensor of the present invention may be specified in the same manner as for the fragements, i.e, by their N-terminal and C-terninal positions or length in contigious amino acid residue. Methods and particular uses of the polypeptides and antibodies of the present invention to detect *Staphylococcus* species, including *S. aureus*, or specific polypeptides using bio chip and biosensor technology include those known in the art, those of the U.S. Patent Nos. and World Patent Nos. listed above for bio chips and biosensors using polynucleotides of the present invention, and those of: U.S. Pat. Nos. 5,658, 732, 5,135,852, 5,567,301, 5,677,196, 5,690,894 and World Patent Nos. WO9729366, WO9612957, each incorporated herein in their entireties.

Treatment

Agonists and Antagonists—Assays and Molecules

The invention also provides a method of screening compounds to identify those which enhance or block the biological activity of the *S. aureus* polypeptides of the present invention. The present invention further provides where the compounds kill or slow the growth of *S. aureus*. The ability of *S. aureus* antagonists, including *S. aureus* ligands, to prophylactically or therapeutically block antibiotic resistance may be easily tested by the skilled artisan. See, e.g. Straden et al. (1997) J Bacteriol. 179(1):9–16.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity.

The antagonists may be employed for instance to inhibit peptidoglycan cross bridge formation. Antibodies against *S. aureus* may be employed to bind to and inhibit *S. aureus* activity to treat antibiotic resistance. Any of the above antagonists may be employed in a composition with a pharmaceutically acceptable carrier.

Polypeptides and polynucleotides of the invention may also be used to assess the binding of small molecule substrates and ligands in, for example, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

Polypeptides and polynucleotides of the present invention are responsible for many biological functions, including many disease states, in particular the Diseases hereinbefore mentioned. It is therefor desirable to devise screening methods to identify compounds which stimulate or which inhibit the function of the polypeptide or polynucleotide. Accordingly, in a further aspect, the present invention provides for a method of screening compounds to identify those which stimulate or which inhibit the function of a polypeptide or a polynucleotide of the invention, as well as related polypeptides and polynucleotides. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of *S. aureus* polypeptides and polynucleotides of the invention; or may be structural or functional mimetics thereof (see Coligan et al., supra).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of known agonists and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further the screening methods may simply comprise the steps of mixing a candidate compound with a solution containing a polypeptide or polynucleotide of the present invention, to form a mixture, measuring S. aureus polypeptide and/or polynucleotide activity in the mixture, and comparing the S. aureus polypeptide and/or polynucleotide activity of the mixture to a standard. Fusion proteins, such as those made from His tag and S. aureus polypeptides of the invention, as described herein, can also be used for high-throughput screening assays to identify antagonists of the polypeptide of the present invention, as well as of phylogenetically and/or functionally related polypeptides (see, e.g., Bennett et al., J. Mol. Recognition 8:52–58 (1995); and Johanson et al., J. Biol. Chem. 270(16):9459–71 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonists, respectively) from suitably manipulated cells or tissues.

The invention also provides a method of screening compounds to identify those which enhance (agonist) or block (antagonist) the action of S. aureus polypeptide or polynucleotide of the invention, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising a S. aureus polypeptide of the invention and a labeled substrate or ligand of such polypeptide is incubated in the absence of the presence of a candidate molecule that may be an agonist or antagonist of a S. aureus polypeptide of the invention. The ability of the candidate molecule to agonize or antagonize the S. aureus polypeptide is reflected in decreased binding of the labeled ligand or decreased production of product from such substrate. Molecules that bind gratuitously, i.e., without inducing the effects of S. aureus polypeptides are most likely to be good antagonists. Molecules that bind well and, as the case may be, increase the rate of product production from substrate, increase signal transduction, or increase chemical channel activity are agonists. Using a reporter system may enhance the detection of the rate or level of, for example, the production of product from substrate, signal transduction, or chemical channel activity. Reporter systems that may be useful in this regard include but are not limited to calorimetric, labeled substrate converted into product, a reporter gene that is responsive to changes in a S. aureus polynucleotide or polypeptide activity, and binding assays known in the art.

S. aureus polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, 125I), chemically modified (for instance, biotinylated), or fused to a peptide sequence suitable for detection or purification (for instance, a His tag), and incubated with a source of the putative receptor (S. aureus or human cells, cell membranes, cell supernatants, tissue extracts, bodily materials). Other methods include biophysical techniques such as surface plasmon resonance and spectroscopy. These screening methods may also be used to identify agonists and antagonists of the polypeptide which compete with the binding of the polypeptide to its receptor (s), if any. Standard methods for conducting such assays are well understood in the art.

The fluorescence polarization value for a fluorescently-tagged molecule depends on the rotational correlation time or tumbling rate. Protein complexes, such as formed by one S. aureus polypeptide of the invention associating with itself or another S. aureus polypeptide of the invention, labeled to comprise a fluorescently-labeled molecule will have higher polarization values than a fluorescently labeled monomeric protein. It is preferred that this method be used to characterize small molecules that disrupt polypeptide complexes.

Fluorescence energy transfer may also be used to characterize small molecules that interfere with the formation of S. aureus polypeptide dimers, trimers, tetramers, or higher order structures, or structures formed by one S. aureus polypeptide bound to another polypeptide. S. aureus polypeptides can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of small molecules on S. aureus polypeptide self-association as well as an association of S. aureus polypeptide and another polypeptide or small molecule. S. aureus polypeptide can be coupled to a sensor chip at low site density such that covalently bound molecules will be monomeric. Solution protein can then be passed over the S. aureus polypeptide-coated surface and specific binding can be detected in real-time by monitoring the change in resonance angle caused by a change in local refractive index. This technique can be used to characterize the effect of small molecules on kinetic rates and equilibrium binding constants for S. aureus polypeptide self-association as well as an association of S. aureus polypeptides with another polypeptide or small molecule.

A scintillation proximity assay may be used to characterize the interaction between an association of S. aureus polypeptide with another S. aureus polypeptide or a different polypeptide. S. aureus polypeptide can be coupled to a scintillation-filled bead. Addition of radio-labeled S. aureus polypeptide results in binding where the radioactive source molecule is in close proximity to the scintillation fluid. Thus, signal is emitted upon S. aureus polypeptide binding and compounds that prevent S. aureus polypeptide self-association or an association of S. aureus polypeptide and another polypeptide or small molecule will diminish signal.

ICS biosensors have been described by AMBRI (Australian Membrane Biotechnology Research Institute). They couple the self-association of macromolecules to the closing of gramacidin-facilitated ion channels in suspended membrane bilayers and hence to a measurable change in the admittance (similar to impedance) of the biosensor. This approach is linear over six decades of admittance change and is ideally suited for large scale, high through-put screening of small molecule combinatorial libraries.

In other embodiments of the invention there are provided methods for identifying compounds which bind to or otherwise interact with and inhibit or activate an activity or expression of a polypeptide and/or polynucleotide of the of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such as binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for S. aureus polypeptide agonists is a competitive assay that combines a S. aureus polypeptide and a potential agonists with S. aureus polypeptide-binding molecules, recombinant S. aureus polypeptide-binding molecules, natural substrates or ligands, or substrate or ligand mimetics, under appropriate conditions for a competitive inhibition assay. S. aureus polypeptide can be labeled, such as by radioactivity or a calorimetric compound, such that the number of S. aureus polypeptide molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing S. aureus polypeptide induced activities, thereby preventing the action or expression of S. aureus polypeptides and/or polynucleotides by excluding S. aureus polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see, e.g., Okano, J. Neurochem. 56:560 (1991); OLIGODEOXYNUCLEOTIDES AS ANTISENSE INHIBITORS OF GENE EXPRESSION, CRC Press, Boca Raton, Fla. (1998)), for a description of these molecules). Preferred potential antagonists include compounds related to and variants of S. aureus polypeptides of the invention.

Other examples of potential S. aureus polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

The invention further comprises biomimetics, or functional mimetics of the natural S. aureus polypeptides of the invention. These functional mimetics may be used for, among other things, antagonizing the activity of S. aureus polypeptide or as an antigen or immunogen in a manner described elsewhere herein. Functional mimetics of the polypeptides of the invention include but are not limited to truncated polypeptides. For example, preferred functional mimetics include, a polypeptide comprising a polypeptide sequence set forth in Table 1 lacking 20, 30, 40, 50, 60, 70, or 80 amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Thus, in another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises: (a) a polypeptide and/or a polynucleotide of the present invention; (b) a recombinant cell expressing a polypeptide and/or polynucleotide of the present invention; (c) a cell membrane expressing a polypeptide and/or a polynucleotide of the present invention; or (d) antibody to a polypeptide and/or polynucleotide of the present invention; which polypeptide is preferably one of the S. aureus polypeptides shown in Table 1, and which polynucleotide is preferably one of the S. aureus polynucleotides shown in Table 1.

It will be appreciated that in any such kit, (a), (b), (c), or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive(s), and/or motif(s); and (d) testing whether the candidate compounds are indeed agonists, antagonists or inhibitors. It will be further appreciated that this will normally be an iterative process, and this iterative process may be performed using automated and computer-controlled steps.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention further encompasses the use of polypeptides, polynucleotides, agonists and/or antagonists of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial *S. aureus* proteins that mediate tissue damage and/or; to block the normal progression of pathogenesis in infections initiated other than by the implantation of in-dwelling devices or by other surgical techniques.

In a specific embodiment, the invention provides *S. aureus* polypeptide agonists and antagonists, preferably bacteristatic or bactericidal agonists and antagonists.

The antagonists and agonists of the invention may be employed, for example, to prevent, inhibit and/or treat diseases.

Vaccines

The present invention also provides vaccines comprising one or more polypeptides of the present invention. Heterogeneity in the composition of a vaccine may be provided by combining *S. aureus* polypeptides of the present invention. Multi-component vaccines of this type are desirable because they are likely to be more effective in eliciting protective immune responses against multiple species and strains of the *Staphylococcus* genus than single polypeptide vaccines.

Multi-component vaccines are known in the art to elicit antibody production to numerous immunogenic components. See, e.g., Decker et al. (1996) J. Infect. Dis. 174: S270–275. In addition, a hepatitis B, diphtheria, tetanus, pertussis tetravalent vaccine has recently been demonstrated to elicit protective levels of antibodies in human infants against all four pathogenic agents. See, e.g., Aristegui, J. et al. (1997) Vaccine 15:7–9.

The present invention in addition to single-component vaccines includes multi-component vaccines. These vaccines comprise more than one polypeptide, immunogen or antigen. Thus, a multi-component vaccine would be a vaccine comprising more than one of the *S. aureus* polypeptides of the present invention.

Further within the scope of the invention are whole cell and whole viral vaccines. Such vaccines may be produced recombinantly and involve the expression of one or more of the *S. aureus* polypeptides described in Table 1. For example, the *S. aureus* polypeptides of the present invention may be either secreted or localized intracellularly, on the cell surface, or in the periplasmic space. Further, when a recombinant virus is used, the *S. aureus* polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al. (1997) Nature Biotech. 15:653–657; Sirard, J. et al. (1997) Infect. Immun. 65:2029–2033; Chabalgoity, J. et al. (1997) Infect. Immun. 65:2402–2412. These cells may be administered live or may be killed prior to administration. Chabalgoity, J. et al., supra, for example, report the successful use in mice of a live attenuated *Salmonella* vaccine strain which expresses a portion of a platyhelminth fatty acid-binding protein as a fusion protein on its cells surface.

A multi-component vaccine can also be prepared using techniques known in the art by combining one or more *S. aureus* polypeptides of the present invention, or fragments thereof, with additional non-staphylococcal components (e.g., diphtheria toxin or tetanus toxin, and/or other compounds known to elicit an immune response). Such vaccines are useful for eliciting protective immune responses to both members of the *Staphylococcus* genus and non-staphylococcal pathogenic agents.

The vaccines of the present invention also include DNA vaccines. DNA vaccines are currently being developed for a number of infectious diseases. See, et al., Boyer, et al. (1997) Nat. Med. 3:526–532; reviewed in Spier, R. (1996) Vaccine 14:1285–1288. Such DNA vaccines contain a nucleotide sequence encoding one or more *S. aureus* polypeptides of the present invention oriented in a manner that allows for expression of the subject polypeptide. For example, the direct administration of plasmid DNA encoding *B. burgdorgeri* OspA has been shown to elicit protective immunity in mice against borrelial challenge. See, Luke et al. (1997) J. Infect. Dis. 175:91–97.

The present invention also relates to the administration of a vaccine which is co-administered with a molecule capable of modulating immune responses. Kim et al. (1997) Nature Biotech. 15:641–646, for example, report the enhancement of immune responses produced by DNA immunizations when DNA sequences encoding molecules which stimulate the immune response are co-administered. In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to staphylococcal infection by either passive or active immunization. When the vaccines of the present invention are used to confer resistance to staphylococcal infection through active immunization, a vaccine of the present invention is administered to an animal to elicit a protective immune response which either prevents or attenuates a staphylococcal infection. When the vaccines of the present invention are used to confer resistance to staphylococcal infection through passive immunization, the vaccine is provided to a host animal (e.g., human, dog, or mouse), and the antisera elicited by this antisera is recovered and directly provided to a recipient suspected of having an infection caused by a member of the *Staphylococcus* genus.

The ability to label antibodies, or fragments of antibodies, with toxin molecules provides an additional method for treating staphylococcal infections when passive immunization is conducted. In this embodiment, antibodies, or fragments of antibodies, capable of recognizing the *S. aureus* polypeptides disclosed herein, or fragments thereof, as well as other *Staphylococcus* proteins, are labeled with toxin molecules prior to their administration to the patient. When such toxin derivatized antibodies bind to *Staphylococcus* cells, toxin moieties will be localized to these cells and will cause their death.

The present invention thus concerns and provides a means for preventing or attenuating a staphylococcal infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the compound(s)

are provided in advance of any symptoms of staphylococcal infection. The prophylactic administration of the compound (s) serves to prevent or attenuate any subsequent infection. When provided therapeutically, the compound(s) is provided upon or after the detection of symptoms which indicate that an animal may be infected with a member of the *Staphylococcus* genus. The therapeutic administration of the compound(s) serves to attenuate any actual infection. Thus, the *S. aureus* polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., ANTIBODIES: A LABORATORY MANUAL, (Cold Spring Harbor Laboratory Press, 2nd ed. 1988).

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the *S. aureus* polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they non-specifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlNH_4(SO_4)$. Examples of materials suitable for use in vaccine compositions are provided in REMINGTON'S PHARMACEUTICAL SCIENCES 1324–1341 (A. Osol, ed, Mack Publishing Co, Easton, Pa., (1980) (incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization using vaccines encapsulated in biodegradable microsphere composed of poly(DL-lactide-co-glycolide). See, Shahin, R. et al. (1995) Infect. Immun. 63:1195–1200. Similarly, orally administered encapsulated *Salmonella typhimurium* antigens can also be used. Allaoui-Attarki, K. et al. (1997) Infect. Immun. 65:853–857. Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

Binding Peptides and Other Molecules

The invention also encompasses screening methods for identifying polypeptides and nonpolypeptides that bind the *S. aureus* polypeptides of the invention, and the *S. aureus* polypeptides binding molecules identified thereby. These binding molecules are useful, for example, as agonists and antagonists of the *S. aureus* polypeptides of the invention.

Such agonists and antagonists can be used, in accordance with the invention, in the therapeutic embodiments described in detail, below.

This method comprises the steps of:
(a) contacting a S. aureus polypeptide with a plurality of molecules; and
(b) identifying a molecule that binds the S. aureus polypeptide.

The step of contacting the S. aureus polypeptide with the plurality of molecules may be effected in a number of ways. For example, one may contemplate immobilizing the S. aureus polypeptide on a solid support and bringing a solution of the plurality of molecules in contact with the immobilized S. aureus polypeptide. Such a procedure would be akin to an affinity chromatographic process, with the affinity matrix being comprised of the immobilized S. aureus polypeptide. The molecules having a selective affinity for the S. aureus polypeptide can then be purified by affinity selection. The nature of the solid support, process for attachment of the S. aureus polypeptide to the solid support, solvent, and conditions of the affinity isolation or selection are largely conventional and well-known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the S. aureus polypeptide, optionally in the presence of an inducer should one be required for expression, to determine if any selective affinity interaction takes place between the S. aureus polypeptide and the individual clone. Prior to contacting the S. aureus polypeptide with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for S. aureus polypeptide. Furthermore, the amino acid sequence of the polypeptide having a selective affinity for any one of the S. aureus polypeptides of the invention can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound S. aureus polypeptide, or alterntatively, unbound polypeptides, from a mixture of the S. aureus polypeptide and the plurality of polypeptides prior to attempting to determine or to detect the presence of a selective affinity interaction. Such a wash step may be particularly desirable when the S. aureus polypeptide or the plurality of polypeptides is bound to a solid support.

The plurality of molecules provided according to this method may be provided by way of diversity libraries, such as random or combinatorial peptide or nonpeptide libraries which can be screened for molecules that specifically bind to a S. aureus polypeptide. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, beta-mercapoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol.

251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and CT Publication No. WO 94/18318.

In a specific embodiment, screening to identify a molecule that binds a S. aureus polypeptide can be carried out by contacting the library members with a S. aureus polypeptide immobilized on a solid phase and harvesting those library members that bind to the S. aureus polypeptide. Examples of such screening methods, termed "panning" techniques are described by way of example in Parmley and Smith, 1988, Gene 73:305–318; Fowlkes et al., 1992, BioTechniques 13:422–427; PCT Publication No. WO 94/183 18; and in references cited herein.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to any one of the S. aureus polypeptides shown in Table 1.

Where the S. aureus polypeptide binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a S. aureus polypeptide binding molecule that is a polypeptide, the polypeptide may have about 6 to less than about 60 amino acid residues, preferably about 6 to about 10 amino acid residues, and most preferably, about 6 to about 22 amino acids. In another embodiment, a S. aureus polypeptide binding polypeptide has in the range of 15–100 amino acids, or 20–50 amino acids.

The selected S. aureus polypeptide binding polypeptide can be obtained by chemical synthesis or recombinant expression.

EXAMPLES

Example 1

Isolation of a Selected DNA Clone from the Deposited Sample

Three approaches can be used to isolate a S. aureus clone comprising a polynucleotide of the present invention from any S. aureus genomic DNA library. The S. aureus strain ISP3 has been deposited as a convienent source for obtaining a S. aureus strain although a wide varity of strains S. aureus strains can be used which are known in the art.

S. aureus genomic DNA is prepared using the following method. A 20 ml overnight bacterial culture grown in a rich medium (e.g., Trypticase Soy Broth, Brain Heart Infusion broth or Super broth), pelleted, washed two times with TES (30 mM Tris-pH 8.0, 25 mM EDTA, 50 mM NaCl), and resuspended in 5 ml high salt TES (2.5M NaCl). Lysostaphin is added to final concentration of approx 50 ug/ml and the mixture is rotated slowly 1 hour at 37° C. to make protoplast cells. The solution is then placed in incubator (or place in a shaking water bath) and warmed to 55° C. Five hundred microliters of 20% sarcosyl in TES (final concentration 2%) is then added to lyse the cells. Next, guanidine HCl is added to a final concentration of 7M (3.69 g in 5.5 ml). The mixture is swirled slowly at 55° C. for 60–90 min (solution should clear). A CsCl gradient is then set up in SW41 ultra clear tubes using 2.0 ml 5.7M CsCl and overlaying with 2.85M CsCl. The gradient is carefully overlayed with the DNA-containing GuHCl solution. The gradient is spun at 30,000 rpm, 20° C. for 24 hr and the lower DNA band is collected. The volume is increased to 5 ml with TE buffer. The DNA is then treated with protease K (10 ug/ml) overnight at 37° C., and precipitated with ethanol. The precipitated DNA is resuspended in a desired buffer.

In the first method, a plasmid is directly isolated by screening a plasmid S. aureus genomic DNA library using a polynucleotide probe corresponding to a polynucleotide of the present invention. Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989). The transformants are plated on 1.5% agar plates (containing the appropriate selection agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, New York 1989) or other techniques known to those of skill in the art.

Alternatively, two primers of 15–25 nucleotides derived from the 5' and 3' ends of a polynucleotide of Table 1 are synthesized and used to amplify the desired DNA by PCR using a S. aureus genomic DNA prep (e.g., the deposited S. aureus ISP3) as a template. PCR is carried out under routine conditions, for instance, in 25 μl of reaction mixture with 0.5 ug of the above DNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are perform with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of Table 1 can be synthesized and used to generate a nucleotide sequence of desired length using PCR methods known in the art.

Example 2(a)

Expression and Purification Staphylococcal Polypeptides in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion of a *S. aureus* protein of the present invention is amplified from *S. aureus* genomic DNA or from the deposited DNA clone using PCR oligonucleotide primers which anneal to the 5' and 3' sequences coding for the portion of the *S. aureus* polynucleotide. Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desired *S. aureus* polynucleotide sequence in Table 1. One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the desired coding sequence of Table 1, excluding a stop codon, with the coding sequence aligned with the restriction site so as to maintain its reading frame with that of the six His codons in the pQE60 vector.

The amplified *S. aureus* DNA fragment and the vector pQE60 are digested with restriction enzymes which recognize the sites in the primers and the digested DNAs are then ligated together. The *S. aureus* DNA is inserted into the restricted pQE60 vector in a manner which places the *S. aureus* protein coding region downstream from the IPTG-inducible promoter and in-frame with an initiating AUG and the six histidine codons.

The ligation mixture is transformed into competent *E. coli* cells using standard procedures such as those described by Sambrook et al., supra. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing a *S. aureus* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the *S. aureus* polypeptide is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the *S. aureus* polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6 M-1 M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at –80° C.

Alternatively, the polypeptides of the present invention can be produced by a non-denaturing method. In this method, after the cells are harvested by centrifugation, the cell pellet from each liter of culture is resuspended in 25 ml of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm is approximately 10–20 O.D./ml. The suspension is then put through three freeze/thaw cycles from –70° C. (using a ethanol-dry ice bath) up to room temperature. The cells are lysed via sonication in short 10 sec bursts over 3 minutes at approximately 80 W while kept on ice. The sonicated sample is then centrifuged at 15,000 RPM for 30 minutes at 4° C. The supernatant is passed through a column containing 1.0 ml of CL-4B resin to pre-clear the sample of any proteins that may bind to agarose non-specifically, and the flow-through fraction is collected.

The pre-cleared flow-through is applied to a nickel-nitrilo-tri-acetic acid ("Ni-NTA") affinity resin column (Quiagen, Inc., supra). Proteins with a 6×His tag bind to the Ni-NTA resin with high affinity and can be purified in a simple one-step procedure. Briefly, the supernatant is loaded onto the column in Lysis Buffer A at 4° C., the column is first washed with 10 volumes of Lysis Buffer A until the A280 of the eluate returns to the baseline. Then, the column is washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5). The protein is eluted off of the column with a series of increasing Imidazole solutions made by adjusting the ratios of Lysis Buffer A to Buffer B. Three different concentrations are used: 3 volumes of 75 mM Imidazole, 3 volumes of 150 mM Imidazole, 5 volumes of 500 mM Imidazole. The fractions containing the purified protein are analyzed using 8%, 10% or 14% SDS-PAGE depending on the protein size. The purified protein is then dialyzed 2× against phosphate-buffered saline (PBS) in order to place it into an easily workable buffer. The purified protein is stored at 4° C. or frozen at −80° C.

The following is another alternative method may be used to purify S. aureus expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the S. aureus polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded S. aureus polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the S. aureus polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the S. aureus polypeptide (determined, for instance, by 16% SDS-PAGE) are then pooled.

The resultant S. aureus polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Example 2(b)

Expression and Purification Staphylococcal Polypeptides in E. coli

Alternatively, the vector pQE10 can be used to clone and express polypeptides of the present invention. The difference being such that an inserted DNA fragment encoding a polypeptide expresses that polypeptide with the six His residues (i.e., a "6×His tag") covalently linked to the amino terminus of that polypeptide. The bacterial expression vector pQE10 (QIAGEN, Inc., 9259 Eton Avenue, Chatsworth, Calif., 91311) is used in this example . The components of the pQE 10 plasmid are arranged such that the inserted DNA sequence encoding a polypeptide of the present invention expresses the polypeptide with the six His residues (i.e., a "6×His tag")) covalently linked to the amino terminus.

The DNA sequences encoding the desired portions of a polypeptide of Table 1 are amplified using PCR oligonucleotide primers from either genomic S. aureus DNA or DNA from the plasmid clones listed in Table 1 clones of the present invention. The PCR primers anneal to the nucleotide sequences encoding the desired amino acid sequence of a polypeptide of the present invention. Additional nucleotides containing restriction sites to facilitate cloning in the pQE10 vector are added to the 5' and 3' primer sequences, respectively.

For cloning a polypeptide of the present invention, the 5' and 3' primers are selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer is designed so the coding sequence of the 6×His tag is aligned with the restriction site so as to maintain its reading frame with that of S. aureus polypeptide. The 3' is designed to include a stop codon. The amplified DNA fragment is then cloned, and the protein expressed, as described above for the pQE60 plasmid.

The DNA sequences encoding the amino acid sequences of Table 1 may also be cloned and expressed as fusion proteins by a protocol similar to that described directly above, wherein the pET-32b(+) vector (Novagen, 601 Science Drive, Madison, Wis. 53711) is preferentially used in place of pQE10.

Example 2(c)

Expression and Purification of Stahphlococcusl Polypeptides in E. coli

The bacterial expression vector pQE60 is used for bacterial expression in this example (QIAGEN, Inc., 9259 Eton Avenue, Chatsworth, Calif., 91311). However, in this example, the polypeptide coding sequence is inserted such that translation of the six His codons is prevented and, therefore, the polypeptide is produced with no 6×His tag.

The DNA sequence encoding the desired portion of the *S. aureus* amino acid sequence is amplified from a *S. aureus* genomic DNA prep using PCR oligonucleotide primers which anneal to the 5' and 3' nucleotide sequences corresponding to the desired portion of the *S. aureus* polypeptides. Additional nucleotides containing restriction sites to facilitate cloning in the pQE60 vector are added to the 5' and 3' primer sequences.

For cloning *S. aureus* polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified *S. aureus* DNA fragments and the vector pQE60 are digested with restriction enzymes recognizing the sites in the primers and the digested DNAs are then ligated together. Insertion of the *S. aureus* DNA into the restricted pQE60 vector places the *S. aureus* protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described by Sambrook et al. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing *S. aureus* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the *S. aureus* polypeptide, the cells are then stirred for 3–4 hours at 4° C. in 6M guanidine-HCl, pH 8. The cell debris is removed by centrifugation, and the supernatant containing the *S. aureus* polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure *S. aureus* polypeptide. The purified protein is stored at 4° C. or frozen at −80° C.

The following alternative method may be used to purify *S. aureus* polypeptides expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the *S. aureus* polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded *S. aureus* polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the *S. aureus* polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the *S. aureus* polypeptide (determined, for instance, by 16% SDS-PAGE) are then pooled.

The resultant *S. aureus* polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2(d)
Cloning and Expression of S. aureus in Other Bacteria

S. aureus polypeptides can also be produced in: S. aureus using the methods of S. Skinner et al., (1988) Mol. Microbiol. 2:289–297 or J. I. Moreno (1996) Protein Expr. Purif. 8(3):332–340; Lactobacillus using the methods of C. Rush et al., 1997 Appl. Microbiol. Biotechnol. 47(5):537–542; or in Bacillus subtilis using the methods Chang et al., U.S. Pat. No. 4,952,508.

Example 3
Cloning and Expression in COS Cells

A S. aureus expression plasmid is made by cloning a portion of the DNA encoding a S. aureus polypeptide into the expression vector pDNAI/Amp or pDNAIII (which can be obtained from Invitrogen, Inc.). The expression vector pDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a S. aureus polypeptide is cloned into the polylinker region of the vector so that recombinant protein expression is directed by the CMV promoter. The plasmid construction strategy is as follows. The DNA from a S. aureus genomic DNA prep is amplified using primers that contain convenient restriction sites, much as described above for construction of vectors for expression of S. aureus in E. coli. The 5' primer contains a Kozak sequence, an AUG start codon, and nucleotides of the 5' coding region of the S. aureus polypeptide. The 3' primer, contains nucleotides complementary to the 3' coding sequence of the S. aureus DNA, a stop codon, and a convenient restriction site.

The PCR amplified DNA fragment and the vector, pDNAI/Amp, are digested with appropriate restriction enzymes and then ligated. The ligation mixture is transformed into an appropriate E. coli strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the S. aureus polypeptide For expression of a recombinant S. aureus polypeptide, COS cells are transfected with an expression vector, as described above, using DEAE-dextran, as described, for instance, by Sambrook et al. (supra). Cells are incubated under conditions for expression of S. aureus by the vector.

Expression of the S. aureus-HA fusion protein is detected by radiolabeling and immunoprecipitation, using methods described in, for example Harlow et al., supra.. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4
Cloning and Expression in CHO Cells

The vector pC4 is used for the expression of S. aureus polypeptide in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the S. aureus polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the S.

*aureus* polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the *S. aureus* polypeptide is synthesized and used. A 3' primer, containing a restriction site, stop codon, and nucleotides complementary to the 3' coding sequence of the *S. aureus* polypeptides is synthesized and used. The amplified fragment is digested with the restriction endonucleases and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using a lipid-mediated transfection agent such as Lipofectin™ or LipofectAMINE.™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 5
Quantitative Murine Soft Tissue Infection Model for *S. aureus*

Compositions of the present invention, including polypeptides and peptides, are assayed for their ability to function as vaccines or to enhance/stimulate an immune response to a bacterial species (e.g., *S. aureus*) using the following quantitative murine soft tissue infection model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

The desired bacterial species used to challenge the mice, such as *S. aureus*, is grown as an overnight culture. The culture is diluted to a concentration of $5 \times 10^8$ cfu/ml, in an appropriate media, mixed well, serially diluted, and titered. The desired doses are further diluted 1:2 with sterilized Cytodex 3 microcarrier beads preswollen in sterile PBS (3 g/100 ml). Mice are anesthetized briefly until docile, but still mobile and injected with 0.2 ml of the Cytodex 3 bead/bacterial mixture into each animal subcutaneously in the inguinal region. After four days, counting the day of injection as day one, mice are sacrificed and the contents of the abscess is excised and placed in a 15 ml conical tube containing 1.0 ml of sterile PBS. The contents of the abscess are then enzymatically treated and plated as follows.

The abscess is first disrupted by vortexing with sterilized glass beads placed in the tubes. 3.0 mls of prepared enzyme mixture (1.0 ml Collagenase D (4.0 mg/ml), 1.0 ml Trypsin (6.0 mg/ml) and 8.0 ml PBS) is then added to each tube followed by 20 min. incubation at 37° C. The solution is then centrifuged and the supernatant drawn off. 0.5 ml $dH_2O$ is then added and the tubes are vortexed and then incubated for 10 min. at room temperature. 0.5 ml media is then added and samples are serially diluted and plated onto agar plates, and grown overnight at 37° C. Plates with distinct and separate colonies are then counted, compared to positive and negative control samples, and quantified. The method can be used to identify composition and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

Example 6
Murine Systemic Neutropenic Model for *S. aureus* Infection

Compositions of the present invention, including polypeptides and peptides, are assayed for their ability to function as vaccines or to enhance/stimulate an immune response to a bacterial species (e.g., *S. aureus*) using the following qualitative murine systemic neutropenic model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

Mice are then injected with 250–300 mg/kg cyclophosphamide intraperitonially. Counting the day of C.P. injection as day one, the mice are left untreated for 5 days to begin recovery of PMNL'S.

The desired bacterial species used to challenge the mice, such as *S. aureus*, is grown as an overnight culture. The culture is diluted to a concentration of $5 \times 10^8$ cfu/ml, in an appropriate media, mixed well, serially diluted, and titered. The desired doses are further diluted 1:2 in 4% Brewer's yeast in media.

Mice are injected with the bacteria/brewer's yeast challenge intraperitonially. The Brewer's yeast solution alone is used as a control. The mice are then monitored twice daily for the first week following challenge, and once a day for the next week to ascertain morbidity and mortality. Mice remaining at the end of the experiment are sacrificed. The method can be used to identify compositions and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to

Example 7
Murine Lethal Sepsis Model

S. aureus polypeptides of he present invention can be evaluated for potential vaccine efficacy using the murine lethal sepsis model. In this model, mice are challenged with extremely low lethal doses (frequently between 1 and 10 colony forming units [cfu]) of virulent strains of S. aureus. Initial studies are conducted to determine a less virulent strain of S. aureus. Polypeptides of the present invention (e.g., such as the polypeptides described in Table 1, fragments thereof and fragments that comprise the epitopes shown in Table 4) produced as Example 2(a)–(d), and optionally conjugated with another immunogen are tested as vaccine candidates. Vaccine candidates immunized mice are then challenged with a lethal dose of S. aureus which protect against death when approximately 100 times the $LD_{50}$ of the strain employed are selected as protective antigens.

More specifically, female C2H/HeJ mices are immunized subcutaneously in groups of 10 with 15 ug of protein formulated in complete Freund's adjuvant (CFA). Twenty one days later, mice are boosted in the same way with protein formulated in incomplete Freund's adjuvant. Twenty-eight days following boost animals are bled and a prechallenge immune titer against S. aureus proteins is determined by ELISA.

35 days following the boost, a freshly prepared culture of S. aureus in BHI are diluted to approximately 35 to 100× $LD_{50}$ in sterile PBS and injected intraperitoneally into mice in a volume of 100 ul. Mice are monitored for 14 days for mortality. Survival rate is compared with a sham group immunized with PBS and adjuvant alone.

Example 8
Identifying Vaccine Antigens Against Prevelant S. aureus Strains It is further determined whether the majority of the most prevalent S. aureus strains express the vaccine antigen(s) and polypeptide(s) identified by the lethal model of Example 7 or the models of Example 5 or 6. Immunoblot analysis is performed with cell lysates prepared from Staphylococcus strains representative of the major capsular serotypes and probed with polyclonal antisera specific for the protective antigens. A preferred vaccine is comprised of a serological epitope of the polypeptide of the present invention that is well conserved among the majority of infective Staphyloccus serotypes.

Example 9
Production of an Antibody
a) Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phages are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

The disclosure of all publications (including patents, patent applications, journal articles, laboratory manuals, books, or other documents) cited herein and the sequence listings are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparent to those skilled in the art from the foregoing description and accompanying drawings. Such modifications are intended to fall within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties. Moreover, the hard copy of and the corresponding computer readable form of the Sequence Listing of U.S. patent application Ser. No. 60/151,933 is also incorporated herein by reference in its entirety.

What is claimed is:

1. An isolated polynucleotide comprising a nucleic acid sequence encoding an amino acid sequence identical to, except for up to five amino acid alterations per 100 amino acids, an amino acid sequence selected from the group consisting of:
   (a) the full-length IspA amino acid sequence encoded by the ORF represented by SEQ ID NO:63; and
   (b) the full-length IspA amino acid sequence represented by SEQ ID NO:64.

2. The isolated polynucleotide of claim 1 wherein the amino acid sequence is (a).

3. The isolated polynucleotide of claim 1, wherein the amino acid sequence is (b).

4. The isolated polynucleotide of claim 1, wherein said polynucleotide comprises a heterologous polynucleotide sequence.

5. The isolated polynucleotide of claim 4, wherein said heterologous polynucleotide sequence encodes a heterologous polypeptide.

6. A method for making a recombinant vector comprising inserting the isolated polynucleotide of claim 1 into a vector.

7. A recombinant vector comprising the isolated polynucleotide of claim 1.

8. The recombinant vector of claim 7, wherein said polynucleotide is operably associated with a heterologous regulatory sequence that controls gene expression.

9. A recombinant host cell comprising the isolated polynucleotide of claim 1.

10. The recombinant host cell of claim 9, wherein said polynucleotide is operably associated with a heterologous regulatory sequence that controls gene expression.

11. A method for producing a polypeptide, comprising:
    (a) culturing a cell under conditions suitable to produce a polypeptide encoded by the polynucleotide of claim 1; and
    (b) recovering the polypeptide.

12. An isolated polynucleotide comprising a nucleic acid sequence encoding at least 15 contiguous amino acid residues of an amino acid sequence selected from the group consisting of:
    (a) the full-length IspA amino acid sequence encoded by the ORF represented by SEQ ID NO:63; and
    (b) the full-length IspA amino acid sequence represented by SEQ ID NO:64.

13. The isolated polynucleotide of claim 12 wherein the amino acid sequence is (a).

14. The isolated polynucleotide of claim 12 wherein the amino acid sequence is (b).

15. The isolated polynucleotide of claim 12, wherein said polynucleotide comprises a heterologous polynucleotide sequence.

16. The isolated polynucleotide of claim 15, wherein said heterologous polynucleotide sequence encodes a heterologous polypeptide.

17. A method for making a recombinant vector comprising inserting the isolated polynucleotide of claim 12 into a vector.

18. A recombinant vector comprising the isolated polynucleotide of claim 12.

19. The recombinant vector of claim 18, wherein said polynucleotide is operably associated with a heterologous regulatory sequence that controls gene expression.

20. A recombinant host cell comprising the isolated polynucleotide of claim 12.

21. The recombinant host cell of claim 20, wherein said polynucleotide is operably associated with a heterologous regulatory sequence that controls gene expression.

22. A method for producing a polypeptide, comprising:
    (a) culturing a cell under conditions suitable to produce a polypeptide encoded by the polynucleotide of claim 12; and
    (b) recovering the polypeptide.

23. The isolated polynucleotide of claim 12, wherein said polynucleotide comprises a nucleic acid sequence encoding at least 30 contiguous amino acid residues of an amino acid sequence selected from the group consisting of:
    (a) the full-length IspA amino acid sequence encoded by the ORF represented by SEQ ID NO:63; and
    (b) the full-length IspA amino acid sequence represented by SEQ ID NO:64.

24. The isolated polynucleotide of claim 23 wherein the amino acid sequence is (a).

25. The isolated polynucleotide of claim 23 wherein the amino acid sequence is (b).

26. The isolated polynucleotide of claim 23, wherein said polynucleotide comprises a heterologous polynucleotide sequence.

27. The isolated polynucleotide of claim 26, wherein said heterologous polynucleotide sequence encodes a heterologous polypeptide.

28. A method for making a recombinant vector comprising inserting the isolated polynucleotide of claim 23 into a vector.

29. A recombinant vector comprising the isolated polynucleotide of claim 23.

30. The recombinant vector of claim 29, wherein said polynucleotide is operably associated with a heterologous regulatory sequence that controls gene expression.

31. A recombinant host cell comprising the isolated polynucleotide of claim 23.

32. The recombinant host cell of claim 31, wherein said polynucleotide is operably associated with a heterologous regulatory sequence that controls gene expression.

33. A method for producing a polypeptide, comprising:
    (a) culturing a cell under conditions suitable to produce a polypeptide encoded by the polynucleotide of claim 23; and
    (b) recovering the polypeptide.

34. An isolated polynucleotide comprising a nucleic acid sequence which hybridizes, at 42° C. in 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing in 0.1×SSC at 65° C., to a nucleic acid sequence complementary to SEQ ID NO:63.

35. The isolated polynucleotide of claim 34, wherein said polynucleotide comprises a heterologous polynucleotide sequence.

36. The isolated polynucleotide of claim 35, wherein said heterologous polynucleotide sequence encodes a heterologous polypeptide.

37. A method for making a recombinant vector comprising inserting the isolated polynucleotide of claim 34 into a vector.

38. A recombinant vector comprising the isolated polynucleotide of claim 34.

39. The recombinant vector of claim 38, wherein said polynucleotide is operably associated with a heterologous regulatory sequence that controls gene expression.

40. A recombinant host cell comprising the isolated polynucleotide of claim 34.

41. The recombinant host cell of claim 40, wherein said polynucleotide is operably associated with a heterologous regulatory sequence that controls gene expression.

42. A method for producing a polypeptide, comprising:
(a) culturing a cell under conditions suitable to produce a polypeptide encoded by the polynucleotide of claim 34; and
(b) recovering the polypeptide.

43. An isolated polynucleotide comprising at least 50 contiguous nucleotides, or the complement thereof, of an ORF encoding an amino acid sequence selected from the group consisting of:
(a) the full-length IspA amino acid sequence encoded by the ORF represented by SEQ ID NO;63; and
(b) the full-length IspA amino acid sequence represented by SEQ ID NO:64.

44. The isolated polynucleotide of claim 43 wherein the amino acid sequence is (a).

45. The isolated polynucleotide of claim 43 wherein the amino acid sequence is (b).

46. The isolated polynucleotide of claim 43, wherein said polynucleotide comprises a heterologous polynucleotide sequence.

47. The isolated polynucleotide of claims 46, wherein said heterologous polynucleotide sequence encodes a heterologous polypeptide.

48. A method for making a recombinant vector comprising inserting the isolated polynucleotide of claim 43 into a vector.

49. A recombinant vector comprising the isolated polynucleotide of claim 43.

50. The recombinant vector of claim 49, wherein said polynucleotide is operably associated with a heterologous regulatory sequence that controls gene expression.

51. A recombinant host cell comprising the isolated polynucleotide of claim 43.

52. The recombinant host cell of claim 51, wherein said polynucleotide is operably associated with a heterologous regulatory sequence that controls gene expression.

53. A method for producing a polypeptide, comprising:
(a) culturing a cell under conditions suitable to produce a polypeptide encoded by the polynucleotide of claim 43; and
(b) recovering the polypeptide.

54. The isolated polynucleotide of claim 43 comprising at least 100 contiguous nucleotides of an ORF encoding an amino acid sequence selected from the group consisting of:
(a) the full-length IspA amino acid sequence encoded by the ORF represented by SEQ ID NO:63; and
(b) the full-length IspA amino acid sequence represented by SEQ ID NO:64.

55. The isolated polynucleotide of claim 54 wherein the amino acid sequence is (a).

56. The isolated polynucleotide of claim 54 wherein the amino acid sequence is (b).

57. The isolated polynucleotide of claim 54, wherein said polynucleotide comprises a heterologous polynucleotide sequence.

58. The isolated polynucleotide of claim 57, wherein said heterologous polynucleotide sequence encodes a heterologous polypeptide.

59. A method for making a recombinant vector comprising inserting the isolated polynucleotide of claim 54 into a vector.

60. A recombinant vector comprising the isolated polynucleotide of claim 54.

61. The recombinant vector of claim 60, wherein said polynucleotide is operably associated with a heterologous regulatory sequence that controls gene expression.

62. A recombinant host cell comprising the isolated polynucleotide of claim 54.

63. The recombinant host cell of claim 62, wherein said polynucleotide is operably associated with a heterologous regulatory sequence that controls gene expression.

64. A method for producing a polypeptide, comprising:
(a) culturing a cell under conditions suitable to produce a polypeptide encoded by the polynucleotide of claim 54; and
(b) recovering the polypeptide.

\* \* \* \* \*